US010444242B2

(12) United States Patent
Ziemann et al.

(10) Patent No.: US 10,444,242 B2
(45) Date of Patent: Oct. 15, 2019

(54) DETECTION METHODS EMPLOYING HCV CORE LIPID AND DNA BINDING DOMAIN MONOCLONAL ANTIBODIES

(71) Applicants: ABBOTT LABORATORIES, Abbott Park, IL (US); Icahn School of Medicine at Mount Sinai, New York, NY (US)

(72) Inventors: Robert Ziemann, Abbott Park, IL (US); April Ahlberg, Abbott Park, IL (US); David Hawksworth, Abbott Park, IL (US); Bryan Tieman, Abbott Park, IL (US); A. Scott Muerhoff, Abbott Park, IL (US); Christopher Marohnic, Abbott Park, IL (US); Kathy Otis, Abbott Park, IL (US); Andrea Branch, New York, NY (US); Francis Eng, New York, NY (US)

(73) Assignees: ABBOTT LABORATORIES, Abbott Park, IL (US); ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 24 days.

(21) Appl. No.: 15/189,646

(22) Filed: Jun. 22, 2016

(65) Prior Publication Data

US 2017/0052184 A1 Feb. 23, 2017

Related U.S. Application Data

(63) Continuation-in-part of application No. 15/079,013, filed on Mar. 23, 2016, now Pat. No. 10,197,573, which is a continuation of application No. 14/138,991, filed on Dec. 23, 2013, now Pat. No. 9,371,374.

(60) Provisional application No. 61/783,529, filed on Mar. 14, 2013.

(51) Int. Cl.
*G01N 33/576* (2006.01)
*C07K 16/10* (2006.01)

(52) U.S. Cl.
CPC ....... *G01N 33/5767* (2013.01); *C07K 16/109* (2013.01); *C07K 2317/34* (2013.01); *C07K 2317/56* (2013.01); *C07K 2317/92* (2013.01); *G01N 2333/186* (2013.01); *G01N 2469/10* (2013.01); *G01N 2800/52* (2013.01)

(58) Field of Classification Search
CPC .......................... G01N 33/5767; C07K 16/109
See application file for complete search history.

(56) References Cited

U.S. PATENT DOCUMENTS

| | | |
|---|---|---|
| 4,338,397 A | 7/1982 | Gilbert et al. |
| 4,425,437 A | 1/1984 | Riggs |
| 4,431,739 A | 2/1984 | Riggs |
| 4,526,938 A | 7/1985 | Churchill |
| 4,554,101 A | 11/1985 | Hopp |
| 4,816,397 A | 3/1989 | Boss |
| 4,816,567 A | 3/1989 | Cabilly |
| 4,880,078 A | 11/1989 | Inoue et al. |
| 4,946,778 A | 8/1990 | Ladner |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner |
| 5,225,539 A | 7/1993 | Winter |
| 5,241,070 A | 8/1993 | Law |
| 5,242,828 A | 9/1993 | Bergstrom |
| 5,258,498 A | 11/1993 | Huston |
| 5,290,540 A | 3/1994 | Prince et al. |
| 5,294,404 A | 3/1994 | Grandone et al. |
| 5,350,671 A | 9/1994 | Houghton et al. |
| 5,352,803 A | 10/1994 | Mattingly |
| 5,359,093 A | 10/1994 | Adamczyk et al. |
| 5,399,346 A | 3/1995 | Anderson et al. |
| 5,403,484 A | 4/1995 | Ladner |
| 5,427,908 A | 6/1995 | Dower |
| 5,468,646 A | 11/1995 | Mattingly |
| 5,496,925 A | 3/1996 | Mattingly |
| 5,516,637 A | 5/1996 | Huang |
| 5,530,101 A | 6/1996 | Queen |

(Continued)

FOREIGN PATENT DOCUMENTS

| | | |
|---|---|---|
| CA | 2450710 | 1/2003 |
| EP | 086631 | 8/1983 |

(Continued)

OTHER PUBLICATIONS

Wang et al. (Journal of Infectious Diseases, 1996, vol. 173, p. 808-821).*
Filatov, V.L. et al., "Epitope mapping of anti-troponin I monoclonal antibodies," Biochem. Mol. Biol. Int. (1998) 45 (6):1179-1187.
Foote, J. et al., "Antibody frame work residues affecting the confirmation of the hypervariable loops," J. Mol. Biol. (1992) 224:487-499.

(Continued)

*Primary Examiner* — Agnieszka Boesen
(74) *Attorney, Agent, or Firm* — Melissa E. Kolom; Casimir Jones, S.C.

(57) ABSTRACT

The present disclosure provides detection methods employing HCV core lipid binding domain and DNA binding domain monoclonal antibodies or antibody fragments. In certain embodiments, the lipid binding domain monoclonal antibody or antibody fragment recognizes an epitope in amino acids 141 to 161 of HCV core protein and the DNA binding domain antibody or antibody fragment recognizes an epitope in amino acids 95-123 (e.g., in amino acids 99-117) of HCV core protein.

8 Claims, 12 Drawing Sheets

Specification includes a Sequence Listing.

(56) References Cited

U.S. PATENT DOCUMENTS

| | | |
|---|---|---|
| 5,543,524 A | 8/1996 | Mattingly |
| 5,565,332 A | 10/1996 | Hoogenboom |
| 5,565,352 A | 10/1996 | Hochstrasser |
| 5,571,698 A | 11/1996 | Ladner |
| 5,573,904 A | 11/1996 | Mattingly |
| 5,580,717 A | 12/1996 | Dower |
| 5,585,089 A | 12/1996 | Queen |
| 5,593,896 A | 1/1997 | Adamczyk et al. |
| 5,624,821 A | 4/1997 | Winter |
| 5,627,052 A | 5/1997 | Schrader |
| 5,641,870 A | 6/1997 | Rinderknecht |
| 5,648,260 A | 7/1997 | Winter |
| 5,658,727 A | 8/1997 | Barbas |
| 5,679,377 A | 10/1997 | Bernstein et al. |
| 5,688,688 A | 11/1997 | Luciw et al. |
| 5,693,762 A | 12/1997 | Queen |
| 5,698,426 A | 12/1997 | Huse |
| 5,705,330 A | 1/1998 | Shah et al. |
| 5,714,350 A | 2/1998 | Co et al. |
| 5,714,352 A | 2/1998 | Jakobovits |
| 5,723,323 A | 3/1998 | Kauffman |
| 5,733,743 A | 3/1998 | Johnson |
| 5,750,753 A | 5/1998 | Kimae |
| 5,753,430 A | 5/1998 | Mehta et al. |
| 5,763,192 A | 6/1998 | Kauffman |
| 5,766,886 A | 6/1998 | Studnicka |
| 5,780,225 A | 7/1998 | Wigler |
| 5,783,699 A | 7/1998 | Mattingly |
| 5,795,784 A | 8/1998 | Amquist et al. |
| 5,807,715 A | 9/1998 | Morrison et al. |
| 5,814,476 A | 9/1998 | Kauffman |
| 5,817,483 A | 10/1998 | Kauffman |
| 5,821,047 A | 10/1998 | Garrard |
| 5,824,514 A | 10/1998 | Kauffman |
| 5,855,913 A | 1/1999 | Hanes et al. |
| 5,856,194 A | 1/1999 | Amquist et al. |
| 5,874,064 A | 2/1999 | Edwards et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori |
| 5,934,272 A | 8/1999 | Lloyd et al. |
| 5,939,598 A | 8/1999 | Kucherlapati |
| 5,969,108 A | 10/1999 | McCafferty |
| 5,976,862 A | 11/1999 | Kauffman |
| 5,985,309 A | 11/1999 | Edwards et al. |
| 5,985,320 A | 11/1999 | Edwards et al. |
| 5,985,615 A | 11/1999 | Jakobovits |
| 5,989,463 A | 11/1999 | Tracy et al. |
| 5,989,905 A | 11/1999 | Houghton et al. |
| 5,998,209 A | 12/1999 | Jokobovits |
| 6,019,968 A | 2/2000 | Platz et al. |
| 6,075,181 A | 6/2000 | Kucherlapati |
| 6,091,001 A | 7/2000 | Jokobovits |
| 6,096,319 A | 8/2000 | Seidel |
| 6,114,598 A | 9/2000 | Kucherlapati |
| 6,130,364 A | 10/2000 | Jokobovits |
| 6,172,189 B1 | 1/2001 | Devare |
| 6,180,370 B1 | 1/2001 | Queen |
| 6,194,222 B1 | 2/2001 | Buechler et al. |
| 6,204,023 B1 | 3/2001 | Robinson |
| 6,225,047 B1 | 5/2001 | Hutchens et al. |
| 6,306,579 B1 | 10/2001 | Seidel |
| 6,329,209 B1 | 12/2001 | Wagner et al. |
| 6,350,861 B1 | 2/2002 | Co et al. |
| 6,555,114 B1 * | 4/2003 | Leroux-Roels ...... C07K 14/005 424/228.1 |
| 6,623,921 B2 | 9/2003 | Aoyagi |
| 6,699,658 B1 | 3/2004 | Wittrup |
| 6,727,092 B2 | 4/2004 | Shah |
| 6,846,905 B2 | 1/2005 | Hackett et al. |
| 6,914,128 B1 | 7/2005 | Salfeld |
| 7,049,060 B2 | 5/2006 | Bahl |
| 7,101,683 B2 | 9/2006 | Shah et al. |
| 7,285,418 B2 | 10/2007 | Katrukha et al. |
| 7,371,383 B2 | 5/2008 | Reed et al. |
| 7,462,354 B2 | 12/2008 | Sette et al. |
| 7,521,542 B2 | 4/2009 | Johnson et al. |
| 7,612,181 B2 | 11/2009 | Wu |
| 7,858,752 B2 | 12/2010 | Tu |
| 7,871,625 B2 | 1/2011 | Chien et al. |
| 7,888,004 B2 | 2/2011 | Coit et al. |
| 8,030,026 B2 | 10/2011 | Brophy |
| 8,193,318 B2 | 6/2012 | Koenig et al. |
| 8,865,398 B2 | 10/2014 | Rodgers et al. |
| 9,194,873 B2 | 11/2015 | Dawson et al. |
| 9,371,374 B2 * | 6/2016 | Ziemann ............ C07K 16/109 |
| 9,841,427 B2 * | 12/2017 | Dawson ............ G01N 33/5767 |
| 2002/0037868 A1 | 3/2002 | Budkowska |
| 2002/0137134 A1 | 9/2002 | Gerngross |
| 2003/0152948 A1 | 8/2003 | Shah et al. |
| 2003/0170881 A1 | 9/2003 | Davis |
| 2003/0186374 A1 | 10/2003 | Hufton |
| 2004/0018577 A1 | 1/2004 | Campbell et al. |
| 2004/0018590 A1 | 1/2004 | Gerngross et al. |
| 2004/0072267 A1 | 4/2004 | Rieunier et al. |
| 2005/0054078 A1 | 3/2005 | Miller et al. |
| 2006/0018897 A1 | 1/2006 | Lee et al. |
| 2006/0160164 A1 | 7/2006 | Miller et al. |
| 2008/0020401 A1 | 1/2008 | Grenier et al. |
| 2008/0113339 A1 | 5/2008 | Rodgers et al. |
| 2008/0248493 A1 | 10/2008 | Mattingly et al. |
| 2010/0297607 A1 | 11/2010 | Zheng |
| 2012/0009196 A1 | 1/2012 | Muerhoff |
| 2012/0046188 A1 | 2/2012 | Berland et al. |
| 2012/0202295 A1 | 8/2012 | Leary et al. |
| 2014/0272932 A1 | 9/2014 | Muerhoff |
| 2014/0272933 A1 | 9/2014 | Dawson et al. |
| 2015/0024457 A1 | 1/2015 | Brophy |
| 2017/0052183 A1 | 2/2017 | Zieman et al. |
| 2017/0052184 A1 | 2/2017 | Zieman et al. |

FOREIGN PATENT DOCUMENTS

| | | |
|---|---|---|
| EP | 0229246 | 7/1987 |
| EP | 0239400 | 9/1987 |
| EP | 0424634 | 5/1991 |
| EP | 0471293 | 2/1992 |
| EP | 0519596 | 12/1992 |
| EP | 0592106 | 4/1994 |
| EP | 0425633 | 5/1998 |
| EP | 0967485 | 12/1999 |
| EP | 1176195 | 1/2002 |
| EP | 1308507 | 5/2003 |
| EP | 1310796 | 5/2003 |
| EP | 2014302 | 1/2009 |
| FR | 2779526 | 12/1999 |
| JP | 2004035534 A | 2/2004 |
| WO | 1990/001443 | 2/1990 |
| WO | 1990/005144 | 5/1990 |
| WO | 1990/005370 | 5/1990 |
| WO | 1990/014424 | 11/1990 |
| WO | 1990/014430 | 11/1990 |
| WO | 1990/014443 | 11/1990 |
| WO | 91/05548 | 5/1991 |
| WO | 91/09630 | 7/1991 |
| WO | 1991/009967 | 7/1991 |
| WO | 1991/010741 | 7/1991 |
| WO | 1991/017271 | 11/1991 |
| WO | 1992/001047 | 1/1992 |
| WO | 1992/002551 | 2/1992 |
| WO | 1992/003461 | 3/1992 |
| WO | 1992/009690 | 6/1992 |
| WO | 1992/011272 | 7/1992 |
| WO | 1992/015679 | 9/1992 |
| WO | 1992/018619 | 10/1992 |
| WO | 92/19244 | 11/1992 |
| WO | 1992/020791 | 11/1992 |
| WO | 1992/022324 | 12/1992 |
| WO | 93/00365 | 1/1993 |
| WO | 1993/001288 | 1/1993 |
| WO | 1993/006213 | 4/1993 |
| WO | 1993/011236 | 6/1993 |
| WO | 94/01778 | 1/1994 |

(56) References Cited

FOREIGN PATENT DOCUMENTS

| | | |
|---|---|---|
| WO | 1994/002602 | 2/1994 |
| WO | 1994/018219 | 8/1994 |
| WO | 1995/015982 | 6/1995 |
| WO | 1995/020401 | 8/1995 |
| WO | 1997/020032 | 6/1996 |
| WO | 96/20698 | 7/1996 |
| WO | 1996/033735 | 10/1996 |
| WO | 1996/034096 | 10/1996 |
| WO | 1997/029131 | 8/1997 |
| WO | 97/32572 | 9/1997 |
| WO | 97/44013 | 11/1997 |
| WO | 1999/006834 | 2/1998 |
| WO | 1998/016654 | 4/1998 |
| WO | 1998/024893 | 6/1998 |
| WO | 98/31346 | 7/1998 |
| WO | 1998/031700 | 7/1998 |
| WO | 98/37200 | 8/1998 |
| WO | 1998/050433 | 11/1998 |
| WO | 99/09148 | 2/1999 |
| WO | 99/15154 | 4/1999 |
| WO | 99/20253 | 4/1999 |
| WO | 1999/045031 | 9/1999 |
| WO | 99/51773 | 10/1999 |
| WO | 99/54342 | 10/1999 |
| WO | 1999/051773 | 10/1999 |
| WO | 1999/053049 | 10/1999 |
| WO | 99/66903 | 12/1999 |
| WO | 00/07023 | 2/2000 |
| WO | 2000/009560 | 2/2000 |
| WO | 2000/037504 | 6/2000 |
| WO | 00/56934 | 9/2000 |
| WO | 2000/056772 | 9/2000 |
| WO | 01/21189 | 3/2001 |
| WO | 01/38360 | 5/2001 |
| WO | 2001/083525 | 11/2001 |
| WO | 01/96875 | 12/2001 |
| WO | 02/072636 | 9/2002 |
| WO | 03/002749 | 1/2003 |
| WO | 03/016466 | 2/2003 |
| WO | 03/035835 | 5/2003 |
| WO | 03/086458 | 10/2003 |
| WO | 2004/070387 | 8/2004 |
| WO | 2005/000901 | 1/2005 |
| WO | 2005/010049 | 2/2005 |
| WO | 2005/03575 | 4/2005 |
| WO | 2005/068503 | 7/2005 |
| WO | 2005/100584 | 10/2005 |
| WO | 2008/028686 | 3/2008 |
| WO | 2008/051762 | 5/2008 |
| WO | 2008/070727 | 6/2008 |
| WO | 2008/120202 | 10/2008 |
| WO | 2010/060186 | 6/2010 |
| WO | 2011/163558 | 12/2011 |
| WO | 01/09609 | 2/2018 |

OTHER PUBLICATIONS

Fuchs et al., "Targeting Recombinant Antibodies to the Surface of *Echerichia coli*: Fusion to a Peptidoglycan Associated Lipoprotein," Biotechnology, 9:1370-1372 (1991).
Garrard et al., FAB Assembly and Enrichment in a Monovalent Phage Display System, Biotechnology, 9:1373-1377 (1991).
Gavilondo et al., "Antibody engineering at the millennium," Biotechniques, (2000) 29(1):128-132, 134-136, 138.
Giege, R. et al., "An introduction to the crystalligenesis of biological macromolecules," Crystallization of Nucleic Acids and Proteins, a Practical Approach, 2nd Edition, Oxford University Press, New York (1999) 20 1-16.
Gillies et al., "High-level expression of chimeric antibodies using adapted cDNA variable region cassettes," J. Immunol. Methods (1989) 125:191-202.
Goodson, J.M. et al., Medical Applications of Controlled Release, Chapter 6, Dental Applications (1984) 2:115-138.
Gorman et al., "The Rous sarcoma virus long terminal repeat is a strong promoter when introduced into a variety of eukaryotic cells by DNA-mediated transfection," Proc. Natl. Acad. Sci. USA (1982) 79(22):6777-6781.
Gram et al., "In vitro selection and affinity maturation of antibodies from a naive combinatorial immunoglobulin library," Proc. Natl. Acad. Sci. USA, 89(8):3576-3580 (1992).
Green et al., "Antigen-specific human monoclonal antibodies from mice engineered with human Ig heavy and light Chain YACs," Nat. Genet., 7(1):13-21 (1994).
Green et al., "Regulation of B cell development by variable gene complexity in mice reconstituted with human immunoglobulin yeast artificial chromosomes," J. Exp. Med., 188(3):483-495 (1998).
Griffiths et al., "Human anti-self antibodies with high specificity from phage display libraries," EMBO J., 12 (2):725-734 (1993).
Gu et al., "Three conformational snapshots of the hepatitis C virus NS3 helicase reveal a ratchet translocation mechanism," Proc. Natl. Acad. Sci. USA (2010) 107(2):521-528.
Hawkins et al., "Selection of phage antibodies by binding affinity. Mimicking affinity maturation," J. Mol. Biol., 226 (3):889-896 (1992).
Hay et al., "Bacteriophage cloning and *Escherichia coli* expression of a human IgM Fab," Hum. Antibodies Hybridomas, 3(2):81-85 (1992).
Higgins et al., "Fast and sensitive multiple sequence alignments on a micro computer," CABIOS (1989) 5(2):151-153.
Hino, "Diagnosis of hepatitis C," Intervirology, 37(2):77-86 (1994).
Hollinger et al., ""Diabodies": small bivalent and bispecific antibody fragments," Proc. Natl. Acad. Sci. USA, 90 (14):6444-6448 (1993).
Hoogenboom et al., "Multi-subunit proteins on the surface of filamentous phage: methodologies for displaying antibody (Fab) heavy and light chains," Nucleic Acids Res., 19(15):4133-4137 (1991).
Hoogenboom et al., "Natural and designer binding sites made by phage display technology," Immunol. Today, 21 (8)371-378 (2000).
Hoogenboom, "Designing and optimizing library selection strategies for generating high-affinity antibodies," Trends Biotechnol., 15(2):62-70 (1997).
Hope, et al., "Sequence motifs required for lipid droplet association and protein stability are 1, 6-9 and 19 unique to the hepatitus C virus core protein". J Gen Virol. 2000 vol. 81(Pt. 8), p. 1913-1925; Abstract; p. 1914, Fig 1; p. 1915, col. 2, last para and Table 1; p. 1916, col. 1 and Fig 2; p. 1917, col. 2, top and middle para; p. 1918, col. 1, para 1; and p. 1919, Fig 3 (13 pages).
Howard, M.A. et al., "Intracerebral drug delivery in rats with lesion-induced memory deficits," J. Neurosurg. (1989) 71:105-112.
Huber et al., "Crystallographic structure studies of an IgG molecule and an Fc fragment," Nature, 264(5585):415-420 (1976).
Huse et al., "Generation of a large combinatorial library of the immunoglobulin repertoire in phage lambda," Science, 246(4935):1275-1281 (1989).
Huston et al., "Protein engineering of single-chain Fv analogs and fusion proteins," Methods Enzymol., 203:46-88 (1991).
Huston et al., "Protein engineering of antibody binding sites: recovery of specific activity in an anti-digoxin single-chain Fv analogue produced in *Escherichia coli*," Proc. Natl. Acad. Sci. USA, 85(16):5879-5883 (1988).
Hytest 1999 Product Catalog, 3 pages.
Jayaraman et al., "Polymerase chain reaction-mediated gene synthesis: synthesis of a gene coding for isozyme C of horseradish peroxidase," Proc. Natl. Acad. Sci. USA (1991) 88(10):4084-4088.
Hytest 2000 General Product Catalog, 3 pages.
Hytest 2001-2002 General Product Catalog, 3 pages.
Hytest 2001 Cardiac Markers Panel, 4 pages.
Hytest 2003 General Product Catalog, 3 pages.
Hytest 2004-2005 General Product Catalog, 3 pages.
Hytest 2004 Cardiac Markers Panel, 4 pages.
Hytest 2005-2006 General Product Catalog, 3 pages.
Hytest 2005 Markers of Cardiovascular Diseases Catalog, 4 pages.
Hytest 2006-2007—General Product Catalog, 3 pages.
Hytest 2007-2008 General Product Catalog, 3 pages.
Hytest 2007 markers of Cardiovascular Diseases Catalog, 4 pages.

(56) References Cited

OTHER PUBLICATIONS

Hytest 2008-2009 General Product Catalog, 3 pages.
Hytest 2008 Markers of Cardiovascular Diseases and Metabolis Syndrome, 4 pages.
International Search Report and Written Opinion for Application No. PCT/US2013/077487 dated Apr. 22, 2014 (23 pages).
International Search Report and Written Opinion for Application No. PCT/US2010/024979 dated May 6, 2010 (16 pages).
International Search Report and Written Opinion for Application No. PCT/US2013/077504 dated Jul. 1, 2014 (14 pages).
Patent Cooperation Treaty, Notification of the International Search Report and Written Opinion for Application No. PCT/US2013/077499 dated May 20, 2014 (21 pages).
Jackson et al., "In vitro antibody maturation. Improvement of a high affinity, neutralizing antibody against IL-1 beta," J. Immunol., 154(7)3310-3319 (1995).
Jay et al., "Chemical synthesis of a biologically active gene for human immune interferon-gamma. Prospect for site-specific mutagenesis and structure-function studies," J. Biol. Chem. (1984) 259(10):6311-6317.
Wallick, S.C. et al., "Glycosylation of a VH residue of a monoclonal antibody against alpha(1-6) dextran increases its affinity for antigens," Exp. Med. (1988) 168:1099-1109.
Wallemacq et al., "Evaluation of the new AxSYM cyclosporine assay: comparison with TDx monoclonal whole blood and Emit cyclosporine assays," Clin. Chem., 45(3):432-435 (1999).
Ward et al., "Binding activities of a repertoire of single immunoglobulin variable domains secreted from *Escherichia coli*," Nature, 341(6242):544-546 (1989).
West et al., "Crystal structure and immunoglobulin G binding properties of the human major histocompatibility complex-related Fc receptor(,)," Biochemistry, 39(32):9698-9708 (2000).
Winnaker et al., From Genes to Cones, Verlagsgesellschaft, Weinheim, Germany (1987).
Wright, A. et al., "Antibody variable region glycosylation: position effects on antigen binding and carbohydrate structure," EMBO J. (1991) 10:2717-2723.
Wu et al, "Receptor-mediated in vitro gene transformation by a soluble DNA carrier system," J. Biol. Chem. (1987) 262:4429-4432.
Yatscoff et al., "Abbott TDx monoclonal antibody assay evaluated for measuring cyclosporine in whole blood," Clin. Chem., 36(11):1969-1973 (1990).
Yelton et al., "Affinity maturation of the BR96 anti-carcinoma antibody by codon-based mutagenesis," J. Immunol., 155(4):1994-2004 (1995).
Ylikotila et al., "Utilization of recombinant fab fragments in a cTnI immunoassay conducted in spot wells," Clinc. Biochem. (2006) 39:843-850.
United States Patent Office Action for U.S. Appl. No. 14/139,053 dated Oct. 6, 2015 (15 pages).
United States Patent Office Action for U.S. Appl. No. 14/139,108 dated Jan. 21, 2015 (11 pages).
United States Patent Office Notice of Allowance for U.S. Appl. No. 14/139,108 dated Jul. 17, 2015 (5 pages).
United States Patent Office Action for U.S. Appl. No. 12/391,937 dated Feb. 24, 2011 (15 pages).
United States Patent Office Notice of Allowance for U.S. Appl. No. 12/391,937 dated Aug. 5, 2011 (13 pages).
United States Patent Office Notice of Allowance for U.S. Appl. No. 14/035,420 dated Feb. 27, 2015 (8 pages).
United States Patent Office Action for U.S. Appl. No. 14/035,420 dated Mar. 18, 2014 (9 pages).
United States Patent Office Action for U.S. Appl. No. 90/012,377 dated Feb. 6, 2013 (15 pages).
United States Patent Office Action for U.S. Appl. No. 14/461,082 dated Apr. 15, 2016 (7 pages).
United States Patent Office Action for U.S. Appl. No. 14/138,053 dated May 4, 2016 (8 pages).
United States Patent Office Advisory Action for U.S. Appl. No. 14/138,053 dated Jul. 20, 2016 (5 pages).
United States Patent Office Action for U.S. Appl. No. 14/138,053 dated Oct. 21, 2016 (6 pages).
United States Patent Office Action for U.S. Appl. No. 14/138,053 dated May 8, 2017 (10 pages).
United States Patent Office Action for U.S. Appl. No. 14/851,471 dated Apr. 20, 2017 (14 pages).
European Patent Office for Application No. 13878437.6 dated Sep. 1, 2017 (6 pages).
United States Patent Office Action for U.S. Appl. No. 14/461,082 dated Aug. 9, 2017 (5 pages).
United States Patent Office Action for U.S. Appl. No. 14/851,471 dated Aug. 9, 2017 (10 pages).
European Patent Office for Application No. 13878042.4 dated Oct. 24, 2017 (4 pages).
European Extended Search Report for Application No. 13878042.4 dated Sep. 29, 2016 (8 pages).
European Extended Search Report for Application No. 13880371.3 dated Oct. 10, 2016 (13 pages).
United States Patent Office Action for U.S. Appl. No. 14/138,991 dated Sep. 21, 2015 (9 pages).
United States Patent Office Action for U.S. Appl. No. 14/138,991 dated Feb. 23, 2016 (7 pages).
Zapata et al., "Engineering linear F(ab')2 fragments for efficient production in *Escherichia coli* and enhanced antiproliferative activity," Protein Eng., 8(10):1057-1062 (1995).
Aach et al., "Hepatitis C virus infection in post-transfusion hepatitis. An analysis with first- and second-generation assays," N. Engl. J. Med., 325(19):1325-1329 (1991).
Adamczyk et al., "Modulation of the Chemiluminescent Signal from N10-(3-Sulfopropyl)-N-Sulfonylacridinium-9-carboxamides," Tetrahedron, 55:10899-10914 (1999).
Adamczyk et al., "Chemiluminescence quenching of pteroic acid-N-sulfonyl-acridinium-9-carboxamide conjugates by folate binding protein," Bioorg. Med. Chem. Lett., 14(9):2313-2317 (2004).
Adamczyk et al., "Chemiluminescent acridinium-9-carboxamide boronic acid probes: application to a homogeneous glycated hemoglobin assay," Bioorg. Med. Chem. Lett., 16(5):1324-1328 (2006).
Adamczyk et al., "Intrinsic factor-mediated modulation of cyanocobalamin-N-sulfonyl-acridinium-9-carboxamide chemiluminescence," Bioorg. Med. Chem. Lett., 14(15):3917-3921 (2004).
Adamczyk et al., "Linker-mediated modulation of the chemiluminescent signal from N(10)-(3-Sulfopropyl)-N-sulfonylacridinium-9-carboxamide tracers," Bioconjug. Chem., 11(5):714-724 (2000).
Adamczyk et al., "Regiodependent luminescence quenching of biotinylated N-sulfonyl-acridinium-9-carboxamides by avidin," Org. Lett., 5(21):3779-3782 (2003).
Adamczyk et al., "Synthesis of a chemiluminescent acridinium hydroxylamine (AHA) for the direct detection of abasic sites in DNA," Org. Lett. 1(5):779-781 (1999).
Adamczyk et al., "Neopentyl 3-Triflyloxypropanesulfonate. A Reactive Sulfopropylation Reagent for the Preparation of Chemiluminescent Labels," J. Org. Chem., 63:5636-5639 (1998).
Alter et al., "The natural history of community-acquired hepatitis C in the United States. The Sentinel Counties Chronic non-A, non-B Hepatitis Study Team," N. Engl. J. Med., 327(27):1899-1905 (1992).
Altschul, S.F. et al., "Gapped BLAST and PSI-BLAST: a new generation of protein database search programs," Nucleic Acids Res. (1997) 25:3389-3402.
Ames et al., "Conversion of murine Fabs isolated from a combinatorial phage display library to full length immunoglobulins," J. Immunol. Methods, 184(2):177-186 (1995).
Anthony et al., "Recapitulation of IVIG anti-inflammatory activity with a recombinant IgG Fc," Science, 320 (5874):373-376 (2008).
Azzazy et al., "Phage display technology: clinical applications and recent innovations," Clin. Biochem., 35(6):425-445 (2002).
Babcook et al., "A novel strategy for generating monoclonal antibodies from single, isolated lymphocytes producing antibodies of defined specificities," Proc. Natl. Acad. Sci. USA, 93(15):7843-7848 (1996).

(56) References Cited

OTHER PUBLICATIONS

Barbas et al., "In vitro evolution of a neutralizing human antibody to human immunodeficiency virus type 1 to enhance affinity and broaden strain cross-reactivity," Proc. Natl. Acad. Sci. USA, 91(9):3809-3813 (1994).
Barbas et al., "Assembly of combinatorial antibody libraries on phage surfaces: the gene III site," Proc. Natl. Acad. Sci. USA, 88(18):7978-7982 (1991).
Beckett et al., "A minimal peptide substrate in biotin holoenzyme synthetase-catalyzed biotinylation," Protein Sci. (1999) 8(4):921-929.
Better et al., "*Escherichia coli* secretion of an active chimeric antibody fragment," Science, 240(4855):1041-1043 (1988).
Biedler et al., "Cloning and high level expression of a chimeric antibody with specificity for human carcinoembryonic antigen," J. Immunol., 141(11):4053-4060 (1988).
Biewenga et al., "IgA1 half molecules in human multiple myeloma and the in vitro production of similar fragments from intact IgA1 molecules," Clin. Exp. Immunol., 51(2):395-400 (1983).
Bird et al., "Single-chain antigen-binding proteins," Science, 242(4877):423-426 (1988).
Bodor, G.S. et al., "Development of monoclonal antibodies for an assay of cardiac Troponin-I and preliminary results in suspected cases of myocardial infarction," Clinical Chem. (1992) 38:2203-2214.
Boder, E.T. et al., "Yeast surface display for screening combinatorial polypeptide libraries," Nature Biotech. (1997) 15:553-557.
Boulant et al., "Hepatitis C virus core protein is a dimeric alpha-helical protein exhibiting membrane protein features," J. Virol., 79(17):11353-11365 (2005).
Bresters et al., "Enhanced sensitivity of a second generation ELISA for antibody to hepatitis C virus," Vox Sang, 62 (4):213-217 (1992).
Brinkmann et al., "Phage display of disulfide-stabilized Fv fragments," J. Immunol. Methods, 182(1):41-50 (1995).
Buchwald, H. et al., "Long-term, continuous intravenous heparin administration by an implantable infusion pump in ambulatory patients with recurrent venous thrombosis," Surgery (1980) 88:507-516.
Burton et al., "Human antibodies from combinatorial libraries," Adv. Immunol., 57:191-280 (1994).
Busch et al., "Committee report. Nucleic acid amplification testing of blood donors for transfusion-transmitted infectious diseases: Report of the Interorganizational Task Force on Nucleic Acid Amplification Testing of Blood Donors," Transfusion, 40(2):143-159 (2000).
Carter et al., "Humanization of an anti-p185HER2 antibody for human cancer therapy," Proc. Natl. Acad. Sci. USA, 89(10):4285-4289 (1992).
Choo et al., "Isolation of a cDNA clone derived from a blood-borne non-A, non-B viral hepatitis genome," Science, 244 (4902):359-362 (1989).
Chothia et al., "Canonical structures for the hypervariable regions of immunoglobulins," J. Mol. Biol., 196(4):901-917 (1987).
Chothia et al., "Conformations of immunoglobulin hypervariable regions," Nature, 342(6252):877-883 (1989).
Chothia, C. et al., "Structural repertoire of the human VH segments," J. Mol. Biol. (1992) 227:799-817.
Clackson et al., "Making antibody fragments using phage display libraries," Nature, 352(6336):624-628 (1991).
Cleek et al., "Biodegradable polymeric carriers for a bFGF antibody for cardiovascular application," Pro. Int. Symp. Control. Rel. Bioact. Mater (1997) 24:853-854.
Co, M.S. et al., "Genetically engineered deglycosylation of the variable domain increases the affinity of an anti-CD33 monoclonal antibody," Mol. Immunol (1993) 30:1361-1367.
Colman, P.M., "Effects of amino acid sequence changes on antibody-antigen interactions," Research in Immunology (1994) 145:33-36.
Courouce et al., "Anti-hepatitis C virus (anti-HCV) seroconversion in patients undergoing hemodialysis: comparison of second- and third-generation anti-HCV assays," Transfusion, 34(9):790-795 (1994).
Courouce et al., "Significance of NS3 and NS5 antigens in screening for HCV antibody," Lancet, 343 (8901):853-854 (1994).
Cummins, B. et al., "Cardiac-specific troponin radioimmunoassay in the diagnosis of acute myocardial infarction," Am. Heart Journal (1987) 113:1333-1344.
Dall'Acqua et al., "Contribution of domain interface residues to the stability of antibody CH3 domain homodimers," Biochemistry, 37(26):9266-9273 (1998).
Ferns et al., "Characterisation of a panel of monoclonal antibodies raised against recombinant 1, 6, 9, and 19 HCV core protein". J Med Virol. 1996 vol. 50(3), p. 221-229. Abstract (9 pages).
Dijkema et al., "Cloning and expression of the chromosomal immune interferon gene of the rat," EMBO J. (1985) 4 (3):761-767.
During et al., "Controlled release of dopamine from a polymeric brain implant: in vivo characterization," Ann. Neurol. (1989) 25:351-356.
El-Emshaty et al., "Diagnostic performance of an immunoassay for simultaneous detection of HCV core antigen and antibodies among haemodialysis patients,"Brazilian Journal of Microbiology (2011) 42: 303-309.
Eng et al., "Internal initiation stimulates production of p8 minicore, a member of a newly discovered family of hepatitis C virus core protein isoforms," J. Virol., 83(7)3104-3114 (2009).
Erikkson, S. et al., "Comparison of cardiac troponin. Immunoassays variably affected by circulating autoantibodies," Clin. Chem. (2005) 51(5):848-855.
Needleman et al., J. Mol. Biol. (1970) 48:443.
Neuberger et al., "Recombinant antibodies possessing novel effector functions," Nature (1984) 312:604-608.
Ning et al., "Intratumoral radioimmunotherapy of a human colon cancer xenograft using a sustained-released gel," Radiotherapy and Oncology (1996) 39:179-189.
Ogata et al., "Nucleide sequence and mutation rate of the H strain of hepatitis C virus," Proc. Natl. Acad. Sci. USA (1991) 88(8):3392-3396.
Padlan et al., "A possible procedure for reducing the immunogenicity of antibody variable domains while preserving their ligand-binding properties," Mol. Immunol., 28(4-5):489-498 (1991).
Padlan et al., "Identification of specificity-determining residues in antibodies," FASEB J., 9(1):133-139 (1995).
Panina-Bordignon et al., "Universally immunogenic T cell epitopes: promiscuous binding to human MHC class II and promiscuous recognition by T cells," Eur. J. Immunol., 19(12):2237-2242 (1989).
Paul, Fundamental Immunology, 3rd Edition (1993) pp. 292-295, under the heading "FV Structure and Diversity in Three Dimensions".
Pearson et al., "Improved tools for biological sequence comparison," Proc. Natl. Acad. Sci. (1988) 85:2444-2448.
Peronnet et al., "Isoelectric point determination of cardiac troponin I forms present 1n plasma from patients with myocardial infarction," (2007) 377(1-2):243-247.
Persic et al., "An integrated vector system for the eukaryotic expression of antibodies or their fragments after selection from phage display libraries," Gene, 187(1):9-18 (1997).
Poljak, "Production and structure of diabodies," Structure, 2(12):1121-1123 (1994).
Presta et al., "Humanization of an antibody directed against IgE," J. Immunol., 151(5):2623-2632 (1993).
Queen et al., "A humanized antibody that binds to the interleukin 2 receptor," Proc. Natl. Acad. Sci. USA (1989) 86 (24):10029-10033.
Quinn, F. et al., "36 Bulk Reagent Random-access analyzer: Architect; 2000," The Immunoassay Handbook, 2nd Edition (2001) 363-367.
Rama, D. et al., "Epitope localization of monoclonal antibodies used in human troponin I immunoenzymometric assay," Hybridoma (1997) 16(2):153-157.
Razavi et al., "Stable and versatile active acridinium esters I," Luminescence, 15(4):239-244 (2000).
Razavi et al., "Stable and versatile active acridinium esters II," Luminescence, 15(4):245-249 (2000).
Reverse Translate a Protein (1998) (www.vivo.colostae.edu/molkit/translate/index.html), 1 page.

(56) References Cited

OTHER PUBLICATIONS

Riechmann et al., "Reshaping human antibodies for therapy," Nature, 332(6162):323-327 (1988).
Roberts et al., "RNA-peptide fusions for the in vitro selection of peptides and proteins," Proc. Natl. Acad. Sci. USA, 94(23):12297-12302 (1997).
Roguska et al, "Humanization of murine monoclonal antibodies through variable domain resurfacing," Proc. Natl. Acad. Sci. USA, 91(3):969-973 (1994).
Rudikoff et al., "Single amino acid substitution altering antigen-binding specificity," Proc. Natl. Acad. Sci USA (1982) 79(6):1979-1983.
Sallberg et al., "Immunogenicity and antigenicity of the ATPase/helicase domain of the hepatitis C virus non-structural 3 protein," J. Gen. Virol. (1996) 77(Pt 11):2721-2728.
Sambrook et al., A Laboratory Manual, Molecular Cloning, 2nd Edition, Cold Spring Harbor Laboratory Press, Cold Spring Harbor, New York (1989) 30 pages.
Saudek et al., "A preliminary trial of the programmable implantable medication system for insulin delivery," N. Engl. J. Med. (1989) 321:574-579.
Sawai et al., "Direct production of the Fab fragment derived from the sperm immobilizing antibody using polymerase chain reaction and cDNA expression vectors," Am. J. Reprod. Immunol., 34(1):26-34 (1995).
Schier et al., "Identification of functional and structural amino-acid residues by parsimonious mutagenesis," Gene, 169 (2):147-155 (1996).
Schiestl et al., "High efficiency transformation of intact yeast cells using single stranded nucleic acids as a carrier," Current Genetics (1989) 16(5-6):339-346.
Seligmann et al., Immunochemical Study of a Human Myeloma IgG1 Half Molecule (*), Ann. Immunol., 129:855-870 (1978).
Shah et al., "Combination HCV core antigen and antibody assay on a fully automated chemiluminescence analyzer," Transfusion (2003) 43:1067-1074.
Shapiro et al., "DNA target motifs of somatic mutagenesis in antibody genes," Crit. Rev. Immunol., 22(3):183-200 (2002).
Shavinskaya et al. (The Journal of Biological Chemistry 2007, p. 37158-37169).
Shields, R.L. et al., "Lack of fucose on human IgG1 N-linked oligosaccharide improves binding to human FcγRIII and antibody dependent cellular toxicity," J. Biol. Chem. (2002) 277:26733-26740.
Shu et al., "Secretion of a single-gene-encoded immunoglobulin from myeloma cells," Proc. Natl. Acad. Sci. USA, 90 (17):7995-7999 (1993).
Sims et al., "A humanized CD18 antibody can block function without cell destruction," J. Immunol., 151(4):2296-2308 (1993).
Skerra et al., "Assembly of a functional immunoglobulin Fv fragment in *Escherichia coli*," Science, 240 (4855):1038-1041 (1988).
Smith et al., "Comparison of biosequences," Appl. Math. (1981) 2:482-489.
Song et al., "Antibody mediated lung targeting of long-circulating emulsions," PDA Journal of Pharmaceutical Science and Technology (1995) 50:372-377.
Studnicka et al., "Human-engineered monoclonal antibodies retain full specific binding activity by preserving non-CDR complementarity-modulating residues," Protein Eng., 7(6):805-814 (1994).
Table Showing Codon-amino acid Abbreviations (www.hgmd.cf.ac.uk/docs/cd_amino.html), printed Jan. 23, 2013, 3 pages.
Tai et al., "Structural-based mutational analysis of the hepatitis C Virus NS3 helicase," J. Virology (2001) 74 (17):8289-8207.
Tamura et al., "MEGA5: molecular evolutionary genetics analysis using maximum likelihood, evolutionary distance, and maximum parsimony methods," Mol. Biol. Evol., 28(10):2731-2739 (2011).
Takeda et al., "Constsruction of chimaeric processed immunoglobulin genes containing mouse variable and human constant region sequences," Nature (1985) 314:452-454.
Taylor et al., "A transgenic mouse that expresses a diversity of human sequence heavy and light chain immunoglobulins," Nucleic Acids Res., 20(23):6287-6295 (1992).
Thies et al., "Folding and association of the antibody domain CH3: prolyl isomerization preceeds dimerization," J. Mol. Biol., 293(1):67-79 (1999).
Thompson et al., "Clustal W: improving the sensitivity of progressive multiple sequence alignment through sequence weighting, position-specific gap penalties and weight matrix choice," Nucleic Acids Res., 22(22):4673-4680 (1994).
Umana et al., "Engineered glycoforms of an antineuro-blastoma IgG1 with optimized antibody-dependent cellular cytotoxic activity," Nat. Biotech. (1999) 17:176-181.
Urlaub et al., "Isolation of Chinese hamster cell mutants deficient in dehydrofolate reductase activity," Proc. Natl. Acad. Sci. (1980) 77:4216-4220.
Verhoeyen et al., "Reshaping human antibodies: grafting an antilysozyme activity," Science, 239(4847):1534-1536 (1988).
Jefferis, R. et al., "Glycosylation of recombinant antibody therapeutics," Biotechnol. Prog. (2005) 21:11-16.
Johnsson et al., "Comparison of methods for immobilization to carboxymethyl dextran sensor surfaces by analysis of the specific activity of monoclonal antibodies," J. Mol. Recognit., 8(1-2):125-131 (1995).
Johnsson et al., "Immobilization of proteins to a carboxymethyldextran-modified gold surface for biospecific interaction analysis in surface plasmon resonance sensors," Anal. Biochem., 198(2):268-277 (1991).
Jones et al., "Replacing the complementarity-determining regions in a human antibody with those from a mouse," Nature, 321(6069):522-525 (1986).
Jonsson et al., "Introducing a biosensor based technology for real-time biospecific interaction analysis," Ann. Biol. Clin. (Paris), 51(1):19-26 (1993).
Jonsson et al., "Real-time biospecific interaction analysis using surface plasmon resonance and a sensor chip technology," Biotechniques, 11(5):620-627 (1991).
Kabat et al., "Attempts to locate complementarity-determining residues in the variable positions of light and heavy chains," Ann. NY Acad. Sci., 190:382-393 (1971).
Kabat et al, Sequences of Proteins of Immunological Interest, National Institutes of Health, Bethesda, Maryland (1987) and (1991), 4th Edition, 4 pages.
Kabat et al., Sequences of Proteins of Immunological Interest, 5th Edition, Department of Health and Human Services, NIH Publication No. 91-3242 (1991), 11 pages.
Katrukha et al., "Degradation of cardiac troponin: implication for reliable immunodetection," Clin. Chem. (1998) 44 (12):2433-2440.
Katrukha, "Troponin. Measurement: the concept of a precise immunoassay," Clin. Lab. Internat. (2006) 30(5):14-16.
Katrukha, "New approach to standardization of human cardiac Troponin I (cTnI)," Scand. J. Clin. Lab. Invest. (1999) 59(Suppl 230):124-127.
Katrukha, "Biochemical factors influencing measurement of cardiac troponin I in serum," Clin. Chem. Lab Med. (1999) 37(11/12):1091-1095.
Katrukha, "Antibody selection strategies in cardiac troponin assays," Cardiac Markers, Second Edition 173-185.
Kaufman, R.J. et al., "Amplification and expression of sequences cotransfected with a modular dihydrofolate reductase complementary DNA gene," Mol. Biol. (1982) 159:601-621.
Kellerman et al., "Antibody discovery: the use of transgenic mice to generate human monoclonal antibodies for therapeutics," Curr. Opin. Biotechnol., 13(6):593-597 (2002).
Kettleborough et al., "Isolation of tumor cell-specific single-chain Fv from immunized mice using phage-antibody ibraries and the re-construction of whole antibodies from these antibody fragments," Eur. J. Immunol., 24(4):952-958 (1994).
Kim et al., "Mutational analysis of the hepatitis C virus RNA helicase," J. Virology (1997) 71(12):9400-9409.
Kim et al., "Template requirements for De Novo RNA synthesis by hepatitis C virus nonstructural protein 5B polymerase on the viral X RNA," J. Virology (2002) 76(14):6944-6956.

(56) References Cited

OTHER PUBLICATIONS

Kim et al., "Identifying amino acid residues that influence plasma clearance of murine IgG1 fragment by site-directed mutagenesis," Eur. J. Immunol. (1994) 24(3):542-548.

Kipriyanov, S.M. et al., "Single-chain antibody streptavidin fusions: tetrameric bifunctional ScFv-complexes with biotin binding activity and enhanced affinity to antigen," Human Antibodies and Hybridomas (1995) 6:93-101.

Kipriyanov, S.M. et al., "Recombinant single-chain Fv fragments carrying c-terminal cysteine residues: production of bivalent and biotinylated miniantibodies," Mol. Immunol. (1994) 31:1047-1058.

Kontermann, Antibody Engineering, p. 790, Springer-Verlag, New York (2001).

Kleinman et al., "Increased detection of hepatitis C virus (HCV)-infected blood donors by a multiple-antigen HCV enzyme immunoassay," Transfusion, 32(9):805-813 (1992).

Kohler et al., "Continuous cultures of fused cells secreting antibody of predefined specificity," Nature, 256 (5517):495-497 (1975).

Kuo et al., "An assay for circulating antibodies to a major etiologic virus of human non-A, non-B hepatitis," Science, 244(4902):362-364 (1989).

Kyte et al., "A simple method for displaying the hydropathic character of a protein," J. Mol. Biol., 157(1):105-132 (1982).

Lam et al., "Microencapsulation of recombinant humanized monoclonal antibody for local delivery," Proc. Int'l Symp. Control Rel. Bioact. Mater. (1997) 24:759-760.

Langer et al., "Chemical physical structure of polymers as carriers for controlled release of bioactive agents: a review," J. Macromol. Sci. Rev. Macromol. Chem. (1983) 23:61-126.

Langer et al., "New methods of drug delivery," Science (1990) 249:1527-1533.

Laperche et al., "Simultaneous Detection of Hepatitis C Virus (HVC) Core Antigen and Anti- 1, 6-9, and 19 HCV Antibodies Improves the Early Detection of HCV Infection". J Clin Microbiol. 2005, vol. 43(8), p. 3877-3883. Entire Documentation, especially Abstract (8 pages).

Lee et al., "Increased detection of hepatitis C virus infection in commercial plasma donors by a third-generation screening assay," Transfusion, 35(10):845-849 (1995).

Levy, R.J. et al., "Inhibition of calcification of bioprosthetic heart valves by local controlled-release diphosphonate," Science (1985) 228:190-192.

Little et al., "Of mice and men: hybridoma and recombinant antibodies," Immunol. Today, 21(8):364-370 (2000).

MacCallum et al., "Antibody-antigen interactions: contact analysis and binding site topography," J. Mol. Biol., 262 (5):732-745 (1996).

Marchalonis et al., "Evolutionary factors in the emergence of the combinatorial germline antibody repertoire," Adv. Exp. Med. Biol., 484:13-30 (2001).

Marks et al., "By-passing immunization: building high affinity human antibodies by chain shuffling," Biotechnology (NY), 10(7):779-783 (1992).

Mattingly, "Chemiluminescent 10-methyl-acridinium-9-(N-sulphonylcarboxamide) salts. Synthesis and kinetics of light emission," J. Biolumin. Chemilumin., 6(2):107-114 (1991).

McCafferty et al., "Phage antibodies: filamentous phage displaying antibody variable domains," Nature, 348 (6301):552-554 (1990).

McCapara et al., "Chemiluminescence Involving Peroxide Decompositions," Photochemistry and Photobiology, 4:1111-1121 (1965).

Medical Applicants of Controlled Release, Langer and Wise (eds), CRC Press, Boca Raton, Florida (1974).

Mendez et al., "Functional transplant of megabase human immunoglobulin loci recapitulates human antibody response in mice," Nat. Genet., 15(2):146-156 (1997).

Mimms et al., "Specificity of anti-HCV ELISA assessed by reactivity to three immunodominant HCV regions," Lancet, 336(8730):1590-1591 (1990).

Mizushima et al., "pEF-BOS, a powerful mammalian expression vector," Nucleic Acids Research (1990) 18:5322-5323.

Morota et al., "A new sensitive and automated chemiluminescent microparticle immunoassay for quantitative determination of hepatitis C virus core antigen," J. Virol. Methods, 157(1):8-14 (2009).

Morrison et al., "Numeric human antibody molecules: mouse antigen-binding domains with human constant region domains," Proc. Natl. Acad. Sci. (1984) 81:6851-6855.

Morrison, "Transfectomas provide novel chimeric antibodies," Science, 229(4719):1202-1207 (1985).

Mullinax et al., "Expression of a heterodimeric Fab antibody protein in one cloning step," Biotechniques, 12 (6):864-869 (1992).

Oellerich, "Enzyme-immunoassay: a review," J. Clin. Chem. Clin. Biochem., 22(12):895-904 (1984).

Oi et al., "Chimeric Antibodies," BioTechniques, 4(3):214 (1986).

\* cited by examiner

FIG. 1A

Figure 1a: Anti-Core134-171 heavy chain variable domain sequences

FIG. 1B

Figure 1b: Anti-Core134-171 light chain variable domain sequences

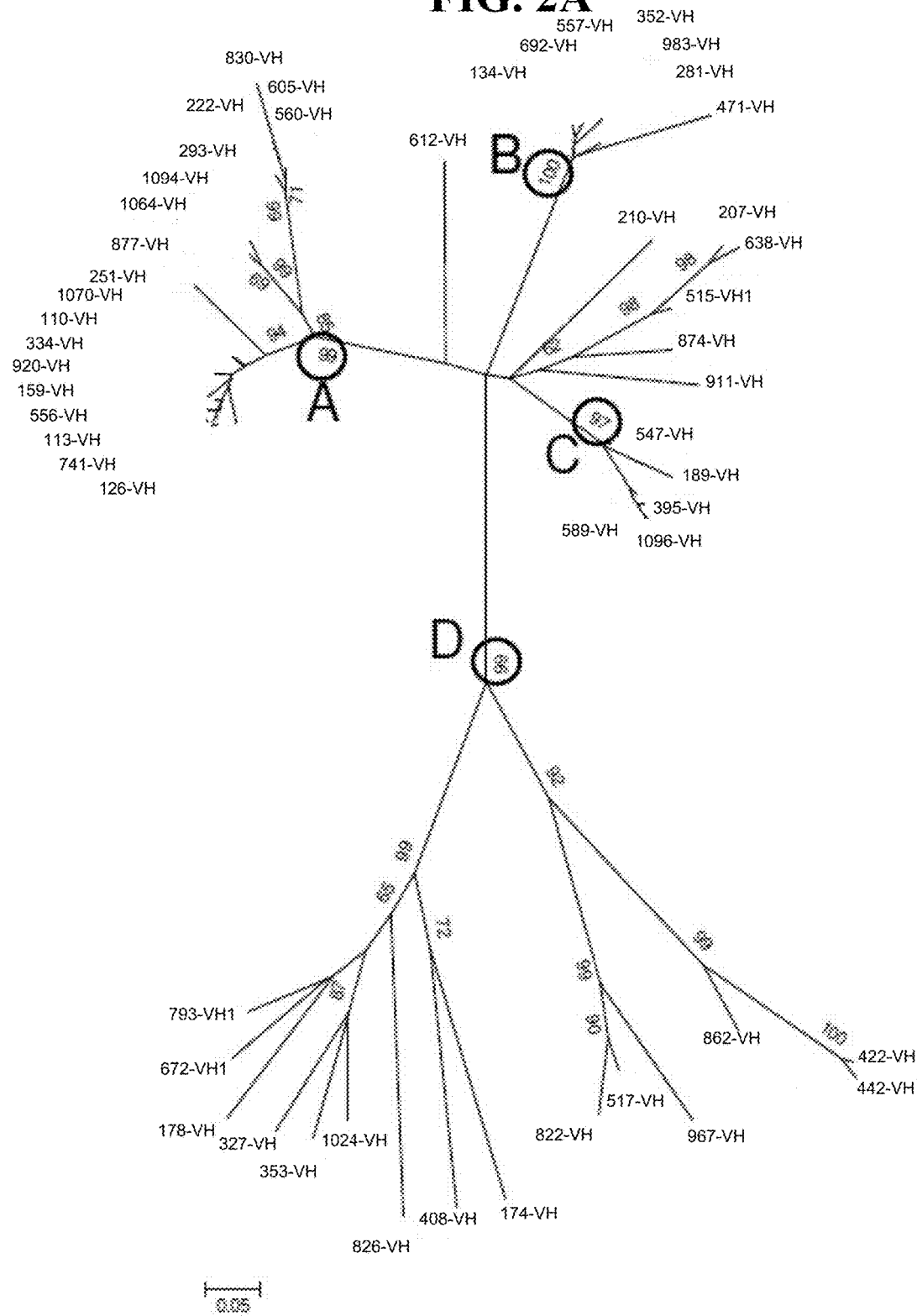

FIG. 8A (SEQ ID NO: 583) Amino acid sequence of Neo4 light chain variable domain:

(CDRL1, SEQ ID NO:585)          (CDRL2, SEQ ID NO:586)
DIVLTQSPASLIVSLGQRATISC<u>RASKSVNEYGYTYMH</u>WYQQKPGLPPKLLIY<u>LASNLDS</u>GVPAR
FSGSGSGTDFTLNIHPVEEEDAATYYC<u>QHSRELPYT</u>FGGGTKLEIKR
                                (CDRL3, SEQ ID NO:587)

FIG. 8B (SEQ ID NO: 584) Amino acid sequence of Neo4 heavy chain variable domain sequence:

(CDRH1, SEQ ID NO:588)          (CDRH2, SEQ ID NO:589)
QIQLKESGPAVIKPSQSLSLTCIVS<u>GFSITSSVYC</u>WQWIRQPPGKGLEWMG<u>RICYDGSVDYSPSITS</u>
RGTISRDTSLNKVFFQLSSVTNEDTAMYYCSR<u>ENHIDYYDTTYPSFDV</u>WGAGTTVTVSS
                               (CDRH3, SEQ ID NO:590)

FIG. 9A (SEQ ID NO:591) Variable light chain nucleotide sequence:

gacattgtgctgacacagtctcctgcttccttaattgtatctctggggcagagggccaccatctcgtgcagggccagcaaaagtgtcaatgaatatggctatacttatatgca
ctggtaccaacagaaaccaggactgccacccaaactcctcatctatcttgcatccaatctagattctggggtccctgccaggttcagtggcagtgggtctgggacagactt
caccctcaacatccatcctgtggaggaggaggatgctgcaacctattactgtcaacacagtagggagcttccgtacacgttcggagggggggaccaagctggaaataaaa
cgg

FIG. 9B (SEQ ID NO:592) Variable heavy chain nucleotide sequence:

cagattcagctgaaggagtctggacctgctgtcatcaagccatcacagtcactgtctctcacgtgcatagtctctggattctccatcacaagtagtgtttattgctggcagtgg
atccgccagccccaggaaagggattagagtggatgggacgcatctgttatgacggttcagttgactatagtccatccatcacaagccgcggcaccatctccagagaca
catctctgaacaaagtcttttccagctgagctctgtgacaaatgaggacacagccatgtactactgttccagggaaaaccatattgattactacgatactacttatccgtcctt
cgatgtctggggcgcagggaccacggtcaccgtctcctca

SEQUENCE LISTING

<160> NUMBER OF SEQ ID NOS: 616

<210> SEQ ID NO 1
<211> LENGTH: 351
<212> TYPE: DNA
<213> ORGANISM: Artificial Sequence
<220> FEATURE:
<223> OTHER INFORMATION: synthetic

<400> SEQUENCE: 1

```
gaggtccagc tgcaacagtc tggacctgag ttggtgaagc ctggggcctc agtgaagata      60
tcttgcaaga cttctggata cactttcact gaatacgcca tgcactggat gaagcagagc     120
catggaaaga gccttgagtg gattggaggt atcaatccta ctaatggtga tacaatctac     180
aaccagaagt tcaaggacaa ggccaaattg actgtagaca ggtcctccag cacagcctac     240
atggagctcc gcagcctgac atctgacgat tctgcattat tttattgtgc aagacgggaa     300
ctggactact ttgcctcctg gggccaaggc accactctca cagtctcctc a              351
```

<210> SEQ ID NO 2
<211> LENGTH: 117
<212> TYPE: PRT
<213> ORGANISM: Artificial Sequence
<220> FEATURE:
<223> OTHER INFORMATION: synthetic

<400> SEQUENCE: 2

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ala Met His Trp Met Lys Gln Ser His Gly Lys Ser Leu Glu Trp Ile
        35                  40                  45

Gly Gly Ile Asn Pro Thr Asn Gly Asp Thr Ile Tyr Asn Gln Lys Phe
    50                  55                  60

Lys Asp Lys Ala Lys Leu Thr Val Asp Arg Ser Ser Ser Thr Ala Tyr
65                  70                  75                  80

Met Glu Leu Arg Ser Leu Thr Ser Asp Asp Ser Ala Leu Phe Tyr Cys
                85                  90                  95

Ala Arg Arg Glu Leu Asp Tyr Phe Ala Ser Trp Gly Gln Gly Thr Thr
            100                 105                 110

Leu Thr Val Ser Ser
        115
```

<210> SEQ ID NO 3
<211> LENGTH: 351
<212> TYPE: DNA
<213> ORGANISM: Artificial Sequence
<220> FEATURE:
<223> OTHER INFORMATION: synthetic

<400> SEQUENCE: 3

```
gaggtccagc tgcaacagtc tggacctgag ctggtgaagc ctggggcctc agtgaagata      60
tcctgcaaga cttctggata cactttcact gaatacgcca tgcactggat gaagcagagc     120
catggaaaga gccttgagtg gattggcggt atcaatccta ctaatggtga tacaatctac     180
aaccagaggt tcaaggacaa ggccaaattg actgtagaca ggtcctccag cacagcctac     240
atggagctcc gcagcctgac atctgacgat tctgcattat tttattgtgc aagacgggaa     300
ctggactact ttgcctcctg gggccaaggc accactctca cagtctcctc a              351
```

<210> SEQ ID NO 4
<211> LENGTH: 117
<212> TYPE: PRT
<213> ORGANISM: Artificial Sequence
<220> FEATURE:
<223> OTHER INFORMATION: synthetic

<400> SEQUENCE: 4

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ala Met His Trp Met Lys Gln Ser His Gly Lys Ser Leu Glu Trp Ile
        35                  40                  45

Gly Gly Ile Asn Pro Thr Asn Gly Asp Thr Ile Tyr Asn Gln Arg Phe
    50                  55                  60

Lys Asp Lys Ala Lys Leu Thr Val Asp Arg Ser Ser Thr Ala Tyr
65                  70                  75                  80

Met Glu Leu Arg Ser Leu Thr Ser Asp Asp Ser Ala Leu Phe Tyr Cys
                85                  90                  95

Ala Arg Arg Glu Leu Asp Tyr Phe Ala Ser Trp Gly Gln Gly Thr Thr
            100                 105                 110

Leu Thr Val Ser Ser
        115
```

<210> SEQ ID NO 5
<211> LENGTH: 351
<212> TYPE: DNA
<213> ORGANISM: Artificial Sequence
<220> FEATURE:
<223> OTHER INFORMATION: synthetic

<400> SEQUENCE: 5

```
gaggtccagc tgcaacagtc tggacctgaa ctggtgaagc ctggggcctc agtgaagata      60
tcctgtaagg cttcgggatt cactttcact gaatacgcca tgcactggat gaaacagagc     120
catggaaaga gccttgagtg gattggaggt atcaatccta ctaacggtga tgcaatctac     180
aaccagaagt tcaaggacaa ggccaagttg actgtagaca ggtcctccag cacagcctac     240
atggagctcc gcagcctgac atctgacgat tctgcattat tttattgtgc aagacgggaa     300
ctggactact ttccctcctg gggccaaggc accactctca cagtctcctc a              351
```

<210> SEQ ID NO 6
<211> LENGTH: 117
<212> TYPE: PRT
<213> ORGANISM: Artificial Sequence
<220> FEATURE:
<223> OTHER INFORMATION: synthetic

<400> SEQUENCE: 6

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Phe Thr Phe Thr Glu Tyr
            20                  25                  30

Ala Met His Trp Met Lys Gln Ser His Gly Lys Ser Leu Glu Trp Ile
        35                  40                  45

Gly Gly Ile Asn Pro Thr Asn Gly Asp Ala Ile Tyr Asn Gln Lys Phe
    50                  55                  60
```

Lys Asp Lys Ala Lys Leu Thr Val Asp Arg Ser Ser Thr Ala Tyr
65                  70                  75                  80

Met Glu Leu Arg Ser Leu Thr Ser Asp Ser Ala Leu Phe Tyr Cys
                85                  90                  95

Ala Arg Arg Glu Leu Asp Tyr Phe Pro Ser Trp Gly Gln Gly Thr Thr
            100                 105                 110

Leu Thr Val Ser Ser
        115

<210> SEQ ID NO 7
<211> LENGTH: 351
<212> TYPE: DNA
<213> ORGANISM: Artificial Sequence
<220> FEATURE:
<223> OTHER INFORMATION: synthetic

<400> SEQUENCE: 7
gaggtccagc tgcaacagtc tggacctgaa ctggaaaagc ctggggcttc agtgaggata      60
tcctgcaaga cttctggata cacattcact gaatacgcca tgcactgggt gaagcagagc     120
catggaaaga gccttgagtg gattggaggt attaatccta caatggcaa tgctatctac      180 aaccagatat tcaaggacaa ggccacactg actgtggaca ggtcctccag cacagcctac     240
atgggcctcc gcagcctgac attcggggat tctggagtct acttctgtgt aagacgacaa     300
ctggactact ttgactattg gggccagggc gcctctctca cagtctcctc a              351

<210> SEQ ID NO 8
<211> LENGTH: 117
<212> TYPE: PRT
<213> ORGANISM: Artificial Sequence
<220> FEATURE:
<223> OTHER INFORMATION: synthetic

<400> SEQUENCE: 8

Glu Val Gln Leu Gln Gln Ser Gly Pro Glu Leu Glu Lys Pro Gly Ala
1               5                   10                  15

Ser Val Arg Ile Ser Cys Lys Thr Ser Gly Tyr Thr Phe Thr Glu Tyr
            20                  25                  30

Ala Met His Trp Val Lys Gln Ser His Gly Lys Ser Leu Glu Trp Ile
        35                  40                  45

Gly Gly Ile Asn Pro Asn Asn Gly Asn Ala Ile Tyr Asn Gln Ile Phe
    50                  55                  60

Lys Asp Lys Ala Thr Leu Thr Val Asp Arg Ser Ser Thr Ala Tyr
65                  70                  75                  80

Met Gly Leu Arg Ser Leu Thr Phe Gly Asp Ser Gly Val Tyr Phe Cys
                85                  90                  95

Val Arg Arg Gln Leu Asp Tyr Phe Asp Tyr Trp Gly Gln Gly Ala Ser
            100                 105                 110

Leu Thr Val Ser Ser
        115

<210> SEQ ID NO 9
<211> LENGTH: 351
<212> TYPE: DNA
<213> ORGANISM: Artificial Sequence
<220> FEATURE:
<223> OTHER INFORMATION: synthetic

<400> SEQUENCE: 9
gaggtccagc tgcaacagtc tggacctgag ctggaaaagc ctggggcttc agtgaagata      60

```
tcctgcaaga cttctggata cacattcact gaatacgcca tacactgggt gaagcagagc      120
catggaatga gccttgagtg gattggaggt attaatccta gcaatggcaa tgctatctac      180
aaccaaatat tcaaggacaa ggccacactg actgtggaca ggtcctccag cacagcctac      240
atgggcctcc gcagcctgac atttggggat tctggagtct acttctgtgt aagacgacaa      300
ctggacttct ttgactattg gggccagggc gcctctctca cagtctcctc a               351
```

```
<210> SEQ ID NO 10
<211> LENGTH: 117
<212> TYPE: PRT
<213> ORGANISM: Artificial Sequence
<220> FEATURE:
<223> OTHER INFORMATION: synthetic

<400> SEQUENCE: 10

Glu Val Gln Leu Gln Gln Ser Gly Pro Glu Leu Glu Lys Pro Gly Ala
1               5                   10                  15

Ser Val Lys Ile Ser Cys Lys Thr Ser Gly Tyr Thr Phe Thr Glu Tyr
            20                  25                  30

Ala Ile His Trp Val Lys Gln Ser His Gly Met Ser Leu Glu Trp Ile
        35                  40                  45

Gly Gly Ile Asn Pro Ser Asn Gly Asn Ala Ile Tyr Asn Gln Ile Phe
    50                  55                  60

Lys Asp Lys Ala Thr Leu Thr Val Asp Arg Ser Ser Ser Thr Ala Tyr
65                  70                  75                  80

Met Gly Leu Arg Ser Leu Thr Phe Gly Asp Ser Gly Val Tyr Phe Cys
                85                  90                  95

Val Arg Arg Gln Leu Asp Phe Phe Asp Tyr Trp Gly Gln Gly Ala Ser
            100                 105                 110

Leu Thr Val Ser Ser
        115
```

```
<210> SEQ ID NO 11
<211> LENGTH: 351
<212> TYPE: DNA
<213> ORGANISM: Artificial Sequence
<220> FEATURE:
<223> OTHER INFORMATION: synthetic

<400> SEQUENCE: 11
gaggtccagc tgcaacagtc tggacctgag ctggaaaagc ctggggcttc agtgaagata      60
tcctgcaaga cttctggata cacattcact gaatacgcca tgcactgggt gaagcagagc      120
catggaatga gccttgagtg gattggaggt attaatccta gcaatggcaa tgctatctac      180
aaccagatat tcaaggacaa ggccacactg actgtggaca ggtcctccag cacagcctac      240
atgggcctcc gcagcctgac atttggggat tctggagtct acttctgtgt aagacgacaa      300
ctggacttct ttgactattg gggccagggc gcctctctca cagtctcctc a               351
```

```
<210> SEQ ID NO 12
<211> LENGTH: 117
<212> TYPE: PRT
<213> ORGANISM: Artificial Sequence
<220> FEATURE:
<223> OTHER INFORMATION: synthetic

<400> SEQUENCE: 12

Glu Val Gln Leu Gln Gln Ser Gly Pro Glu Leu Glu Lys Pro Gly Ala
1               5                   10                  15
```

Ser Val Lys Ile Ser Cys Lys Thr Ser Gly Tyr Thr Phe Thr Glu Tyr
            20                  25                  30

Ala Met His Trp Val Lys Gln Ser His Gly Met Ser Leu Glu Trp Ile
        35                  40                  45

Gly Gly Ile Asn Pro Ser Asn Gly Asn Ala Ile Tyr Asn Gln Ile Phe
    50                  55                  60

Lys Asp Lys Ala Thr Leu Thr Val Asp Arg Ser Ser Thr Ala Tyr
65                  70                  75                  80

Met Gly Leu Arg Ser Leu Thr Phe Gly Asp Ser Gly Val Tyr Phe Cys
                85                  90                  95

Val Arg Arg Gln Leu Asp Phe Phe Asp Tyr Trp Gly Gln Gly Ala Ser
                100                 105                 110

Leu Thr Val Ser Ser
        115

<210> SEQ ID NO 13
<211> LENGTH: 351
<212> TYPE: DNA
<213> ORGANISM: Artificial Sequence
<220> FEATURE:
<223> OTHER INFORMATION: synthetic

<400> SEQUENCE: 13
gaggtccggc tgcagcagcc tggacctgag gtggaaaagc ctggggcttc agtgaagata     60
tcctgcaaga cttctggata cacattcact gaatacgcca tccactgggt gaaacagagc    120
catggagaga gccttgagtg gattggaggt attaatccta gcaatggcga tcctatctat    180
aaccagatat tcaaggacaa ggccacactg actgtggaca ggtcctccaa cacagcctac    240
atgggcctcc gcagcctgac agttggggat tctggagtct acttctgtgt tagacgacaa    300
ctggactact ttgacttttg gggccagggc gcctctctca cagtctcctc a             351

<210> SEQ ID NO 14
<211> LENGTH: 117
<212> TYPE: PRT
<213> ORGANISM: Artificial Sequence
<220> FEATURE:
<223> OTHER INFORMATION: synthetic

<400> SEQUENCE: 14

Glu Val Arg Leu Gln Gln Pro Gly Pro Glu Val Glu Lys Pro Gly Ala
1               5                   10                  15

Ser Val Lys Ile Ser Cys Lys Thr Ser Gly Tyr Thr Phe Thr Glu Tyr
            20                  25                  30

Ala Ile His Trp Val Lys Gln Ser His Gly Glu Ser Leu Glu Trp Ile
        35                  40                  45

Gly Gly Ile Asn Pro Ser Asn Gly Asp Pro Ile Tyr Asn Gln Ile Phe
    50                  55                  60

Lys Asp Lys Ala Thr Leu Thr Val Asp Arg Ser Ser Asn Thr Ala Tyr
65                  70                  75                  80

Met Gly Leu Arg Ser Leu Thr Val Gly Asp Ser Gly Val Tyr Phe Cys
                85                  90                  95

Val Arg Arg Gln Leu Asp Tyr Phe Asp Phe Trp Gly Gln Gly Ala Ser
                100                 105                 110

Leu Thr Val Ser Ser
        115

<210> SEQ ID NO 15
<211> LENGTH: 351
<212> TYPE: DNA
<213> ORGANISM: Artificial Sequence
<220> FEATURE:
<223> OTHER INFORMATION: synthetic

<400> SEQUENCE: 15

```
cagggtcaga tgcagcagtc tggagctgaa ctggcgaagc ctggggcttc agtgaagctg      60
tcctgcaaga cttctggctt caccttcagc agtagttata aagttggtt gaagcaaaag      120
cctggacaga gtcttgagtg gattgcatgg atttatgctg gaactggtaa tactaactat     180
aatcagaagt tcacagacaa ggcccaactg actgtagaca catcctccag tacagcctac    240
atgcaactca gcagcctgac aactgaggac tctgccatct attactgtgc gataagtggg    300
acgggattta cttactgggg ccaagggact ctggtcactg tctctgcaac a              351
```

<210> SEQ ID NO 16
<211> LENGTH: 116
<212> TYPE: PRT
<213> ORGANISM: Artificial Sequence
<220> FEATURE:
<223> OTHER INFORMATION: synthetic

<400> SEQUENCE: 16

```
Gln Gly Gln Met Gln Gln Ser Gly Ala Glu Leu Ala Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Leu Thr Val Asp Thr Ser Ser Thr Ala Tyr
65                  70                  75                  80

Met Gln Leu Ser Ser Leu Thr Thr Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115
```

<210> SEQ ID NO 17
<211> LENGTH: 351
<212> TYPE: DNA
<213> ORGANISM: Artificial Sequence
<220> FEATURE:
<223> OTHER INFORMATION: synthetic

<400> SEQUENCE: 17

```
cagggtcaga tgcagcagtc tggagctgaa ctggtgaagc ctggggcttc agtgaagctg      60
tcctgcaaga cttctggctt caccttcagc agtagttata aagttggtt gaagcaaaag      120
cctggacaga gtcttgagtg gattgcatgg atttatgctg gaactggtaa tactaactat     180
aatcagaagt tcacagacaa ggcccaactg actgtagaca catcctccag tacagcctac    240
atgcaactca gcagcctgac aactgaggac tctgccatct attactgtgc gataagtggg    300
acgggattta cttactgggg ccaagggact ctggtcactg tctctgcaac a              351
```

<210> SEQ ID NO 18

```
<211> LENGTH: 116
<212> TYPE: PRT
<213> ORGANISM: Artificial Sequence
<220> FEATURE:
<223> OTHER INFORMATION: synthetic

<400> SEQUENCE: 18

Gln Gly Gln Met Gln Gln Ser Gly Ala Glu Leu Ala Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Phe Ala Gly Thr Gly Asn Thr Asn Tyr Asn Gln Lys Phe
    50                  55                  60

Thr Asp Lys Ala Gln Leu Thr Val Asp Thr Ser Ser Thr Ala Tyr
65                  70                  75                  80

Met Gln Leu Ser Ser Leu Thr Thr Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115

<210> SEQ ID NO 19
<211> LENGTH: 348
<212> TYPE: DNA
<213> ORGANISM: Artificial Sequence
<220> FEATURE:
<223> OTHER INFORMATION: synthetic

<400> SEQUENCE: 19
cagggtcaga tgcagcagtc tggagctgag ctggcgaagc ctggggcttc agtgaaactg        60
tcctgcaaga cttctggctt caccttcagc agtagttata taagttggtt gaagcaaaag      120
cctggacaga gtcttgagtg gattgcatgg attttgctg gaactggtaa tactaattat       180
aatcagaagt tcacagacaa ggcccaactg actgtagaca catcctccag tacagcctac      240
atgcaactca gcagcctgac aactgaggac tctgccatct attactgtgc gataagtggg      300 acgggatta cttactgggg ccaagggact ctggtcactg tctctgca                    348

<210> SEQ ID NO 20
<211> LENGTH: 116
<212> TYPE: PRT
<213> ORGANISM: Artificial Sequence
<220> FEATURE:
<223> OTHER INFORMATION: synthetic

<400> SEQUENCE: 20

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Leu Thr Val Asp Thr Ser Ser Thr Ala Tyr
65                  70                  75                  80
```

```
Met Gln Leu Ser Ser Leu Thr Thr Glu Asp Ser Ala Ile Tyr Tyr Cys
             85                  90                  95

Ala Ile Ser Gly Thr Gly Phe Thr Tyr Trp Gly Gln Gly Thr Leu Val
            100                 105                 110

Thr Val Ser Ala
        115

<210> SEQ ID NO 21
<211> LENGTH: 348
<212> TYPE: DNA
<213> ORGANISM: Artificial Sequence
<220> FEATURE:
<223> OTHER INFORMATION: synthetic

<400> SEQUENCE: 21
cagggtcaga tgcagcagtc tggagctgag ctggtgaagc ctggggcttc agtgaagctg      60
tcctgcaaga cttctggctt caccttcagc agtagtttta taagttggtt gaagcaaaag     120
cctggacaga gtcttgagtg gattgcatgg atttatgctg aactggaaaa tactaactat     180
aatcagaagt tcacagacaa ggcccaactg actgtagaca tcctccagac acagcctac     240 atgcaattca gcagcctgac gactgaggac tctgccatct attactgtgc gataagtggg     300
acggggttta cttactgggg ccaagggact ctggtcactg tctctgca                  348

<210> SEQ ID NO 22
<211> LENGTH: 116
<212> TYPE: PRT
<213> ORGANISM: Artificial Sequence
<220> FEATURE:
<223> OTHER INFORMATION: synthetic

<400> SEQUENCE: 22

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Phe Ile Ser Trp Leu Lys Gln Lys Pro Gly Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Leu Thr Val Asp Thr Ser Ser Thr Ala Tyr
65                  70                  75                  80

Met Gln Phe Ser Ser Leu Thr Thr Glu Asp Ser Ala Ile Tyr Tyr Cys
             85                  90                  95

Ala Ile Ser Gly Thr Gly Phe Thr Tyr Trp Gly Gln Gly Thr Leu Val
            100                 105                 110

Thr Val Ser Ala
        115

<210> SEQ ID NO 23
<211> LENGTH: 351
<212> TYPE: DNA
<213> ORGANISM: Artificial Sequence
<220> FEATURE:
<223> OTHER INFORMATION: synthetic

<400> SEQUENCE: 23
cagggtcaga tgcagcagtc tggagctgag ctggtgaagc ctggggcttc agtgaagctg      60
tcctgcaaga cttctggctt caccttcagc agtagttatt ttagttggtt gaagcaaaag     120
```

```
cctggacaga gtcttgagtg gattgcatgg atttatgctg gaactggtaa tactatctat      180
aatcagaagt tcacagacaa ggcccaactg actgtagaca cagcctccag cacagccttc      240
atgcaactca gcagcctgac aattgaggac tctgccatct actactgtgc gataagtggg      300
acggggttta cttactgggg ccaagggact ctggtcactg tctctgcaac a               351
```

<210> SEQ ID NO 24
<211> LENGTH: 116
<212> TYPE: PRT
<213> ORGANISM: Artificial Sequence
<220> FEATURE:
<223> OTHER INFORMATION: synthetic

<400> SEQUENCE: 24

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Phe Ser Trp Leu Lys Gln Lys Pro Gly Gln Ser Leu Glu Trp Ile
        35                  40                  45

Ala Trp Ile Tyr Ala Gly Thr Gly Asn Thr Ile Tyr Asn Gln Lys Phe
    50                  55                  60

Thr Asp Lys Ala Gln Leu Thr Val Asp Thr Ala Ser Ser Thr Ala Phe
65                  70                  75                  80

Met Gln Leu Ser Ser Leu Thr Ile Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115
```

<210> SEQ ID NO 25
<211> LENGTH: 348
<212> TYPE: DNA
<213> ORGANISM: Artificial Sequence
<220> FEATURE:
<223> OTHER INFORMATION: synthetic

<400> SEQUENCE: 25

```
cagggtcagc tgcagcagtc tggagctgag ctggtgaagc ctggggcttc agtgaagctg       60
tcctgcaaga cttctggctt caccttcagc agtagttata aagttggtt gaagcaaagg      120 cctggacaga gtcttgagtg gattgcatgg atttatgctg gaactggtgg tactaactat      180
aatcagaagt tcacagacaa ggcccaactg actgtagaca catcctccag cacagcctac      240
atgcaattca gcagcctgac aactgaggac tctgccatct attactgtgc gataagtggg      300
acggggttta tttactgggg ccaagggact ctggtcactg tctctgca                   348
```

<210> SEQ ID NO 26
<211> LENGTH: 116
<212> TYPE: PRT
<213> ORGANISM: Artificial Sequence
<220> FEATURE:
<223> OTHER INFORMATION: synthetic

<400> SEQUENCE: 26

```
Gln Gly Gln Leu Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30
```

Tyr Ile Ser Trp Leu Lys Gln Arg Pro Gly Gln Ser Leu Glu Trp Ile
            35                  40                  45

Ala Trp Ile Tyr Ala Gly Thr Gly Gly Thr Asn Tyr Asn Gln Lys Phe
    50                  55                  60

Thr Asp Lys Ala Gln Leu Thr Val Asp Thr Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Ile Ser Gly Thr Gly Phe Ile Tyr Trp Gly Gln Gly Thr Leu Val
            100                 105                 110

Thr Val Ser Ala
        115

<210> SEQ ID NO 27
<211> LENGTH: 345
<212> TYPE: DNA
<213> ORGANISM: Artificial Sequence
<220> FEATURE:
<223> OTHER INFORMATION: synthetic

<400> SEQUENCE: 27
cagggtcagt tgcagcagtc tggaccagta ctggtgaagc ctggggcttc agaaatacta      60
tactgcaaga cttctggctt caccttcagc agtacctata aagttggtt gaagcaaaag     120 cctggacaga gtcttgagtg gattgcgtgg atttatgctg gaactggtgc tactaattat    180
aatcagaagt tcacaggcaa ggcccaactg actgtagacg cttcctccaa cacagcctac    240
atgcacttca gcggcctgac acctgaggac tctgccatct attactgtgc aatttctggg    300
gcggggggtt actggggcca aggactctg gtcactgtct ctgca                     345

<210> SEQ ID NO 28
<211> LENGTH: 115
<212> TYPE: PRT
<213> ORGANISM: Artificial Sequence
<220> FEATURE:
<223> OTHER INFORMATION: synthetic

<400> SEQUENCE: 28

Gln Gly Gln Leu Gln Gln Ser Gly Pro Val Leu Val Lys Pro Gly Ala
1               5                   10                  15

Ser Glu Ile Leu Tyr Cys Lys Thr Ser Gly Phe Thr Phe Ser Ser Thr
            20                  25                  30

Tyr Ile Ser Trp Leu Lys Gln Lys Pro Gly Gln Ser Leu Glu Trp Ile
            35                  40                  45

Ala Trp Ile Tyr Ala Gly Thr Gly Ala Thr Asn Tyr Asn Gln Lys Phe
    50                  55                  60

Thr Gly Lys Ala Gln Leu Thr Val Asp Ala Ser Ser Asn Thr Ala Tyr
65                  70                  75                  80

Met His Phe Ser Gly Leu Thr Pro Glu Asp Ser Ala Ile Tyr Tyr Cys
                85                  90                  95

Ala Ile Ser Gly Ala Gly Val Tyr Trp Gly Gln Gly Thr Leu Val Thr
            100                 105                 110

Val Ser Ala
        115

<210> SEQ ID NO 29
<211> LENGTH: 354
<212> TYPE: DNA

```
<213> ORGANISM: Artificial Sequence
<220> FEATURE:
<223> OTHER INFORMATION: synthetic

<400> SEQUENCE: 29
cagggccaac tgcagcagcc tggggctgag tttgtgaagc ctggggcttc actgaagctg      60
tcctgcaggg cttctggcta caccttcacc agctactgga tacactgggt gaagcagagg     120
cctggacaag gccttgagtg gattggagaa attgatcctt ctgacagtta tattaaccag     180
aatcaaaagt tcaggggcaa ggccacattg actgtggaca atcctccag cacagcctac      240 atggaactca gcggcctgac atctgaagac tctgcggtct attactgtgc aagacattac     300
tacggtgttc ttgactcctg gggccaaggt accactctca cagtctcctc aaca           354

<210> SEQ ID NO 30
<211> LENGTH: 117
<212> TYPE: PRT
<213> ORGANISM: Artificial Sequence
<220> FEATURE:
<223> OTHER INFORMATION: synthetic

<400> SEQUENCE: 30

Gln Gly Gln Leu Gln Gln Pro Gly Ala Glu Phe Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Ile Asn Gln Asn Gln Lys Phe
    50                  55                  60

Arg Gly Lys Ala Thr Leu Thr Val Asp Lys Ser Ser Thr Ala Tyr
65                  70                  75                  80

Met Glu Leu Ser Gly Leu Thr Ser Glu Asp Ser Ala Val Tyr Tyr Cys
                85                  90                  95

Ala Arg His Tyr Tyr Gly Val Leu Asp Ser Trp Gly Gln Gly Thr Thr
            100                 105                 110

Leu Thr Val Ser Ser
        115

<210> SEQ ID NO 31
<211> LENGTH: 351
<212> TYPE: DNA
<213> ORGANISM: Artificial Sequence
<220> FEATURE:
<223> OTHER INFORMATION: synthetic

<400> SEQUENCE: 31
cagggccaac tgcagcagcc tggggctgag tttgtgaagc ctggggcttc actgaagctg      60
tcctgcaggg cttctggcta caccttcacc agctactgga ttcactgggt gaagcagagg     120
cctggacaag gccttgagtg gatcggagaa gttgatcctt ctgacagtta tattaaccag     180
aatgaaaagt tcaggggcaa ggccacattg actgtggaca atcctccag cacagcctac      240 atgcagctcg gcagcctgac atctgaagac tctgcggtct attactgtgc aagacattac     300
tacggtgttc ttgactcctg gggccaaggc accgctctca cagtctcctc a              351

<210> SEQ ID NO 32
<211> LENGTH: 117
<212> TYPE: PRT
<213> ORGANISM: Artificial Sequence
```

```
<220> FEATURE:
<223> OTHER INFORMATION: synthetic

<400> SEQUENCE: 32

Gln Gly Gln Leu Gln Gln Pro Gly Ala Glu Phe Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Val Asp Pro Ser Asp Ser Tyr Ile Asn Gln Asn Glu Lys Phe
    50                  55                  60

Arg Gly Lys Ala Thr Leu Thr Val Asp Lys Ser Ser Ser Thr Ala Tyr
65                  70                  75                  80

Met Gln Leu Gly Ser Leu Thr Ser Glu Asp Ser Ala Val Tyr Tyr Cys
                85                  90                  95

Ala Arg His Tyr Tyr Gly Val Leu Asp Ser Trp Gly Gln Gly Thr Ala
            100                 105                 110

Leu Thr Val Ser Ser
            115

<210> SEQ ID NO 33
<211> LENGTH: 351
<212> TYPE: DNA
<213> ORGANISM: Artificial Sequence
<220> FEATURE:
<223> OTHER INFORMATION: synthetic

<400> SEQUENCE: 33
caggtccaac tgcagcagcc tggggctgaa cttgtgaagc ctggggcttc actgaagctg      60
tcctgcaggg cctctggcta caccttcacc agctactgga ttcactgggt gaagcagagg     120
cctggacaag gccttgagtg gatcggagag attgatcctt ctgatagtta tactaactac     180
aatcaaaagt tcaagggcaa ggccacattg actgtagaca atcctccag ggcagcctac      240 atgcagctca gcagcctgac atctgaggac tctgcggtct attactgtgc aagacattac     300
tacggtgtct tgactcctg gggccaaggc accaaactca cagtctcctc a               351

<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34

Gln Val Gln Leu Gln Gln Pro Gly Ala Glu Leu Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Arg Ala Ala Tyr
65                  70                  75                  80

Met Gln Leu Ser Ser Leu Thr Ser Glu Asp Ser Ala Val Tyr Tyr Cys
                85                  90                  95
```

Ala Arg His Tyr Tyr Gly Val Phe Asp Ser Trp Gly Gln Gly Thr Lys
                100                 105                 110

Leu Thr Val Ser Ser
        115

<210> SEQ ID NO 35
<211> LENGTH: 360
<212> TYPE: DNA
<213> ORGANISM: Artificial Sequence
<220> FEATURE:
<223> OTHER INFORMATION: synthetic

<400> SEQUENCE: 35
caggtccaac tgcagcagcc tggggctgag cttgtgaagc ctggggcttc agtgaagctg      60
tcctgcaagg cttctggcta caccctcagt agctattgga tgcactgggt gaagcagagg     120
cctggacaag gccttgagtg gatcggagag attcatcctt ctgatagtta ctactagctac    180 aatcaaaagt tcaaggacaa ggccacattg actgtagaca atcctccag cacagcctac      240 atgcagctca gcagcctgac atctgaggac tctgcagtct attactgtgc aagggggggc     300
tactataggt acgacgagtt tgcttactgg ggccaaggga ctctggtcac tgtctctgca     360

<210> SEQ ID NO 36
<211> LENGTH: 120
<212> TYPE: PRT
<213> ORGANISM: Artificial Sequence
<220> FEATURE:
<223> OTHER INFORMATION: synthetic

<400> SEQUENCE: 36

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Leu Ser Ser Tyr
            20                  25                  30

Trp Met His Trp Val Lys Gln Arg Pro Gly Gln Gly Leu Glu Trp Ile
        35                  40                  45

Gly Glu Ile His Pro Ser Asp Ser Tyr Thr Ser Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Tyr Arg Tyr Asp Glu Phe Ala Tyr Trp Gly Gln
                100                 105                 110

Gly Thr Leu Val Thr Val Ser Ala
        115                 120

<210> SEQ ID NO 37
<211> LENGTH: 348
<212> TYPE: DNA
<213> ORGANISM: Artificial Sequence
<220> FEATURE:
<223> OTHER INFORMATION: synthetic

<400> SEQUENCE: 37
caggtccatc tgcagcagcc tggggctgag ctggtgaggc ctggggtttc agtgaagctg      60
tcctgcaagg cttctggcta caccttcacc acctactcga taaactggat gaagcagagg     120
cctggacaag gccttgagtg gatcggaaat atttatcctt ctaccagtca tactaactac     180
aatcaaaagt tcagggacaa ggccacaatg actgtagaca atcctccag cacagcctac      240

```
atgcagctca gcagcccgac atctgaggac tctgcggtct attattgtac aataaatgcc      300
tattctatgg actactgggg tcaaggaacc tcagtcaccg tctcctca                   348
```

<210> SEQ ID NO 38
<211> LENGTH: 116
<212> TYPE: PRT
<213> ORGANISM: Artificial Sequence
<220> FEATURE:
<223> OTHER INFORMATION: synthetic

<400> SEQUENCE: 38

```
Gln Val His Leu Gln Gln Pro Gly Ala Glu Leu Val Arg Pro Gly Val
1               5                  10                  15

Ser Val Lys Leu Ser Cys Lys Ala Ser Gly Tyr Thr Phe Thr Thr Tyr
            20                  25                  30

Ser Ile Asn Trp Met Lys Gln Arg Pro Gly Gln Gly Leu Glu Trp Ile
        35                  40                  45

Gly Asn Ile Tyr Pro Ser Thr Ser His Thr Asn Tyr Asn Gln Lys Phe
    50                  55                  60

Arg Asp Lys Ala Thr Met Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Ile Asn Ala Tyr Ser Met Asp Tyr Trp Gly Gln Gly Thr Ser Val
                100                 105                 110

Thr Val Ser Ser
            115
```

<210> SEQ ID NO 39
<211> LENGTH: 339
<212> TYPE: DNA
<213> ORGANISM: Artificial Sequence
<220> FEATURE:
<223> OTHER INFORMATION: synthetic

<400> SEQUENCE: 39

```
caggtccagc ttcagcagtc tggggctgga ctggcaaaac ctggggcctc agtgaagatg       60
tcctgcaagg cttctggcta cacctttact gccaacaaga tgcactgggc aaaacagcgg      120
cctggacagg gtctggaatg gattggatac attgatccta gctctggtta tactgaatac      180
aatcataaga tccagtacaa ggccactttg actgcagaca catcctccag cacagcctac      240
atgcaactga gcaccctaac atttgaagac tctgcagtct attactgtac aaattttgct      300
tactggggcc aagggactct ggtcactgtc tcagcaaca                             339
```

<210> SEQ ID NO 40
<211> LENGTH: 112
<212> TYPE: PRT
<213> ORGANISM: Artificial Sequence
<220> FEATURE:
<223> OTHER INFORMATION: synthetic

<400> SEQUENCE: 40

```
Gln Val Gln Leu Gln Gln Ser Gly Ala Gly Leu Ala Lys Pro Gly Ala
1               5                  10                  15

Ser Val Lys Met Ser Cys Lys Ala Ser Gly Tyr Thr Phe Thr Ala Asn
            20                  25                  30

Lys Met His Trp Ala Lys Gln Arg Pro Gly Gln Gly Leu Glu Trp Ile
        35                  40                  45
```

```
Gly Tyr Ile Asp Pro Ser Ser Gly Tyr Thr Glu Tyr Asn His Lys Ile
            50                  55                  60

Gln Tyr Lys Ala Thr Leu Thr Ala Asp Thr Ser Ser Thr Ala Tyr
 65                  70                  75                  80

Met Gln Leu Ser Thr Leu Thr Phe Glu Asp Ser Ala Val Tyr Tyr Cys
                    85                  90                  95

Thr Asn Phe Ala Tyr Trp Gly Gln Gly Thr Leu Val Thr Val Ser Ala
                100                 105                 110
```

<210> SEQ ID NO 41
<211> LENGTH: 336
<212> TYPE: DNA
<213> ORGANISM: Artificial Sequence
<220> FEATURE:
<223> OTHER INFORMATION: synthetic

<400> SEQUENCE: 41

```
caggtccagc ttcagcagtc tggggctgga ctggcaaaac ctggggcctc agtgaagatg    60
tcctgcaagg cttctggcta cacctttact gccaacaaga tgcactgggc aaaacagcgg   120
cctggacagg gtctggaatg gattggatac attgatccta gctctggtta tactgaatac   180
aatcataaga tccaggacaa ggccacattg actgcagaca catcctccag cacagcctac   240
atgcaactga gcagcctaac atttgaagac tctgcagtct attactgtac aaattttgct   300
tactggggcc aagggactct ggtcactgtc tcagca                             336
```

<210> SEQ ID NO 42
<211> LENGTH: 112
<212> TYPE: PRT
<213> ORGANISM: Artificial Sequence
<220> FEATURE:
<223> OTHER INFORMATION: synthetic

<400> SEQUENCE: 42

```
Gln Val Gln Leu Gln Gln Ser Gly Ala Gly Leu Ala Lys Pro Gly Ala
  1               5                  10                  15

Ser Val Lys Met Ser Cys Lys Ala Ser Gly Tyr Thr Phe Thr Ala Asn
                20                  25                  30

Lys Met His Trp Ala Lys Gln Arg Pro Gly Gln Gly Leu Glu Trp Ile
            35                  40                  45

Gly Tyr Ile Asp Pro Ser Ser Gly Tyr Thr Glu Tyr Asn His Lys Ile
        50                  55                  60

Gln Asp Lys Ala Thr Leu Thr Ala Asp Thr Ser Ser Thr Ala Tyr
 65                 70                  75                  80

Met Gln Leu Ser Ser Leu Thr Phe Glu Asp Ser Ala Val Tyr Tyr Cys
                    85                  90                  95

Thr Asn Phe Ala Tyr Trp Gly Gln Gly Thr Leu Val Thr Val Ser Ala
                100                 105                 110
```

<210> SEQ ID NO 43
<211> LENGTH: 336
<212> TYPE: DNA
<213> ORGANISM: Artificial Sequence
<220> FEATURE:
<223> OTHER INFORMATION: synthetic

<400> SEQUENCE: 43

```
caggtccagc ttcagcagtc tggggctgga ctggcaaaac ctggggcctc agtgaagatg    60
tcctgcaagg cttctggcta cacctttact gccaacaaga tgcactggac aaaacagcgg   120
```

```
cctggacagg gtctggaatg gattggatac attgatccta gctctggtta tactcaatac    180
aatcataaga tccaggacaa ggccacattg actgcagaca catcctccag cacagcctac    240
atgcaactga gcagcctaac atttgaagac tctgcagtct attactgtac aaattttgct    300
tactggggcc aagggactct ggtcactgtc tcagca                              336
```

<210> SEQ ID NO 44
<211> LENGTH: 112
<212> TYPE: PRT
<213> ORGANISM: Artificial Sequence
<220> FEATURE:
<223> OTHER INFORMATION: synthetic

<400> SEQUENCE: 44

```
Gln Val Gln Leu Gln Gln Ser Gly Ala Gly Leu Ala Lys Pro Gly Ala
1               5                   10                  15

Ser Val Lys Met Ser Cys Lys Ala Ser Gly Tyr Thr Phe Thr Ala Asn
            20                  25                  30

Lys Met His Trp Thr Lys Gln Arg Pro Gly Gln Gly Leu Glu Trp Ile
        35                  40                  45

Gly Tyr Ile Asp Pro Ser Ser Gly Tyr Thr Gln Tyr Asn His Lys Ile
    50                  55                  60

Gln Asp Lys Ala Thr Leu Thr Ala Asp Thr Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Thr Asn Phe Ala Tyr Trp Gly Gln Gly Thr Leu Val Thr Val Ser Ala
            100                 105                 110
```

<210> SEQ ID NO 45
<211> LENGTH: 339
<212> TYPE: DNA
<213> ORGANISM: Artificial Sequence
<220> FEATURE:
<223> OTHER INFORMATION: synthetic

<400> SEQUENCE: 45

```
caggtccacc ttcagcagtc tggggctgaa ctggccaaac ctggggcctc agtgcagatg     60
tcctgcaagg cttctggcta cacctttact gccaacaaga tgcactgggc aagacagcgg    120
cctagacagg gtctggaatg gattggatac attgatcctg cctctggcta tactgaatac    180
aatcagaaga tcaaggacag gccacattg actgcagaca atcctccag cacagcctac     240 atgcaactga gcagcctgac atctgaggac tctgcagtct attactgtac aaattttgct    300
tactggggcc aagggactct ggtcactgtc tctacaaca                           339
```

<210> SEQ ID NO 46
<211> LENGTH: 112
<212> TYPE: PRT
<213> ORGANISM: Artificial Sequence
<220> FEATURE:
<223> OTHER INFORMATION: synthetic

<400> SEQUENCE: 46

```
Gln Val His Leu Gln Gln Ser Gly Ala Glu Leu Ala Lys Pro Gly Ala
1               5                   10                  15

Ser Val Gln Met Ser Cys Lys Ala Ser Gly Tyr Thr Phe Thr Ala Asn
            20                  25                  30

Lys Met His Trp Ala Arg Gln Arg Pro Arg Gln Gly Leu Glu Trp Ile
```

```
                    35                  40                  45
Gly Tyr Ile Asp Pro Ala Ser Gly Tyr Thr Glu Tyr Asn Gln Lys Ile
         50                  55                  60
Lys Asp Arg Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Thr Asn Phe Ala Tyr Trp Gly Gln Gly Thr Leu Val Thr Val Ser Thr
            100                 105                 110
```

<210> SEQ ID NO 47
<211> LENGTH: 339
<212> TYPE: DNA
<213> ORGANISM: Artificial Sequence
<220> FEATURE:
<223> OTHER INFORMATION: synthetic

<400> SEQUENCE: 47

```
caggtccagc ttcagcagtc tggggctgaa ctggcaaaac ctggggcctc agtgaagatg      60
tcctgcaagg cttctggcta cacctttact agcaacaaga tgcactgggc aaaacagcgg     120
cctggacagg gtctggaatg gattggatac attgatccta gctctggtta tactgaatac     180
aatcagaaga tcaaggacaa ggccacattg actgcagaca atcctccag cacagcctac     240
atgcaactga gcagcctgac atctgaggac tctgcagtct attactgtac aaattttgct     300
tactggggcc aagggactct ggtcactgtc tctgcaaca                            339
```

<210> SEQ ID NO 48
<211> LENGTH: 112
<212> TYPE: PRT
<213> ORGANISM: Artificial Sequence
<220> FEATURE:
<223> OTHER INFORMATION: synthetic

<400> SEQUENCE: 48

```
Gln Val Gln Leu Gln Gln Ser Gly Ala Glu Leu Ala Lys Pro Gly Ala
 1               5                  10                  15
Ser Val Lys Met Ser Cys Lys Ala Ser Gly Tyr Thr Phe Thr Ser Asn
             20                  25                  30
Lys Met His Trp Ala Lys Gln Arg Pro Gly Gln Gly Leu Glu Trp Ile
         35                  40                  45
Gly Tyr Ile Asp Pro Ser Ser Gly Tyr Thr Glu Tyr Asn Gln Lys Ile
     50                  55                  60
Lys Asp Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Thr Asn Phe Ala Tyr Trp Gly Gln Gly Thr Leu Val Thr Val Ser Ala
            100                 105                 110
```

<210> SEQ ID NO 49
<211> LENGTH: 351
<212> TYPE: DNA
<213> ORGANISM: Artificial Sequence
<220> FEATURE:
<223> OTHER INFORMATION: synthetic

<400> SEQUENCE: 49

```
caggtccagt tgcagcagtc tggacctgag ttggtgaagc ctggggcttc aatgaggata      60
```

```
tcctgcaagg cttctggcta caccttcaca agctactatg tacactggat aaagcagagg    120
cctggacagg gacttgagtg gattggatgt atttatcctg gagatgttaa tactgactat    180
aatgagaagt tcaagggcaa ggccacgctg actgcagaca atcctccag cacagcctac     240 atgcaggtca gcaccctgac ctctgaggac tctgcgatct atttctgtgt cctttattac    300
tacggtagtt ttgcttactg gggccaaggg actctggtca ctgtctctgc a             351

<210> SEQ ID NO 50
<211> LENGTH: 117
<212> TYPE: PRT
<213> ORGANISM: Artificial Sequence
<220> FEATURE:
<223> OTHER INFORMATION: synthetic

<400> SEQUENCE: 50

Gln Val Gln Leu Gln Gln Ser Gly Pro Glu Leu Val Lys Pro Gly Ala
1               5                   10                  15

Ser Met Arg Ile Ser Cys Lys Ala Ser Gly Tyr Thr Phe Thr Ser Tyr
            20                  25                  30

Tyr Val His Trp Ile Lys Gln Arg Pro Gly Gln Gly Leu Glu Trp Ile
        35                  40                  45

Gly Cys Ile Tyr Pro Gly Asp Val Asn Thr Asp Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Val Ser Thr Leu Thr Ser Glu Asp Ser Ala Ile Tyr Phe Cys
                85                  90                  95

Val Leu Tyr Tyr Tyr Gly Ser Phe Ala Tyr Trp Gly Gln Gly Thr Leu
            100                 105                 110

Val Thr Val Ser Ala
        115

<210> SEQ ID NO 51
<211> LENGTH: 348
<212> TYPE: DNA
<213> ORGANISM: Artificial Sequence
<220> FEATURE:
<223> OTHER INFORMATION: synthetic

<400> SEQUENCE: 51
gatgtacagc ttcaggagtc aggacctggc ctcgtgaatc cttctcagtc tctgtctctc     60
acctgctctg tcactggcta ctccatcacc agtggttatt actggatctg gatccagcag    120
tctccaggaa acaaactgga atggatgggc tacataaagt acgacggtgg caataactac    180 agccatctc tcaaaaatcg aatctccatc gctcgtgaca catctaagaa ccagtgtttc     240
ctgaagttga attctgtgac tattgaggac acagctcat attactgtac aagagggtcg     300
gactcctttg actactgggg ccaaggcacc actctcacag tctcctca                 348

<210> SEQ ID NO 52
<211> LENGTH: 116
<212> TYPE: PRT
<213> ORGANISM: Artificial Sequence
<220> FEATURE:
<223> OTHER INFORMATION: synthetic

<400> SEQUENCE: 52

Asp Val Gln Leu Gln Glu Ser Gly Pro Gly Leu Val Asn Pro Ser Gln
1               5                   10                  15
```

```
Ser Leu Ser Leu Thr Cys Ser Val Thr Gly Tyr Ser Ile Thr Ser Gly
            20                  25                  30

Tyr Tyr Trp Ile Trp Ile Gln Gln Ser Pro Gly Asn Lys Leu Glu Trp
        35                  40                  45

Met Gly Tyr Ile Lys Tyr Asp Gly Gly Asn Asn Tyr Ser Pro Ser Leu
    50                  55                  60

Lys Asn Arg Ile Ser Ile Ala Arg Asp Thr Ser Lys Asn Gln Cys Phe
65              70                  75                  80

Leu Lys Leu Asn Ser Val Thr Ile Glu Asp Thr Ala Thr Tyr Tyr Cys
                85                  90                  95

Thr Arg Gly Ser Asp Ser Phe Asp Tyr Trp Gly Gln Gly Thr Thr Leu
            100                 105                 110

Thr Val Ser Ser
        115

<210> SEQ ID NO 53
<211> LENGTH: 348
<212> TYPE: DNA
<213> ORGANISM: Artificial Sequence
<220> FEATURE:
<223> OTHER INFORMATION: synthetic

<400> SEQUENCE: 53
gatgtacagc ttcaggagtc aggacctggc ctcgtgaatc cttctcagtc tctgtctctc     60
acctgctctg tcactggcta ctccatcacc agtggttatt actggatctg gatccggcag    120
tttccaggaa acaaactgga atggatgggc tacataaagt acgacggtgg caataactac    180
agcccatctc tcaaaaatcg aatctccatc gctcgtgaca catctaagaa ccagttttc    240 ctgaagttga attctgtgac tattgaggac acagctacat attactgtac aagagggtcg    300
gactcctttg actactgggg ccaaggcacc actctcacag tctcctca                 348

<210> SEQ ID NO 54
<211> LENGTH: 116
<212> TYPE: PRT
<213> ORGANISM: Artificial Sequence
<220> FEATURE:
<223> OTHER INFORMATION: synthetic

<400> SEQUENCE: 54

Asp Val Gln Leu Gln Glu Ser Gly Pro Gly Leu Val Asn Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Ile Trp Ile Arg Gln Phe Pro Gly Asn Lys Leu Glu Trp
        35                  40                  45

Met Gly Tyr Ile Lys Tyr Asp Gly Gly Asn Asn Tyr Ser Pro Ser Leu
    50                  55                  60

Lys Asn Arg Ile Ser Ile Ala Arg Asp Thr Ser Lys Asn Gln Phe Phe
65              70                  75                  80

Leu Lys Leu Asn Ser Val Thr Ile Glu Asp Thr Ala Thr Tyr Tyr Cys
                85                  90                  95

Thr Arg Gly Ser Asp Ser Phe Asp Tyr Trp Gly Gln Gly Thr Thr Leu
            100                 105                 110

Thr Val Ser Ser
        115

<210> SEQ ID NO 55
```

<211> LENGTH: 333
<212> TYPE: DNA
<213> ORGANISM: Artificial Sequence
<220> FEATURE:
<223> OTHER INFORMATION: synthetic

<400> SEQUENCE: 55

```
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttcctggaa acaaactgga gtggatgggc tacataagct acagtggtac cactgtctac     180
agcccatctc tcaaaagtcg aatctccatc actcgggaca catccaaaaa ccagttcttc     240
ctgcaattga attctgtgac tattgaggac tcagccacgt attattgtgg gggtaattac     300
tggggccaag ggactctggt cactgtctct gca                                  333
```

<210> SEQ ID NO 56
<211> LENGTH: 111
<212> TYPE: PRT
<213> ORGANISM: Artificial Sequence
<220> FEATURE:
<223> OTHER INFORMATION: synthetic

<400> SEQUENCE: 56

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Ser Ala Thr Tyr Tyr Cys
                85                  90                  95

Gly Gly Asn Tyr Trp Gly Gln Gly Thr Leu Val Thr Val Ser Ala
            100                 105                 110
```

<210> SEQ ID NO 57
<211> LENGTH: 366
<212> TYPE: DNA
<213> ORGANISM: Artificial Sequence
<220> FEATURE:
<223> OTHER INFORMATION: synthetic

<400> SEQUENCE: 57

```
caggtgcagc tggaggagtc aggacctggc ctggtggcgc cctcacagag cctgtccatc      60
acttgcactg tctctggatt ttcattaacc agctatggtg tacactgggt tcgccagcct     120
ccaggaaagg gtctggagtg gctgggagta atatgggctt tggaagtat aaattataat      180
tcggctctca tgtccagact gagcatcagc aaagacaact ccaagagcca gttttctta      240
aaaatgaaca gtctacgaac tgatgacaca gccatgtact actgtgccag agatcggact     300
acggctaccc ccttctttga ctactggggc caaggcacca ctctcacagt ctcctcatcc     360
aaaaca                                                                366
```

<210> SEQ ID NO 58
<211> LENGTH: 119
<212> TYPE: PRT

```
<213> ORGANISM: Artificial Sequence
<220> FEATURE:
<223> OTHER INFORMATION: synthetic

<400> SEQUENCE: 58

Gln Val Gln Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Val Gly Ser Ile Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Asp Thr Ala Met Tyr Tyr Cys Ala
                85                  90                  95

Arg Asp Arg Thr Thr Ala Thr Pro Phe Phe Asp Tyr Trp Gly Gln Gly
            100                 105                 110

Thr Thr Leu Thr Val Ser Ser
        115

<210> SEQ ID NO 59
<211> LENGTH: 351
<212> TYPE: DNA
<213> ORGANISM: Artificial Sequence
<220> FEATURE:
<223> OTHER INFORMATION: synthetic

<400> SEQUENCE: 59
caggtgcagc tgaagcagtc aggacctggc ctagtgcagc cctcacagag cctgtccatc      60
acctgcacag tctctggttt ctcattaatt acccatggtg tacactgggt tcgccagtct     120
ccaggaaagg gtctggagtg gctgggagtg atatggagtg gtggaagcac agactataat     180
gcagctttca tatccagact gagcatcagc aaggacacct ccaagagcca agttttcctt     240
aaaatgagca gtctgcaagc tgatgacaca gccatatact actgtgccag aaatgggggg     300
gctacggcct ttgactactg gggccaaggc accactctca cagtctcctc a              351

<210> SEQ ID NO 60
<211> LENGTH: 117
<212> TYPE: PRT
<213> ORGANISM: Artificial Sequence
<220> FEATURE:
<223> OTHER INFORMATION: synthetic

<400> SEQUENCE: 60

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Thr His
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Thr Ser Lys Ser Gln Val Phe Leu
65                  70                  75                  80

Lys Met Ser Ser Leu Gln Ala Asp Asp Thr Ala Ile Tyr Tyr Cys Ala
                85                  90                  95
```

Arg Asn Gly Gly Ala Thr Ala Phe Asp Tyr Trp Gly Gln Gly Thr Thr
            100                 105                 110

Leu Thr Val Ser Ser
        115

<210> SEQ ID NO 61
<211> LENGTH: 351
<212> TYPE: DNA
<213> ORGANISM: Artificial Sequence
<220> FEATURE:
<223> OTHER INFORMATION: synthetic

<400> SEQUENCE: 61
caggtacagc tgaagcagtc aggacctggc ctagtgcagc cctcacagag cctgtccatc    60
acctgcacag tctctggttt ctcattaatt acctatggtg tacactgggt tcgccagtct   120
ccaggaaagg gtctggagtg gctgggagtg atatggggtg gtggaagcac aggctataat   180
gcagctttcg tatccagact gaacatcacc aaggacaact ccaagagcca agttttcttt   240
aaaatgaaca gtctgcaacc tgatgacaca gccatatact actgtgccag aaatggaggg   300
gctacggtct tgactactgg ggccaaggc accactctca cagtctcctc a             351

<210> SEQ ID NO 62
<211> LENGTH: 117
<212> TYPE: PRT
<213> ORGANISM: Artificial Sequence
<220> FEATURE:
<223> OTHER INFORMATION: synthetic

<400> SEQUENCE: 62

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Thr Tyr
            20                  25                  30

Gly Val His Trp Val Arg Gln Ser Pro Gly Lys Gly Leu Glu Trp Leu
        35                  40                  45

Gly Val Ile Trp Gly Gly Gly Ser Thr Gly Tyr Asn Ala Ala Phe Val
    50                  55                  60

Ser Arg Leu Asn Ile Thr Lys Asp Asn Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Arg Asn Gly Gly Ala Thr Val Phe Asp Tyr Trp Gly Gln Gly Thr Thr
            100                 105                 110

Leu Thr Val Ser Ser
        115

<210> SEQ ID NO 63
<211> LENGTH: 351
<212> TYPE: DNA
<213> ORGANISM: Artificial Sequence
<220> FEATURE:
<223> OTHER INFORMATION: synthetic

<400> SEQUENCE: 63
gaggtgcagc tggtggagtc tgggggagac ttagtgaagc ctggagggtc cctgaaactc    60
tcctgtgcag cctctggatt cactttcagt aactatggca tgtcttgggt tcgccagact   120
ccagacaaga ggctggagtg gtcgcaacc attagtagtg gtggtagtta tagctactat   180

```
ccagacagtg taaaggggcg gttcaccatc tccagagaca atgccaagaa catcctgtac        240
ctgcaaatga gcagtctgaa gtctgaggac acagccatgt attactgtgc aagtctctac        300
tacggctacg gggactactg gggccaaggc accgctttca cagtctcctc a                 351
```

<210> SEQ ID NO 64
<211> LENGTH: 117
<212> TYPE: PRT
<213> ORGANISM: Artificial Sequence
<220> FEATURE:
<223> OTHER INFORMATION: synthetic

<400> SEQUENCE: 64

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Ser Tyr Tyr Pro Asp Ser Val
    50                  55                  60

Lys Gly Arg Phe Thr Ile Ser Arg Asp Asn Ala Lys Asn Ile Leu Tyr
65                  70                  75                  80

Leu Gln Met Ser Ser Leu Lys Ser Glu Asp Thr Ala Met Tyr Tyr Cys
                85                  90                  95

Ala Ser Leu Tyr Tyr Gly Tyr Gly Asp Tyr Trp Gly Gln Gly Thr Ala
            100                 105                 110

Phe Thr Val Ser Ser
        115
```

<210> SEQ ID NO 65
<211> LENGTH: 360
<212> TYPE: DNA
<213> ORGANISM: Artificial Sequence
<220> FEATURE:
<223> OTHER INFORMATION: synthetic

<400> SEQUENCE: 65

```
gaagtgcagc tggtggagtc tgggggaggc ttggtgaagc ctggagggtc cctgaaactc        60
tcctgtgcag cctctggatt cactttcagt gactctttata tgtattgggt tcgccagact       120
ccggaccaga ggctggagtg gtcgcaacc attagtgatg gtggtagtta caccttctat        180
ccagacagtg tgaagggacg attcaccatc tccagagaca atgcccagaa caacctgtac        240
ctgcaaatga gcagtctgaa gtctgaggac acagccatgt attactgtgc atccccccat        300
gctggctact cggctggttt tgcttactgg ggccgaggga ctctggtcac tgtctctgca        360
```

<210> SEQ ID NO 66
<211> LENGTH: 120
<212> TYPE: PRT
<213> ORGANISM: Artificial Sequence
<220> FEATURE:
<223> OTHER INFORMATION: synthetic

<400> SEQUENCE: 66

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Ser
            20                  25                  30

Tyr Met Tyr Trp Val Arg Gln Thr Pro Asp Gln Arg Leu Glu Trp Val
```

```
                    35                  40                  45
Ala Thr Ile Ser Asp Gly Gly Ser Tyr Thr Phe Tyr Pro Asp Ser Val
        50                  55                  60
Lys Gly Arg Phe Thr Ile Ser Arg Asp Asn Ala Gln Asn Asn Leu Tyr
65                  70                  75                  80
Leu Gln Met Ser Ser Leu Lys Ser Glu Asp Thr Ala Met Tyr Tyr Cys
                85                  90                  95
Ala Ser Pro His Ala Gly Tyr Phe Gly Trp Phe Ala Tyr Trp Gly Arg
                100                 105                 110
Gly Thr Leu Val Thr Val Ser Ala
            115                 120

<210> SEQ ID NO 67
<211> LENGTH: 351
<212> TYPE: DNA
<213> ORGANISM: Artificial Sequence
<220> FEATURE:
<223> OTHER INFORMATION: synthetic

<400> SEQUENCE: 67
gaggtgcagc tggtggagtc tgggggagac ttagtgaagc ctggagggtc cctgaaactc    60
tcctgtgcag cctctggatt cactttcaat cactatggca tgtcttgggt tcgccagcct   120
ccagacaaga gactggagtg ggtcgcaacc attagtagtg gtggtggtta cacctactat   180
ccagacagtg tgaaggggcg cttcaccatc tccagagaca atgccaagga caccctgtcc   240
ctgcaaatga gcagtctgag gtctggggac acagccgtgt attactgtgc aagcctatac   300
ggtagcctgt ttgcttactg gggccaaggg actctggtca ctgtctctgc a             351

<210> SEQ ID NO 68
<211> LENGTH: 117
<212> TYPE: PRT
<213> ORGANISM: Artificial Sequence
<220> FEATURE:
<223> OTHER INFORMATION: synthetic

<400> SEQUENCE: 68

Glu Val Gln Leu Val Glu Ser Gly Gly Asp Leu Val Lys Pro Gly Gly
1               5                   10                  15
Ser Leu Lys Leu Ser Cys Ala Ala Ser Gly Phe Thr Phe Asn His Tyr
            20                  25                  30
Gly Met Ser Trp Val Arg Gln Pro Pro Asp Lys Arg Leu Glu Trp Val
        35                  40                  45
Ala Thr Ile Ser Ser Gly Gly Gly Tyr Thr Tyr Tyr Pro Asp Ser Val
        50                  55                  60
Lys Gly Arg Phe Thr Ile Ser Arg Asp Asn Ala Lys Asp Thr Leu Ser
65                  70                  75                  80
Leu Gln Met Ser Ser Leu Arg Ser Gly Asp Thr Ala Val Tyr Tyr Cys
                85                  90                  95
Ala Ser Leu Tyr Gly Ser Leu Phe Ala Tyr Trp Gly Gln Gly Thr Leu
                100                 105                 110
Val Thr Val Ser Ala
        115

<210> SEQ ID NO 69
<211> LENGTH: 366
<212> TYPE: DNA
<213> ORGANISM: Artificial Sequence
<220> FEATURE:
```

<223> OTHER INFORMATION: synthetic

<400> SEQUENCE: 69

```
gacgtgaagc tcgtggagtc tgggggaggc ttagtgaagc ttggagggtc cctgaaactc    60
tcctgtgcag cctctggatt cactttcagt agctattaca tgtcttgggt tcgccagact   120
ccagagaaga ggctggagtt ggtcgcagcc attaatagta atggtggtag cacctactat   180
ccagacactg tgaagggccg attcaccatc tccagacaca tgccaagaa caccctgtac    240
ctgcaaatga gcagtctgaa gtctgaggac acagccttgt attactgtgc aagacatggg   300
ggactgggac gtagggactg gtacttcgat gtctggggcg cagggaccac ggtcaccgtc   360
tcctca                                                              366
```

<210> SEQ ID NO 70
<211> LENGTH: 122
<212> TYPE: PRT
<213> ORGANISM: Artificial Sequence
<220> FEATURE:
<223> OTHER INFORMATION: synthetic

<400> SEQUENCE: 70

```
Asp Val Lys Leu Val Glu Ser Gly Gly Gly Leu Val Lys Leu Gly Gly
1               5                   10                  15
Ser Leu Lys Leu Ser Cys Ala Ala Ser Gly Phe Thr Phe Ser Ser Tyr
            20                  25                  30
Tyr Met Ser Trp Val Arg Gln Thr Pro Glu Lys Arg Leu Glu Leu Val
        35                  40                  45
Ala Ala Ile Asn Ser Asn Gly Gly Ser Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Leu Tyr Tyr Cys
                85                  90                  95
Ala Arg His Gly Gly Leu Gly Arg Arg Asp Trp Tyr Phe Asp Val Trp
            100                 105                 110
Gly Ala Gly Thr Thr Val Thr Val Ser Ser
        115                 120
```

<210> SEQ ID NO 71
<211> LENGTH: 360
<212> TYPE: DNA
<213> ORGANISM: Artificial Sequence
<220> FEATURE:
<223> OTHER INFORMATION: synthetic

<400> SEQUENCE: 71

```
gaagtgaaac tggtggagtc tgggggaagt ttagtgcagc ctggagggtc cctgaaactc    60
tcctgcgcag cctctggatt caatttcaat acctatgcca tgtcttgggt tcgccagact   120
ccagagaaga ggctggagtg ggtcgcatac attagtaatg gtggtggtaa cacctactat   180
gtagacactg taaagggccg attcaccatc tccagagaca tgccaagaa caccctgtac    240
ctgcgaatga gcagtctgaa gtctgaggac acggccatgt attactgtgc aagacatggg   300
ctctactggg gctattctat ggactactgg ggtcaaggaa cctcagtcac cgtctcctca   360
```

<210> SEQ ID NO 72
<211> LENGTH: 120
<212> TYPE: PRT
<213> ORGANISM: Artificial Sequence
<220> FEATURE:
<223> OTHER INFORMATION: synthetic

<400> SEQUENCE: 72

Glu Val Lys Leu Val Glu Ser Gly Gly Ser Leu Val Gln Pro Gly Gly
1               5                   10                  15

Ser Leu Lys Leu Ser Cys Ala Ala Ser Gly Phe Asn Phe Asn Thr Tyr
            20                  25                  30

Ala Met Ser Trp Val Arg Gln Thr Pro Glu Lys Arg Leu Glu Trp Val
        35                  40                  45

Ala Tyr Ile Ser Asn Gly Gly Asn Thr Tyr Tyr Val Asp Thr Val
    50                  55                  60

Lys Gly Arg Phe Thr Ile Ser Arg Asp Asn Ala Lys Asn Thr Leu Tyr
65                  70                  75                  80

Leu Arg Met Ser Ser Leu Lys Ser Glu Asp Thr Ala Met Tyr Tyr Cys
                85                  90                  95

Ala Arg His Gly Leu Tyr Trp Gly Tyr Ser Met Asp Tyr Trp Gly Gln
            100                 105                 110

Gly Thr Ser Val Thr Val Ser Ser
        115                 120

<210> SEQ ID NO 73
<211> LENGTH: 357
<212> TYPE: DNA
<213> ORGANISM: Artificial Sequence
<220> FEATURE:
<223> OTHER INFORMATION: synthetic

<400> SEQUENCE: 73
gaagtgaagc tggtggagtc tgggggaggt ttagtgcagc caggagggtc cctgaaactc      60
tcctgtgcag cctctggatt cactttcagt agctatgcca tgtcttgggt tcgccagact     120
ccagagagga ggctggagtg ggtcacatac attagtaatg gtggtggtag cacctactat     180
tcagacactg taaagggccg attcaccttc tccagagaca atgccaagaa cacCCtgtac     240
ctgcaaatga gcagtctgaa gtctgaggac acggccatgt attactgtgc aagacatgga     300
ctgggaagga cagggtttgc ttcctggggc caagggactc tggtcactgt ctctgca       357

<210> SEQ ID NO 74
<211> LENGTH: 119
<212> TYPE: PRT
<213> ORGANISM: Artificial Sequence
<220> FEATURE:
<223> OTHER INFORMATION: synthetic

<400> SEQUENCE: 74

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Arg Arg Leu Glu Trp Val
        35                  40                  45

Thr Tyr Ile Ser Asn Gly Gly Gly Ser Thr Tyr Tyr Ser Asp Thr Val
    50                  55                  60

Lys Gly Arg Phe Thr Phe Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Leu Gly Arg Thr Gly Phe Ala Ser Trp Gly Gln Gly
            100                 105                 110

Thr Leu Val Thr Val Ser Ala
        115

<210> SEQ ID NO 75
<211> LENGTH: 363
<212> TYPE: DNA
<213> ORGANISM: Artificial Sequence
<220> FEATURE:
<223> OTHER INFORMATION: synthetic

<400> SEQUENCE: 75
gatgtgcagc tggtggagtc tgggggaggc ctagtgcagg ctggagggtc ccggaaactc      60
tcctgtgcag cctctggatt ccctttcagt tcctttggaa tgcactgggt tcgtcaggct     120
ccagagaagg ggctggagtg ggtcgcctcc attagtagtc gcactagtaa gatctactat     180
gcagacaacc tgaagggccg attcaccatc tccagagaca atcccaagaa caccctgttc     240
ctgcaaatga ccagtcttgg atctgaggac acggccatgt attactgtgt aagatccgtc     300
tttggtaatt cttactggtt tttcgatgtc tggggcgcag ggaccacggt caccgtctcc     360
tca                                                                  363

<210> SEQ ID NO 76
<211> LENGTH: 121
<212> TYPE: PRT
<213> ORGANISM: Artificial Sequence
<220> FEATURE:
<223> OTHER INFORMATION: synthetic

<400> SEQUENCE: 76

Asp Val Gln Leu Val Glu Ser Gly Gly Gly Leu Val Gln Ala Gly Gly
1               5                   10                  15

Ser Arg Lys Leu Ser Cys Ala Ala Ser Gly Phe Pro Phe Ser Ser Phe
            20                  25                  30

Gly Met His Trp Val Arg Gln Ala Pro Glu Lys Gly Leu Glu Trp Val
        35                  40                  45

Ala Ser Ile Ser Ser Arg Thr Ser Lys Ile Tyr Tyr Ala Asp Asn Leu
    50                  55                  60

Lys Gly Arg Phe Thr Ile Ser Arg Asp Asn Pro Lys Asn Thr Leu Phe
65                  70                  75                  80

Leu Gln Met Thr Ser Leu Gly Ser Glu Asp Thr Ala Met Tyr Tyr Cys
                85                  90                  95

Val Arg Ser Val Phe Gly Asn Ser Tyr Trp Phe Phe Asp Val Trp Gly
            100                 105                 110

Ala Gly Thr Thr Val Thr Val Ser Ser
        115                 120

<210> SEQ ID NO 77
<211> LENGTH: 345
<212> TYPE: DNA
<213> ORGANISM: Artificial Sequence
<220> FEATURE:
<223> OTHER INFORMATION: synthetic

<400> SEQUENCE: 77
gaagtgaagc ttgaggagtc tgaggaggc ttggtacaac ctgggggatc catgaaactc       60
tcctgtgtag cctctggatt tctttcagt agctactgga tgtcttgggt ccgccagtct     120
ccagagaagg ggcttgactg ggttgctgaa attagattga gatctgataa ttatgcaacc     180

```
cattatgcgg agtctgtgaa agggaggttc accatctcaa gagatgattc cataagtcgt    240
ctctacctgc aaatgaacac cttaagagct gaagacactg gaatttatta ctgtacatgg    300
atgacgtact ggggccaagg gactctggtc actgtctctg caaca                    345
```

<210> SEQ ID NO 78
<211> LENGTH: 114
<212> TYPE: PRT
<213> ORGANISM: Artificial Sequence
<220> FEATURE:
<223> OTHER INFORMATION: synthetic

<400> SEQUENCE: 78

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ser Phe Ser Ser Tyr
            20                  25                  30

Trp Met Ser Trp Val Arg Gln Ser Pro Glu Lys Gly Leu Asp Trp Val
        35                  40                  45

Ala Glu Ile Arg Leu Arg Ser Asp Asn Tyr Ala Thr His Tyr Ala Glu
    50                  55                  60

Ser Val Lys Gly Arg Phe Thr Ile Ser Arg Asp Asp Ser Ile Ser Arg
65                  70                  75                  80

Leu Tyr Leu Gln Met Asn Thr Leu Arg Ala Glu Asp Thr Gly Ile Tyr
                85                  90                  95

Tyr Cys Thr Trp Met Thr Tyr Trp Gly Gln Gly Thr Leu Val Thr Val
                100                 105                 110

Ser Ala

<210> SEQ ID NO 79
<211> LENGTH: 366
<212> TYPE: DNA
<213> ORGANISM: Artificial Sequence
<220> FEATURE:
<223> OTHER INFORMATION: synthetic

<400> SEQUENCE: 79

```
gaggtgaagc tggtggagtc tggaggaggc ttggtacagc ctgggggttc tctgagactc    60
tcctgtgcaa gttctgggtt caccttcact gattactaca tgagctgggt ccgccagcct    120
ccaggaaagg cacttgagtg gttgggtttt attagaaaca agcttatgg ttacacgacc     180 gagttcagtg catctgtgaa cggtcggttc accatctcca gagatgattc ccaaagcgtc    240
ccctatcttc aaatgaacac cctgagagct gaggacagtg ccacttatta ctgtgcgaga    300
gtcctctact atgattacgg gggatttgct tactggggcc aagggactct ggtcactgtc    360
tctaca                                                               366
```

<210> SEQ ID NO 80
<211> LENGTH: 122
<212> TYPE: PRT
<213> ORGANISM: Artificial Sequence
<220> FEATURE:
<223> OTHER INFORMATION: synthetic

<400> SEQUENCE: 80

Glu Val Lys Leu Val Glu Ser Gly Gly Gly Leu Val Gln Pro Gly Gly
1               5                   10                  15

Ser Leu Arg Leu Ser Cys Ala Ser Ser Gly Phe Thr Phe Thr Asp Tyr
            20                  25                  30

```
Tyr Met Ser Trp Val Arg Gln Pro Pro Gly Lys Ala Leu Glu Trp Leu
            35                  40                  45

Gly Phe Ile Arg Asn Lys Ala Tyr Gly Tyr Thr Thr Glu Phe Ser Ala
        50                  55                  60

Ser Val Asn Gly Arg Phe Thr Ile Ser Arg Asp Asp Ser Gln Ser Val
65                  70                  75                  80

Pro Tyr Leu Gln Met Asn Thr Leu Arg Ala Glu Asp Ser Ala Thr Tyr
                85                  90                  95

Tyr Cys Ala Arg Val Leu Tyr Tyr Asp Tyr Gly Gly Phe Ala Tyr Trp
                100                 105                 110

Gly Gln Gly Thr Leu Val Thr Val Ser Thr
            115                 120
```

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81

```
gaggtccagc tgcagcagtc tggacctgag ctggtaaagc ctggggcttc agtgaagatg      60
tcctgtaagg cttccggata cagattcact agctatgtta tgcactgggt gaggcagaag    120
cctggacagg gccttgagtg gattggatat attgatcctc acaatgatga tacaaaatac    180
agtgagaagt tcagaggtaa ggccacactg acttcagaca gtcctccaca cacagcctac    240
atggagctca gcagcctgac ctctgaggac tctgcggtct attactgtgt gagatattct    300
tacgacaggg attacagtcc tatggactac tggggtcaag gaacctcagt caccgtctcc    360
tca                                                                  363
```

<210> SEQ ID NO 82
<211> LENGTH: 121
<212> TYPE: PRT
<213> ORGANISM: Artificial Sequence
<220> FEATURE:
<223> OTHER INFORMATION: synthetic

<400> SEQUENCE: 82

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Thr Ser Tyr
            20                  25                  30

Val Met His Trp Val Arg Gln Lys Pro Gly Gln Gly Leu Glu Trp Ile
            35                  40                  45

Gly Tyr Ile Asp Pro His Asn Asp Asp Thr Lys Tyr Ser Glu Lys Phe
        50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Val Arg Tyr Ser Tyr Asp Arg Asp Tyr Ser Pro Met Asp Tyr Trp Gly
                100                 105                 110

Gln Gly Thr Ser Val Thr Val Ser Ser
            115                 120
```

<210> SEQ ID NO 83

<211> LENGTH: 345
<212> TYPE: DNA
<213> ORGANISM: Artificial Sequence
<220> FEATURE:
<223> OTHER INFORMATION: synthetic

<400> SEQUENCE: 83

```
cagctgcaac agtctggacc tgagctggtg aagcctgggg cttcagtgaa aatttcctgc      60
aagacttctg gatacacatt cactgaaaac gccatgcact gggtgaagca gagccgtgga     120
aagagccttg agtggattgg aggtgttaat cctaacaatg gtgatactgt ctacacccag     180
aagttcaagg gcaaggccac attgactgta gccaagtctt ccagcacagc ctacatggag     240
ctccgcacca tgacatgtga ggaatctaca gtgattact gtgcaagccg ggaaccggac      300
ttctttgact actggggcca aggctcctct gtcacagtct cctca                     345
```

<210> SEQ ID NO 84
<211> LENGTH: 115
<212> TYPE: PRT
<213> ORGANISM: Artificial Sequence
<220> FEATURE:
<223> OTHER INFORMATION: synthetic

<400> SEQUENCE: 84

```
Gln Leu Gln Gln Ser Gly Pro Glu Leu Val Lys Pro Gly Ala Ser Val
1               5                   10                  15
Lys Ile Ser Cys Lys Thr Ser Gly Tyr Thr Phe Thr Glu Asn Ala Met
            20                  25                  30
His Trp Val Lys Gln Ser Arg Gly Lys Ser Leu Glu Trp Ile Gly Gly
        35                  40                  45
Val Asn Pro Asn Asn Gly Asp Thr Val Tyr Thr Gln Lys Phe Lys Gly
    50                  55                  60
Lys Ala Thr Leu Thr Val Ala Lys Ser Ser Ser Thr Ala Tyr Met Glu
65                  70                  75                  80
Leu Arg Thr Met Thr Cys Glu Glu Ser Thr Val Tyr Tyr Cys Ala Ser
                85                  90                  95
Arg Glu Pro Asp Phe Phe Asp Tyr Trp Gly Gln Gly Ser Ser Val Thr
            100                 105                 110
Val Ser Ser
        115
```

<210> SEQ ID NO 85
<211> LENGTH: 345
<212> TYPE: DNA
<213> ORGANISM: Artificial Sequence
<220> FEATURE:
<223> OTHER INFORMATION: synthetic

<400> SEQUENCE: 85

```
cagctgcaac agtctggacc tgtactggtg aagcctgggg cttcagtgaa aatttcctgc      60
aagacttctg gatacacatt cactgaaaac gccatgcact gggtgaagca gagccatgga    120
aagagccttg agtggattgg aggtgttaat cctaacaatg gtgatactat ctacaaccag    180
aagttcaagg gcaaggccac attgactgta gacaagtcct ccagcacagc cttcatggag    240
ctccgcagcc tgacatctga agaatcccca gtctatttct gtgtaagacg ggaactggac    300
ttctttgact actggggcca aggcacctct gtcacagtct cctca                    345
```

<210> SEQ ID NO 86
<211> LENGTH: 115

<212> TYPE: PRT
<213> ORGANISM: Artificial Sequence
<220> FEATURE:
<223> OTHER INFORMATION: synthetic

<400> SEQUENCE: 86

Gln Leu Gln Gln Ser Gly Pro Val Leu Val Lys Pro Gly Ala Ser Val
1               5                   10                  15

Lys Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Tyr Asn Gln Lys Phe Lys Gly
    50                  55                  60

Lys Ala Thr Leu Thr Val Asp Lys Ser Ser Thr Ala Phe Met Glu
65                  70                  75                  80

Leu Arg Ser Leu Thr Ser Glu Glu Ser Pro Val Tyr Phe Cys Val Arg
                85                  90                  95

Arg Glu Leu Asp Phe Phe Asp Tyr Trp Gly Gln Gly Thr Ser Val Thr
            100                 105                 110

Val Ser Ser
        115

<210> SEQ ID NO 87
<211> LENGTH: 345
<212> TYPE: DNA
<213> ORGANISM: Artificial Sequence
<220> FEATURE:
<223> OTHER INFORMATION: synthetic

<400> SEQUENCE: 87
cagctgcaac agtctggccc tgtcctggtg aagtctggga cttcagttaa aatttcctgc      60
aagacttctg gatacacatt cactgaaaac gccatgcact gggtgaaaca gagccatgga    120
cagagccttg agtggattgg aggtgttaat cctaacaatg gtgatactat cttcaaccag    180
aagttcaagg gcaaggccac attgactgta gacaagtcct ccagcacagc cttcatggag    240
ctccgcagcc tgacatctga gaatccaca gtctattact gtgtaagacg ggaactggac    300
ttctttgact actggggtca aggcacctct gtcacagtct cctca                    345

<210> SEQ ID NO 88
<211> LENGTH: 115
<212> TYPE: PRT
<213> ORGANISM: Artificial Sequence
<220> FEATURE:
<223> OTHER INFORMATION: synthetic

<400> SEQUENCE: 88

Gln Leu Gln Gln Ser Gly Pro Val Leu Val Lys Ser Gly Thr Ser Val
1               5                   10                  15

Lys Ile Ser Cys Lys Thr Ser Gly Tyr Thr Phe Thr Glu Asn Ala Met
            20                  25                  30

His Trp Val Lys Gln Ser His Gly Gln Ser Leu Glu Trp Ile Gly Gly
        35                  40                  45

Val Asn Pro Asn Asn Gly Asp Thr Ile Phe Asn Gln Lys Phe Lys Gly
    50                  55                  60

Lys Ala Thr Leu Thr Val Asp Lys Ser Ser Thr Ala Phe Met Glu
65                  70                  75                  80

Leu Arg Ser Leu Thr Ser Glu Glu Ser Thr Val Tyr Tyr Cys Val Arg

```
                    85                  90                  95

Arg Glu Leu Asp Phe Phe Asp Tyr Trp Gly Gln Gly Thr Ser Val Thr
                100                 105                 110

Val Ser Ser
        115

<210> SEQ ID NO 89
<211> LENGTH: 345
<212> TYPE: DNA
<213> ORGANISM: Artificial Sequence
<220> FEATURE:
<223> OTHER INFORMATION: synthetic

<400> SEQUENCE: 89
cagctgcaac agtctggccc tgtcctggtg aagcctggga cttcagtgaa aatttcctgc     60
aagacttctg gatacacatt cactgaaaac gccatgcact gggtgaaaca gagccatgga    120
aagagccttg agtggattgg aggtgttaat cctaacaatg gtgatactat cttcaaccag    180
aagttcaagg gcaaggccac attgactgta gacaagtcct ccagcacagc cttcatggag    240
ctccgcagcc tgacatctga gaatccacag tctattact gtgtaagacg ggaactggac     300
ttctttgact actggggcca aggcacctct gtcacagtct cctca                    345

<210> SEQ ID NO 90
<211> LENGTH: 115
<212> TYPE: PRT
<213> ORGANISM: Artificial Sequence
<220> FEATURE:
<223> OTHER INFORMATION: synthetic

<400> SEQUENCE: 90

Gln Leu Gln Gln Ser Gly Pro Val Leu Val Lys Pro Gly Thr Ser Val
1               5                   10                  15

Lys Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
    50                  55                  60

Lys Ala Thr Leu Thr Val Asp Lys Ser Ser Ser Thr Ala Phe Met Glu
65                  70                  75                  80

Leu Arg Ser Leu Thr Ser Glu Glu Ser Thr Val Tyr Tyr Cys Val Arg
                85                  90                  95

Arg Glu Leu Asp Phe Phe Asp Tyr Trp Gly Gln Gly Thr Ser Val Thr
                100                 105                 110

Val Ser Ser
        115

<210> SEQ ID NO 91
<211> LENGTH: 345
<212> TYPE: DNA
<213> ORGANISM: Artificial Sequence
<220> FEATURE:
<223> OTHER INFORMATION: synthetic

<400> SEQUENCE: 91
cagctgcaac agtctggacc tgcccaggtg aagcctgggg cttcagtgat gatttcctgc     60
aagacttctg gatacacatt cactgaaaac gccatgcact gggtgaaaca gagccatgga    120
aagagccttg agtggattgg aggtgttaat cctaacaatg gtgatactat tttcaaccag    180
```

```
aagttcaagg acaaggccgc attgactgta gacaagtcct ccagcacagc cttcatggag      240
ctccgcagcc tgacatctga ggagtccaca gtctattact gtgtaagacg ggaattggac      300
ttctttgact actggggcca aggcacctct gtcacagtct cctca                     345
```

<210> SEQ ID NO 92
<211> LENGTH: 115
<212> TYPE: PRT
<213> ORGANISM: Artificial Sequence
<220> FEATURE:
<223> OTHER INFORMATION: synthetic

<400> SEQUENCE: 92

```
Gln Leu Gln Gln Ser Gly Pro Ala Gln Val Lys Pro Gly Ala Ser Val
1               5                   10                  15

Met Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Phe Asn Gln Lys Phe Lys Asp
    50                  55                  60

Lys Ala Ala Leu Thr Val Asp Lys Ser Ser Thr Ala Phe Met Glu
65                  70                  75                  80

Leu Arg Ser Leu Thr Ser Glu Glu Ser Thr Val Tyr Tyr Cys Val Arg
                85                  90                  95

Arg Glu Leu Asp Phe Phe Asp Tyr Trp Gly Gln Gly Thr Ser Val Thr
            100                 105                 110

Val Ser Ser
        115
```

<210> SEQ ID NO 93
<211> LENGTH: 345
<212> TYPE: DNA
<213> ORGANISM: Artificial Sequence
<220> FEATURE:
<223> OTHER INFORMATION: synthetic

<400> SEQUENCE: 93

```
cagctgcaac agtctggacc tgtcctggtg aagcctgggg cttcagtgat gatttcctgc      60
aagacttctg gatacacatt cactgaaaac gccatgcact gggtgaaaca gagccatgga      120
aagagccttg agtggattgg aggtgttaat cctaacaatg gtgatactat tttcaaccag      180
aagttcaagg caaggccac attgactgta gacaagtcct ccaacacagc cttcacggag       240
ctccgcagcc tgccatctga gaatccaca gtctattact gtgttagacg gggattggac       300
ttctttgact actggggcca aggcacctct gtcacagtct cctca                     345
```

<210> SEQ ID NO 94
<211> LENGTH: 115
<212> TYPE: PRT
<213> ORGANISM: Artificial Sequence
<220> FEATURE:
<223> OTHER INFORMATION: synthetic

<400> SEQUENCE: 94

```
Gln Leu Gln Gln Ser Gly Pro Val Leu Val Lys Pro Gly Ala Ser Val
1               5                   10                  15

Met Ile Ser Cys Lys Thr Ser Gly Tyr Thr Phe Thr Glu Asn Ala Met
            20                  25                  30
```

His Trp Val Lys Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
 50                  55                  60

Lys Ala Thr Leu Thr Val Asp Lys Ser Ser Asn Thr Ala Phe Thr Glu
 65                  70                  75                  80

Leu Arg Ser Leu Pro Ser Glu Glu Ser Thr Val Tyr Tyr Cys Val Arg
                 85                  90                  95

Arg Gly Leu Asp Phe Phe Asp Tyr Trp Gly Gln Gly Thr Ser Val Thr
                100                 105                 110

Val Ser Ser
        115

<210> SEQ ID NO 95
<211> LENGTH: 345
<212> TYPE: DNA
<213> ORGANISM: Artificial Sequence
<220> FEATURE:
<223> OTHER INFORMATION: synthetic

<400> SEQUENCE: 95
cagctgcaac agtctggccc tgtcctggtg gggcctgggg cttcagtgat gatttcctgc      60
aagacttctg gatacacatt cactgaaaac gccatgcact gggtggaaca gagccatgga    120
aagagccttg agtggattgg aggtgttaat cctaacaatg gtgatactat tttcaaccag    180
aagttcaagg gcaaggccac attgactgta gacaagtcct ccagcacagc cttcatggag    240
ttccgcagcc tgacatctga gaatccacag tctattact gtgtaagacg ggaattggac    300
ttctttgact actggggcca aggcacctct gtcacagtct cctca                    345

<210> SEQ ID NO 96
<211> LENGTH: 115
<212> TYPE: PRT
<213> ORGANISM: Artificial Sequence
<220> FEATURE:
<223> OTHER INFORMATION: synthetic

<400> SEQUENCE: 96

Gln Leu Gln Gln Ser Gly Pro Val Leu Val Gly Pro Gly Ala Ser Val
 1               5                  10                  15

Met Ile Ser Cys Lys Thr Ser Gly Tyr Thr Phe Thr Glu Asn Ala Met
             20                  25                  30

His Trp Val Glu Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
 50                  55                  60

Lys Ala Thr Leu Thr Val Asp Lys Ser Ser Ser Thr Ala Phe Met Glu
 65                  70                  75                  80

Phe Arg Ser Leu Thr Ser Glu Glu Ser Thr Val Tyr Tyr Cys Val Arg
                 85                  90                  95

Arg Glu Leu Asp Phe Phe Asp Tyr Trp Gly Gln Gly Thr Ser Val Thr
                100                 105                 110

Val Ser Ser
        115

<210> SEQ ID NO 97
<211> LENGTH: 348
<212> TYPE: DNA
<213> ORGANISM: Artificial Sequence
<220> FEATURE:
<223> OTHER INFORMATION: synthetic

<400> SEQUENCE: 97

```
cagctgcaac agtctggacc tgtcctggtg aagcctgggg cttcagtgat gatttcctgc      60
aagacttctg gatacacatt cactgaaaac gccatgcact gggtgaaaca gagccatgga     120
aagagccttg agtggattgg aggtgttaat cctaacaatg gtgatactat tttcaaccag     180
aagttcaagg gcaaggccac attgactgta gacaagtcct ccagcacagc cttcatggag     240
ttccgcagcc tgacatctga agaatccaca gtctattact gtgtaagacg ggaattggac     300
ttctttgact actggggcca aggcacctct gtcacagtct cctcaaca                  348
```

<210> SEQ ID NO 98
<211> LENGTH: 115
<212> TYPE: PRT
<213> ORGANISM: Artificial Sequence
<220> FEATURE:
<223> OTHER INFORMATION: synthetic

<400> SEQUENCE: 98

```
Gln Leu Gln Gln Ser Gly Pro Val Leu Val Lys Pro Gly Ala Ser Val
1               5                   10                  15
Met Ile Ser Cys Lys Thr Ser Gly Tyr Thr Phe Thr Glu Asn Ala Met
            20                  25                  30
His Trp Val Lys Gln Ser His Gly Lys Ser Leu Glu Trp Ile Gly Gly
        35                  40                  45
Val Asn Pro Asn Asn Gly Asp Thr Ile Phe Asn Gln Lys Phe Lys Gly
    50                  55                  60
Lys Ala Thr Leu Thr Val Asp Lys Ser Ser Ser Thr Ala Phe Met Glu
65                  70                  75                  80
Phe Arg Ser Leu Thr Ser Glu Glu Ser Thr Val Tyr Tyr Cys Val Arg
                85                  90                  95
Arg Glu Leu Asp Phe Phe Asp Tyr Trp Gly Gln Gly Thr Ser Val Thr
            100                 105                 110
Val Ser Ser
        115
```

<210> SEQ ID NO 99
<211> LENGTH: 345
<212> TYPE: DNA
<213> ORGANISM: Artificial Sequence
<220> FEATURE:
<223> OTHER INFORMATION: synthetic

<400> SEQUENCE: 99

```
cagctgcaac agtctggacc tgtcctggtg aagcctgggg cttcagtgat gatttcctgc      60
aagacttctg gatacacatt cactgaaaac gccatgcact gggtgaaaca gagccatgga     120
aagagccttg agtggattgg aggtgttaat cctaacaatg gtgatactat tttcaaccag     180
aagttcaagg gcaaggccac attgactgta gacaagtcct ccagcacagc cttcatggag     240
ctccgcagcc tgacatctga agaatccaca gtctattact gtgtaagacg ggaattggac     300
ttctttgact actggggcca aggcacctct gtcacagtct cctca                     345
```

<210> SEQ ID NO 100
<211> LENGTH: 115
<212> TYPE: PRT
<213> ORGANISM: Artificial Sequence
<220> FEATURE:

<223> OTHER INFORMATION: synthetic

<400> SEQUENCE: 100

Gln Leu Gln Gln Ser Gly Pro Val Leu Val Lys Pro Gly Ala Ser Val
1               5                   10                  15
Met Ile Ser Cys Lys Thr Ser Gly Tyr Thr Phe Thr Glu Asn Ala Met
            20                  25                  30
His Trp Val Lys Gln Ser His Gly Lys Ser Leu Glu Trp Ile Gly Gly
        35                  40                  45
Val Asn Pro Asn Asn Gly Asp Thr Ile Phe Asn Gln Lys Phe Lys Gly
    50                  55                  60
Lys Ala Thr Leu Thr Val Asp Lys Ser Ser Thr Ala Phe Met Glu
65                  70                  75                  80
Leu Arg Ser Leu Thr Ser Glu Glu Ser Thr Val Tyr Tyr Cys Val Arg
                85                  90                  95
Arg Glu Leu Asp Phe Phe Asp Tyr Trp Gly Gln Gly Thr Ser Val Thr
            100                 105                 110
Val Ser Ser
        115

<210> SEQ ID NO 101
<211> LENGTH: 15
<212> TYPE: DNA
<213> ORGANISM: Artificial Sequence
<220> FEATURE:
<223> OTHER INFORMATION: synthetic

<400> SEQUENCE: 101
gaatacgcca tgcac                                                    15

<210> SEQ ID NO 102
<211> LENGTH: 5
<212> TYPE: PRT
<213> ORGANISM: Artificial Sequence
<220> FEATURE:
<223> OTHER INFORMATION: synthetic

<400> SEQUENCE: 102

Glu Tyr Ala Met His
1               5

<210> SEQ ID NO 103
<211> LENGTH: 15
<212> TYPE: DNA
<213> ORGANISM: Artificial Sequence
<220> FEATURE:
<223> OTHER INFORMATION: synthetic

<400> SEQUENCE: 103
gaatacgcca tacac                                                    15

<210> SEQ ID NO 104
<211> LENGTH: 5
<212> TYPE: PRT
<213> ORGANISM: Artificial Sequence
<220> FEATURE:
<223> OTHER INFORMATION: synthetic

<400> SEQUENCE: 104

Glu Tyr Ala Ile His
1               5

-continued

```
<210> SEQ ID NO 105
<211> LENGTH: 15
<212> TYPE: DNA
<213> ORGANISM: Artificial Sequence
<220> FEATURE:
<223> OTHER INFORMATION: synthetic

<400> SEQUENCE: 105
agtagttata taagt                                                    15

<210> SEQ ID NO 106
<211> LENGTH: 5
<212> TYPE: PRT
<213> ORGANISM: Artificial Sequence
<220> FEATURE:
<223> OTHER INFORMATION: synthetic

<400> SEQUENCE: 106

Ser Ser Tyr Ile Ser
1               5

<210> SEQ ID NO 107
<211> LENGTH: 15
<212> TYPE: DNA
<213> ORGANISM: Artificial Sequence
<220> FEATURE:
<223> OTHER INFORMATION: synthetic

<400> SEQUENCE: 107
agtagtttta taagt                                                    15

<210> SEQ ID NO 108
<211> LENGTH: 5
<212> TYPE: PRT
<213> ORGANISM: Artificial Sequence
<220> FEATURE:
<223> OTHER INFORMATION: synthetic

<400> SEQUENCE: 108

Ser Ser Phe Ile Ser
1               5

<210> SEQ ID NO 109
<211> LENGTH: 15
<212> TYPE: DNA
<213> ORGANISM: Artificial Sequence
<220> FEATURE:
<223> OTHER INFORMATION: synthetic

<400> SEQUENCE: 109
agtagttatt ttagt                                                    15

<210> SEQ ID NO 110
<211> LENGTH: 5
<212> TYPE: PRT
<213> ORGANISM: Artificial Sequence
<220> FEATURE:
<223> OTHER INFORMATION: synthetic

<400> SEQUENCE: 110

Ser Ser Tyr Phe Ser
1               5

<210> SEQ ID NO 111
<211> LENGTH: 18
<212> TYPE: DNA
<213> ORGANISM: Artificial Sequence
```

<220> FEATURE:
<223> OTHER INFORMATION: synthetic

<400> SEQUENCE: 111
agcagtacct atataagt                                                   18

<210> SEQ ID NO 112
<211> LENGTH: 5
<212> TYPE: PRT
<213> ORGANISM: Artificial Sequence
<220> FEATURE:
<223> OTHER INFORMATION: synthetic

<400> SEQUENCE: 112

Ser Thr Tyr Ile Ser
1               5

<210> SEQ ID NO 113
<211> LENGTH: 15
<212> TYPE: DNA
<213> ORGANISM: Artificial Sequence
<220> FEATURE:
<223> OTHER INFORMATION: synthetic

<400> SEQUENCE: 113
agctactgga tacac                                                      15

<210> SEQ ID NO 114
<211> LENGTH: 5
<212> TYPE: PRT
<213> ORGANISM: Artificial Sequence
<220> FEATURE:
<223> OTHER INFORMATION: synthetic

<400> SEQUENCE: 114

Ser Tyr Trp Ile His
1               5

<210> SEQ ID NO 115
<211> LENGTH: 15
<212> TYPE: DNA
<213> ORGANISM: Artificial Sequence
<220> FEATURE:
<223> OTHER INFORMATION: synthetic

<400> SEQUENCE: 115
agctattgga tgcac                                                      15

<210> SEQ ID NO 116
<211> LENGTH: 5
<212> TYPE: PRT
<213> ORGANISM: Artificial Sequence
<220> FEATURE:
<223> OTHER INFORMATION: synthetic

<400> SEQUENCE: 116

Ser Tyr Trp Met His
1               5

<210> SEQ ID NO 117
<211> LENGTH: 14
<212> TYPE: DNA
<213> ORGANISM: Artificial Sequence
<220> FEATURE:
<223> OTHER INFORMATION: synthetic

<400> SEQUENCE: 117

```
cctactcgat aaac                                                    14
```

<210> SEQ ID NO 118
<211> LENGTH: 5
<212> TYPE: PRT
<213> ORGANISM: Artificial Sequence
<220> FEATURE:
<223> OTHER INFORMATION: synthetic

<400> SEQUENCE: 118

```
Thr Tyr Ser Ile Asn
1               5
```

<210> SEQ ID NO 119
<211> LENGTH: 15
<212> TYPE: DNA
<213> ORGANISM: Artificial Sequence
<220> FEATURE:
<223> OTHER INFORMATION: synthetic

<400> SEQUENCE: 119

```
gccaacaaga tgcac                                                   15
```

<210> SEQ ID NO 120
<211> LENGTH: 5
<212> TYPE: PRT
<213> ORGANISM: Artificial Sequence
<220> FEATURE:
<223> OTHER INFORMATION: synthetic

<400> SEQUENCE: 120

```
Ala Asn Lys Met His
1               5
```

<210> SEQ ID NO 121
<211> LENGTH: 15
<212> TYPE: DNA
<213> ORGANISM: Artificial Sequence
<220> FEATURE:
<223> OTHER INFORMATION: synthetic

<400> SEQUENCE: 121

```
agcaacaaga tgcac                                                   15
```

<210> SEQ ID NO 122
<211> LENGTH: 5
<212> TYPE: PRT
<213> ORGANISM: Artificial Sequence
<220> FEATURE:
<223> OTHER INFORMATION: synthetic

<400> SEQUENCE: 122

```
Ser Asn Lys Met His
1               5
```

<210> SEQ ID NO 123
<211> LENGTH: 15
<212> TYPE: DNA
<213> ORGANISM: Artificial Sequence
<220> FEATURE:
<223> OTHER INFORMATION: synthetic

<400> SEQUENCE: 123

```
agctactatg tacac                                                   15
```

```
<210> SEQ ID NO 124
<211> LENGTH: 5
<212> TYPE: PRT
<213> ORGANISM: Artificial Sequence
<220> FEATURE:
<223> OTHER INFORMATION: synthetic

<400> SEQUENCE: 124

Ser Tyr Tyr Val His
1               5

<210> SEQ ID NO 125
<211> LENGTH: 18
<212> TYPE: DNA
<213> ORGANISM: Artificial Sequence
<220> FEATURE:
<223> OTHER INFORMATION: synthetic

<400> SEQUENCE: 125
agtggttatt actggatc                                                 18

<210> SEQ ID NO 126
<211> LENGTH: 6
<212> TYPE: PRT
<213> ORGANISM: Artificial Sequence
<220> FEATURE:
<223> OTHER INFORMATION: synthetic

<400> SEQUENCE: 126

Ser Gly Tyr Tyr Trp Ile
1               5

<210> SEQ ID NO 127
<211> LENGTH: 18
<212> TYPE: DNA
<213> ORGANISM: Artificial Sequence
<220> FEATURE:
<223> OTHER INFORMATION: synthetic

<400> SEQUENCE: 127
agtgattatg cctggaac                                                 18

<210> SEQ ID NO 128
<211> LENGTH: 6
<212> TYPE: PRT
<213> ORGANISM: Artificial Sequence
<220> FEATURE:
<223> OTHER INFORMATION: synthetic

<400> SEQUENCE: 128

Ser Asp Tyr Ala Trp Asn
1               5

<210> SEQ ID NO 129
<211> LENGTH: 15
<212> TYPE: DNA
<213> ORGANISM: Artificial Sequence
<220> FEATURE:
<223> OTHER INFORMATION: synthetic

<400> SEQUENCE: 129
agctatggtg tacac                                                    15

<210> SEQ ID NO 130
<211> LENGTH: 5
<212> TYPE: PRT
<213> ORGANISM: Artificial Sequence
```

```
<220> FEATURE:
<223> OTHER INFORMATION: synthetic

<400> SEQUENCE: 130

Ser Tyr Gly Val His
1               5

<210> SEQ ID NO 131
<211> LENGTH: 15
<212> TYPE: DNA
<213> ORGANISM: Artificial Sequence
<220> FEATURE:
<223> OTHER INFORMATION: synthetic

<400> SEQUENCE: 131
acccatggtg tacac                                            15

<210> SEQ ID NO 132
<211> LENGTH: 5
<212> TYPE: PRT
<213> ORGANISM: Artificial Sequence
<220> FEATURE:
<223> OTHER INFORMATION: synthetic

<400> SEQUENCE: 132

Thr His Gly Val His
1               5

<210> SEQ ID NO 133
<211> LENGTH: 15
<212> TYPE: DNA
<213> ORGANISM: Artificial Sequence
<220> FEATURE:
<223> OTHER INFORMATION: synthetic

<400> SEQUENCE: 133
acctatggtg tacac                                            15

<210> SEQ ID NO 134
<211> LENGTH: 5
<212> TYPE: PRT
<213> ORGANISM: Artificial Sequence
<220> FEATURE:
<223> OTHER INFORMATION: synthetic

<400> SEQUENCE: 134

Thr Tyr Gly Val His
1               5

<210> SEQ ID NO 135
<211> LENGTH: 15
<212> TYPE: DNA
<213> ORGANISM: Artificial Sequence
<220> FEATURE:
<223> OTHER INFORMATION: synthetic

<400> SEQUENCE: 135
aactatggca tgtct                                            15

<210> SEQ ID NO 136
<211> LENGTH: 5
<212> TYPE: PRT
<213> ORGANISM: Artificial Sequence
<220> FEATURE:
<223> OTHER INFORMATION: synthetic

<400> SEQUENCE: 136
```

```
Asn Tyr Gly Met Ser
1               5

<210> SEQ ID NO 137
<211> LENGTH: 15
<212> TYPE: DNA
<213> ORGANISM: Artificial Sequence
<220> FEATURE:
<223> OTHER INFORMATION: synthetic

<400> SEQUENCE: 137
gactcttata tgtat                                                    15

<210> SEQ ID NO 138
<211> LENGTH: 5
<212> TYPE: PRT
<213> ORGANISM: Artificial Sequence
<220> FEATURE:
<223> OTHER INFORMATION: synthetic

<400> SEQUENCE: 138

Asp Ser Tyr Met Tyr
1               5

<210> SEQ ID NO 139
<211> LENGTH: 15
<212> TYPE: DNA
<213> ORGANISM: Artificial Sequence
<220> FEATURE:
<223> OTHER INFORMATION: synthetic

<400> SEQUENCE: 139
cactatggca tgtct                                                    15

<210> SEQ ID NO 140
<211> LENGTH: 5
<212> TYPE: PRT
<213> ORGANISM: Artificial Sequence
<220> FEATURE:
<223> OTHER INFORMATION: synthetic

<400> SEQUENCE: 140

His Tyr Gly Met Ser
1               5

<210> SEQ ID NO 141
<211> LENGTH: 15
<212> TYPE: DNA
<213> ORGANISM: Artificial Sequence
<220> FEATURE:
<223> OTHER INFORMATION: synthetic

<400> SEQUENCE: 141
agctattaca tgtct                                                    15

<210> SEQ ID NO 142
<211> LENGTH: 5
<212> TYPE: PRT
<213> ORGANISM: Artificial Sequence
<220> FEATURE:
<223> OTHER INFORMATION: synthetic

<400> SEQUENCE: 142

Ser Tyr Tyr Met Ser
1               5
```

<210> SEQ ID NO 143
<211> LENGTH: 15
<212> TYPE: DNA
<213> ORGANISM: Artificial Sequence
<220> FEATURE:
<223> OTHER INFORMATION: synthetic

<400> SEQUENCE: 143
acctatgcca tgtct                                                        15

<210> SEQ ID NO 144
<211> LENGTH: 5
<212> TYPE: PRT
<213> ORGANISM: Artificial Sequence
<220> FEATURE:
<223> OTHER INFORMATION: synthetic

<400> SEQUENCE: 144

Thr Tyr Ala Met Ser
1               5

<210> SEQ ID NO 145
<211> LENGTH: 15
<212> TYPE: DNA
<213> ORGANISM: Artificial Sequence
<220> FEATURE:
<223> OTHER INFORMATION: synthetic

<400> SEQUENCE: 145
agctatgcca tgtct                                                        15

<210> SEQ ID NO 146
<211> LENGTH: 5
<212> TYPE: PRT
<213> ORGANISM: Artificial Sequence
<220> FEATURE:
<223> OTHER INFORMATION: synthetic

<400> SEQUENCE: 146

Ser Tyr Ala Met Ser
1               5

<210> SEQ ID NO 147
<211> LENGTH: 15
<212> TYPE: DNA
<213> ORGANISM: Artificial Sequence
<220> FEATURE:
<223> OTHER INFORMATION: synthetic

<400> SEQUENCE: 147
tcctttggaa tgcac                                                        15

<210> SEQ ID NO 148
<211> LENGTH: 5
<212> TYPE: PRT
<213> ORGANISM: Artificial Sequence
<220> FEATURE:
<223> OTHER INFORMATION: synthetic

<400> SEQUENCE: 148

Ser Phe Gly Met His
1               5

<210> SEQ ID NO 149
<211> LENGTH: 15
<212> TYPE: DNA

```
<213> ORGANISM: Artificial Sequence
<220> FEATURE:
<223> OTHER INFORMATION: synthetic

<400> SEQUENCE: 149
agctactgga tgtct                                                    15

<210> SEQ ID NO 150
<211> LENGTH: 5
<212> TYPE: PRT
<213> ORGANISM: Artificial Sequence
<220> FEATURE:
<223> OTHER INFORMATION: synthetic

<400> SEQUENCE: 150

Ser Tyr Trp Met Ser
1               5

<210> SEQ ID NO 151
<211> LENGTH: 15
<212> TYPE: DNA
<213> ORGANISM: Artificial Sequence
<220> FEATURE:
<223> OTHER INFORMATION: synthetic

<400> SEQUENCE: 151
gattactaca tgagc                                                    15

<210> SEQ ID NO 152
<211> LENGTH: 5
<212> TYPE: PRT
<213> ORGANISM: Artificial Sequence
<220> FEATURE:
<223> OTHER INFORMATION: synthetic

<400> SEQUENCE: 152

Asp Tyr Tyr Met Ser
1               5

<210> SEQ ID NO 153
<211> LENGTH: 15
<212> TYPE: DNA
<213> ORGANISM: Artificial Sequence
<220> FEATURE:
<223> OTHER INFORMATION: synthetic

<400> SEQUENCE: 153
agctatgtta tgcac                                                    15

<210> SEQ ID NO 154
<211> LENGTH: 5
<212> TYPE: PRT
<213> ORGANISM: Artificial Sequence
<220> FEATURE:
<223> OTHER INFORMATION: synthetic

<400> SEQUENCE: 154

Ser Tyr Val Met His
1               5

<210> SEQ ID NO 155
<211> LENGTH: 15
<212> TYPE: DNA
<213> ORGANISM: Artificial Sequence
<220> FEATURE:
<223> OTHER INFORMATION: synthetic
```

<400> SEQUENCE: 155
gaaaacgcca tgcac                                                                            15

<210> SEQ ID NO 156
<211> LENGTH: 5
<212> TYPE: PRT
<213> ORGANISM: Artificial Sequence
<220> FEATURE:
<223> OTHER INFORMATION: synthetic

<400> SEQUENCE: 156

Glu Asn Ala Met His
1               5

<210> SEQ ID NO 157
<211> LENGTH: 51
<212> TYPE: DNA
<213> ORGANISM: Artificial Sequence
<220> FEATURE:
<223> OTHER INFORMATION: synthetic

<400> SEQUENCE: 157
ggtatcaatc ctactaatgg tgatacaatc tacaaccaga agttcaagga c            51

<210> SEQ ID NO 158
<211> LENGTH: 17
<212> TYPE: PRT
<213> ORGANISM: Artificial Sequence
<220> FEATURE:
<223> OTHER INFORMATION: synthetic

<400> SEQUENCE: 158

Gly Ile Asn Pro Thr Asn Gly Asp Thr Ile Tyr Asn Gln Lys Phe Lys
1               5                   10                  15

Asp

<210> SEQ ID NO 159
<211> LENGTH: 51
<212> TYPE: DNA
<213> ORGANISM: Artificial Sequence
<220> FEATURE:
<223> OTHER INFORMATION: synthetic

<400> SEQUENCE: 159
ggtatcaatc ctactaatgg tgatacaatc tacaaccaga ggttcaagga c            51

<210> SEQ ID NO 160
<211> LENGTH: 17
<212> TYPE: PRT
<213> ORGANISM: Artificial Sequence
<220> FEATURE:
<223> OTHER INFORMATION: synthetic

<400> SEQUENCE: 160

Gly Ile Asn Pro Thr Asn Gly Asp Thr Ile Tyr Asn Gln Arg Phe Lys
1               5                   10                  15

Asp

<210> SEQ ID NO 161
<211> LENGTH: 51
<212> TYPE: DNA
<213> ORGANISM: Artificial Sequence
<220> FEATURE:
<223> OTHER INFORMATION: synthetic

<400> SEQUENCE: 161
ggtattaatc ctaacaatgg caatgctatc tacaaccaga tattcaagga c               51

<210> SEQ ID NO 162
<211> LENGTH: 17
<212> TYPE: PRT
<213> ORGANISM: Artificial Sequence
<220> FEATURE:
<223> OTHER INFORMATION: synthetic

<400> SEQUENCE: 162

Gly Ile Asn Pro Asn Asn Gly Asn Ala Ile Tyr Asn Gln Ile Phe Lys
1               5                   10                  15
Asp

<210> SEQ ID NO 163
<211> LENGTH: 51
<212> TYPE: DNA
<213> ORGANISM: Artificial Sequence
<220> FEATURE:
<223> OTHER INFORMATION: synthetic

<400> SEQUENCE: 163
ggtattaatc ctagcaatgg caatgctatc tacaaccaaa tattcaagga c               51

<210> SEQ ID NO 164
<211> LENGTH: 17
<212> TYPE: PRT
<213> ORGANISM: Artificial Sequence
<220> FEATURE:
<223> OTHER INFORMATION: synthetic

<400> SEQUENCE: 164

Gly Ile Asn Pro Ser Asn Gly Asn Ala Ile Tyr Asn Gln Ile Phe Lys
1               5                   10                  15
Asp

<210> SEQ ID NO 165
<211> LENGTH: 51
<212> TYPE: DNA
<213> ORGANISM: Artificial Sequence
<220> FEATURE:
<223> OTHER INFORMATION: synthetic

<400> SEQUENCE: 165
ggtattaatc ctagcaatgg cgatcctatc tataaccaga tattcaagga c               51

<210> SEQ ID NO 166
<211> LENGTH: 17
<212> TYPE: PRT
<213> ORGANISM: Artificial Sequence
<220> FEATURE:
<223> OTHER INFORMATION: synthetic

<400> SEQUENCE: 166

Gly Ile Asn Pro Ser Asn Gly Asp Pro Ile Tyr Asn Gln Ile Phe Lys
1               5                   10                  15
Asp

<210> SEQ ID NO 167
<211> LENGTH: 51
<212> TYPE: DNA
<213> ORGANISM: Artificial Sequence
<220> FEATURE:

<223> OTHER INFORMATION: synthetic

<400> SEQUENCE: 167
tggatttatg ctggaactgg taatactaac tataatcaga agttcacaga c    51

<210> SEQ ID NO 168
<211> LENGTH: 17
<212> TYPE: PRT
<213> ORGANISM: Artificial Sequence
<220> FEATURE:
<223> OTHER INFORMATION: synthetic

<400> SEQUENCE: 168

Trp Ile Tyr Ala Gly Thr Gly Asn Thr Asn Tyr Asn Gln Lys Phe Thr
1               5                   10                  15
Asp

<210> SEQ ID NO 169
<211> LENGTH: 51
<212> TYPE: DNA
<213> ORGANISM: Artificial Sequence
<220> FEATURE:
<223> OTHER INFORMATION: synthetic

<400> SEQUENCE: 169
tggatttttg ctggaactgg taatactaat tataatcaga agttcacaga c    51

<210> SEQ ID NO 170
<211> LENGTH: 17
<212> TYPE: PRT
<213> ORGANISM: Artificial Sequence
<220> FEATURE:
<223> OTHER INFORMATION: synthetic

<400> SEQUENCE: 170

Trp Ile Phe Ala Gly Thr Gly Asn Thr Asn Tyr Asn Gln Lys Phe Thr
1               5                   10                  15
Asp

<210> SEQ ID NO 171
<211> LENGTH: 51
<212> TYPE: DNA
<213> ORGANISM: Artificial Sequence
<220> FEATURE:
<223> OTHER INFORMATION: synthetic

<400> SEQUENCE: 171
tggatttatg ctggaactgg taatactatc tataatcaga agttcacaga c    51

<210> SEQ ID NO 172
<211> LENGTH: 17
<212> TYPE: PRT
<213> ORGANISM: Artificial Sequence
<220> FEATURE:
<223> OTHER INFORMATION: synthetic

<400> SEQUENCE: 172

Trp Ile Tyr Ala Gly Thr Gly Asn Thr Ile Tyr Asn Gln Lys Phe Thr
1               5                   10                  15
Asp

<210> SEQ ID NO 173
<211> LENGTH: 51
<212> TYPE: DNA

<213> ORGANISM: Artificial Sequence
<220> FEATURE:
<223> OTHER INFORMATION: synthetic

<400> SEQUENCE: 173
tggatttatg ctggaactgg tggtactaac tataatcaga agttcacaga c       51

<210> SEQ ID NO 174
<211> LENGTH: 17
<212> TYPE: PRT
<213> ORGANISM: Artificial Sequence
<220> FEATURE:
<223> OTHER INFORMATION: synthetic

<400> SEQUENCE: 174

Trp Ile Tyr Ala Gly Thr Gly Gly Thr Asn Tyr Asn Gln Lys Phe Thr
1               5                   10                  15
Asp

<210> SEQ ID NO 175
<211> LENGTH: 51
<212> TYPE: DNA
<213> ORGANISM: Artificial Sequence
<220> FEATURE:
<223> OTHER INFORMATION: synthetic

<400> SEQUENCE: 175
tggatttatg ctggaactgg tgctactaat tataatcaga agttcacagg c       51

<210> SEQ ID NO 176
<211> LENGTH: 17
<212> TYPE: PRT
<213> ORGANISM: Artificial Sequence
<220> FEATURE:
<223> OTHER INFORMATION: synthetic

<400> SEQUENCE: 176

Trp Ile Tyr Ala Gly Thr Gly Ala Thr Asn Tyr Asn Gln Lys Phe Thr
1               5                   10                  15
Gly

<210> SEQ ID NO 177
<211> LENGTH: 51
<212> TYPE: DNA
<213> ORGANISM: Artificial Sequence
<220> FEATURE:
<223> OTHER INFORMATION: synthetic

<400> SEQUENCE: 177
gaaattgatc cttctgacag ttatattaac cagaatcaaa agttcagggg c       51

<210> SEQ ID NO 178
<211> LENGTH: 17
<212> TYPE: PRT
<213> ORGANISM: Artificial Sequence
<220> FEATURE:
<223> OTHER INFORMATION: synthetic

<400> SEQUENCE: 178

Glu Ile Asp Pro Ser Asp Ser Tyr Ile Asn Gln Asn Gln Lys Phe Arg
1               5                   10                  15
Gly

<210> SEQ ID NO 179

```
<211> LENGTH: 51
<212> TYPE: DNA
<213> ORGANISM: Artificial Sequence
<220> FEATURE:
<223> OTHER INFORMATION: synthetic

<400> SEQUENCE: 179
gaagttgatc cttctgacag ttatattaac cagaatgaaa agttcagggg c          51

<210> SEQ ID NO 180
<211> LENGTH: 17
<212> TYPE: PRT
<213> ORGANISM: Artificial Sequence
<220> FEATURE:
<223> OTHER INFORMATION: synthetic

<400> SEQUENCE: 180

Glu Val Asp Pro Ser Asp Ser Tyr Ile Asn Gln Asn Glu Lys Phe Arg
1               5                   10                  15

Gly

<210> SEQ ID NO 181
<211> LENGTH: 51
<212> TYPE: DNA
<213> ORGANISM: Artificial Sequence
<220> FEATURE:
<223> OTHER INFORMATION: synthetic

<400> SEQUENCE: 181
gagattgatc cttctgatag ttatactaac tacaatcaaa agttcaaggg c          51

<210> SEQ ID NO 182
<211> LENGTH: 17
<212> TYPE: PRT
<213> ORGANISM: Artificial Sequence
<220> FEATURE:
<223> OTHER INFORMATION: synthetic

<400> SEQUENCE: 182

Glu Ile Asp Pro Ser Asp Ser Tyr Thr Asn Tyr Asn Gln Lys Phe Lys
1               5                   10                  15

Gly

<210> SEQ ID NO 183
<211> LENGTH: 51
<212> TYPE: DNA
<213> ORGANISM: Artificial Sequence
<220> FEATURE:
<223> OTHER INFORMATION: synthetic

<400> SEQUENCE: 183
gagattcatc cttctgatag ttatactagc tacaatcaaa agttcaagga c          51

<210> SEQ ID NO 184
<211> LENGTH: 17
<212> TYPE: PRT
<213> ORGANISM: Artificial Sequence
<220> FEATURE:
<223> OTHER INFORMATION: synthetic

<400> SEQUENCE: 184

Glu Ile His Pro Ser Asp Ser Tyr Thr Ser Tyr Asn Gln Lys Phe Lys
1               5                   10                  15

Asp
```

```
<210> SEQ ID NO 185
<211> LENGTH: 51
<212> TYPE: DNA
<213> ORGANISM: Artificial Sequence
<220> FEATURE:
<223> OTHER INFORMATION: synthetic

<400> SEQUENCE: 185
aatatttatc cttctaccag tcatactaac tacaatcaaa agttcaggga c         51

<210> SEQ ID NO 186
<211> LENGTH: 17
<212> TYPE: PRT
<213> ORGANISM: Artificial Sequence
<220> FEATURE:
<223> OTHER INFORMATION: synthetic

<400> SEQUENCE: 186

Asn Ile Tyr Pro Ser Thr Ser His Thr Asn Tyr Asn Gln Lys Phe Arg
1               5                   10                  15
Asp

<210> SEQ ID NO 187
<211> LENGTH: 51
<212> TYPE: DNA
<213> ORGANISM: Artificial Sequence
<220> FEATURE:
<223> OTHER INFORMATION: synthetic

<400> SEQUENCE: 187
tacattgatc ctagctctgg ttatactgaa tacaatcata agatccagta c         51

<210> SEQ ID NO 188
<211> LENGTH: 17
<212> TYPE: PRT
<213> ORGANISM: Artificial Sequence
<220> FEATURE:
<223> OTHER INFORMATION: synthetic

<400> SEQUENCE: 188

Tyr Ile Asp Pro Ser Ser Gly Tyr Thr Glu Tyr Asn His Lys Ile Gln
1               5                   10                  15
Tyr

<210> SEQ ID NO 189
<211> LENGTH: 51
<212> TYPE: DNA
<213> ORGANISM: Artificial Sequence
<220> FEATURE:
<223> OTHER INFORMATION: synthetic

<400> SEQUENCE: 189
tacattgatc ctagctctgg ttatactgaa tacaatcata agatccagga c         51

<210> SEQ ID NO 190
<211> LENGTH: 17
<212> TYPE: PRT
<213> ORGANISM: Artificial Sequence
<220> FEATURE:
<223> OTHER INFORMATION: synthetic

<400> SEQUENCE: 190

Tyr Ile Asp Pro Ser Ser Gly Tyr Thr Glu Tyr Asn His Lys Ile Gln
1               5                   10                  15
```

Asp

<210> SEQ ID NO 191
<211> LENGTH: 51
<212> TYPE: DNA
<213> ORGANISM: Artificial Sequence
<220> FEATURE:
<223> OTHER INFORMATION: synthetic

<400> SEQUENCE: 191
tacattgatc ctagctctgg ttatactcaa tacaatcata agatccagga c    51

<210> SEQ ID NO 192
<211> LENGTH: 17
<212> TYPE: PRT
<213> ORGANISM: Artificial Sequence
<220> FEATURE:
<223> OTHER INFORMATION: synthetic

<400> SEQUENCE: 192

Tyr Ile Asp Pro Ser Ser Gly Tyr Thr Gln Tyr Asn His Lys Ile Gln
1               5                   10                  15
Asp

<210> SEQ ID NO 193
<211> LENGTH: 51
<212> TYPE: DNA
<213> ORGANISM: Artificial Sequence
<220> FEATURE:
<223> OTHER INFORMATION: synthetic

<400> SEQUENCE: 193
tacattgatc ctgcctctgg ctatactgaa tacaatcaga agatcaagga c    51

<210> SEQ ID NO 194
<211> LENGTH: 17
<212> TYPE: PRT
<213> ORGANISM: Artificial Sequence
<220> FEATURE:
<223> OTHER INFORMATION: synthetic

<400> SEQUENCE: 194

Tyr Ile Asp Pro Ala Ser Gly Tyr Thr Glu Tyr Asn Gln Lys Ile Lys
1               5                   10                  15
Asp

<210> SEQ ID NO 195
<211> LENGTH: 51
<212> TYPE: DNA
<213> ORGANISM: Artificial Sequence
<220> FEATURE:
<223> OTHER INFORMATION: synthetic

<400> SEQUENCE: 195
tacattgatc ctagctctgg ttatactgaa tacaatcaga agatcaagga c    51

<210> SEQ ID NO 196
<211> LENGTH: 17
<212> TYPE: PRT
<213> ORGANISM: Artificial Sequence
<220> FEATURE:
<223> OTHER INFORMATION: synthetic

<400> SEQUENCE: 196

Tyr Ile Asp Pro Ser Ser Gly Tyr Thr Glu Tyr Asn Gln Lys Ile Lys

Asp

<210> SEQ ID NO 197
<211> LENGTH: 51
<212> TYPE: DNA
<213> ORGANISM: Artificial Sequence
<220> FEATURE:
<223> OTHER INFORMATION: synthetic

<400> SEQUENCE: 197
tgtatttatc ctggagatgt taatactgac tataatgaga agttcaaggg c           51

<210> SEQ ID NO 198
<211> LENGTH: 17
<212> TYPE: PRT
<213> ORGANISM: Artificial Sequence
<220> FEATURE:
<223> OTHER INFORMATION: synthetic

<400> SEQUENCE: 198

Cys Ile Tyr Pro Gly Asp Val Asn Thr Asp Tyr Asn Glu Lys Phe Lys
1               5                   10                  15
Gly

<210> SEQ ID NO 199
<211> LENGTH: 48
<212> TYPE: DNA
<213> ORGANISM: Artificial Sequence
<220> FEATURE:
<223> OTHER INFORMATION: synthetic

<400> SEQUENCE: 199
tacataaagt acgacggtgg caataactac agcccatctc tcaaaaat              48

<210> SEQ ID NO 200
<211> LENGTH: 16
<212> TYPE: PRT
<213> ORGANISM: Artificial Sequence
<220> FEATURE:
<223> OTHER INFORMATION: synthetic

<400> SEQUENCE: 200

Tyr Ile Lys Tyr Asp Gly Gly Asn Asn Tyr Ser Pro Ser Leu Lys Asn
1               5                   10                  15

<210> SEQ ID NO 201
<211> LENGTH: 48
<212> TYPE: DNA
<213> ORGANISM: Artificial Sequence
<220> FEATURE:
<223> OTHER INFORMATION: synthetic

<400> SEQUENCE: 201
tacataagct acagtggtac cactgtctac agcccatctc tcaaaagt              48

<210> SEQ ID NO 202
<211> LENGTH: 16
<212> TYPE: PRT
<213> ORGANISM: Artificial Sequence
<220> FEATURE:
<223> OTHER INFORMATION: synthetic

<400> SEQUENCE: 202

Tyr Ile Ser Tyr Ser Gly Thr Thr Val Tyr Ser Pro Ser Leu Lys Ser

<210> SEQ ID NO 203
<211> LENGTH: 48
<212> TYPE: DNA
<213> ORGANISM: Artificial Sequence
<220> FEATURE:
<223> OTHER INFORMATION: synthetic

<400> SEQUENCE: 203
gtaatatggg ctgttggaag tataaattat aattcggctc tcatgtcc                48

<210> SEQ ID NO 204
<211> LENGTH: 16
<212> TYPE: PRT
<213> ORGANISM: Artificial Sequence
<220> FEATURE:
<223> OTHER INFORMATION: synthetic

<400> SEQUENCE: 204

Val Ile Trp Ala Val Gly Ser Ile Asn Tyr Asn Ser Ala Leu Met Ser
1               5                   10                  15

<210> SEQ ID NO 205
<211> LENGTH: 48
<212> TYPE: DNA
<213> ORGANISM: Artificial Sequence
<220> FEATURE:
<223> OTHER INFORMATION: synthetic

<400> SEQUENCE: 205
gtgatatgga gtggtggaag cacagactat aatgcagctt tcatatcc                48

<210> SEQ ID NO 206
<211> LENGTH: 16
<212> TYPE: PRT
<213> ORGANISM: Artificial Sequence
<220> FEATURE:
<223> OTHER INFORMATION: synthetic

<400> SEQUENCE: 206

Val Ile Trp Ser Gly Gly Ser Thr Asp Tyr Asn Ala Ala Phe Ile Ser
1               5                   10                  15

<210> SEQ ID NO 207
<211> LENGTH: 48
<212> TYPE: DNA
<213> ORGANISM: Artificial Sequence
<220> FEATURE:
<223> OTHER INFORMATION: synthetic

<400> SEQUENCE: 207
gtgatatggg gtggtggaag cacaggctat aatgcagctt tcgtatcc                48

<210> SEQ ID NO 208
<211> LENGTH: 16
<212> TYPE: PRT
<213> ORGANISM: Artificial Sequence
<220> FEATURE:
<223> OTHER INFORMATION: synthetic

<400> SEQUENCE: 208

Val Ile Trp Gly Gly Gly Ser Thr Gly Tyr Asn Ala Ala Phe Val Ser
1               5                   10                  15

<210> SEQ ID NO 209

```
<211> LENGTH: 51
<212> TYPE: DNA
<213> ORGANISM: Artificial Sequence
<220> FEATURE:
<223> OTHER INFORMATION: synthetic

<400> SEQUENCE: 209
accattagta gtggtggtag ttatagctac tatccagaca gtgtaaaggg g          51

<210> SEQ ID NO 210
<211> LENGTH: 17
<212> TYPE: PRT
<213> ORGANISM: Artificial Sequence
<220> FEATURE:
<223> OTHER INFORMATION: synthetic

<400> SEQUENCE: 210

Thr Ile Ser Ser Gly Gly Ser Tyr Ser Tyr Tyr Pro Asp Ser Val Lys
 1               5                  10                  15

Gly

<210> SEQ ID NO 211
<211> LENGTH: 51
<212> TYPE: DNA
<213> ORGANISM: Artificial Sequence
<220> FEATURE:
<223> OTHER INFORMATION: synthetic

<400> SEQUENCE: 211
accattagtg atggtggtag ttacaccttc tatccagaca gtgtgaaggg a          51

<210> SEQ ID NO 212
<211> LENGTH: 17
<212> TYPE: PRT
<213> ORGANISM: Artificial Sequence
<220> FEATURE:
<223> OTHER INFORMATION: synthetic

<400> SEQUENCE: 212

Thr Ile Ser Asp Gly Gly Ser Tyr Thr Phe Tyr Pro Asp Ser Val Lys
 1               5                  10                  15

Gly

<210> SEQ ID NO 213
<211> LENGTH: 51
<212> TYPE: DNA
<213> ORGANISM: Artificial Sequence
<220> FEATURE:
<223> OTHER INFORMATION: synthetic

<400> SEQUENCE: 213
accattagta gtggtggtgg ttacacctac tatccagaca gtgtgaaggg g          51

<210> SEQ ID NO 214
<211> LENGTH: 17
<212> TYPE: PRT
<213> ORGANISM: Artificial Sequence
<220> FEATURE:
<223> OTHER INFORMATION: synthetic

<400> SEQUENCE: 214

Thr Ile Ser Ser Gly Gly Gly Tyr Thr Tyr Tyr Pro Asp Ser Val Lys
 1               5                  10                  15

Gly
```

<210> SEQ ID NO 215
<211> LENGTH: 51
<212> TYPE: DNA
<213> ORGANISM: Artificial Sequence
<220> FEATURE:
<223> OTHER INFORMATION: synthetic

<400> SEQUENCE: 215
gccattaata gtaatggtgg tagcacctac tatccagaca ctgtgaaggg c        51

<210> SEQ ID NO 216
<211> LENGTH: 17
<212> TYPE: PRT
<213> ORGANISM: Artificial Sequence
<220> FEATURE:
<223> OTHER INFORMATION: synthetic

<400> SEQUENCE: 216

Ala Ile Asn Ser Asn Gly Gly Ser Thr Tyr Tyr Pro Asp Thr Val Lys
1               5                   10                  15

Gly

<210> SEQ ID NO 217
<211> LENGTH: 51
<212> TYPE: DNA
<213> ORGANISM: Artificial Sequence
<220> FEATURE:
<223> OTHER INFORMATION: synthetic

<400> SEQUENCE: 217
tacattagta atggtggtgg taacacctac tatgtagaca ctgtaaaggg c        51

<210> SEQ ID NO 218
<211> LENGTH: 17
<212> TYPE: PRT
<213> ORGANISM: Artificial Sequence
<220> FEATURE:
<223> OTHER INFORMATION: synthetic

<400> SEQUENCE: 218

Tyr Ile Ser Asn Gly Gly Gly Asn Thr Tyr Tyr Val Asp Thr Val Lys
1               5                   10                  15

Gly

<210> SEQ ID NO 219
<211> LENGTH: 51
<212> TYPE: DNA
<213> ORGANISM: Artificial Sequence
<220> FEATURE:
<223> OTHER INFORMATION: synthetic

<400> SEQUENCE: 219
tacattagta atggtggtgg tagcacctac tattcagaca ctgtaaaggg c        51

<210> SEQ ID NO 220
<211> LENGTH: 17
<212> TYPE: PRT
<213> ORGANISM: Artificial Sequence
<220> FEATURE:
<223> OTHER INFORMATION: synthetic

<400> SEQUENCE: 220

Tyr Ile Ser Asn Gly Gly Gly Ser Thr Tyr Tyr Ser Asp Thr Val Lys
1               5                   10                  15

Gly

<210> SEQ ID NO 221
<211> LENGTH: 51
<212> TYPE: DNA
<213> ORGANISM: Artificial Sequence
<220> FEATURE:
<223> OTHER INFORMATION: synthetic

<400> SEQUENCE: 221
tccattagta gtcgcactag taagatctac tatgcagaca acctgaaggg c        51

<210> SEQ ID NO 222
<211> LENGTH: 17
<212> TYPE: PRT
<213> ORGANISM: Artificial Sequence
<220> FEATURE:
<223> OTHER INFORMATION: synthetic

<400> SEQUENCE: 222

Ser Ile Ser Ser Arg Thr Ser Lys Ile Tyr Tyr Ala Asp Asn Leu Lys
1               5                   10                  15
Gly

<210> SEQ ID NO 223
<211> LENGTH: 57
<212> TYPE: DNA
<213> ORGANISM: Artificial Sequence
<220> FEATURE:
<223> OTHER INFORMATION: synthetic

<400> SEQUENCE: 223
gaaattagat tgagatctga taattatgca acccattatg cggagtctgt gaaaggg        57

<210> SEQ ID NO 224
<211> LENGTH: 19
<212> TYPE: PRT
<213> ORGANISM: Artificial Sequence
<220> FEATURE:
<223> OTHER INFORMATION: synthetic

<400> SEQUENCE: 224

Glu Ile Arg Leu Arg Ser Asp Asn Tyr Ala Thr His Tyr Ala Glu Ser
1               5                   10                  15
Val Lys Gly

<210> SEQ ID NO 225
<211> LENGTH: 57
<212> TYPE: DNA
<213> ORGANISM: Artificial Sequence
<220> FEATURE:
<223> OTHER INFORMATION: synthetic

<400> SEQUENCE: 225
tttattagaa acaaagctta tggttacacg accgagttca gtgcatctgt gaacggt        57

<210> SEQ ID NO 226
<211> LENGTH: 19
<212> TYPE: PRT
<213> ORGANISM: Artificial Sequence
<220> FEATURE:
<223> OTHER INFORMATION: synthetic

<400> SEQUENCE: 226

Phe Ile Arg Asn Lys Ala Tyr Gly Tyr Thr Thr Glu Phe Ser Ala Ser

<210> SEQ ID NO 227
<211> LENGTH: 51
<212> TYPE: DNA
<213> ORGANISM: Artificial Sequence
<220> FEATURE:
<223> OTHER INFORMATION: synthetic

<400> SEQUENCE: 227
tatattgatc ctcacaatga tgatacaaaa tacagtgaga agttcagagg t    51

<210> SEQ ID NO 228
<211> LENGTH: 17
<212> TYPE: PRT
<213> ORGANISM: Artificial Sequence
<220> FEATURE:
<223> OTHER INFORMATION: synthetic

<400> SEQUENCE: 228

Tyr Ile Asp Pro His Asn Asp Asp Thr Lys Tyr Ser Glu Lys Phe Arg
1               5                   10                  15

Gly

<210> SEQ ID NO 229
<211> LENGTH: 51
<212> TYPE: DNA
<213> ORGANISM: Artificial Sequence
<220> FEATURE:
<223> OTHER INFORMATION: synthetic

<400> SEQUENCE: 229
ggtgttaatc ctaacaatgg tgatactgtc tacacccaga agttcaaggg c    51

<210> SEQ ID NO 230
<211> LENGTH: 17
<212> TYPE: PRT
<213> ORGANISM: Artificial Sequence
<220> FEATURE:
<223> OTHER INFORMATION: synthetic

<400> SEQUENCE: 230

Gly Val Asn Pro Asn Asn Gly Asp Thr Val Tyr Thr Gln Lys Phe Lys
1               5                   10                  15

Gly

<210> SEQ ID NO 231
<211> LENGTH: 51
<212> TYPE: DNA
<213> ORGANISM: Artificial Sequence
<220> FEATURE:
<223> OTHER INFORMATION: synthetic

<400> SEQUENCE: 231
ggtgttaatc ctaacaatgg tgatactatc tacaaccaga agttcaaggg c    51

<210> SEQ ID NO 232
<211> LENGTH: 17
<212> TYPE: PRT
<213> ORGANISM: Artificial Sequence
<220> FEATURE:
<223> OTHER INFORMATION: synthetic

<400> SEQUENCE: 232

Gly Val Asn Pro Asn Asn Gly Asp Thr Ile Tyr Asn Gln Lys Phe Lys
1               5                   10                  15

Gly

<210> SEQ ID NO 233
<211> LENGTH: 51
<212> TYPE: DNA
<213> ORGANISM: Artificial Sequence
<220> FEATURE:
<223> OTHER INFORMATION: synthetic

<400> SEQUENCE: 233
ggtgttaatc ctaacaatgg tgatactatc ttcaaccaga agttcaaggg c        51

<210> SEQ ID NO 234
<211> LENGTH: 17
<212> TYPE: PRT
<213> ORGANISM: Artificial Sequence
<220> FEATURE:
<223> OTHER INFORMATION: synthetic

<400> SEQUENCE: 234

Gly Val Asn Pro Asn Asn Gly Asp Thr Ile Phe Asn Gln Lys Phe Lys
1               5                   10                  15

Gly

<210> SEQ ID NO 235
<211> LENGTH: 51
<212> TYPE: DNA
<213> ORGANISM: Artificial Sequence
<220> FEATURE:
<223> OTHER INFORMATION: synthetic

<400> SEQUENCE: 235
ggtgttaatc ctaacaatgg tgatactatt ttcaaccaga agttcaagga c        51

<210> SEQ ID NO 236
<211> LENGTH: 17
<212> TYPE: PRT
<213> ORGANISM: Artificial Sequence
<220> FEATURE:
<223> OTHER INFORMATION: synthetic

<400> SEQUENCE: 236

Gly Val Asn Pro Asn Asn Gly Asp Thr Ile Phe Asn Gln Lys Phe Lys
1               5                   10                  15

Asp

<210> SEQ ID NO 237
<211> LENGTH: 24
<212> TYPE: DNA
<213> ORGANISM: Artificial Sequence
<220> FEATURE:
<223> OTHER INFORMATION: synthetic

<400> SEQUENCE: 237
cgggaactgg actactttgc ctcc                                      24

<210> SEQ ID NO 238
<211> LENGTH: 8
<212> TYPE: PRT
<213> ORGANISM: Artificial Sequence
<220> FEATURE:
<223> OTHER INFORMATION: synthetic -continued

<400> SEQUENCE: 238

Arg Glu Leu Asp Tyr Phe Ala Ser
1               5

<210> SEQ ID NO 239
<211> LENGTH: 24
<212> TYPE: DNA
<213> ORGANISM: Artificial Sequence
<220> FEATURE:
<223> OTHER INFORMATION: synthetic

<400> SEQUENCE: 239
cgggaactgg actactttcc ctcc                                              24

<210> SEQ ID NO 240
<211> LENGTH: 8
<212> TYPE: PRT
<213> ORGANISM: Artificial Sequence
<220> FEATURE:
<223> OTHER INFORMATION: synthetic

<400> SEQUENCE: 240

Arg Glu Leu Asp Tyr Phe Pro Ser
1               5

<210> SEQ ID NO 241
<211> LENGTH: 24
<212> TYPE: DNA
<213> ORGANISM: Artificial Sequence
<220> FEATURE:
<223> OTHER INFORMATION: synthetic

<400> SEQUENCE: 241
cgacaactgg actactttga ctat                                              24

<210> SEQ ID NO 242
<211> LENGTH: 8
<212> TYPE: PRT
<213> ORGANISM: Artificial Sequence
<220> FEATURE:
<223> OTHER INFORMATION: synthetic

<400> SEQUENCE: 242

Arg Gln Leu Asp Tyr Phe Asp Tyr
1               5

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
cgacaactgg acttctttga ctat                                              24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Arg Gln Leu Asp Phe Phe Asp Tyr

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
cgacaactgg actactttga cttt                                       24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Arg Gln Leu Asp Tyr Phe Asp Phe
1               5

<210> SEQ ID NO 247
<211> LENGTH: 21
<212> TYPE: DNA
<213> ORGANISM: Artificial Sequence
<220> FEATURE:
<223> OTHER INFORMATION: synthetic

<400> SEQUENCE: 247
agtgggacgg ggtttactta c                                          21

<210> SEQ ID NO 248
<211> LENGTH: 7
<212> TYPE: PRT
<213> ORGANISM: Artificial Sequence
<220> FEATURE:
<223> OTHER INFORMATION: synthetic

<400> SEQUENCE: 248

Ser Gly Thr Gly Phe Thr Tyr
1               5

<210> SEQ ID NO 249
<211> LENGTH: 21
<212> TYPE: DNA
<213> ORGANISM: Artificial Sequence
<220> FEATURE:
<223> OTHER INFORMATION: synthetic

<400> SEQUENCE: 249
agtgggacgg ggtttattta c                                          21

<210> SEQ ID NO 250
<211> LENGTH: 7
<212> TYPE: PRT
<213> ORGANISM: Artificial Sequence
<220> FEATURE:
<223> OTHER INFORMATION: synthetic

<400> SEQUENCE: 250

Ser Gly Thr Gly Phe Ile Tyr
1               5

<210> SEQ ID NO 251

```
<211> LENGTH: 18
<212> TYPE: DNA
<213> ORGANISM: Artificial Sequence
<220> FEATURE:
<223> OTHER INFORMATION: synthetic

<400> SEQUENCE: 251
tctggggcgg gggtttac                                              18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Ser Gly Ala Gly Val Tyr
1               5

<210> SEQ ID NO 253
<211> LENGTH: 24
<212> TYPE: DNA
<213> ORGANISM: Artificial Sequence
<220> FEATURE:
<223> OTHER INFORMATION: synthetic

<400> SEQUENCE: 253
cattactacg gtgttcttga ctcc                                       24

<210> SEQ ID NO 254
<211> LENGTH: 8
<212> TYPE: PRT
<213> ORGANISM: Artificial Sequence
<220> FEATURE:
<223> OTHER INFORMATION: synthetic

<400> SEQUENCE: 254

His Tyr Tyr Gly Val Leu Asp Ser
1               5

<210> SEQ ID NO 255
<211> LENGTH: 24
<212> TYPE: DNA
<213> ORGANISM: Artificial Sequence
<220> FEATURE:
<223> OTHER INFORMATION: synthetic

<400> SEQUENCE: 255
cattactacg gtgtctttga ctcc                                       24

<210> SEQ ID NO 256
<211> LENGTH: 8
<212> TYPE: PRT
<213> ORGANISM: Artificial Sequence
<220> FEATURE:
<223> OTHER INFORMATION: synthetic

<400> SEQUENCE: 256

His Tyr Tyr Gly Val Phe Asp Ser
1               5

<210> SEQ ID NO 257
<211> LENGTH: 33
<212> TYPE: DNA
<213> ORGANISM: Artificial Sequence
<220> FEATURE:
```

<223> OTHER INFORMATION: synthetic

<400> SEQUENCE: 257
gggggctact ataggtacga cgagtttgct tac                33

<210> SEQ ID NO 258
<211> LENGTH: 11
<212> TYPE: PRT
<213> ORGANISM: Artificial Sequence
<220> FEATURE:
<223> OTHER INFORMATION: synthetic

<400> SEQUENCE: 258

Gly Gly Tyr Tyr Arg Tyr Asp Glu Phe Ala Tyr
1               5                   10

<210> SEQ ID NO 259
<211> LENGTH: 21
<212> TYPE: DNA
<213> ORGANISM: Artificial Sequence
<220> FEATURE:
<223> OTHER INFORMATION: synthetic

<400> SEQUENCE: 259
aatgcctatt ctatggacta c                21

<210> SEQ ID NO 260
<211> LENGTH: 7
<212> TYPE: PRT
<213> ORGANISM: Artificial Sequence
<220> FEATURE:
<223> OTHER INFORMATION: synthetic

<400> SEQUENCE: 260

Asn Ala Tyr Ser Met Asp Tyr
1               5

<210> SEQ ID NO 261
<211> LENGTH: 9
<212> TYPE: DNA
<213> ORGANISM: Artificial Sequence
<220> FEATURE:
<223> OTHER INFORMATION: synthetic

<400> SEQUENCE: 261 tttgcttac                9

<210> SEQ ID NO 262
<211> LENGTH: 3
<212> TYPE: PRT
<213> ORGANISM: Artificial Sequence
<220> FEATURE:
<223> OTHER INFORMATION: synthetic

<400> SEQUENCE: 262

Phe Ala Tyr
1

<210> SEQ ID NO 263
<211> LENGTH: 24
<212> TYPE: DNA
<213> ORGANISM: Artificial Sequence
<220> FEATURE:
<223> OTHER INFORMATION: synthetic

<400> SEQUENCE: 263
tattactacg gtagttttgc ttac        24

<210> SEQ ID NO 264
<211> LENGTH: 8
<212> TYPE: PRT
<213> ORGANISM: Artificial Sequence
<220> FEATURE:
<223> OTHER INFORMATION: synthetic

<400> SEQUENCE: 264

Tyr Tyr Tyr Gly Ser Phe Ala Tyr
1               5

<210> SEQ ID NO 265
<211> LENGTH: 21
<212> TYPE: DNA
<213> ORGANISM: Artificial Sequence
<220> FEATURE:
<223> OTHER INFORMATION: synthetic

<400> SEQUENCE: 265
gggtcggact cctttgacta c        21

<210> SEQ ID NO 266
<211> LENGTH: 7
<212> TYPE: PRT
<213> ORGANISM: Artificial Sequence
<220> FEATURE:
<223> OTHER INFORMATION: synthetic

<400> SEQUENCE: 266

Gly Ser Asp Ser Phe Asp Tyr
1               5

<210> SEQ ID NO 267
<211> LENGTH: 6
<212> TYPE: DNA
<213> ORGANISM: Artificial Sequence
<220> FEATURE:
<223> OTHER INFORMATION: synthetic

<400> SEQUENCE: 267 aattac        6

<210> SEQ ID NO 268
<211> LENGTH: 2
<212> TYPE: PRT
<213> ORGANISM: Artificial Sequence
<220> FEATURE:
<223> OTHER INFORMATION: synthetic

<400> SEQUENCE: 268

Asn Tyr
1

<210> SEQ ID NO 269
<211> LENGTH: 33
<212> TYPE: DNA
<213> ORGANISM: Artificial Sequence
<220> FEATURE:
<223> OTHER INFORMATION: synthetic

<400> SEQUENCE: 269
gatcggacta cggctacccc cttctttgac tac        33

<210> SEQ ID NO 270

```
<211> LENGTH: 11
<212> TYPE: PRT
<213> ORGANISM: Artificial Sequence
<220> FEATURE:
<223> OTHER INFORMATION: synthetic

<400> SEQUENCE: 270

Asp Arg Thr Thr Ala Thr Pro Phe Phe Asp Tyr
1               5                   10

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271 aatgggggggg ctacggcctt tgactac                                        27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Asn Gly Gly Ala Thr Ala Phe Asp Tyr
1               5

<210> SEQ ID NO 273
<211> LENGTH: 27
<212> TYPE: DNA
<213> ORGANISM: Artificial Sequence
<220> FEATURE:
<223> OTHER INFORMATION: synthetic

<400> SEQUENCE: 273
aatggagggg ctacggtctt tgactac                                         27

<210> SEQ ID NO 274
<211> LENGTH: 9
<212> TYPE: PRT
<213> ORGANISM: Artificial Sequence
<220> FEATURE:
<223> OTHER INFORMATION: synthetic

<400> SEQUENCE: 274

Asn Gly Gly Ala Thr Val Phe Asp Tyr
1               5

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
ctctactacg gctacgggga ctac                                            24

<210> SEQ ID NO 276
<211> LENGTH: 8
<212> TYPE: PRT
<213> ORGANISM: Artificial Sequence
<220> FEATURE:
```

<223> OTHER INFORMATION: synthetic

<400> SEQUENCE: 276

Leu Tyr Tyr Gly Tyr Gly Asp Tyr
1               5

<210> SEQ ID NO 277
<211> LENGTH: 33
<212> TYPE: DNA
<213> ORGANISM: Artificial Sequence
<220> FEATURE:
<223> OTHER INFORMATION: synthetic

<400> SEQUENCE: 277
ccccatgctg gctacttcgg ctggtttgct tac                                      33

<210> SEQ ID NO 278
<211> LENGTH: 11
<212> TYPE: PRT
<213> ORGANISM: Artificial Sequence
<220> FEATURE:
<223> OTHER INFORMATION: synthetic

<400> SEQUENCE: 278

Pro His Ala Gly Tyr Phe Gly Trp Phe Ala Tyr
1               5                   10

<210> SEQ ID NO 279
<211> LENGTH: 24
<212> TYPE: DNA
<213> ORGANISM: Artificial Sequence
<220> FEATURE:
<223> OTHER INFORMATION: synthetic

<400> SEQUENCE: 279
ctatacggta gcctgtttgc ttac                                                24

<210> SEQ ID NO 280
<211> LENGTH: 8
<212> TYPE: PRT
<213> ORGANISM: Artificial Sequence
<220> FEATURE:
<223> OTHER INFORMATION: synthetic

<400> SEQUENCE: 280

Leu Tyr Gly Ser Leu Phe Ala Tyr
1               5

<210> SEQ ID NO 281
<211> LENGTH: 39
<212> TYPE: DNA
<213> ORGANISM: Artificial Sequence
<220> FEATURE:
<223> OTHER INFORMATION: synthetic

<400> SEQUENCE: 281
catgggggac tgggacgtag ggactggtac ttcgatgtc                                39

<210> SEQ ID NO 282
<211> LENGTH: 13
<212> TYPE: PRT
<213> ORGANISM: Artificial Sequence
<220> FEATURE:
<223> OTHER INFORMATION: synthetic

<400> SEQUENCE: 282

His Gly Gly Leu Gly Arg Arg Asp Trp Tyr Phe Asp Val
1               5                   10

<210> SEQ ID NO 283
<211> LENGTH: 33
<212> TYPE: DNA
<213> ORGANISM: Artificial Sequence
<220> FEATURE:
<223> OTHER INFORMATION: synthetic

<400> SEQUENCE: 283
catgggctct actggggcta ttctatggac tac                                    33

<210> SEQ ID NO 284
<211> LENGTH: 11
<212> TYPE: PRT
<213> ORGANISM: Artificial Sequence
<220> FEATURE:
<223> OTHER INFORMATION: synthetic

<400> SEQUENCE: 284

His Gly Leu Tyr Trp Gly Tyr Ser Met Asp Tyr
1               5                   10

<210> SEQ ID NO 285
<211> LENGTH: 30
<212> TYPE: DNA
<213> ORGANISM: Artificial Sequence
<220> FEATURE:
<223> OTHER INFORMATION: synthetic

<400> SEQUENCE: 285
catggactgg gaaggacagg gtttgcttcc                                        30

<210> SEQ ID NO 286
<211> LENGTH: 10
<212> TYPE: PRT
<213> ORGANISM: Artificial Sequence
<220> FEATURE:
<223> OTHER INFORMATION: synthetic

<400> SEQUENCE: 286

His Gly Leu Gly Arg Thr Gly Phe Ala Ser
1               5                   10

<210> SEQ ID NO 287
<211> LENGTH: 21
<212> TYPE: DNA
<213> ORGANISM: Artificial Sequence
<220> FEATURE:
<223> OTHER INFORMATION: synthetic

<400> SEQUENCE: 287
tccgtctttg gtaattctta c                                                 21

<210> SEQ ID NO 288
<211> LENGTH: 12
<212> TYPE: PRT
<213> ORGANISM: Artificial Sequence
<220> FEATURE:
<223> OTHER INFORMATION: synthetic

<400> SEQUENCE: 288

Ser Val Phe Gly Asn Ser Tyr Trp Phe Asp Val
1               5                   10

<210> SEQ ID NO 289
<211> LENGTH: 9
<212> TYPE: DNA
<213> ORGANISM: Artificial Sequence
<220> FEATURE:
<223> OTHER INFORMATION: synthetic

<400> SEQUENCE: 289 atgacgtac                                                                9

<210> SEQ ID NO 290
<211> LENGTH: 3
<212> TYPE: PRT
<213> ORGANISM: Artificial Sequence
<220> FEATURE:
<223> OTHER INFORMATION: synthetic

<400> SEQUENCE: 290

Met Thr Tyr
1

<210> SEQ ID NO 291
<211> LENGTH: 33
<212> TYPE: DNA
<213> ORGANISM: Artificial Sequence
<220> FEATURE:
<223> OTHER INFORMATION: synthetic

<400> SEQUENCE: 291
gtcctctact atgattacgg gggatttgct tac                                    33

<210> SEQ ID NO 292
<211> LENGTH: 11
<212> TYPE: PRT
<213> ORGANISM: Artificial Sequence
<220> FEATURE:
<223> OTHER INFORMATION: synthetic

<400> SEQUENCE: 292

Val Leu Tyr Tyr Asp Tyr Gly Gly Phe Ala Tyr
1               5                   10

<210> SEQ ID NO 293
<211> LENGTH: 36
<212> TYPE: DNA
<213> ORGANISM: Artificial Sequence
<220> FEATURE:
<223> OTHER INFORMATION: synthetic

<400> SEQUENCE: 293
tattcttacg acagggatta cagtcctatg gactac                                 36

<210> SEQ ID NO 294
<211> LENGTH: 12
<212> TYPE: PRT
<213> ORGANISM: Artificial Sequence
<220> FEATURE:
<223> OTHER INFORMATION: synthetic

<400> SEQUENCE: 294

Tyr Ser Tyr Asp Arg Asp Tyr Ser Pro Met Asp Tyr
1               5                   10

<210> SEQ ID NO 295
<211> LENGTH: 24
<212> TYPE: DNA
<213> ORGANISM: Artificial Sequence

```
<220> FEATURE:
<223> OTHER INFORMATION: synthetic

<400> SEQUENCE: 295
cgggaaccgg acttctttga ctac                                              24

<210> SEQ ID NO 296
<211> LENGTH: 8
<212> TYPE: PRT
<213> ORGANISM: Artificial Sequence
<220> FEATURE:
<223> OTHER INFORMATION: synthetic

<400> SEQUENCE: 296

Arg Glu Pro Asp Phe Phe Asp Tyr
1               5

<210> SEQ ID NO 297
<211> LENGTH: 24
<212> TYPE: DNA
<213> ORGANISM: Artificial Sequence
<220> FEATURE:
<223> OTHER INFORMATION: synthetic

<400> SEQUENCE: 297
cgggaattgg acttctttga ctac                                              24

<210> SEQ ID NO 298
<211> LENGTH: 8
<212> TYPE: PRT
<213> ORGANISM: Artificial Sequence
<220> FEATURE:
<223> OTHER INFORMATION: synthetic

<400> SEQUENCE: 298

Arg Glu Leu Asp Phe Phe Asp Tyr
1               5

<210> SEQ ID NO 299
<211> LENGTH: 24
<212> TYPE: DNA
<213> ORGANISM: Artificial Sequence
<220> FEATURE:
<223> OTHER INFORMATION: synthetic

<400> SEQUENCE: 299
cggggattgg acttctttga ctac                                              24

<210> SEQ ID NO 300
<211> LENGTH: 8
<212> TYPE: PRT
<213> ORGANISM: Artificial Sequence
<220> FEATURE:
<223> OTHER INFORMATION: synthetic

<400> SEQUENCE: 300

Arg Gly Leu Asp Phe Phe Asp Tyr
1               5

<210> SEQ ID NO 301
<211> LENGTH: 347
<212> TYPE: DNA
<213> ORGANISM: Artificial Sequence
<220> FEATURE:
<223> OTHER INFORMATION: synthetic

<400> SEQUENCE: 301
```

```
gacattgtgc tgacacagtc tcctgcttcc ttaattgttt ctctggggca gacggccacc    60
atctcatgca gggccagcca aagtgtcagt acatctaggt ttagttatct gcactggatc   120
caacagaaac cagggcagcc acccaaactc ctcatcaagt atgcatccaa ccttgaatct   180
ggggtccctg tcaggttcag tggcagtggg tctgggacag acttcaccct caacatccat   240
cctgtggagg aggaggatac tgcaacatat ttctgtcagc acagttggga gtttccattc   300
acgttcggct cggggacaaa gttgaaaata aaacgggctg atgctgc                 347
```

<210> SEQ ID NO 302
<211> LENGTH: 112
<212> TYPE: PRT
<213> ORGANISM: Artificial Sequence
<220> FEATURE:
<223> OTHER INFORMATION: synthetic

<400> SEQUENCE: 302

```
Asp Ile Val Leu Thr Gln Ser Pro Ala Ser Leu Ile Val Ser Leu Gly
1               5                   10                  15

Gln Thr Ala Thr Ile Ser Cys Arg Ala Ser Gln Ser Val Ser Thr Ser
            20                  25                  30

Arg Phe Ser Tyr Leu His Trp Ile Gln Gln Lys Pro Gly Gln Pro Pro
        35                  40                  45

Lys Leu Leu Ile Lys Tyr Ala Ser Asn Leu Glu Ser Gly Val Pro Val
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Phe Cys Gln His Ser Trp
                85                  90                  95

Glu Phe Pro Phe Thr Phe Gly Ser Gly Thr Lys Leu Lys Ile Lys Arg
            100                 105                 110
```

<210> SEQ ID NO 303
<211> LENGTH: 347
<212> TYPE: DNA
<213> ORGANISM: Artificial Sequence
<220> FEATURE:
<223> OTHER INFORMATION: synthetic

<400> SEQUENCE: 303

```
gacattgtgc tgacacagtc tcctgcttcc ttaattgttt ctctggggca gacggccacc    60
atctcatgca gggccagcca aagtctcagt acatctaggt ttagctatgt gcactggatc   120
caacagaaac cagggcagcc acccaaactc ctcatcaagt atgcatccaa ccttgaatct   180
ggggtccctg tcaggttcag tggcagtggg tctgggacag acttcaccct caacatccat   240
cctgtggagg aggaggatac tgcaacatat ttctgtcagc acagttggga gtttccattc   300
acgttcggct cggggacaaa gttgaaaata aaacgggctg atgctgc                 347
```

<210> SEQ ID NO 304
<211> LENGTH: 112
<212> TYPE: PRT
<213> ORGANISM: Artificial Sequence
<220> FEATURE:
<223> OTHER INFORMATION: synthetic

<400> SEQUENCE: 304

```
Asp Ile Val Leu Thr Gln Ser Pro Ala Ser Leu Ile Val Ser Leu Gly
1               5                   10                  15
```

```
Gln Thr Ala Thr Ile Ser Cys Arg Ala Ser Gln Ser Leu Thr Ser
            20                  25                  30

Arg Phe Ser Tyr Val His Trp Ile Gln Gln Lys Pro Gly Gln Pro Pro
        35                  40                  45

Lys Leu Leu Ile Lys Tyr Ala Ser Asn Leu Glu Ser Gly Val Pro Val
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Phe Cys Gln His Ser Trp
                85                  90                  95

Glu Phe Pro Phe Thr Phe Gly Ser Gly Thr Lys Leu Lys Ile Lys Arg
            100                 105                 110
```

<210> SEQ ID NO 305
<211> LENGTH: 347
<212> TYPE: DNA
<213> ORGANISM: Artificial Sequence
<220> FEATURE:
<223> OTHER INFORMATION: synthetic

<400> SEQUENCE: 305

```
gacattgtgc tgacacagtc tcctgcttcc ttaattgtat ctctggggca gagggccacc      60
atctcatgta gggccagcca aagtgtcagt acatccaggt ttagttatgt gcactggatc     120
caacagaaac cagggcagcc acccaaactc ctcatcaagt atgcatccaa ccttgaatct     180
ggggtccctg tcaggttcag tggcagtggg tctgggacag acttcatcct caacatccat     240
cctgtggagg aggaggatac tgcaacatat ttctgtcagc acagtgggga gtttccattc     300
acgttcggct cggggacaaa gttggaaata aaacgggctg atgctgc                   347
```

<210> SEQ ID NO 306
<211> LENGTH: 112
<212> TYPE: PRT
<213> ORGANISM: Artificial Sequence
<220> FEATURE:
<223> OTHER INFORMATION: synthetic

<400> SEQUENCE: 306

```
Asp Ile Val Leu Thr Gln Ser Pro Ala Ser Leu Ile Val Ser Leu Gly
 1               5                  10                  15

Gln Arg Ala Thr Ile Ser Cys Arg Ala Ser Gln Ser Val Ser Thr Ser
            20                  25                  30

Arg Phe Ser Tyr Val His Trp Ile Gln Gln Lys Pro Gly Gln Pro Pro
        35                  40                  45

Lys Leu Leu Ile Lys Tyr Ala Ser Asn Leu Glu Ser Gly Val Pro Val
 50                  55                  60

Arg Phe Ser Gly Ser Gly Ser Gly Thr Asp Phe Ile Leu Asn Ile His
 65                  70                  75                  80

Pro Val Glu Glu Glu Asp Thr Ala Thr Tyr Phe Cys Gln His Ser Trp
                85                  90                  95

Glu Phe Pro Phe Thr Phe Gly Ser Gly Thr Lys Leu Glu Ile Lys Arg
            100                 105                 110
```

<210> SEQ ID NO 307
<211> LENGTH: 350
<212> TYPE: DNA
<213> ORGANISM: Artificial Sequence
<220> FEATURE:
<223> OTHER INFORMATION: synthetic

<400> SEQUENCE: 307

```
gaagttttga tgacccaaag tccactctcc ctgcctgtca gtcttggaga tcaggcctcc    60
atctcttgca gatctagtca gagccttgaa catactaatg gaaacaccta tttagagtgg   120
ttcctgcaga gaccaggcca gcctccaaag ctcctgatct acaaagtttc cagccgattt   180
tctggggtcc cagacaggtt cagtggcagt ggatcaggga cagatttcac actcaagatc   240
agcagagtgg aggctgagga tctgggagtt tattactgtt ttcaaggttc acatgttcca   300
ttcacgttcg gctcggggac aaagttggca ataaaacggg ctgatgctgc              350
```

<210> SEQ ID NO 308
<211> LENGTH: 113
<212> TYPE: PRT
<213> ORGANISM: Artificial Sequence
<220> FEATURE:
<223> OTHER INFORMATION: synthetic

<400> SEQUENCE: 308

```
Glu Val Leu Met Thr Gln Ser Pro Leu Ser Leu Pro Val Ser Leu Gly
1               5                   10                  15
Asp Gln Ala Ser Ile Ser Cys Arg Ser Ser Gln Ser Leu Glu His Thr
            20                  25                  30
Asn Gly Asn Thr Tyr Leu Glu Trp Phe Leu Gln Arg Pro Gly Gln Pro
        35                  40                  45
Pro Lys Leu Leu Ile Tyr Lys Val Ser Ser Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Phe Thr Phe Gly Ser Gly Thr Lys Leu Ala Ile Lys
            100                 105                 110
Arg
```

<210> SEQ ID NO 309
<211> LENGTH: 350
<212> TYPE: DNA
<213> ORGANISM: Artificial Sequence
<220> FEATURE:
<223> OTHER INFORMATION: synthetic

<400> SEQUENCE: 309

```
gaagttttga tgacccaaag tccactctcc ctgcctgtca gtcttggaga tcaggcctcc    60
atctcttgca gatctagtca gagccttgaa catagtaatg gaaacaccta tttagagtgg   120
ttcctgcaga gaccaggcca gcctccaaag ctcctgatct acaaagtttc cagccgattt   180
tctggggtcc cagacaggtt cagtggcagt ggatcaggga cagatttcac actcaagatc   240
agcagagtgg aggctgagga tctgggagtt tattactgtt ttcaaggttc acatgttcca   300
ttcacgttcg gctcggggac aaagttggca ataaaacggg ctgatgctgc              350
```

<210> SEQ ID NO 310
<211> LENGTH: 113
<212> TYPE: PRT
<213> ORGANISM: Artificial Sequence
<220> FEATURE:
<223> OTHER INFORMATION: synthetic

<400> SEQUENCE: 310

Glu Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Leu Glu His Ser
            20                  25                  30

Asn Gly Asn Thr Tyr Leu Glu Trp Phe Leu Gln Arg Pro Gly Gln Pro
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Ala Ile Lys
            100                 105                 110

Arg

<210> SEQ ID NO 311
<211> LENGTH: 350
<212> TYPE: DNA
<213> ORGANISM: Artificial Sequence
<220> FEATURE:
<223> OTHER INFORMATION: synthetic

<400> SEQUENCE: 311
gatgttttga tggcccaaac tccactctcc ctgcctgtca cccttggaga tcaagcctcc      60
atctcttgca gatctagtca gagccttgta catagtaatg aaacaccta tttagagtgg     120 ttcctgcaga accaggcca gtctccaaag ctcctgatct acaacgtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ctcacgttcg gctcggggac aaagttggaa ataaaacggg ctgatgctgc              350

<210> SEQ ID NO 312
<211> LENGTH: 113
<212> TYPE: PRT
<213> ORGANISM: Artificial Sequence
<220> FEATURE:
<223> OTHER INFORMATION: synthetic

<400> SEQUENCE: 312

Asp Val Leu Met Ala Gln Thr Pro Leu Ser Leu Pro Val Thr Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Asn Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ser Gly Thr Lys Leu Glu Ile Lys
            100                 105                 110

Arg

<210> SEQ ID NO 313
<211> LENGTH: 350
<212> TYPE: DNA
<213> ORGANISM: Artificial Sequence
<220> FEATURE:
<223> OTHER INFORMATION: synthetic

<400> SEQUENCE: 313

```
gatgttttga tgacccaaac tccactctcc ctgcctgtca atcttggaga tcaggcctcc      60
atctcttgca gatctagtca gagccttcta catagtaatg aaacaccta tttagagtgg     120
ttcctgcaga aaccaggcca gtctccaaag ctcctgatct acaatgtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gctcggggac aaagttggca ataaaacggg ctgatgctgc                350
```

<210> SEQ ID NO 314
<211> LENGTH: 113
<212> TYPE: PRT
<213> ORGANISM: Artificial Sequence
<220> FEATURE:
<223> OTHER INFORMATION: synthetic

<400> SEQUENCE: 314

Asp Val Leu Met Thr Gln Thr Pro Leu Ser Leu Pro Val Asn Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Asn Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Ala Ile Lys
            100                 105                 110

Arg

<210> SEQ ID NO 315
<211> LENGTH: 350
<212> TYPE: DNA
<213> ORGANISM: Artificial Sequence
<220> FEATURE:
<223> OTHER INFORMATION: synthetic

<400> SEQUENCE: 315

```
gatgttttga tgacccaaac tccactctcc ctgcctgtca gtcttggaga tcaagcctcc      60
atctcttgca gatctagtca gagccttgta cataataatg aaacaccta tttagaatgg     120
ttcctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gctcggggac aaagttggaa ataaaacggg ctgatgctgc                350
```

<210> SEQ ID NO 316
<211> LENGTH: 113

```
<212> TYPE: PRT
<213> ORGANISM: Artificial Sequence
<220> FEATURE:
<223> OTHER INFORMATION: synthetic

<400> SEQUENCE: 316

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg

<210> SEQ ID NO 317
<211> LENGTH: 350
<212> TYPE: DNA
<213> ORGANISM: Artificial Sequence
<220> FEATURE:
<223> OTHER INFORMATION: synthetic

<400> SEQUENCE: 317
gatgttttga tgacccaaac tccactctcc ctgcctgtca gtcttggaga tcaagcctcc      60
atctcttgca gatctagtca gagcattgta cacagtaatg gaaacaccta tttagagtgg     120
tacctgcaga aactaggcca gtctccaaag ctcctgatct acagagtttc caaccgattt     180
tctgggtcc cagacaggtt cagtggcagt ggatcaggga cagatttcac actcaagatc      240
agcagagtgg aggctgagga tctgggagtt tattactgct ttcaaggttc acatgttccg     300
tggacgttcg gtggaggcac caagctggaa atcaaacggg ctgatgctgc                350

<210> SEQ ID NO 318
<211> LENGTH: 113
<212> TYPE: PRT
<213> ORGANISM: Artificial Sequence
<220> FEATURE:
<223> OTHER INFORMATION: synthetic

<400> SEQUENCE: 318

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Leu Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

Ser His Val Pro Trp Thr Phe Gly Gly Gly Thr Lys Leu Glu Ile Lys
            100                 105                 110

Arg

<210> SEQ ID NO 319
<211> LENGTH: 350
<212> TYPE: DNA
<213> ORGANISM: Artificial Sequence
<220> FEATURE:
<223> OTHER INFORMATION: synthetic

<400> SEQUENCE: 319
gatgttgtga tgacccaaac tccactctcc ctgcctgtca gtcttggaga tcaagcctcc      60
atctcttgca gatctagtca gagccttcta catagtaatg aaacaccta tttagaatgg     120 tacctgcaga aacctggcca gtctccaaac ctcctgatct acaatgtttc caaccgattt    180
tctggggtcc cagacaggtt cagtggcagt ggatcaggga cagatttcgc actcaagatc    240
agcagagtgg gggctgagga tctggagagt tattactgct ttcaaggttc acatgttccg    300
ctcacgttcg gtgctgggac caagctggag ctgaaacggg ctgatgctgc                350

<210> SEQ ID NO 320
<211> LENGTH: 113
<212> TYPE: PRT
<213> ORGANISM: Artificial Sequence
<220> FEATURE:
<223> OTHER INFORMATION: synthetic

<400> SEQUENCE: 320

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Asn Val Ser Asn Arg Phe Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Gly Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg

<210> SEQ ID NO 321
<211> LENGTH: 350
<212> TYPE: DNA
<213> ORGANISM: Artificial Sequence
<220> FEATURE:
<223> OTHER INFORMATION: synthetic

<400> SEQUENCE: 321
gatgttgtgc tgacccaaac tccactctcc ctgcctctca gtcttggaga tcaggcctcc      60
atctcttgca gatctagtca gaccttcta cacagtgatg agacaccta tttacattgg     120 tacctgcaga agccaggcca gtctccaaag ctcctgatct acaaactttc caaccgattt    180
tctggggtcc cagacaggtt cagtggcagt ggatcaggga cagatttcac actcaagatc    240

```
agcagagtgg aggctgagga tctgggagtt tatttctgct ctcaaagtac acatgttccg    300
tacacgttcg gagggggac caagctggaa ataaaacggg ctgatgctgc                350
```

<210> SEQ ID NO 322
<211> LENGTH: 113
<212> TYPE: PRT
<213> ORGANISM: Artificial Sequence
<220> FEATURE:
<223> OTHER INFORMATION: synthetic

<400> SEQUENCE: 322

```
Asp Val Val Leu Thr Gln Thr Pro Leu Ser Leu Pro Phe Ser Phe Gly
1               5                   10                  15

Asn Lys Ala Ser Ile Phe Cys Lys Phe Ser Gln Thr Leu Leu His Arg
            20                  25                  30

Asp Gly Asn Pro Phe Leu Leu Trp Tyr Leu Gln Lys Pro Gly Gln Ser
        35                  40                  45

Pro Lys Leu Leu Ile Tyr Lys Leu Ser Asn Arg Phe Phe Gly Val Pro
    50                  55                  60

Lys Arg Phe Arg Gly Arg Gly Ser Gly Thr Asn Phe Pro Leu Lys Ile
65                  70                  75                  80

Ser Lys Gly Glu Ala Glu Asp Leu Gly Val Phe Phe Cys Ser Gln Ser
                85                  90                  95

Thr His Val Pro Tyr Thr Phe Gly Gly Gly Thr Lys Leu Glu Ile Lys
            100                 105                 110

Arg
```

<210> SEQ ID NO 323
<211> LENGTH: 350
<212> TYPE: DNA
<213> ORGANISM: Artificial Sequence
<220> FEATURE:
<223> OTHER INFORMATION: synthetic

<400> SEQUENCE: 323

```
gatattgtga tgacccagac tccactcact ttgtcggtta ccattggaca accagcttcc    60
atctcttgca agtcaagtca gagcctctta tttactaatg gaaaaaccta tttaaattgg    120
tttttacaga ggccaggcca gtctccaaaa cgcctaatct atctgctgtc taaattggac    180
tctggagtcc ctgacaggtt cagtggcagt ggatcaggga cagatttcac actgaaaatc    240
agcagagtgg aggctgagga tttgggagtt tattactgct tgcagagtac atattttcct    300
ctcacgttcg gtgctgggac caagctggag ctgaaacggg ctgatgctgc                350
```

<210> SEQ ID NO 324
<211> LENGTH: 113
<212> TYPE: PRT
<213> ORGANISM: Artificial Sequence
<220> FEATURE:
<223> OTHER INFORMATION: synthetic

<400> SEQUENCE: 324

```
Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Phe Thr
            20                  25                  30

Asn Gly Lys Thr Tyr Leu Asn Trp Phe Leu Gln Arg Pro Gly Gln Ser
        35                  40                  45

Pro Lys Arg Leu Ile Tyr Leu Leu Ser Lys Leu Asp Ser Gly Val Pro
```

```
                50                  55                  60
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                    85                  90                  95

Thr Tyr Phe Pro Leu Thr Phe Gly Ala Gly Thr Lys Leu Glu Leu Lys
                100                 105                 110

Arg

<210> SEQ ID NO 325
<211> LENGTH: 350
<212> TYPE: DNA
<213> ORGANISM: Artificial Sequence
<220> FEATURE:
<223> OTHER INFORMATION: synthetic

<400> SEQUENCE: 325
gatgttgtga tgacccagac tccactcact ttgtcggtta ccattggaca accagcttcc      60
atctcttgca agtcaagtca gagcctctta tactaatg aaagaccta tttgaattgg       120 ttattacaga ggccaggcca gtctccaaaa cgcctaatct atctggtgtc aaaattggac     180
tctggagtcc ctgacaggtt cagtggcagt ggatcaggga cagatttcac actgaaaatc     240
agcagagtgg aggctgagga tttgggagtt tattactgct tgcagagtat acattttccg     300
tacacgttcg gaggggggac caagctggac ataaaacggg ctgatgctgc                350

<210> SEQ ID NO 326
<211> LENGTH: 113
<212> TYPE: PRT
<213> ORGANISM: Artificial Sequence
<220> FEATURE:
<223> OTHER INFORMATION: synthetic

<400> SEQUENCE: 326

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                    85                  90                  95

Ile His Phe Pro Tyr Thr Phe Gly Gly Gly Thr Lys Leu Asp Ile Lys
                100                 105                 110

Arg

<210> SEQ ID NO 327
<211> LENGTH: 350
<212> TYPE: DNA
<213> ORGANISM: Artificial Sequence
<220> FEATURE:
<223> OTHER INFORMATION: synthetic

<400> SEQUENCE: 327
gatattgtga tgacgcaggc tgcattctcc aatccagtca ctcctggaac atcagtttcc      60
```

```
atctcctgca ggtctagtaa gagtctccta catagtaatg gcatcactta tttgtattgg    120
tatctgcaga agccaggcca gtctcctcag ctcctgattt atcagatgtc caagattgcc    180
tcaggagtcc cagacaggtt caggagcagt gggtcaggaa ctgatttcac actgagaatc    240
agcagagtgg aggctgcgga tgtgggtgtt tattactgtg ctcaaaatct agaacttccg    300
tggacgttcg gtggaggcac caagctggaa atcaaacggg ctgatgctgc              350
```

<210> SEQ ID NO 328
<211> LENGTH: 113
<212> TYPE: PRT
<213> ORGANISM: Artificial Sequence
<220> FEATURE:
<223> OTHER INFORMATION: synthetic

<400> SEQUENCE: 328

Asp Ile Val Met Thr Gln Ala Ala Phe Ser Asn Pro Val Thr Pro Gly
1               5                   10                  15

Thr Ser Val Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Lys Ile Ala Ser Gly Val Pro
    50                  55                  60

Asp Arg Phe Arg Ser Ser Gly Ser Gly Thr Asp Phe Thr Leu Arg Ile
65                  70                  75                  80

Ser Arg Val Glu Ala Ala Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

Arg

<210> SEQ ID NO 329
<211> LENGTH: 335
<212> TYPE: DNA
<213> ORGANISM: Artificial Sequence
<220> FEATURE:
<223> OTHER INFORMATION: synthetic

<400> SEQUENCE: 329

```
gacattgtga tgacccagtc tcacaaattc atgtccacat caataggaga cagggtcagc    60
atcacctgca aggccagtca gaatgtgagt cctgctgtag cctggtatca acagaaacca    120
ggacaatctc ctaaactact gatttactcg gcatcctccc gatacactgg agtccctgat    180
cgcttcactg gcagtggatc tgggacggct tcactttca ccatcagcag tgtgcaggct    240
gaagacctgg cagtttattt ctgtcagcaa cattttagta ctccgtggac gttcggtgga    300
ggcaccatgc tggaaatcaa acgggctgat gctgc                              335
```

<210> SEQ ID NO 330
<211> LENGTH: 108
<212> TYPE: PRT
<213> ORGANISM: Artificial Sequence
<220> FEATURE:
<223> OTHER INFORMATION: synthetic

<400> SEQUENCE: 330

Asp Ile Val Met Thr Gln Ser His Lys Phe Met Ser Thr Ser Ile Gly
1               5                   10                  15

Asp Arg Val Ser Ile Thr Cys Lys Ala Ser Gln Asn Val Ser Pro Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Asp Arg Phe Thr Gly
    50                  55                  60

Ser Gly Ser Gly Thr Ala Phe Thr Phe Thr Ile Ser Ser Val Gln Ala
65                  70                  75                  80

Glu Asp Leu Ala Val Tyr Phe Cys Gln Gln His Phe Ser Thr Pro Trp
                85                  90                  95

Thr Phe Gly Gly Gly Thr Met Leu Glu Ile Lys Arg
            100                 105

<210> SEQ ID NO 331
<211> LENGTH: 335
<212> TYPE: DNA
<213> ORGANISM: Artificial Sequence
<220> FEATURE:
<223> OTHER INFORMATION: synthetic

<400> SEQUENCE: 331
gacattgtga tgacccagtc tcaaaaattc atgtccacaa cagttgggga cagggtcaga    60
gtcacctgca aggccagtca gaatgtgggt actgctgtag cctggtatca acagaaacca   120
ggacaatctc ctaaactact gatttactca gcatccaatc ggtacactgg agtccctgat   180
cgcttcacag gcagtggatc tgggacagat ttcactctca ccattaccaa tatgcagtct   240
gaagacctgg cagattattt ctgtcagcaa tatagcacct atcctctcac gttcggctcg   300
ggggcaaagt tggaaataaa acgggctgat gctgc                              335

<210> SEQ ID NO 332
<211> LENGTH: 108
<212> TYPE: PRT
<213> ORGANISM: Artificial Sequence
<220> FEATURE:
<223> OTHER INFORMATION: synthetic

<400> SEQUENCE: 332

Asp Ile Val Met Thr Gln Ser Gln Lys Phe Met Ser Thr Thr Val Gly
1               5                   10                  15

Asp Arg Val Arg Val Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Thr Tyr Pro Leu
                85                  90                  95

Thr Phe Gly Ser Gly Ala Lys Leu Glu Ile Lys Arg
            100                 105

<210> SEQ ID NO 333
<211> LENGTH: 332
<212> TYPE: DNA
<213> ORGANISM: Artificial Sequence
<220> FEATURE:
<223> OTHER INFORMATION: synthetic

<400> SEQUENCE: 333

```
gacattgtga tgacccagtc tcacaaattc atgtccacat cagtaggaga cagggtcagc      60
atcacctgca aggccagtca ggatgtgggt actgctgtag cctggtatca acagaaacca     120
ggacaatctc ctaaactact gatttactgg gcatccaccc ggcacactgg agtccctgat     180
cgcttcacag gcagtggatc tgggacagat ttcactctca ccattagcaa tgtgcagtct     240
gaagacttgg cagattattt ctgtcagcaa tatagcaact atctcacgtt cggtgctggg     300
accaagctgg aggtgaaacg ggctgatgct gc                                   332
```

<210> SEQ ID NO 334
<211> LENGTH: 107
<212> TYPE: PRT
<213> ORGANISM: Artificial Sequence
<220> FEATURE:
<223> OTHER INFORMATION: synthetic

<400> SEQUENCE: 334

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Leu Thr
                85                  90                  95

Phe Gly Ala Gly Thr Lys Leu Glu Val Lys Arg
            100                 105
```

<210> SEQ ID NO 335
<211> LENGTH: 335
<212> TYPE: DNA
<213> ORGANISM: Artificial Sequence
<220> FEATURE:
<223> OTHER INFORMATION: synthetic

<400> SEQUENCE: 335

```
gacatccaga tgacccagtc tccatcctcc ttatctgcct ctctgggcga aagagtcagt      60
ctcacttgtc gggcaagtca ggacattggt ggtagcataa actggcttca gcaggaacca     120
gatggaacta ttaaacgcct gatctacgcc acatccagtt tagattctgg tgtccccaaa     180
aggttcagtg gcagtaggtc tgggtcagat tattctctca ccatcagcag ccttgagtct     240
gaagattttg tagactatta ctgtctacaa tatgctagtt ctcctccgac gttcggtgga     300
ggcaccaaac tggaaatcaa acgggctgat gctgc                                335
```

<210> SEQ ID NO 336
<211> LENGTH: 108
<212> TYPE: PRT
<213> ORGANISM: Artificial Sequence
<220> FEATURE:
<223> OTHER INFORMATION: synthetic

<400> SEQUENCE: 336

```
Asp Ile Gln Met Thr Gln Ser Pro Ser Ser Leu Ser Ala Ser Leu Gly
1               5                   10                  15
```

Glu Arg Val Ser Leu Thr Cys Arg Ala Ser Gln Asp Ile Gly Gly Ser
            20                  25                  30

Ile Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
 50                      55                  60

Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Ser Ser Pro Pro
                85                  90                  95

Thr Phe Gly Gly Gly Thr Lys Leu Glu Ile Lys Arg
                100                 105

<210> SEQ ID NO 337
<211> LENGTH: 335
<212> TYPE: DNA
<213> ORGANISM: Artificial Sequence
<220> FEATURE:
<223> OTHER INFORMATION: synthetic

<400> SEQUENCE: 337
gacatccaga tgactcagtc tccagcctcc ctatctgcat ctgtgggaga aactgtcacc      60
atcacatgtc gagcaagtgg gaatattcac acttatttag catggtatca gcagaaacag     120
ggaaaatctc ctcagctcct ggtctacaat gcaaacacct tggcagatgg tgtgccatca     180
aggttcagtg gcagtggatc aggaacacaa ttttctctca agatcaacag tctgcagcct     240
gacgattttg ggagttatta ctgtcaacat ttttggagtg ctccgtggac gttcggtgga     300
ggcacccagc tggaaatcaa acgggctgat gctgc                                335

<210> SEQ ID NO 338
<211> LENGTH: 108
<212> TYPE: PRT
<213> ORGANISM: Artificial Sequence
<220> FEATURE:
<223> OTHER INFORMATION: synthetic

<400> SEQUENCE: 338

Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Thr Tyr
            20                  25                  30

Leu Ala Trp Tyr Gln Gln Lys Gln Gly Lys Ser Pro Gln Leu Leu Val
            35                  40                  45

Tyr Asn Ala Asn Thr Leu Ala Asp Gly Val Pro Ser Arg Phe Ser Gly
 50                      55                  60

Ser Gly Ser Gly Thr Gln Phe Ser Leu Lys Ile Asn Ser Leu Gln Pro
 65                  70                  75                  80

Asp Asp Phe Gly Ser Tyr Tyr Cys Gln His Phe Trp Ser Ala Pro Trp
                85                  90                  95

Thr Phe Gly Gly Gly Thr Gln Leu Glu Ile Lys Arg
                100                 105

<210> SEQ ID NO 339
<211> LENGTH: 335
<212> TYPE: DNA
<213> ORGANISM: Artificial Sequence
<220> FEATURE:
<223> OTHER INFORMATION: synthetic

<400> SEQUENCE: 339

```
gatattgtgt taactcagtc tccagccacc ctgtctgtga ctccaggaga tagagtcagt    60
ctttcctgca gggccagtca agaatttac aactacctac actggtatca acaaaaatca   120
catgagtctc caaggcttct caccaagtat gcttcccagt ccatctctgg gatcccctcc   180
aggttcagtg gcagtggctc agggacagat ttcattctca ctatcaacag tgtggagact   240
gaagattttg gaatgtattt ctgtcaacag agtaacagct ggcctctcac gttcggtgct   300
gggaccaagc tggagctgag acgggctgat gctgc                             335
```

<210> SEQ ID NO 340
<211> LENGTH: 108
<212> TYPE: PRT
<213> ORGANISM: Artificial Sequence
<220> FEATURE:
<223> OTHER INFORMATION: synthetic

<400> SEQUENCE: 340

```
Asp Ile Val Leu Thr Gln Ser Pro Ala Thr Leu Ser Val Thr Pro Gly
1               5                   10                  15
Asp Arg Val Ser Leu Ser Cys Arg Ala Ser Gln Arg Ile Tyr Asn Tyr
            20                  25                  30
Leu His Trp Tyr Gln Gln Lys Ser His Glu Ser Pro Arg Leu Leu Thr
        35                  40                  45
Lys Tyr Ala Ser Gln Ser Ile Ser Gly Ile Pro Ser Arg Phe Ser Gly
    50                  55                  60
Ser Gly Ser Gly Thr Asp Phe Ile Leu Thr Ile Asn Ser Val Glu Thr
65                  70                  75                  80
Glu Asp Phe Gly Met Tyr Phe Cys Gln Gln Ser Asn Ser Trp Pro Leu
                85                  90                  95
Thr Phe Gly Ala Gly Thr Lys Leu Glu Leu Arg Arg
            100                 105
```

<210> SEQ ID NO 341
<211> LENGTH: 335
<212> TYPE: DNA
<213> ORGANISM: Artificial Sequence
<220> FEATURE:
<223> OTHER INFORMATION: synthetic

<400> SEQUENCE: 341

```
gatattgtgt taactcagtc tccagccacc ctgtctgtga ctccaggaga tagagtcagt    60
ctttcctgca gggccagtca agaatttac aactacctac actggtatca acaaaaatca   120
catgagtctc caaggcttct catcaagtat gcttcccagt ccatctctgg gatcccctcc   180
aggttcagtg gcagtggctc agggacagat ttcattctca ctatcaacag tgtggagact   240
gaagattttg gaatgtattt ctgtcaacag agtaacagct ggcctctcac gttcggtgct   300
gggaccaagc tggagctgag acgggctgat gctgc                             335
```

<210> SEQ ID NO 342
<211> LENGTH: 108
<212> TYPE: PRT
<213> ORGANISM: Artificial Sequence
<220> FEATURE:
<223> OTHER INFORMATION: synthetic

<400> SEQUENCE: 342

```
Asp Ile Val Leu Thr Gln Ser Pro Ala Thr Leu Ser Val Thr Pro Gly
```

```
              1               5                  10                 15
Asp Arg Val Ser Leu Ser Cys Arg Ala Ser Gln Arg Ile Tyr Asn Tyr
             20                  25                 30

Leu His Trp Tyr Gln Gln Lys Ser His Glu Ser Pro Arg Leu Leu Ile
             35                  40                 45

Lys Tyr Ala Ser Gln Ser Ile Ser Gly Ile Pro Ser Arg Phe Ser Gly
             50                  55                 60

Ser Gly Ser Gly Thr Asp Phe Ile Leu Thr Ile Asn Ser Val Glu Thr
65                   70                  75                 80

Glu Asp Phe Gly Met Tyr Phe Cys Gln Gln Ser Asn Ser Trp Pro Leu
                     85                  90                 95

Thr Phe Gly Ala Gly Thr Lys Leu Glu Leu Arg Arg
                100                 105
```

<210> SEQ ID NO 343
<211> LENGTH: 335
<212> TYPE: DNA
<213> ORGANISM: Artificial Sequence
<220> FEATURE:
<223> OTHER INFORMATION: synthetic

<400> SEQUENCE: 343

```
gacattgtga tgactcagtc tccagccacc ctgtctgtga ctccaggaga tagagtctct    60
ctttcctgca gggccagcca gagtattagc gactacttac actggtatca acaaaaatca   120
catgagtctc caaggcttct catcaaatat gcttcccaat ccatctctgg atcccctcc    180
aggttccgtg gcagtggatc agggtcacat ttcactctca gtatcaacag tgtggaacct   240
gaagatgttg gagtgtatta ctgtcaaaat ggtcacagtt ttccgtggac gttcggtgga   300
ggcaccaagc tggaaatcaa acgggctgat gctgc                              335
```

<210> SEQ ID NO 344
<211> LENGTH: 108
<212> TYPE: PRT
<213> ORGANISM: Artificial Sequence
<220> FEATURE:
<223> OTHER INFORMATION: synthetic

<400> SEQUENCE: 344

```
Asp Ile Val Met Thr Gln Ser Pro Ala Thr Leu Ser Val Thr Pro Gly
1               5                  10                 15

Asp Arg Val Ser Leu Ser Cys Arg Ala Ser Gln Ser Ile Ser Asp Tyr
             20                  25                 30

Leu His Trp Tyr Gln Gln Lys Ser His Glu Ser Pro Arg Leu Leu Ile
             35                  40                 45

Lys Tyr Ala Ser Gln Ser Ile Ser Gly Ile Pro Ser Arg Phe Arg Gly
             50                  55                 60

Ser Gly Ser Gly Ser His Phe Thr Leu Ser Ile Asn Ser Val Glu Pro
65                   70                  75                 80

Glu Asp Val Gly Val Tyr Tyr Cys Gln Asn Gly His Ser Phe Pro Trp
                     85                  90                 95

Thr Phe Gly Gly Gly Thr Lys Leu Glu Ile Lys Arg
                100                 105
```

<210> SEQ ID NO 345
<211> LENGTH: 335
<212> TYPE: DNA
<213> ORGANISM: Artificial Sequence
<220> FEATURE:

<223> OTHER INFORMATION: synthetic

<400> SEQUENCE: 345

```
gacattgtga tgactcagtc tccagccacc ctgtctgtga ctccaggaga tagagtctct    60
ctttcctgca gggccagcca gactattagc gactacttac actggtatca acaaaaatcg  120
catgagtctc caaggcttct catcaaatat gcttcccaat ccatctctgg gatcccctcc  180
aggttcagtg gcagtggatc agggtcacat ttcactctca gtatcaacag tgtggaacct  240
gaagatgttg gagtgtatta ctgtcaaaat ggtcacagtt ttccgtggac gttcggtgga  300
ggcaccaagc tggaaatcaa acgggctgat gctgc                              335
```

<210> SEQ ID NO 346
<211> LENGTH: 108
<212> TYPE: PRT
<213> ORGANISM: Artificial Sequence
<220> FEATURE:
<223> OTHER INFORMATION: synthetic

<400> SEQUENCE: 346

```
Asp Ile Val Met Thr Gln Ser Pro Ala Thr Leu Ser Val Thr Pro Gly
1               5                   10                  15
Asp Arg Val Ser Leu Ser Cys Arg Ala Ser Gln Thr Ile Ser Asp Tyr
            20                  25                  30
Leu His Trp Tyr Gln Gln Lys Ser His Glu Ser Pro Arg Leu Leu Ile
        35                  40                  45
Lys Tyr Ala Ser Gln Ser Ile Ser Gly Ile Pro Ser Arg Phe Ser Gly
    50                  55                  60
Ser Gly Ser Gly Ser His Phe Thr Leu Ser Ile Asn Ser Val Glu Pro
65                  70                  75                  80
Glu Asp Val Gly Val Tyr Tyr Cys Gln Asn Gly His Ser Phe Pro Trp
                85                  90                  95
Thr Phe Gly Gly Gly Thr Lys Leu Glu Ile Lys Arg
            100                 105
```

<210> SEQ ID NO 347
<211> LENGTH: 329
<212> TYPE: DNA
<213> ORGANISM: Artificial Sequence
<220> FEATURE:
<223> OTHER INFORMATION: synthetic

<400> SEQUENCE: 347

```
gagattgtgc tcactcagtc tccagccatc acagctgcat ctctgggca aaacgtcacc     60
atcacctgca gagccagctc aagtgtaagt tacatgcatt ggtaccggca gaagtccggc   120
acctccccc aactatggat ttatgagata tccagacggg cttctggagt cccagctcgc    180
ttccgtgcca gtgggtctgg gacctcttat tctctcacaa tcagcagcat ggaggctgaa   240
gatgctgcca tttattactg ccagcagtgg aattatcctc tcacgttcgg tgctgggacc   300
aagctggagg tgaaacgggc tgatgctgc                                      329
```

<210> SEQ ID NO 348
<211> LENGTH: 106
<212> TYPE: PRT
<213> ORGANISM: Artificial Sequence
<220> FEATURE:
<223> OTHER INFORMATION: synthetic

<400> SEQUENCE: 348

```
Glu Ile Val Leu Thr Gln Ser Pro Ala Ile Thr Ala Ala Ser Leu Gly
1               5                   10                  15

Gln Asn Val Thr Ile Thr Cys Arg Ala Ser Ser Val Ser Tyr Met
            20                  25                  30

His Trp Tyr Arg Gln Lys Ser Gly Thr Ser Pro Gln Leu Trp Ile Tyr
            35                  40                  45

Glu Ile Ser Arg Arg Ala Ser Gly Val Pro Ala Arg Phe Arg Ala Ser
50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Thr Phe
                85                  90                  95

Gly Ala Gly Thr Lys Leu Glu Val Lys Arg
            100                 105
```

<210> SEQ ID NO 349
<211> LENGTH: 329
<212> TYPE: DNA
<213> ORGANISM: Artificial Sequence
<220> FEATURE:
<223> OTHER INFORMATION: synthetic

<400> SEQUENCE: 349

```
gaagttgtgc tcactcagtc tccagccatc acagctgcat ctctggggca aaaggtcacc    60
atcacctgca gagccagctc aagtgtaagt tacatgcact ggtaccggca gaagtcaggc   120
acctccccc agccatggat ttatgaaata tccactggg cttctggagt cccaactcgc    180
ttccgtgcca gtgggtctgg gacctcttat tctctcacaa tcagcagcat ggaggctgaa   240
gatgctgcca tttattactg ccagcagtgg aattatcctc tcacgttcgg tgctgggacc   300
aagctggaac tgaaacgggc tgatgctgc                                     329
```

<210> SEQ ID NO 350
<211> LENGTH: 106
<212> TYPE: PRT
<213> ORGANISM: Artificial Sequence
<220> FEATURE:
<223> OTHER INFORMATION: synthetic

<400> SEQUENCE: 350

```
Glu Val Val Leu Thr Gln Ser Pro Ala Ile Thr Ala Ala Ser Leu Gly
1               5                   10                  15

Gln Lys Val Thr Ile Thr Cys Arg Ala Ser Ser Val Ser Tyr Met
            20                  25                  30

His Trp Tyr Arg Gln Lys Ser Gly Thr Ser Pro Gln Pro Trp Ile Tyr
            35                  40                  45

Glu Ile Ser Thr Leu Ala Ser Gly Val Pro Thr Arg Phe Arg Ala Ser
50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Thr Phe
                85                  90                  95

Gly Ala Gly Thr Lys Leu Glu Leu Lys Arg
            100                 105
```

<210> SEQ ID NO 351
<211> LENGTH: 338
<212> TYPE: DNA
<213> ORGANISM: Artificial Sequence
<220> FEATURE:
<223> OTHER INFORMATION: synthetic

<400> SEQUENCE: 351

```
caaattgttc tcacccagtc tccaacaatc atgtctgcat ctctagggga acgggtcacc    60
atgacctgca ctgccagctc aagtgtgagt tccagttact gcactggtt ccagcagaag    120
ccaggatcct cccccaaact ctggatttat agcacatcca acctggcttc tggagtccca   180
cctcgcttca gtggcagtgg gtctgggacc tcttactctc tctcaatcag cagcgtggag   240
gctgaagatg ttgccactta ttactgcctc cagtttcatc gttccccgtg gacgttcggt   300
ggaggcgcca agttggaaat caaacgggct gatgctgc                          338
```

<210> SEQ ID NO 352
<211> LENGTH: 109
<212> TYPE: PRT
<213> ORGANISM: Artificial Sequence
<220> FEATURE:
<223> OTHER INFORMATION: synthetic

<400> SEQUENCE: 352

```
Gln Ile Val Leu Thr Gln Ser Pro Thr Ile Met Ser Ala Ser Leu Gly
  1               5                  10                  15
Glu Arg Val Thr Met Thr Cys Thr Ala Ser Ser Val Ser Ser Ser
             20                  25                  30
Tyr Leu His Trp Phe Gln Gln Lys Pro Gly Ser Ser Pro Lys Leu Trp
         35                  40                  45
Ile Tyr Ser Thr Ser Asn Leu Ala Ser Gly Val Pro Pro Arg Phe Ser
     50                  55                  60
Gly Ser Gly Ser Gly Thr Ser Tyr Ser Leu Ser Ile Ser Ser Val Glu
 65                  70                  75                  80
Ala Glu Asp Val Ala Thr Tyr Tyr Cys Leu Gln Phe His Arg Ser Pro
                 85                  90                  95
Trp Thr Phe Gly Gly Gly Ala Lys Leu Glu Ile Lys Arg
            100                 105
```

<210> SEQ ID NO 353
<211> LENGTH: 338
<212> TYPE: DNA
<213> ORGANISM: Artificial Sequence
<220> FEATURE:
<223> OTHER INFORMATION: synthetic

<400> SEQUENCE: 353

```
caaattgttt tcacccagta tccagcaata atgtctgcat ctctagggga acgggtcacc    60
atgacctgca cagccagctc aagtgtaact tccagttact gcactggtt ccagcagaag    120
ccaggatcct cccccaaact ctggatttat agcacgtcca acccgggttc tggagtccca   180
gctcgcttca gtggcagagg atctgggacc tcttactctc tctcaatcag cagcatggag   240
gctgaagatg ctgccactta ttactgcctc cagtttcatc gttccccgtg gacgttcggt   300
ggaggcacca agctggaaat cagacgggct gatgctgc                          338
```

<210> SEQ ID NO 354
<211> LENGTH: 109
<212> TYPE: PRT
<213> ORGANISM: Artificial Sequence
<220> FEATURE:
<223> OTHER INFORMATION: synthetic

<400> SEQUENCE: 354

Gln Ile Val Phe Thr Gln Tyr Pro Ala Ile Met Ser Ala Ser Leu Gly
1               5                   10                  15

Glu Arg Val Thr Met Thr Cys Thr Ala Ser Ser Val Thr Ser Ser
            20                  25                  30

Tyr Leu His Trp Phe Gln Gln Lys Pro Gly Ser Ser Pro Lys Leu Trp
            35                  40                  45

Ile Tyr Ser Thr Ser Asn Pro Gly Ser Gly Val Pro Ala Arg Phe Ser
50                  55                  60

Gly Arg Gly Ser Gly Thr Ser Tyr Ser Leu Ser Ile Ser Met Glu
65                  70                  75                  80

Ala Glu Asp Ala Ala Thr Tyr Tyr Cys Leu Gln Phe His Arg Ser Pro
            85                  90                  95

Trp Thr Phe Gly Gly Gly Thr Lys Leu Glu Ile Arg Arg
            100                 105

<210> SEQ ID NO 355
<211> LENGTH: 332
<212> TYPE: DNA
<213> ORGANISM: Artificial Sequence
<220> FEATURE:
<223> OTHER INFORMATION: synthetic

<400> SEQUENCE: 355
caaattgttc tcacccagtc tccagcaatc atgtctgtat ctccagggga gaaggtctcc     60
atgacctgca gtgccagctc aagtgtcact tacatgcact ggtatcagca gaagtcaggc    120
acctccccca aaagatggat ttatgacaca tccgagctgg cttctggagt ccctgctcgc    180
ttcagtggca gtgggtctgg gaccacttac tctctcacaa tcagcagcat ggaggctgaa    240
gatgctgcca cttattactg ccagcagtgg agtaataaac cgctcacgtt cggtgctggg    300
accaagctgg agctgaaacg ggctgatgct gc                                  332

<210> SEQ ID NO 356
<211> LENGTH: 107
<212> TYPE: PRT
<213> ORGANISM: Artificial Sequence
<220> FEATURE:
<223> OTHER INFORMATION: synthetic

<400> SEQUENCE: 356

Gln Ile Val Leu Thr Gln Ser Pro Ala Ile Met Ser Val Ser Pro Gly
1               5                   10                  15

Glu Lys Val Ser Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
            35                  40                  45

Asp Thr Ser Glu Leu Ala Ser Gly Val Pro Ala Arg Phe Ser Gly Ser
50                  55                  60

Gly Ser Gly Thr Thr Tyr Ser Leu Thr Ile Ser Ser Met Glu Ala Glu
65                  70                  75                  80

Asp Ala Ala Thr Tyr Tyr Cys Gln Gln Trp Ser Asn Lys Pro Leu Thr
            85                  90                  95

Phe Gly Ala Gly Thr Lys Leu Glu Leu Lys Arg
            100                 105

<210> SEQ ID NO 357
<211> LENGTH: 332
<212> TYPE: DNA

<213> ORGANISM: Artificial Sequence
<220> FEATURE:
<223> OTHER INFORMATION: synthetic

<400> SEQUENCE: 357

```
caaaatgttc tcacccagtc tccagcaatc atgtctgcat ctccagggga gaaggtcacc    60
atgtcctgca gtgccagctc aagtgtcact tacatgttct ggtaccagct gaagccagaa   120
tcctccccca gactcctgat ttatgacaca tccaatttgg cttctggcgt ccctgttcgc   180
ttcagtggca gtgggtctgg gacctcttac tctctcacaa tcagccgtat ggaggctgaa   240
gatgctgcca cttattactg ccaggagtgg agtagttacc cactcacgtt cggtgctggg   300
accaagctgg acctgaaacg ggctgatgct gc                                 332
```

<210> SEQ ID NO 358
<211> LENGTH: 107
<212> TYPE: PRT
<213> ORGANISM: Artificial Sequence
<220> FEATURE:
<223> OTHER INFORMATION: synthetic

<400> SEQUENCE: 358

Gln Asn Val Leu Thr Gln Ser Pro Ala Ile Met Ser Ala Ser Pro Gly
1               5                   10                  15
Glu Lys Val Thr Met Ser Cys Ser Ala Ser Ser Ser Val Thr Tyr Met
            20                  25                  30
Phe Trp Tyr Gln Leu Lys Pro Glu Ser Ser Pro Arg Leu Leu Ile Tyr
        35                  40                  45
Asp Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Glu Trp Ser Ser Tyr Pro Leu Thr
                85                  90                  95
Phe Gly Ala Gly Thr Lys Leu Asp Leu Lys Arg
            100                 105

<210> SEQ ID NO 359
<211> LENGTH: 332
<212> TYPE: DNA
<213> ORGANISM: Artificial Sequence
<220> FEATURE:
<223> OTHER INFORMATION: synthetic

<400> SEQUENCE: 359

```
caaattgttc tcacccagtc tccaacactc atgtctgcat cgccaggaga aaggtcacc     60
atgacctgca gtgccagctc aactgtgact tacatttact ggtaccaaca gaagcccggc   120
tcctccccca gactctggat gtatgacaca ttcaacctgg tttctggagt ccctgctcgc   180
ttcagtggca gtaggtctgg gacctcttat tttctcacaa tcagtagcat ggaggtgaa    240
gatgctgcca cttattactg ccaacagtac agtgattccc cgtacacgtt cggaggggg    300
accaagctgg agataaaacg ggctgatgct gc                                 332
```

<210> SEQ ID NO 360
<211> LENGTH: 107
<212> TYPE: PRT
<213> ORGANISM: Artificial Sequence
<220> FEATURE:
<223> OTHER INFORMATION: synthetic -continued

<400> SEQUENCE: 360

Gln Ile Val Leu Thr Gln Ser Pro Thr Leu Met Ser Ala Ser Pro Gly
1               5                   10                  15

Glu Lys Val Thr Met Thr Cys Ser Ala Ser Ser Thr Val Thr Tyr Ile
            20                  25                  30

Tyr Trp Tyr Gln Gln Lys Pro Gly Ser Ser Pro Arg Leu Trp Met Tyr
        35                  40                  45

Asp Thr Phe Asn Leu Val Ser Gly Val Pro Ala Arg Phe Ser Gly Ser
    50                  55                  60

Arg Ser Gly Thr Ser Tyr Phe Leu Thr Ile Ser Ser Met Glu Gly Glu
65                  70                  75                  80

Asp Ala Ala Thr Tyr Tyr Cys Gln Gln Tyr Ser Asp Ser Pro Tyr Thr
                85                  90                  95

Phe Gly Gly Gly Thr Lys Leu Glu Ile Lys Arg
            100                 105

<210> SEQ ID NO 361
<211> LENGTH: 332
<212> TYPE: DNA
<213> ORGANISM: Artificial Sequence
<220> FEATURE:
<223> OTHER INFORMATION: synthetic

<400> SEQUENCE: 361
caaattgttc tcacccagtc tccagagatc atgtctgcat ctccagggga gaaggtcacc      60
ataacctgca gtgccagctc aagtgtaagt tcatgtatt ggttccagca gaagccaggc     120
acttctccca aactctggat ttatatcaca tccaacctgg cttctggagt ccctactcgc     180
ttcagtggca gtggatctgg gacctcttac tctctcacaa tcagccgaat ggaggctgaa     240
gatgctgcca cttattactg ccagcaaagg agtagtttcc cgtacacgtt cggagggggg     300
accaaactgg aaatgaaacg gctgatgct gc                                    332

<210> SEQ ID NO 362
<211> LENGTH: 107
<212> TYPE: PRT
<213> ORGANISM: Artificial Sequence
<220> FEATURE:
<223> OTHER INFORMATION: synthetic

<400> SEQUENCE: 362

Gln Ile Val Leu Thr Gln Ser Pro Glu Ile Met Ser Ala Ser Pro Gly
1               5                   10                  15

Glu Lys Val Thr Ile Thr Cys Ser Ala Ser Ser Ser Val Ser Phe Met
            20                  25                  30

Tyr Trp Phe Gln Gln Lys Pro Gly Thr Ser Pro Lys Leu Trp Ile Tyr
        35                  40                  45

Ile Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Phe Pro Tyr Thr
                85                  90                  95

Phe Gly Gly Gly Thr Lys Leu Glu Met Lys Arg
            100                 105

<210> SEQ ID NO 363
<211> LENGTH: 344

<212> TYPE: DNA
<213> ORGANISM: Artificial Sequence
<220> FEATURE:
<223> OTHER INFORMATION: synthetic

<400> SEQUENCE: 363

```
gacattgtgc tgacccaatc tccagcttct ttggctgtgt ctctagggca gagggccatc      60
atctcctgca aggccagcca aagtgtcagt tttgctggta ctaatttaat gcactggtac     120
caacagaaac caggacagca acccaaactc ctcatctatc gtgcatccaa cctagaaact     180
ggggttccta ccaggtttag tggcagtggg tctaggacag acttcaccct caatatccat     240
cctgtggagg aagatgatgc tgcaacctat tactgtcagc aaagtaggga atattacacg     300
ttcggagggg ggaccaagct ggaaataaaa cgggctgatg ctgc                      344
```

<210> SEQ ID NO 364
<211> LENGTH: 111
<212> TYPE: PRT
<213> ORGANISM: Artificial Sequence
<220> FEATURE:
<223> OTHER INFORMATION: synthetic

<400> SEQUENCE: 364

```
Asp Ile Val Leu Thr Gln Ser Pro Ala Ser Leu Ala Val Ser Leu Gly
1               5                   10                  15
Gln Arg Ala Ile Ile Ser Cys Lys Ala Ser Gln Ser Val Ser Phe Ala
            20                  25                  30
Gly Thr Asn Leu Met His Trp Tyr Gln Gln Lys Pro Gly Gln Gln Pro
        35                  40                  45
Lys Leu Leu Ile Tyr Arg Ala Ser Asn Leu Glu Thr Gly Val Pro Thr
    50                  55                  60
Arg Phe Ser Gly Ser Gly Ser Arg Thr Asp Phe Thr Leu Asn Ile His
65                  70                  75                  80
Pro Val Glu Glu Asp Asp Ala Ala Thr Tyr Tyr Cys Gln Gln Ser Arg
                85                  90                  95
Glu Tyr Tyr Thr Phe Gly Gly Gly Thr Lys Leu Glu Ile Lys Arg
            100                 105                 110
```

<210> SEQ ID NO 365
<211> LENGTH: 347
<212> TYPE: DNA
<213> ORGANISM: Artificial Sequence
<220> FEATURE:
<223> OTHER INFORMATION: synthetic

<400> SEQUENCE: 365

```
gacattgtgc tgacccaatc tccagcttct ttggctgggt ctctagggaa aagggccccc      60
atctcctgca aagccagcga aagtgtcaat ttttttggta ctaatttaat acactggtac     120
caacaaaaac caggacagcc ccccaaactc ctcatctatc atgcatccaa cctaaaaact     180
ggagtccctg ccaggttcag gggcagggggt tctaaaacaa acttccccct ccccattgat     240
cctgtggagg aaaatgatgt tgcaatctat tactgtctgc aaaataggaa aattcctctc     300
acgttcgggg ttgggaccaa gctggagctg aaacgggctg atgctgc                    347
```

<210> SEQ ID NO 366
<211> LENGTH: 112
<212> TYPE: PRT
<213> ORGANISM: Artificial Sequence
<220> FEATURE:
<223> OTHER INFORMATION: synthetic

<400> SEQUENCE: 366

Asp Ile Val Leu Thr Gln Ser Pro Ala Ser Leu Ala Gly Ser Leu Gly
1               5                   10                  15

Lys Arg Ala Pro Ile Ser Cys Lys Ala Ser Glu Ser Val Asn Phe Phe
                20                  25                  30

Gly Thr Asn Leu Ile His Trp Tyr Gln Gln Lys Pro Gly Gln Pro Pro
            35                  40                  45

Lys Leu Leu Ile Tyr His Ala Ser Asn Leu Lys Thr Gly Val Pro Ala
        50                  55                  60

Arg Phe Arg Gly Arg Gly Ser Lys Thr Asn Phe Pro Leu Pro Ile Asp
65                  70                  75                  80

Pro Val Glu Glu Asn Asp Val Ala Ile Tyr Tyr Cys Leu Gln Asn Arg
                85                  90                  95

Lys Ile Pro Leu Thr Phe Gly Val Gly Thr Lys Leu Glu Leu Lys Arg
                100                 105                 110

<210> SEQ ID NO 367
<211> LENGTH: 347
<212> TYPE: DNA
<213> ORGANISM: Artificial Sequence
<220> FEATURE:
<223> OTHER INFORMATION: synthetic

<400> SEQUENCE: 367
gacattgtgc tgacccaatc tccagcttct ttggctgtgt ctctagggca gagggccacc      60
atctcctgca gagccagcga aagtgttgat aattatggca ttagttttat gcactggtac     120
cagcagaaac aggacagcc acccaaactc ctcatctatc gtgcatccaa cctagaatct      180
gggatccctg ccaggttcag tggcagtggg tctaggacag acttcaccct caccattaat     240
cctgtggaga ctgatgatgt tgcaacctat tactgtcagc aaagtaataa ggatccattc     300
acgttcggct cggggcaaa gttggaaata aaacgggctg atgctgc                    347

<210> SEQ ID NO 368
<211> LENGTH: 112
<212> TYPE: PRT
<213> ORGANISM: Artificial Sequence
<220> FEATURE:
<223> OTHER INFORMATION: synthetic

<400> SEQUENCE: 368

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Phe Thr Phe Gly Ser Gly Ala Lys Leu Glu Ile Lys Arg
                100                 105                 110

<210> SEQ ID NO 369

<211> LENGTH: 347
<212> TYPE: DNA
<213> ORGANISM: Artificial Sequence
<220> FEATURE:
<223> OTHER INFORMATION: synthetic

<400> SEQUENCE: 369

```
gacattgtgg tgacacagtc tcctgcttcc ttagctgtat ctctggggca gagggccacc      60
atctcatgca gggccagcca aagtgtcagt acatctagat atagttatct gcactggtac     120
caacagaaac caggacaacc tcccaaactc ctcatcaagt atgcatccaa cctagaatct     180
ggggtccctg ccaggttcag tggcagtggg tctgggacag acttcaccct caatatccat     240
cctgtggggg aggaggatac tgcaacatat tactgtcagc acagttggga gtttccattc     300
acgttcggct cggggacaaa gttggaaata aaacgggctg atgctgc                   347
```

<210> SEQ ID NO 370
<211> LENGTH: 112
<212> TYPE: PRT
<213> ORGANISM: Artificial Sequence
<220> FEATURE:
<223> OTHER INFORMATION: synthetic

<400> SEQUENCE: 370

```
Asp Ile Val Val Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Leu His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Thr Ala Thr Tyr Tyr Cys Gln His Ser Trp
                85                  90                  95

Glu Phe Pro Phe Thr Phe Gly Ser Gly Thr Lys Leu Glu Ile Lys Arg
            100                 105                 110
```

<210> SEQ ID NO 371
<211> LENGTH: 347
<212> TYPE: DNA
<213> ORGANISM: Artificial Sequence
<220> FEATURE:
<223> OTHER INFORMATION: synthetic

<400> SEQUENCE: 371

```
gacattgtac tgacacagtc tcctgcttcc ttagctgtat ctctggggca gagggccacc      60
atctcatgca ggtccagcca aagtgtcagt acatctagat atagttattt gcactggtac     120
caacagaaac caggacaacc tcccaaactc ctcatcaagt atgcatccaa cctagaatct     180
ggggtccctg ccaggttcag tggcagtggg tctgggacag acttcaccct caacatccat     240
cctgtggggg aggaggatcc tgcaacatat tactgtcagc acagttggga gtttccattc     300
acgttcggct cggggacaaa gttggaaata aaacgggctg atgctgc                   347
```

<210> SEQ ID NO 372
<211> LENGTH: 112
<212> TYPE: PRT
<213> ORGANISM: Artificial Sequence
<220> FEATURE:

<223> OTHER INFORMATION: synthetic

<400> SEQUENCE: 372

Asp Ile Val Leu Thr Gln Ser Pro Ala Ser Leu Ala Val Ser Leu Gly
1               5                   10                  15

Gln Arg Ala Thr Ile Ser Cys Arg Ser Ser Gln Ser Val Ser Thr Ser
            20                  25                  30

Arg Tyr Ser Tyr Leu His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Pro Ala Thr Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 373
<211> LENGTH: 347
<212> TYPE: DNA
<213> ORGANISM: Artificial Sequence
<220> FEATURE:
<223> OTHER INFORMATION: synthetic

<400> SEQUENCE: 373
gacattgccc tgacacagtc tcctgcttcg ttagctgtat ctctggggca gagggccacc    60
atctcatgca gggccagcca agtgtcagt acatctaggt atagttatat gcactggtac    120
caacagaaac caggacaacc acccgaactc ctcatcaagt atgcatccaa cctagaatct    180
ggggtccctg ccaggttcag tggcagtggg tctgggacag acttcaccct caacatccat    240
cctgtggggg aggaggatac tgcaacatat tactgtcagc acagttggga ttttccattc    300
acgttcggct cggggacaaa gttggaaata aaacgggctg atgctgc                  347

<210> SEQ ID NO 374
<211> LENGTH: 112
<212> TYPE: PRT
<213> ORGANISM: Artificial Sequence
<220> FEATURE:
<223> OTHER INFORMATION: synthetic

<400> SEQUENCE: 374

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Glu Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Thr Ala Thr Tyr Tyr Cys Gln His Ser Trp
                85                  90                  95

Asp Phe Pro Phe Thr Phe Gly Ser Gly Thr Lys Leu Glu Ile Lys Arg
            100                 105                 110

<210> SEQ ID NO 375
<211> LENGTH: 347
<212> TYPE: DNA
<213> ORGANISM: Artificial Sequence
<220> FEATURE:
<223> OTHER INFORMATION: synthetic

<400> SEQUENCE: 375

```
gacattgtgc tgacacagtc tcctgcttcc ttagctgttt ctctggggca gagggccacc      60
atctcatgca gggccagcca agtgtcagt acatctaggt atagctacat gcactggtac     120
caacagaaac caggacagcc acccaaactc ctcatcaagt atgcatccaa cctagaatct    180
ggggtccctg ccaggttcag tggcagtggg tctgggacag acttcaccct caacatccat    240
cctgtggcgg aggaggatac tgcaacatat tactgtcagc acagttggga gtttccattc    300
acgttcggct cggggacaaa gttggaaata aaacgggctg atgctgc                   347
```

<210> SEQ ID NO 376
<211> LENGTH: 112
<212> TYPE: PRT
<213> ORGANISM: Artificial Sequence
<220> FEATURE:
<223> OTHER INFORMATION: synthetic

<400> SEQUENCE: 376

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Ala Glu Glu Asp Thr Ala Thr Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 377
<211> LENGTH: 347
<212> TYPE: DNA
<213> ORGANISM: Artificial Sequence
<220> FEATURE:
<223> OTHER INFORMATION: synthetic

<400> SEQUENCE: 377

```
gacattgtgc tgacacagtc tcttgcttcc ttagctgttt ctctggggca gagggccacc      60
atctcatgca gggccagcca agtgtcagt acatctaggt atagttatat gcactggtac     120
caacagaaac caggacagcc acccaaactc ctcatcaagt atgcatccaa ccttgaatgt    180
ggggtccgtg ccaggttcag tggcagtggg tgtgggacag acttcaccct caacatccat    240
cctgtggagg aggaggatac tgcagcatat tactgtcagc acagttggga gtttccattc    300
acgttcggct cggggacaaa attggaaata aaacgggctg atgctgc                   347
```

<210> SEQ ID NO 378
<211> LENGTH: 112
<212> TYPE: PRT
<213> ORGANISM: Artificial Sequence

```
<220> FEATURE:
<223> OTHER INFORMATION: synthetic

<400> SEQUENCE: 378

Asp Ile Val Leu Thr Gln Ser Leu Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Cys Gly Val Arg Ala
    50                  55                  60

Arg Phe Ser Gly Ser Gly Cys Gly Thr Asp Phe Thr Leu Asn Ile His
65                  70                  75                  80

Pro Val Glu Glu Glu Asp Thr Ala Ala Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 379
<211> LENGTH: 347
<212> TYPE: DNA
<213> ORGANISM: Artificial Sequence
<220> FEATURE:
<223> OTHER INFORMATION: synthetic

<400> SEQUENCE: 379
gacattgtac tgacacagtc tcctgcttcc ttagctgttt ctctggggca gagggccacc     60
atctcctgca gggccagcca agtgtcagt  acatctaggt atagttatgt gcactggtat    120
caacagaaac caggacagcc acccaaactc ctcatcaagt atgcagccaa cctagaatct    180
ggggtccctg ccaggttcag tggcagtggg tctgggacag acttcaccct caacatccat    240
cctgtggcgg aggaggatgc tgcagcatat tactgtcagc acagttggga gtttccattc    300
acgttcggct cggggacaaa gttggaaata aaacgggctg atgctgc                  347

<210> SEQ ID NO 380
<211> LENGTH: 112
<212> TYPE: PRT
<213> ORGANISM: Artificial Sequence
<220> FEATURE:
<223> OTHER INFORMATION: synthetic

<400> SEQUENCE: 380

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Val His Trp Tyr Gln Gln Lys Pro Gly Gln Pro Pro
        35                  40                  45

Lys Leu Leu Ile Lys Tyr Ala Ala Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Ala Glu Glu Asp Ala Ala Ala Tyr Tyr Cys Gln His Ser Trp
                85                  90                  95

Glu Phe Pro Phe Thr Phe Gly Ser Gly Thr Lys Leu Glu Ile Lys Arg
            100                 105                 110
```

<210> SEQ ID NO 381
<211> LENGTH: 347
<212> TYPE: DNA
<213> ORGANISM: Artificial Sequence
<220> FEATURE:
<223> OTHER INFORMATION: synthetic

<400> SEQUENCE: 381

```
gacattgtgc tgacacagtc tcctgcttcc ttagctgttt ctctggggca gaggaccacc    60
atctcatgcg gggccagcca agtgtcagt acatctaggt ttagttatat gcactggtac   120
caacagaaac caggacagcc acccaaactc ctcatcaagt atgcatccaa cctagaatct   180
ggggtccctg ccaggttcag tggcagtggg tctgggacag acttcaccct caacatccat   240
cctgtggcgg aggaggatac tgcagcatat tactgtcagc acagttggga gtttccattc   300
acgttcggct cggggacaaa gttggaaata aaacgggctg atgctgc                 347
```

<210> SEQ ID NO 382
<211> LENGTH: 112
<212> TYPE: PRT
<213> ORGANISM: Artificial Sequence
<220> FEATURE:
<223> OTHER INFORMATION: synthetic

<400> SEQUENCE: 382

Asp Ile Val Leu Thr Gln Ser Pro Ala Ser Leu Ala Val Ser Leu Gly
1               5                   10                  15
Gln Arg Thr Thr Ile Ser Cys Gly Ala Ser Gln Ser Val Ser Thr Ser
            20                  25                  30
Arg Phe Ser Tyr Met His Trp Tyr Gln Gln Lys Pro Gly Gln Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Ala Glu Glu Asp Thr Ala Ala Tyr Tyr Cys Gln His Ser Trp
                85                  90                  95
Glu Phe Pro Phe Thr Phe Gly Ser Gly Thr Lys Leu Glu Ile Lys Arg
            100                 105                 110

<210> SEQ ID NO 383
<211> LENGTH: 347
<212> TYPE: DNA
<213> ORGANISM: Artificial Sequence
<220> FEATURE:
<223> OTHER INFORMATION: synthetic

<400> SEQUENCE: 383

```
gacattgtgc tgacacagtc tcctgcttcc ttagctgttt ctctggggca gagggccacc    60
atctcatgca gggccagcca agtgtcagt acatctaggt atagttatat gcactggtac   120
caacagaaac caggacagcc acccaaactc ctcatcaagt atgcatccaa cctagaatct   180
ggggtccctg ccaggttcag tggcagtggg tctgggacag acttcaccct caacatccat   240
cctgtggcgg aggaggatac tgcagcatat tactgtcagc acagtgggg gtttccattc   300
acgttcggct cggggacaaa gttggaaata aagcgggctg atgctgc                 347
```

<210> SEQ ID NO 384
<211> LENGTH: 112
<212> TYPE: PRT

<213> ORGANISM: Artificial Sequence
<220> FEATURE:
<223> OTHER INFORMATION: synthetic

<400> SEQUENCE: 384

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Gln Ser Val Ser Thr Ser
            20                  25                  30
Arg Tyr Ser Tyr Met His Trp Tyr Gln Gln Lys Pro Gly Gln Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Ala Glu Glu Asp Thr Ala Ala Tyr Tyr Cys Gln His Ser Trp
                85                  90                  95
Gly Phe Pro Phe Thr Phe Gly Ser Gly Thr Lys Leu Glu Ile Lys Arg
            100                 105                 110
```

<210> SEQ ID NO 385
<211> LENGTH: 347
<212> TYPE: DNA
<213> ORGANISM: Artificial Sequence
<220> FEATURE:
<223> OTHER INFORMATION: synthetic

<400> SEQUENCE: 385

```
gacattgtgc tgacacagtc tcctgcttcc ttagctgtat ctttgggaaa aaaggccacc    60
atctcatgca gggccagcca agtgtcagt acatctaggt atagttatat gcactggtac   120
caacagaaac caggacaccc acccaaactc ctcatcaaat atgcatccaa cctagaatct   180
ggggtccctg ccaggttcag tgcagtggg tctgggacag acttcaccct caacatccat   240
cctgtggcgg aggaggatac tgcagcatat tactgtcagc acagttggga gtttccattc   300
acgttcggct cggggacaaa gttggaaata aaacgggctg atgctgc                347
```

<210> SEQ ID NO 386
<211> LENGTH: 112
<212> TYPE: PRT
<213> ORGANISM: Artificial Sequence
<220> FEATURE:
<223> OTHER INFORMATION: synthetic

<400> SEQUENCE: 386

```
Asp Ile Val Leu Thr Gln Ser Pro Ala Ser Leu Ala Val Ser Leu Gly
1               5                   10                  15
Lys Lys Ala Thr Ile Ser Cys Arg Ala Ser Gln Ser Val Ser Thr Ser
            20                  25                  30
Arg Tyr Ser Tyr Met His Trp Tyr Gln Gln Lys Pro Gly His Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Ala Glu Glu Asp Thr Ala Ala Tyr Tyr Cys Gln His Ser Trp
                85                  90                  95
Glu Phe Pro Phe Thr Phe Gly Ser Gly Thr Lys Leu Glu Ile Lys Arg
            100                 105                 110
```

<210> SEQ ID NO 387
<211> LENGTH: 347
<212> TYPE: DNA
<213> ORGANISM: Artificial Sequence
<220> FEATURE:
<223> OTHER INFORMATION: synthetic

<400> SEQUENCE: 387

```
gacattgtgc tgacacagtc tcctgcttcc ttagctgttt ctctggggca gagggccacc      60
atctcatgca gggccagcca aagtgtcagt acatctaggt atagttatat gcactggtac     120
caacagaaac caggacagcc acccaaactc ctcatcaagt atgcatccaa ccttgaatct     180
ggggtccctg ccaggttcag tggcagtggg tctgggacag acttcaccct caacatccat     240
cctgtggcgg aggaggatac tgcagcatat tactgtcagc acagttggga gtttccattc     300
acgttcggct cggggacaaa attggaaata aaacgggctg atgctgc                   347
```

<210> SEQ ID NO 388
<211> LENGTH: 112
<212> TYPE: PRT
<213> ORGANISM: Artificial Sequence
<220> FEATURE:
<223> OTHER INFORMATION: synthetic

<400> SEQUENCE: 388

Asp Ile Val Leu Thr Gln Ser Pro Ala Ser Leu Ala Val Ser Leu Gly
1               5                   10                  15
Gln Arg Ala Thr Ile Ser Cys Arg Ala Ser Gln Ser Val Ser Thr Ser
            20                  25                  30
Arg Tyr Ser Tyr Met His Trp Tyr Gln Gln Lys Pro Gly Gln Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Ala Glu Glu Asp Thr Ala Ala Tyr Tyr Cys Gln His Ser Trp
                85                  90                  95
Glu Phe Pro Phe Thr Phe Gly Ser Gly Thr Lys Leu Glu Ile Lys Arg
            100                 105                 110

<210> SEQ ID NO 389
<211> LENGTH: 48
<212> TYPE: DNA
<213> ORGANISM: Artificial Sequence
<220> FEATURE:
<223> OTHER INFORMATION: synthetic

<400> SEQUENCE: 389

```
agatctagtc agagccttga acatagtaat ggaaacacct atttagag                   48
```

<210> SEQ ID NO 390
<211> LENGTH: 16
<212> TYPE: PRT
<213> ORGANISM: Artificial Sequence
<220> FEATURE:
<223> OTHER INFORMATION: synthetic

<400> SEQUENCE: 390

Arg Ser Ser Gln Ser Leu Glu His Ser Asn Gly Asn Thr Tyr Leu Glu
1               5                   10                  15

```
<210> SEQ ID NO 391
<211> LENGTH: 48
<212> TYPE: DNA
<213> ORGANISM: Artificial Sequence
<220> FEATURE:
<223> OTHER INFORMATION: synthetic

<400> SEQUENCE: 391
agatctagtc agagccttgt acatagtaat ggaaacacct atttagag          48

<210> SEQ ID NO 392
<211> LENGTH: 16
<212> TYPE: PRT
<213> ORGANISM: Artificial Sequence
<220> FEATURE:
<223> OTHER INFORMATION: synthetic

<400> SEQUENCE: 392

Arg Ser Ser Gln Ser Leu Val His Ser Asn Gly Asn Thr Tyr Leu Glu
1               5                   10                  15

<210> SEQ ID NO 393
<211> LENGTH: 48
<212> TYPE: DNA
<213> ORGANISM: Artificial Sequence
<220> FEATURE:
<223> OTHER INFORMATION: synthetic

<400> SEQUENCE: 393
agatctagtc agagccttgt acatagtaat ggaaacacct atttagag          48

<210> SEQ ID NO 394
<211> LENGTH: 16
<212> TYPE: PRT
<213> ORGANISM: Artificial Sequence
<220> FEATURE:
<223> OTHER INFORMATION: synthetic

<400> SEQUENCE: 394

Arg Ser Ser Gln Ser Leu Leu His Ser Asn Gly Asn Thr Tyr Leu Glu
1               5                   10                  15

<210> SEQ ID NO 395
<211> LENGTH: 48
<212> TYPE: DNA
<213> ORGANISM: Artificial Sequence
<220> FEATURE:
<223> OTHER INFORMATION: synthetic

<400> SEQUENCE: 395
agatctagtc agagcattgt acacagtaat ggaaacacct atttagag          48

<210> SEQ ID NO 396
<211> LENGTH: 16
<212> TYPE: PRT
<213> ORGANISM: Artificial Sequence
<220> FEATURE:
<223> OTHER INFORMATION: synthetic

<400> SEQUENCE: 396

Arg Ser Ser Gln Ser Ile Val His Ser Asn Gly Asn Thr Tyr Leu Glu
1               5                   10                  15

<210> SEQ ID NO 397
<211> LENGTH: 48
<212> TYPE: DNA
```

```
<213> ORGANISM: Artificial Sequence
<220> FEATURE:
<223> OTHER INFORMATION: synthetic

<400> SEQUENCE: 397
agatctagtc agagccttga acatactaat ggaaacacct atttagag         48

<210> SEQ ID NO 398
<211> LENGTH: 16
<212> TYPE: PRT
<213> ORGANISM: Artificial Sequence
<220> FEATURE:
<223> OTHER INFORMATION: synthetic

<400> SEQUENCE: 398

Arg Ser Ser Gln Ser Leu Glu His Thr Asn Gly Asn Thr Tyr Leu Glu
 1               5                  10                  15

<210> SEQ ID NO 399
<211> LENGTH: 48
<212> TYPE: DNA
<213> ORGANISM: Artificial Sequence
<220> FEATURE:
<223> OTHER INFORMATION: synthetic

<400> SEQUENCE: 399
agatctagtc agagccttgt acataataat ggaaacacct atttagaa         48

<210> SEQ ID NO 400
<211> LENGTH: 16
<212> TYPE: PRT
<213> ORGANISM: Artificial Sequence
<220> FEATURE:
<223> OTHER INFORMATION: synthetic

<400> SEQUENCE: 400

Arg Ser Ser Gln Ser Leu Val His Asn Asn Gly Asn Thr Tyr Leu Glu
 1               5                  10                  15

<210> SEQ ID NO 401
<211> LENGTH: 48
<212> TYPE: DNA
<213> ORGANISM: Artificial Sequence
<220> FEATURE:
<223> OTHER INFORMATION: synthetic

<400> SEQUENCE: 401
aggtctagta agagtctcct acatagtaat ggcatcactt atttgtat         48

<210> SEQ ID NO 402
<211> LENGTH: 16
<212> TYPE: PRT
<213> ORGANISM: Artificial Sequence
<220> FEATURE:
<223> OTHER INFORMATION: synthetic

<400> SEQUENCE: 402

Arg Ser Ser Lys Ser Leu Leu His Ser Asn Gly Ile Thr Tyr Leu Tyr
 1               5                  10                  15

<210> SEQ ID NO 403
<211> LENGTH: 48
<212> TYPE: DNA
<213> ORGANISM: Artificial Sequence
<220> FEATURE:
<223> OTHER INFORMATION: synthetic
```

<400> SEQUENCE: 403
agatctagtc agacccttct acacagtgat ggagacacct atttacat 48

<210> SEQ ID NO 404
<211> LENGTH: 16
<212> TYPE: PRT
<213> ORGANISM: Artificial Sequence
<220> FEATURE:
<223> OTHER INFORMATION: synthetic

<400> SEQUENCE: 404

Lys Phe Ser Gln Thr Leu Leu His Arg Asp Gly Asn Pro Phe Leu Leu
1               5                   10                  15

<210> SEQ ID NO 405
<211> LENGTH: 48
<212> TYPE: DNA
<213> ORGANISM: Artificial Sequence
<220> FEATURE:
<223> OTHER INFORMATION: synthetic

<400> SEQUENCE: 405
aagtcaagtc agagcctctt atttactaat ggaaaaacct atttaaat 48

<210> SEQ ID NO 406
<211> LENGTH: 16
<212> TYPE: PRT
<213> ORGANISM: Artificial Sequence
<220> FEATURE:
<223> OTHER INFORMATION: synthetic

<400> SEQUENCE: 406

Lys Ser Ser Gln Ser Leu Leu Phe Thr Asn Gly Lys Thr Tyr Leu Asn
1               5                   10                  15

<210> SEQ ID NO 407
<211> LENGTH: 48
<212> TYPE: DNA
<213> ORGANISM: Artificial Sequence
<220> FEATURE:
<223> OTHER INFORMATION: synthetic

<400> SEQUENCE: 407
aagtcaagtc agagcctctt atatactaat ggaaagacct atttgaat 48

<210> SEQ ID NO 408
<211> LENGTH: 16
<212> TYPE: PRT
<213> ORGANISM: Artificial Sequence
<220> FEATURE:
<223> OTHER INFORMATION: synthetic

<400> SEQUENCE: 408

Lys Ser Ser Gln Ser Leu Leu Tyr Thr Asn Gly Lys Thr Tyr Leu Asn
1               5                   10                  15

<210> SEQ ID NO 409
<211> LENGTH: 33
<212> TYPE: DNA
<213> ORGANISM: Artificial Sequence
<220> FEATURE:
<223> OTHER INFORMATION: synthetic

<400> SEQUENCE: 409
aaggccagtc agaatgtgag tcctgctgta gcc 33

<210> SEQ ID NO 410
<211> LENGTH: 11
<212> TYPE: PRT
<213> ORGANISM: Artificial Sequence
<220> FEATURE:
<223> OTHER INFORMATION: synthetic

<400> SEQUENCE: 410

Lys Ala Ser Gln Asn Val Ser Pro Ala Val Ala
1               5                   10

<210> SEQ ID NO 411
<211> LENGTH: 33
<212> TYPE: DNA
<213> ORGANISM: Artificial Sequence
<220> FEATURE:
<223> OTHER INFORMATION: synthetic

<400> SEQUENCE: 411
aaggccagtc agaatgtggg tactgctgta gcc                                     33

<210> SEQ ID NO 412
<211> LENGTH: 11
<212> TYPE: PRT
<213> ORGANISM: Artificial Sequence
<220> FEATURE:
<223> OTHER INFORMATION: synthetic

<400> SEQUENCE: 412

Lys Ala Ser Gln Asn Val Gly Thr Ala Val Ala
1               5                   10

<210> SEQ ID NO 413
<211> LENGTH: 33
<212> TYPE: DNA
<213> ORGANISM: Artificial Sequence
<220> FEATURE:
<223> OTHER INFORMATION: synthetic

<400> SEQUENCE: 413
aaggccagtc aggatgtggg tactgctgta gcc                                     33

<210> SEQ ID NO 414
<211> LENGTH: 11
<212> TYPE: PRT
<213> ORGANISM: Artificial Sequence
<220> FEATURE:
<223> OTHER INFORMATION: synthetic

<400> SEQUENCE: 414

Lys Ala Ser Gln Asp Val Gly Thr Ala Val Ala
1               5                   10

<210> SEQ ID NO 415
<211> LENGTH: 33
<212> TYPE: DNA
<213> ORGANISM: Artificial Sequence
<220> FEATURE:
<223> OTHER INFORMATION: synthetic

<400> SEQUENCE: 415
cgggcaagtc aggacattgg tggtagcata aac                                     33

<210> SEQ ID NO 416
<211> LENGTH: 11
<212> TYPE: PRT

<213> ORGANISM: Artificial Sequence
<220> FEATURE:
<223> OTHER INFORMATION: synthetic

<400> SEQUENCE: 416

Arg Ala Ser Gln Asp Ile Gly Gly Ser Ile Asn
1               5                   10

<210> SEQ ID NO 417
<211> LENGTH: 33
<212> TYPE: DNA
<213> ORGANISM: Artificial Sequence
<220> FEATURE:
<223> OTHER INFORMATION: synthetic

<400> SEQUENCE: 417
cgagcaagtg ggaatattca cacttattta gca                                    33

<210> SEQ ID NO 418
<211> LENGTH: 11
<212> TYPE: PRT
<213> ORGANISM: Artificial Sequence
<220> FEATURE:
<223> OTHER INFORMATION: synthetic

<400> SEQUENCE: 418

Arg Ala Ser Gly Asn Ile His Thr Tyr Leu Ala
1               5                   10

<210> SEQ ID NO 419
<211> LENGTH: 33
<212> TYPE: DNA
<213> ORGANISM: Artificial Sequence
<220> FEATURE:
<223> OTHER INFORMATION: synthetic

<400> SEQUENCE: 419
agggccagtc aaagaattta caactaccta cac                                    33

<210> SEQ ID NO 420
<211> LENGTH: 11
<212> TYPE: PRT
<213> ORGANISM: Artificial Sequence
<220> FEATURE:
<223> OTHER INFORMATION: synthetic

<400> SEQUENCE: 420

Arg Ala Ser Gln Arg Ile Tyr Asn Tyr Leu His
1               5                   10

<210> SEQ ID NO 421
<211> LENGTH: 33
<212> TYPE: DNA
<213> ORGANISM: Artificial Sequence
<220> FEATURE:
<223> OTHER INFORMATION: synthetic

<400> SEQUENCE: 421
agggccagcc agagtattag cgactactta cac                                    33

<210> SEQ ID NO 422
<211> LENGTH: 11
<212> TYPE: PRT
<213> ORGANISM: Artificial Sequence
<220> FEATURE:
<223> OTHER INFORMATION: synthetic

<400> SEQUENCE: 422

Arg Ala Ser Gln Ser Ile Ser Asp Tyr Leu His
1               5                   10

<210> SEQ ID NO 423
<211> LENGTH: 33
<212> TYPE: DNA
<213> ORGANISM: Artificial Sequence
<220> FEATURE:
<223> OTHER INFORMATION: synthetic

<400> SEQUENCE: 423
agggccagcc agactattag cgactactta cac                                33

<210> SEQ ID NO 424
<211> LENGTH: 11
<212> TYPE: PRT
<213> ORGANISM: Artificial Sequence
<220> FEATURE:
<223> OTHER INFORMATION: synthetic

<400> SEQUENCE: 424

Arg Ala Ser Gln Thr Ile Ser Asp Tyr Leu His
1               5                   10

<210> SEQ ID NO 425
<211> LENGTH: 30
<212> TYPE: DNA
<213> ORGANISM: Artificial Sequence
<220> FEATURE:
<223> OTHER INFORMATION: synthetic

<400> SEQUENCE: 425
agagccagct caagtgtaag ttacatgcat                                    30

<210> SEQ ID NO 426
<211> LENGTH: 10
<212> TYPE: PRT
<213> ORGANISM: Artificial Sequence
<220> FEATURE:
<223> OTHER INFORMATION: synthetic

<400> SEQUENCE: 426

Arg Ala Ser Ser Ser Val Ser Tyr Met His
1               5                   10

<210> SEQ ID NO 427
<211> LENGTH: 30
<212> TYPE: DNA
<213> ORGANISM: Artificial Sequence
<220> FEATURE:
<223> OTHER INFORMATION: synthetic

<400> SEQUENCE: 427
agagccagct caagtgtaag ttacatgcat                                    30

<210> SEQ ID NO 428
<211> LENGTH: 10
<212> TYPE: PRT
<213> ORGANISM: Artificial Sequence
<220> FEATURE:
<223> OTHER INFORMATION: synthetic

<400> SEQUENCE: 428

Arg Ala Ser Ser Ser Val Ser Tyr Met His
1               5                   10

<210> SEQ ID NO 429
<211> LENGTH: 36
<212> TYPE: DNA
<213> ORGANISM: Artificial Sequence
<220> FEATURE:
<223> OTHER INFORMATION: synthetic

<400> SEQUENCE: 429
actgccagct caagtgtgag ttccagttac ttgcac        36

<210> SEQ ID NO 430
<211> LENGTH: 12
<212> TYPE: PRT
<213> ORGANISM: Artificial Sequence
<220> FEATURE:
<223> OTHER INFORMATION: synthetic

<400> SEQUENCE: 430

Thr Ala Ser Ser Ser Val Ser Ser Ser Tyr Leu His
1               5                   10

<210> SEQ ID NO 431
<211> LENGTH: 36
<212> TYPE: DNA
<213> ORGANISM: Artificial Sequence
<220> FEATURE:
<223> OTHER INFORMATION: synthetic

<400> SEQUENCE: 431
acagccagct caagtgtaac ttccagttac ttgcac        36

<210> SEQ ID NO 432
<211> LENGTH: 12
<212> TYPE: PRT
<213> ORGANISM: Artificial Sequence
<220> FEATURE:
<223> OTHER INFORMATION: synthetic

<400> SEQUENCE: 432

Thr Ala Ser Ser Ser Val Thr Ser Ser Tyr Leu His
1               5                   10

<210> SEQ ID NO 433
<211> LENGTH: 30
<212> TYPE: DNA
<213> ORGANISM: Artificial Sequence
<220> FEATURE:
<223> OTHER INFORMATION: synthetic

<400> SEQUENCE: 433
agtgccagct caagtgtcac ttacatgcac        30

<210> SEQ ID NO 434
<211> LENGTH: 10
<212> TYPE: PRT
<213> ORGANISM: Artificial Sequence
<220> FEATURE:
<223> OTHER INFORMATION: synthetic

<400> SEQUENCE: 434

Ser Ala Ser Ser Ser Val Thr Tyr Met His
1               5                   10

<210> SEQ ID NO 435
<211> LENGTH: 30

<212> TYPE: DNA
<213> ORGANISM: Artificial Sequence
<220> FEATURE:
<223> OTHER INFORMATION: synthetic

<400> SEQUENCE: 435
agtgccagct caagtgtcac ttacatgttc        30

<210> SEQ ID NO 436
<211> LENGTH: 10
<212> TYPE: PRT
<213> ORGANISM: Artificial Sequence
<220> FEATURE:
<223> OTHER INFORMATION: synthetic

<400> SEQUENCE: 436

Ser Ala Ser Ser Ser Val Thr Tyr Met Phe
1               5                   10

<210> SEQ ID NO 437
<211> LENGTH: 30
<212> TYPE: DNA
<213> ORGANISM: Artificial Sequence
<220> FEATURE:
<223> OTHER INFORMATION: synthetic

<400> SEQUENCE: 437
agtgccagct caactgtgac ttacatttac        30

<210> SEQ ID NO 438
<211> LENGTH: 10
<212> TYPE: PRT
<213> ORGANISM: Artificial Sequence
<220> FEATURE:
<223> OTHER INFORMATION: synthetic

<400> SEQUENCE: 438

Ser Ala Ser Ser Thr Val Thr Tyr Ile Tyr
1               5                   10

<210> SEQ ID NO 439
<211> LENGTH: 30
<212> TYPE: DNA
<213> ORGANISM: Artificial Sequence
<220> FEATURE:
<223> OTHER INFORMATION: synthetic

<400> SEQUENCE: 439
agtgccagct caagtgtaag tttcatgtat        30

<210> SEQ ID NO 440
<211> LENGTH: 10
<212> TYPE: PRT
<213> ORGANISM: Artificial Sequence
<220> FEATURE:
<223> OTHER INFORMATION: synthetic

<400> SEQUENCE: 440

Ser Ala Ser Ser Ser Val Ser Phe Met Tyr
1               5                   10

<210> SEQ ID NO 441
<211> LENGTH: 45
<212> TYPE: DNA
<213> ORGANISM: Artificial Sequence
<220> FEATURE:
<223> OTHER INFORMATION: synthetic

```
<400> SEQUENCE: 441
aaggccagcc aaagtgtcag ttttgctggt actaatttaa tgcac          45

<210> SEQ ID NO 442
<211> LENGTH: 15
<212> TYPE: PRT
<213> ORGANISM: Artificial Sequence
<220> FEATURE:
<223> OTHER INFORMATION: synthetic

<400> SEQUENCE: 442

Lys Ala Ser Gln Ser Val Ser Phe Ala Gly Thr Asn Leu Met His
1               5                   10                  15

<210> SEQ ID NO 443
<211> LENGTH: 45
<212> TYPE: DNA
<213> ORGANISM: Artificial Sequence
<220> FEATURE:
<223> OTHER INFORMATION: synthetic

<400> SEQUENCE: 443
aaagccagcg aaagtgtcaa tttttttggt actaatttaa tacac          45

<210> SEQ ID NO 444
<211> LENGTH: 15
<212> TYPE: PRT
<213> ORGANISM: Artificial Sequence
<220> FEATURE:
<223> OTHER INFORMATION: synthetic

<400> SEQUENCE: 444

Lys Ala Ser Glu Ser Val Asn Phe Phe Gly Thr Asn Leu Ile His
1               5                   10                  15

<210> SEQ ID NO 445
<211> LENGTH: 45
<212> TYPE: DNA
<213> ORGANISM: Artificial Sequence
<220> FEATURE:
<223> OTHER INFORMATION: synthetic

<400> SEQUENCE: 445
agagccagcg aaagtgttga taattatggc attagttttg tgcac          45

<210> SEQ ID NO 446
<211> LENGTH: 15
<212> TYPE: PRT
<213> ORGANISM: Artificial Sequence
<220> FEATURE:
<223> OTHER INFORMATION: synthetic

<400> SEQUENCE: 446

Arg Ala Ser Glu Ser Val Asp Asn Tyr Gly Ile Ser Phe Met His
1               5                   10                  15

<210> SEQ ID NO 447
<211> LENGTH: 45
<212> TYPE: DNA
<213> ORGANISM: Artificial Sequence
<220> FEATURE:
<223> OTHER INFORMATION: synthetic

<400> SEQUENCE: 447
agggccagcc aaagtgtcag tacatctaga tatagttatc tgcac          45
```

<210> SEQ ID NO 448
<211> LENGTH: 15
<212> TYPE: PRT
<213> ORGANISM: Artificial Sequence
<220> FEATURE:
<223> OTHER INFORMATION: synthetic

<400> SEQUENCE: 448

Arg Ala Ser Gln Ser Val Ser Thr Ser Arg Tyr Ser Tyr Leu His
1               5                   10                  15

<210> SEQ ID NO 449
<211> LENGTH: 45
<212> TYPE: DNA
<213> ORGANISM: Artificial Sequence
<220> FEATURE:
<223> OTHER INFORMATION: synthetic

<400> SEQUENCE: 449
agggccagcc aaagtgtcag tacatctagg tatagttata tgcac           45

<210> SEQ ID NO 450
<211> LENGTH: 15
<212> TYPE: PRT
<213> ORGANISM: Artificial Sequence
<220> FEATURE:
<223> OTHER INFORMATION: synthetic

<400> SEQUENCE: 450

Arg Ala Ser Gln Ser Val Ser Thr Ser Arg Tyr Ser Tyr Met His
1               5                   10                  15

<210> SEQ ID NO 451
<211> LENGTH: 45
<212> TYPE: DNA
<213> ORGANISM: Artificial Sequence
<220> FEATURE:
<223> OTHER INFORMATION: synthetic

<400> SEQUENCE: 451
ggggccagcc aaagtgtcag tacatctagg tttagttata tgcac           45

<210> SEQ ID NO 452
<211> LENGTH: 15
<212> TYPE: PRT
<213> ORGANISM: Artificial Sequence
<220> FEATURE:
<223> OTHER INFORMATION: synthetic

<400> SEQUENCE: 452

Gly Ala Ser Gln Ser Val Ser Thr Ser Arg Phe Ser Tyr Met His
1               5                   10                  15

<210> SEQ ID NO 453
<211> LENGTH: 45
<212> TYPE: DNA
<213> ORGANISM: Artificial Sequence
<220> FEATURE:
<223> OTHER INFORMATION: synthetic

<400> SEQUENCE: 453
aggtccagcc aaagtgtcag tacatctaga tatagttatt tgcac           45

<210> SEQ ID NO 454
<211> LENGTH: 15

```
<212> TYPE: PRT
<213> ORGANISM: Artificial Sequence
<220> FEATURE:
<223> OTHER INFORMATION: synthetic

<400> SEQUENCE: 454

Arg Ser Ser Gln Ser Val Ser Thr Ser Arg Tyr Ser Tyr Leu His
1               5                   10                  15

<210> SEQ ID NO 455
<211> LENGTH: 45
<212> TYPE: DNA
<213> ORGANISM: Artificial Sequence
<220> FEATURE:
<223> OTHER INFORMATION: synthetic

<400> SEQUENCE: 455
agggccagcc aaagtgtcag tacatctagg tttagttatc tgcac            45

<210> SEQ ID NO 456
<211> LENGTH: 15
<212> TYPE: PRT
<213> ORGANISM: Artificial Sequence
<220> FEATURE:
<223> OTHER INFORMATION: synthetic

<400> SEQUENCE: 456

Arg Ala Ser Gln Ser Val Ser Thr Ser Arg Phe Ser Tyr Leu His
1               5                   10                  15

<210> SEQ ID NO 457
<211> LENGTH: 48
<212> TYPE: DNA
<213> ORGANISM: Artificial Sequence
<220> FEATURE:
<223> OTHER INFORMATION: synthetic

<400> SEQUENCE: 457
agggccagcc aaagtgtcag tacatctagg tatagttatg tgcactgg            48

<210> SEQ ID NO 458
<211> LENGTH: 15
<212> TYPE: PRT
<213> ORGANISM: Artificial Sequence
<220> FEATURE:
<223> OTHER INFORMATION: synthetic

<400> SEQUENCE: 458

Arg Ala Ser Gln Ser Val Ser Thr Ser Arg Tyr Ser Tyr Val His
1               5                   10                  15

<210> SEQ ID NO 459
<211> LENGTH: 45
<212> TYPE: DNA
<213> ORGANISM: Artificial Sequence
<220> FEATURE:
<223> OTHER INFORMATION: synthetic

<400> SEQUENCE: 459
agggccagcc aaagtgtcag tacatccagg tttagttatg tgcac            45

<210> SEQ ID NO 460
<211> LENGTH: 15
<212> TYPE: PRT
<213> ORGANISM: Artificial Sequence
<220> FEATURE:
<223> OTHER INFORMATION: synthetic
```

<400> SEQUENCE: 460

Arg Ala Ser Gln Ser Val Ser Thr Ser Arg Phe Ser Tyr Val His
1               5                   10                  15

<210> SEQ ID NO 461
<211> LENGTH: 45
<212> TYPE: DNA
<213> ORGANISM: Artificial Sequence
<220> FEATURE:
<223> OTHER INFORMATION: synthetic

<400> SEQUENCE: 461
agggccagcc aaagtctcag tacatctagg tttagctatg tgcac            45

<210> SEQ ID NO 462
<211> LENGTH: 15
<212> TYPE: PRT
<213> ORGANISM: Artificial Sequence
<220> FEATURE:
<223> OTHER INFORMATION: synthetic

<400> SEQUENCE: 462

Arg Ala Ser Gln Ser Leu Ser Thr Ser Arg Phe Ser Tyr Val His
1               5                   10                  15

<210> SEQ ID NO 463
<211> LENGTH: 21
<212> TYPE: DNA
<213> ORGANISM: Artificial Sequence
<220> FEATURE:
<223> OTHER INFORMATION: synthetic

<400> SEQUENCE: 463
aaagtttcca gccgattttc t                                       21

<210> SEQ ID NO 464
<211> LENGTH: 7
<212> TYPE: PRT
<213> ORGANISM: Artificial Sequence
<220> FEATURE:
<223> OTHER INFORMATION: synthetic

<400> SEQUENCE: 464

Lys Val Ser Ser Arg Phe Ser
1               5

<210> SEQ ID NO 465
<211> LENGTH: 21
<212> TYPE: DNA
<213> ORGANISM: Artificial Sequence
<220> FEATURE:
<223> OTHER INFORMATION: synthetic

<400> SEQUENCE: 465
aaagtttcca accgattttc t                                       21

<210> SEQ ID NO 466
<211> LENGTH: 7
<212> TYPE: PRT
<213> ORGANISM: Artificial Sequence
<220> FEATURE:
<223> OTHER INFORMATION: synthetic

<400> SEQUENCE: 466

Lys Val Ser Asn Arg Phe Ser

```
<210> SEQ ID NO 467
<211> LENGTH: 21
<212> TYPE: DNA
<213> ORGANISM: Artificial Sequence
<220> FEATURE:
<223> OTHER INFORMATION: synthetic

<400> SEQUENCE: 467
aaactttcca accgattttc t                                              21

<210> SEQ ID NO 468
<211> LENGTH: 7
<212> TYPE: PRT
<213> ORGANISM: Artificial Sequence
<220> FEATURE:
<223> OTHER INFORMATION: synthetic

<400> SEQUENCE: 468

Lys Leu Ser Asn Arg Phe Phe
1               5

<210> SEQ ID NO 469
<211> LENGTH: 21
<212> TYPE: DNA
<213> ORGANISM: Artificial Sequence
<220> FEATURE:
<223> OTHER INFORMATION: synthetic

<400> SEQUENCE: 469
aatgtttcca accgattttc t                                              21

<210> SEQ ID NO 470
<211> LENGTH: 7
<212> TYPE: PRT
<213> ORGANISM: Artificial Sequence
<220> FEATURE:
<223> OTHER INFORMATION: synthetic

<400> SEQUENCE: 470

Asn Val Ser Asn Arg Phe Ser
1               5

<210> SEQ ID NO 471
<211> LENGTH: 21
<212> TYPE: DNA
<213> ORGANISM: Artificial Sequence
<220> FEATURE:
<223> OTHER INFORMATION: synthetic

<400> SEQUENCE: 471
agagtttcca accgattttc t                                              21

<210> SEQ ID NO 472
<211> LENGTH: 7
<212> TYPE: PRT
<213> ORGANISM: Artificial Sequence
<220> FEATURE:
<223> OTHER INFORMATION: synthetic

<400> SEQUENCE: 472

Arg Val Ser Asn Arg Phe Ser
1               5

<210> SEQ ID NO 473
```

```
<211> LENGTH: 21
<212> TYPE: DNA
<213> ORGANISM: Artificial Sequence
<220> FEATURE:
<223> OTHER INFORMATION: synthetic

<400> SEQUENCE: 473
cagatgtcca agattgcctc a                                              21

<210> SEQ ID NO 474
<211> LENGTH: 7
<212> TYPE: PRT
<213> ORGANISM: Artificial Sequence
<220> FEATURE:
<223> OTHER INFORMATION: synthetic

<400> SEQUENCE: 474

Gln Met Ser Lys Ile Ala Ser
1               5

<210> SEQ ID NO 475
<211> LENGTH: 21
<212> TYPE: DNA
<213> ORGANISM: Artificial Sequence
<220> FEATURE:
<223> OTHER INFORMATION: synthetic

<400> SEQUENCE: 475
ctgctgtcta aattggactc t                                              21

<210> SEQ ID NO 476
<211> LENGTH: 7
<212> TYPE: PRT
<213> ORGANISM: Artificial Sequence
<220> FEATURE:
<223> OTHER INFORMATION: synthetic

<400> SEQUENCE: 476

Leu Leu Ser Lys Leu Asp Ser
1               5

<210> SEQ ID NO 477
<211> LENGTH: 21
<212> TYPE: DNA
<213> ORGANISM: Artificial Sequence
<220> FEATURE:
<223> OTHER INFORMATION: synthetic

<400> SEQUENCE: 477
ctggtgtcaa aattggactc t                                              21

<210> SEQ ID NO 478
<211> LENGTH: 7
<212> TYPE: PRT
<213> ORGANISM: Artificial Sequence
<220> FEATURE:
<223> OTHER INFORMATION: synthetic

<400> SEQUENCE: 478

Leu Val Ser Lys Leu Asp Ser
1               5

<210> SEQ ID NO 479
<211> LENGTH: 21
<212> TYPE: DNA
<213> ORGANISM: Artificial Sequence
<220> FEATURE:
```

<223> OTHER INFORMATION: synthetic

<400> SEQUENCE: 479
tcggcatcct cccgatacac t                                              21

<210> SEQ ID NO 480
<211> LENGTH: 7
<212> TYPE: PRT
<213> ORGANISM: Artificial Sequence
<220> FEATURE:
<223> OTHER INFORMATION: synthetic

<400> SEQUENCE: 480

Ser Ala Ser Ser Arg Tyr Thr
1               5

<210> SEQ ID NO 481
<211> LENGTH: 21
<212> TYPE: DNA
<213> ORGANISM: Artificial Sequence
<220> FEATURE:
<223> OTHER INFORMATION: synthetic

<400> SEQUENCE: 481
tcagcatcca atcggtacac t                                              21

<210> SEQ ID NO 482
<211> LENGTH: 7
<212> TYPE: PRT
<213> ORGANISM: Artificial Sequence
<220> FEATURE:
<223> OTHER INFORMATION: synthetic

<400> SEQUENCE: 482

Ser Ala Ser Asn Arg Tyr Thr
1               5

<210> SEQ ID NO 483
<211> LENGTH: 21
<212> TYPE: DNA
<213> ORGANISM: Artificial Sequence
<220> FEATURE:
<223> OTHER INFORMATION: synthetic

<400> SEQUENCE: 483
tgggcatcca cccggcacac t                                              21

<210> SEQ ID NO 484
<211> LENGTH: 7
<212> TYPE: PRT
<213> ORGANISM: Artificial Sequence
<220> FEATURE:
<223> OTHER INFORMATION: synthetic

<400> SEQUENCE: 484

Trp Ala Ser Thr Arg His Thr
1               5

<210> SEQ ID NO 485
<211> LENGTH: 21
<212> TYPE: DNA
<213> ORGANISM: Artificial Sequence
<220> FEATURE:
<223> OTHER INFORMATION: synthetic

<400> SEQUENCE: 485
gccacatcca gtttagattc t                                              21

<210> SEQ ID NO 486
<211> LENGTH: 7
<212> TYPE: PRT
<213> ORGANISM: Artificial Sequence
<220> FEATURE:
<223> OTHER INFORMATION: synthetic

<400> SEQUENCE: 486

Ala Thr Ser Ser Leu Asp Ser
1               5

<210> SEQ ID NO 487
<211> LENGTH: 21
<212> TYPE: DNA
<213> ORGANISM: Artificial Sequence
<220> FEATURE:
<223> OTHER INFORMATION: synthetic

<400> SEQUENCE: 487
aatgcaaaca ccttggcaga t                                              21

<210> SEQ ID NO 488
<211> LENGTH: 7
<212> TYPE: PRT
<213> ORGANISM: Artificial Sequence
<220> FEATURE:
<223> OTHER INFORMATION: synthetic

<400> SEQUENCE: 488

Asn Ala Asn Thr Leu Ala Asp
1               5

<210> SEQ ID NO 489
<211> LENGTH: 21
<212> TYPE: DNA
<213> ORGANISM: Artificial Sequence
<220> FEATURE:
<223> OTHER INFORMATION: synthetic

<400> SEQUENCE: 489
gcttcccagt ccatctctgg g                                              21

<210> SEQ ID NO 490
<211> LENGTH: 7
<212> TYPE: PRT
<213> ORGANISM: Artificial Sequence
<220> FEATURE:
<223> OTHER INFORMATION: synthetic

<400> SEQUENCE: 490

Ala Ser Gln Ser Ile Ser Gly
1               5

<210> SEQ ID NO 491
<211> LENGTH: 21
<212> TYPE: DNA
<213> ORGANISM: Artificial Sequence
<220> FEATURE:
<223> OTHER INFORMATION: synthetic

<400> SEQUENCE: 491
tatgcttccc aatccatctc t                                              21

<210> SEQ ID NO 492

```
<211> LENGTH: 7
<212> TYPE: PRT
<213> ORGANISM: Artificial Sequence
<220> FEATURE:
<223> OTHER INFORMATION: synthetic

<400> SEQUENCE: 492

Tyr Ala Ser Gln Ser Ile Ser
1               5

<210> SEQ ID NO 493
<211> LENGTH: 21
<212> TYPE: DNA
<213> ORGANISM: Artificial Sequence
<220> FEATURE:
<223> OTHER INFORMATION: synthetic

<400> SEQUENCE: 493
gagatatcca gacgggcttc t                                              21

<210> SEQ ID NO 494
<211> LENGTH: 7
<212> TYPE: PRT
<213> ORGANISM: Artificial Sequence
<220> FEATURE:
<223> OTHER INFORMATION: synthetic

<400> SEQUENCE: 494

Glu Ile Ser Arg Arg Ala Ser
1               5

<210> SEQ ID NO 495
<211> LENGTH: 21
<212> TYPE: DNA
<213> ORGANISM: Artificial Sequence
<220> FEATURE:
<223> OTHER INFORMATION: synthetic

<400> SEQUENCE: 495
gaaatatcca cactggcttc t                                              21

<210> SEQ ID NO 496
<211> LENGTH: 7
<212> TYPE: PRT
<213> ORGANISM: Artificial Sequence
<220> FEATURE:
<223> OTHER INFORMATION: synthetic

<400> SEQUENCE: 496

Glu Ile Ser Thr Leu Ala Ser
1               5

<210> SEQ ID NO 497
<211> LENGTH: 21
<212> TYPE: DNA
<213> ORGANISM: Artificial Sequence
<220> FEATURE:
<223> OTHER INFORMATION: synthetic

<400> SEQUENCE: 497
agcacatcca acctggcttc t                                              21

<210> SEQ ID NO 498
<211> LENGTH: 7
<212> TYPE: PRT
<213> ORGANISM: Artificial Sequence
<220> FEATURE:
```

<223> OTHER INFORMATION: synthetic

<400> SEQUENCE: 498

Ser Thr Ser Asn Leu Ala Ser
1               5

<210> SEQ ID NO 499
<211> LENGTH: 21
<212> TYPE: DNA
<213> ORGANISM: Artificial Sequence
<220> FEATURE:
<223> OTHER INFORMATION: synthetic

<400> SEQUENCE: 499
agcacgtcca acccgggttc t                                        21

<210> SEQ ID NO 500
<211> LENGTH: 7
<212> TYPE: PRT
<213> ORGANISM: Artificial Sequence
<220> FEATURE:
<223> OTHER INFORMATION: synthetic

<400> SEQUENCE: 500

Ser Thr Ser Asn Pro Gly Ser
1               5

<210> SEQ ID NO 501
<211> LENGTH: 21
<212> TYPE: DNA
<213> ORGANISM: Artificial Sequence
<220> FEATURE:
<223> OTHER INFORMATION: synthetic

<400> SEQUENCE: 501
gacacatccg agctggcttc t                                        21

<210> SEQ ID NO 502
<211> LENGTH: 7
<212> TYPE: PRT
<213> ORGANISM: Artificial Sequence
<220> FEATURE:
<223> OTHER INFORMATION: synthetic

<400> SEQUENCE: 502

Asp Thr Ser Glu Leu Ala Ser
1               5

<210> SEQ ID NO 503
<211> LENGTH: 21
<212> TYPE: DNA
<213> ORGANISM: Artificial Sequence
<220> FEATURE:
<223> OTHER INFORMATION: synthetic

<400> SEQUENCE: 503
gacacatcca atttggcttc t                                        21

<210> SEQ ID NO 504
<211> LENGTH: 7
<212> TYPE: PRT
<213> ORGANISM: Artificial Sequence
<220> FEATURE:
<223> OTHER INFORMATION: synthetic

<400> SEQUENCE: 504

Asp Thr Ser Asn Leu Ala Ser
1               5

<210> SEQ ID NO 505
<211> LENGTH: 21
<212> TYPE: DNA
<213> ORGANISM: Artificial Sequence
<220> FEATURE:
<223> OTHER INFORMATION: synthetic

<400> SEQUENCE: 505
gacacattca acctggtttc t                                             21

<210> SEQ ID NO 506
<211> LENGTH: 7
<212> TYPE: PRT
<213> ORGANISM: Artificial Sequence
<220> FEATURE:
<223> OTHER INFORMATION: synthetic

<400> SEQUENCE: 506

Asp Thr Phe Asn Leu Val Ser
1               5

<210> SEQ ID NO 507
<211> LENGTH: 21
<212> TYPE: DNA
<213> ORGANISM: Artificial Sequence
<220> FEATURE:
<223> OTHER INFORMATION: synthetic

<400> SEQUENCE: 507
atcacatcca acctggcttc t                                             21

<210> SEQ ID NO 508
<211> LENGTH: 7
<212> TYPE: PRT
<213> ORGANISM: Artificial Sequence
<220> FEATURE:
<223> OTHER INFORMATION: synthetic

<400> SEQUENCE: 508

Ile Thr Ser Asn Leu Ala Ser
1               5

<210> SEQ ID NO 509
<211> LENGTH: 21
<212> TYPE: DNA
<213> ORGANISM: Artificial Sequence
<220> FEATURE:
<223> OTHER INFORMATION: synthetic

<400> SEQUENCE: 509
cgtgcatcca acctagaaac t                                             21

<210> SEQ ID NO 510
<211> LENGTH: 7
<212> TYPE: PRT
<213> ORGANISM: Artificial Sequence
<220> FEATURE:
<223> OTHER INFORMATION: synthetic

<400> SEQUENCE: 510

Arg Ala Ser Asn Leu Glu Thr
1               5

```
<210> SEQ ID NO 511
<211> LENGTH: 21
<212> TYPE: DNA
<213> ORGANISM: Artificial Sequence
<220> FEATURE:
<223> OTHER INFORMATION: synthetic

<400> SEQUENCE: 511
catgcatcca acctaaaaac t                                        21

<210> SEQ ID NO 512
<211> LENGTH: 7
<212> TYPE: PRT
<213> ORGANISM: Artificial Sequence
<220> FEATURE:
<223> OTHER INFORMATION: synthetic

<400> SEQUENCE: 512

His Ala Ser Asn Leu Lys Thr
1               5

<210> SEQ ID NO 513
<211> LENGTH: 21
<212> TYPE: DNA
<213> ORGANISM: Artificial Sequence
<220> FEATURE:
<223> OTHER INFORMATION: synthetic

<400> SEQUENCE: 513
cgtgcatcca acctagaatc t                                        21

<210> SEQ ID NO 514
<211> LENGTH: 7
<212> TYPE: PRT
<213> ORGANISM: Artificial Sequence
<220> FEATURE:
<223> OTHER INFORMATION: synthetic

<400> SEQUENCE: 514

Arg Ala Ser Asn Leu Glu Ser
1               5

<210> SEQ ID NO 515
<211> LENGTH: 21
<212> TYPE: DNA
<213> ORGANISM: Artificial Sequence
<220> FEATURE:
<223> OTHER INFORMATION: synthetic

<400> SEQUENCE: 515
tatgcatcca acctagaatc t                                        21

<210> SEQ ID NO 516
<211> LENGTH: 7
<212> TYPE: PRT
<213> ORGANISM: Artificial Sequence
<220> FEATURE:
<223> OTHER INFORMATION: synthetic

<400> SEQUENCE: 516

Tyr Ala Ser Asn Leu Glu Ser
1               5

<210> SEQ ID NO 517
<211> LENGTH: 21
<212> TYPE: DNA
<213> ORGANISM: Artificial Sequence
```

<220> FEATURE:
<223> OTHER INFORMATION: synthetic

<400> SEQUENCE: 517
tatgcatcca accttgaatg t                                              21

<210> SEQ ID NO 518
<211> LENGTH: 7
<212> TYPE: PRT
<213> ORGANISM: Artificial Sequence
<220> FEATURE:
<223> OTHER INFORMATION: synthetic

<400> SEQUENCE: 518

Tyr Ala Ser Asn Leu Glu Cys
1               5

<210> SEQ ID NO 519
<211> LENGTH: 27
<212> TYPE: DNA
<213> ORGANISM: Artificial Sequence
<220> FEATURE:
<223> OTHER INFORMATION: synthetic

<400> SEQUENCE: 519
tttcaaggtt cacatgttcc attcacg                                        27

<210> SEQ ID NO 520
<211> LENGTH: 9
<212> TYPE: PRT
<213> ORGANISM: Artificial Sequence
<220> FEATURE:
<223> OTHER INFORMATION: synthetic

<400> SEQUENCE: 520

Phe Gln Gly Ser His Val Pro Phe Thr
1               5

<210> SEQ ID NO 521
<211> LENGTH: 27
<212> TYPE: DNA
<213> ORGANISM: Artificial Sequence
<220> FEATURE:
<223> OTHER INFORMATION: synthetic

<400> SEQUENCE: 521
tttcaaggtt cacatgttcc actcacg                                        27

<210> SEQ ID NO 522
<211> LENGTH: 9
<212> TYPE: PRT
<213> ORGANISM: Artificial Sequence
<220> FEATURE:
<223> OTHER INFORMATION: synthetic

<400> SEQUENCE: 522

Phe Gln Gly Ser His Val Pro Leu Thr
1               5

<210> SEQ ID NO 523
<211> LENGTH: 27
<212> TYPE: DNA
<213> ORGANISM: Artificial Sequence
<220> FEATURE:
<223> OTHER INFORMATION: synthetic

<400> SEQUENCE: 523

```
tttcaaggtt cacatgttcc gtggacg                                27
```

<210> SEQ ID NO 524
<211> LENGTH: 10
<212> TYPE: PRT
<213> ORGANISM: Artificial Sequence
<220> FEATURE:
<223> OTHER INFORMATION: synthetic

<400> SEQUENCE: 524

```
Phe Gln Gly Ser His Val Pro Trp Thr Phe
1               5                   10
```

<210> SEQ ID NO 525
<211> LENGTH: 27
<212> TYPE: DNA
<213> ORGANISM: Artificial Sequence
<220> FEATURE:
<223> OTHER INFORMATION: synthetic

<400> SEQUENCE: 525

```
gctcaaaatc tagaacttcc gtggacg                                27
```

<210> SEQ ID NO 526
<211> LENGTH: 9
<212> TYPE: PRT
<213> ORGANISM: Artificial Sequence
<220> FEATURE:
<223> OTHER INFORMATION: synthetic

<400> SEQUENCE: 526

```
Ala Gln Asn Leu Glu Leu Pro Trp Thr
1               5
```

<210> SEQ ID NO 527
<211> LENGTH: 27
<212> TYPE: DNA
<213> ORGANISM: Artificial Sequence
<220> FEATURE:
<223> OTHER INFORMATION: synthetic

<400> SEQUENCE: 527

```
tctcaaagta cacatgttcc gtacacg                                27
```

<210> SEQ ID NO 528
<211> LENGTH: 9
<212> TYPE: PRT
<213> ORGANISM: Artificial Sequence
<220> FEATURE:
<223> OTHER INFORMATION: synthetic

<400> SEQUENCE: 528

```
Ser Gln Ser Thr His Val Pro Tyr Thr
1               5
```

<210> SEQ ID NO 529
<211> LENGTH: 27
<212> TYPE: DNA
<213> ORGANISM: Artificial Sequence
<220> FEATURE:
<223> OTHER INFORMATION: synthetic

<400> SEQUENCE: 529

```
ttgcagagta catattttcc tctcacg                                27
```

```
<210> SEQ ID NO 530
<211> LENGTH: 9
<212> TYPE: PRT
<213> ORGANISM: Artificial Sequence
<220> FEATURE:
<223> OTHER INFORMATION: synthetic

<400> SEQUENCE: 530

Leu Gln Ser Thr Tyr Phe Pro Leu Thr
1               5

<210> SEQ ID NO 531
<211> LENGTH: 27
<212> TYPE: DNA
<213> ORGANISM: Artificial Sequence
<220> FEATURE:
<223> OTHER INFORMATION: synthetic

<400> SEQUENCE: 531
ttgcagagta catttttcc gtacacg                                         27

<210> SEQ ID NO 532
<211> LENGTH: 9
<212> TYPE: PRT
<213> ORGANISM: Artificial Sequence
<220> FEATURE:
<223> OTHER INFORMATION: synthetic

<400> SEQUENCE: 532

Leu Gln Ser Ile His Phe Pro Tyr Thr
1               5

<210> SEQ ID NO 533
<211> LENGTH: 27
<212> TYPE: DNA
<213> ORGANISM: Artificial Sequence
<220> FEATURE:
<223> OTHER INFORMATION: synthetic

<400> SEQUENCE: 533
ctacaatatg ctagttctcc tccgacg                                        27

<210> SEQ ID NO 534
<211> LENGTH: 9
<212> TYPE: PRT
<213> ORGANISM: Artificial Sequence
<220> FEATURE:
<223> OTHER INFORMATION: synthetic

<400> SEQUENCE: 534

Leu Gln Tyr Ala Ser Ser Pro Pro Thr
1               5

<210> SEQ ID NO 535
<211> LENGTH: 27
<212> TYPE: DNA
<213> ORGANISM: Artificial Sequence
<220> FEATURE:
<223> OTHER INFORMATION: synthetic

<400> SEQUENCE: 535
ctccagtttc atcgttcccc gtggacg                                        27

<210> SEQ ID NO 536
<211> LENGTH: 9
<212> TYPE: PRT
<213> ORGANISM: Artificial Sequence
```

```
<220> FEATURE:
<223> OTHER INFORMATION: synthetic

<400> SEQUENCE: 536

Leu Gln Phe His Arg Ser Pro Trp Thr
1               5

<210> SEQ ID NO 537
<211> LENGTH: 27
<212> TYPE: DNA
<213> ORGANISM: Artificial Sequence
<220> FEATURE:
<223> OTHER INFORMATION: synthetic

<400> SEQUENCE: 537
ctgcaaaata ggaaaattcc tctcacg                                      27

<210> SEQ ID NO 538
<211> LENGTH: 9
<212> TYPE: PRT
<213> ORGANISM: Artificial Sequence
<220> FEATURE:
<223> OTHER INFORMATION: synthetic

<400> SEQUENCE: 538

Leu Gln Asn Arg Lys Ile Pro Leu Thr
1               5

<210> SEQ ID NO 539
<211> LENGTH: 27
<212> TYPE: DNA
<213> ORGANISM: Artificial Sequence
<220> FEATURE:
<223> OTHER INFORMATION: synthetic

<400> SEQUENCE: 539
cagcaacatt ttagtactcc gtggacg                                      27

<210> SEQ ID NO 540
<211> LENGTH: 9
<212> TYPE: PRT
<213> ORGANISM: Artificial Sequence
<220> FEATURE:
<223> OTHER INFORMATION: synthetic

<400> SEQUENCE: 540

Gln Gln His Phe Ser Thr Pro Trp Thr
1               5

<210> SEQ ID NO 541
<211> LENGTH: 27
<212> TYPE: DNA
<213> ORGANISM: Artificial Sequence
<220> FEATURE:
<223> OTHER INFORMATION: synthetic

<400> SEQUENCE: 541
cagcaatata gcacctatcc tctcacg                                      27

<210> SEQ ID NO 542
<211> LENGTH: 9
<212> TYPE: PRT
<213> ORGANISM: Artificial Sequence
<220> FEATURE:
<223> OTHER INFORMATION: synthetic

<400> SEQUENCE: 542
```

Gln Gln Tyr Ser Thr Tyr Pro Leu Thr
1               5

<210> SEQ ID NO 543
<211> LENGTH: 24
<212> TYPE: DNA
<213> ORGANISM: Artificial Sequence
<220> FEATURE:
<223> OTHER INFORMATION: synthetic

<400> SEQUENCE: 543
cagcaatata gcaactatct cacg                    24

<210> SEQ ID NO 544
<211> LENGTH: 8
<212> TYPE: PRT
<213> ORGANISM: Artificial Sequence
<220> FEATURE:
<223> OTHER INFORMATION: synthetic

<400> SEQUENCE: 544

Gln Gln Tyr Ser Asn Tyr Leu Thr
1               5

<210> SEQ ID NO 545
<211> LENGTH: 27
<212> TYPE: DNA
<213> ORGANISM: Artificial Sequence
<220> FEATURE:
<223> OTHER INFORMATION: synthetic

<400> SEQUENCE: 545
caacagagta acagctggcc tctcacg                    27

<210> SEQ ID NO 546
<211> LENGTH: 9
<212> TYPE: PRT
<213> ORGANISM: Artificial Sequence
<220> FEATURE:
<223> OTHER INFORMATION: synthetic

<400> SEQUENCE: 546

Gln Gln Ser Asn Ser Trp Pro Leu Thr
1               5

<210> SEQ ID NO 547
<211> LENGTH: 24
<212> TYPE: DNA
<213> ORGANISM: Artificial Sequence
<220> FEATURE:
<223> OTHER INFORMATION: synthetic

<400> SEQUENCE: 547
cagcagtgga attatcctct cacg                    24

<210> SEQ ID NO 548
<211> LENGTH: 8
<212> TYPE: PRT
<213> ORGANISM: Artificial Sequence
<220> FEATURE:
<223> OTHER INFORMATION: synthetic

<400> SEQUENCE: 548

Gln Gln Trp Asn Tyr Pro Leu Thr
1               5

<210> SEQ ID NO 549
<211> LENGTH: 27
<212> TYPE: DNA
<213> ORGANISM: Artificial Sequence
<220> FEATURE:
<223> OTHER INFORMATION: synthetic

<400> SEQUENCE: 549
cagcagtgga gtaataaacc gctcacg         27

<210> SEQ ID NO 550
<211> LENGTH: 9
<212> TYPE: PRT
<213> ORGANISM: Artificial Sequence
<220> FEATURE:
<223> OTHER INFORMATION: synthetic

<400> SEQUENCE: 550

Gln Gln Trp Ser Asn Lys Pro Leu Thr
1               5

<210> SEQ ID NO 551
<211> LENGTH: 27
<212> TYPE: DNA
<213> ORGANISM: Artificial Sequence
<220> FEATURE:
<223> OTHER INFORMATION: synthetic

<400> SEQUENCE: 551
caacagtaca gtgattcccc gtacacg         27

<210> SEQ ID NO 552
<211> LENGTH: 9
<212> TYPE: PRT
<213> ORGANISM: Artificial Sequence
<220> FEATURE:
<223> OTHER INFORMATION: synthetic

<400> SEQUENCE: 552

Gln Gln Tyr Ser Asp Ser Pro Tyr Thr
1               5

<210> SEQ ID NO 553
<211> LENGTH: 27
<212> TYPE: DNA
<213> ORGANISM: Artificial Sequence
<220> FEATURE:
<223> OTHER INFORMATION: synthetic

<400> SEQUENCE: 553
cagcaaagga gtagtttccc gtacacg         27

<210> SEQ ID NO 554
<211> LENGTH: 9
<212> TYPE: PRT
<213> ORGANISM: Artificial Sequence
<220> FEATURE:
<223> OTHER INFORMATION: synthetic

<400> SEQUENCE: 554

Gln Gln Arg Ser Ser Phe Pro Tyr Thr
1               5

<210> SEQ ID NO 555
<211> LENGTH: 24
<212> TYPE: DNA

```
<213> ORGANISM: Artificial Sequence
<220> FEATURE:
<223> OTHER INFORMATION: synthetic

<400> SEQUENCE: 555
cagcaaagta gggaatatta cacg                                          24

<210> SEQ ID NO 556
<211> LENGTH: 8
<212> TYPE: PRT
<213> ORGANISM: Artificial Sequence
<220> FEATURE:
<223> OTHER INFORMATION: synthetic

<400> SEQUENCE: 556

Gln Gln Ser Arg Glu Tyr Tyr Thr
1               5

<210> SEQ ID NO 557
<211> LENGTH: 27
<212> TYPE: DNA
<213> ORGANISM: Artificial Sequence
<220> FEATURE:
<223> OTHER INFORMATION: synthetic

<400> SEQUENCE: 557
cagcaaagta ataaggatcc attcacg                                       27

<210> SEQ ID NO 558
<211> LENGTH: 9
<212> TYPE: PRT
<213> ORGANISM: Artificial Sequence
<220> FEATURE:
<223> OTHER INFORMATION: synthetic

<400> SEQUENCE: 558

Gln Gln Ser Asn Lys Asp Pro Phe Thr
1               5

<210> SEQ ID NO 559
<211> LENGTH: 27
<212> TYPE: DNA
<213> ORGANISM: Artificial Sequence
<220> FEATURE:
<223> OTHER INFORMATION: synthetic

<400> SEQUENCE: 559
caaaatggtc acagttttcc gtggacg                                       27

<210> SEQ ID NO 560
<211> LENGTH: 9
<212> TYPE: PRT
<213> ORGANISM: Artificial Sequence
<220> FEATURE:
<223> OTHER INFORMATION: synthetic

<400> SEQUENCE: 560

Gln Asn Gly His Ser Phe Pro Trp Thr
1               5

<210> SEQ ID NO 561
<211> LENGTH: 27
<212> TYPE: DNA
<213> ORGANISM: Artificial Sequence
<220> FEATURE:
<223> OTHER INFORMATION: synthetic
```

```
<400> SEQUENCE: 561
caacattttt ggagtgctcc gtggacg                                          27

<210> SEQ ID NO 562
<211> LENGTH: 9
<212> TYPE: PRT
<213> ORGANISM: Artificial Sequence
<220> FEATURE:
<223> OTHER INFORMATION: synthetic

<400> SEQUENCE: 562

Gln His Phe Trp Ser Ala Pro Trp Thr
1               5

<210> SEQ ID NO 563
<211> LENGTH: 27
<212> TYPE: DNA
<213> ORGANISM: Artificial Sequence
<220> FEATURE:
<223> OTHER INFORMATION: synthetic

<400> SEQUENCE: 563
caggagtgga gtagttaccc actcacg                                          27

<210> SEQ ID NO 564
<211> LENGTH: 9
<212> TYPE: PRT
<213> ORGANISM: Artificial Sequence
<220> FEATURE:
<223> OTHER INFORMATION: synthetic

<400> SEQUENCE: 564

Gln Glu Trp Ser Ser Tyr Pro Leu Thr
1               5

<210> SEQ ID NO 565
<211> LENGTH: 27
<212> TYPE: DNA
<213> ORGANISM: Artificial Sequence
<220> FEATURE:
<223> OTHER INFORMATION: synthetic

<400> SEQUENCE: 565
cagcacagtt gggagtttcc attcacg                                          27

<210> SEQ ID NO 566
<211> LENGTH: 9
<212> TYPE: PRT
<213> ORGANISM: Artificial Sequence
<220> FEATURE:
<223> OTHER INFORMATION: synthetic

<400> SEQUENCE: 566

Gln His Ser Trp Glu Phe Pro Phe Thr
1               5

<210> SEQ ID NO 567
<211> LENGTH: 27
<212> TYPE: DNA
<213> ORGANISM: Artificial Sequence
<220> FEATURE:
<223> OTHER INFORMATION: synthetic

<400> SEQUENCE: 567
cagcacagtt gggattttcc attcacg                                          27
```

<210> SEQ ID NO 568
<211> LENGTH: 9
<212> TYPE: PRT
<213> ORGANISM: Artificial Sequence
<220> FEATURE:
<223> OTHER INFORMATION: synthetic

<400> SEQUENCE: 568

Gln His Ser Trp Asp Phe Pro Phe Thr
1               5

<210> SEQ ID NO 569
<211> LENGTH: 27
<212> TYPE: DNA
<213> ORGANISM: Artificial Sequence
<220> FEATURE:
<223> OTHER INFORMATION: synthetic

<400> SEQUENCE: 569
cagcacagtt gggatttttcc attcacg                                           27

<210> SEQ ID NO 570
<211> LENGTH: 9
<212> TYPE: PRT
<213> ORGANISM: Artificial Sequence
<220> FEATURE:
<223> OTHER INFORMATION: synthetic

<400> SEQUENCE: 570

Gln His Ser Trp Gly Phe Pro Phe Thr
1               5

<210> SEQ ID NO 571
<211> LENGTH: 507
<212> TYPE: DNA
<213> ORGANISM: Artificial Sequence
<220> FEATURE:
<223> OTHER INFORMATION: synthetic

<400> SEQUENCE: 571
atgtctacca acccgaaacc gcagaaaaaa aacaaacgta acaccaaccg tcgtccgcag         60
gacgttaaat tcccgggtgg tggtcagatc gttggtggtg tttacctgct gccgcgtcgt        120
ggtccgcgtc tgggtgttcg tgctacgcgt aaaacctctg aacgttctca gccgcgtggg        180
cgtcgtcagc cgatcccgaa agctcgtcgt ccggaaggtc gtacctgggc tcagccgggt        240
tacccgtggc cgctgtacgg taacgaaggt tgcggttggg ctggttggct gctgtctccg        300
cgtggatctc gtccgtcttg gggtccgacc gacccgcgtc gtcgttctcg taaccttggt        360
aaagttatcg ataccctgac ctgcggtttc gctgacctga tggttacat accgctggtt         420 ggagctccgc tgggtggtgc tgctcgtgct ctggcgcatg gcgtgcgtgt tctggaagat        480
ggcgtcaact atgccaccgg taatctg                                           507

<210> SEQ ID NO 572
<211> LENGTH: 169
<212> TYPE: PRT
<213> ORGANISM: Artificial Sequence
<220> FEATURE:
<223> OTHER INFORMATION: synthetic

<400> SEQUENCE: 572

Met Ser Thr Asn Pro Lys Pro Gln Lys Lys Asn Lys Arg Asn Thr Asn
1               5                   10                  15

```
Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu
                165

<210> SEQ ID NO 573
<211> LENGTH: 21
<212> TYPE: PRT
<213> ORGANISM: Artificial Sequence
<220> FEATURE:
<223> OTHER INFORMATION: synthetic

<400> SEQUENCE: 573

Met Gly Tyr Ile Pro Leu Val Gly Ala Pro Leu Gly Gly Ala Ala Arg
1               5                   10                  15

Ala Leu Ala His Gly
            20

<210> SEQ ID NO 574
<211> LENGTH: 21
<212> TYPE: PRT
<213> ORGANISM: Artificial Sequence
<220> FEATURE:
<223> OTHER INFORMATION: synthetic

<400> SEQUENCE: 574

Gly Ala Pro Leu Gly Gly Ala Ala Arg Ala Leu Ala His Gly Val Arg
1               5                   10                  15

Val Leu Glu Asp Gly
            20

<210> SEQ ID NO 575
<211> LENGTH: 21
<212> TYPE: PRT
<213> ORGANISM: Artificial Sequence
<220> FEATURE:
<223> OTHER INFORMATION: synthetic

<400> SEQUENCE: 575

Leu Ala His Gly Val Arg Val Leu Glu Asp Gly Val Asn Tyr Ala Thr
1               5                   10                  15

Gly Asn Leu Pro Gly
            20
```

-continued

```
<210> SEQ ID NO 576
<211> LENGTH: 39
<212> TYPE: PRT
<213> ORGANISM: Artificial Sequence
<220> FEATURE:
<223> OTHER INFORMATION: synthetic

<400> SEQUENCE: 576

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly Cys
        35

<210> SEQ ID NO 577
<211> LENGTH: 53
<212> TYPE: PRT
<213> ORGANISM: Artificial Sequence
<220> FEATURE:
<223> OTHER INFORMATION: synthetic

<400> SEQUENCE: 577

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly Gln Tyr Ile Lys Ala Asn Ser Lys Phe Ile
        35                  40                  45

Gly Ile Thr Glu Leu
    50

<210> SEQ ID NO 578
<211> LENGTH: 38
<212> TYPE: PRT
<213> ORGANISM: Artificial Sequence
<220> FEATURE:
<223> OTHER INFORMATION: Synthetic

<400> SEQUENCE: 578

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly
        35

<210> SEQ ID NO 579
<211> LENGTH: 48
<212> TYPE: PRT
<213> ORGANISM: Artificial Sequence
<220> FEATURE:
<223> OTHER INFORMATION: Synthetic

<400> SEQUENCE: 579

Gly Tyr Ile Pro Leu Val Gly Ala Pro Leu Gly Gly Ala Ala Arg Ala
1               5                   10                  15

Leu Ala His Gly Val Arg Val Leu Glu Asp Gly Val Asn Tyr Ala Thr
            20                  25                  30

Gly Asn Leu Pro Gly Gln Gln Lys Phe Gln Phe Gln Phe Glu Gln Gln
        35                  40                  45
```

```
<210> SEQ ID NO 580
<211> LENGTH: 6
<212> TYPE: PRT
<213> ORGANISM: Artificial Sequence
<220> FEATURE:
<223> OTHER INFORMATION: Synthetic

<400> SEQUENCE: 580

His His His His His His
1               5

<210> SEQ ID NO 581
<211> LENGTH: 41
<212> TYPE: DNA
<213> ORGANISM: Artificial Sequence
<220> FEATURE:
<223> OTHER INFORMATION: Synthetic

<400> SEQUENCE: 581
aagcagtggt atcaacgcag agtaccccccc cccccccccc c          41

<210> SEQ ID NO 582
<211> LENGTH: 13
<212> TYPE: PRT
<213> ORGANISM: Artificial Sequence;
<220> FEATURE:
<223> OTHER INFORMATION: Synthetic

<400> SEQUENCE: 582

Leu Ser Pro Arg Gly Ser Arg Pro Ser Trp Gly Pro Thr
1               5                   10

<210> SEQ ID NO 583
<211> LENGTH: 112
<212> TYPE: PRT
<213> ORGANISM: Artificial Sequence;
<220> FEATURE:
<223> OTHER INFORMATION: Synthetic

<400> SEQUENCE: 583

Asp Ile Val Leu Thr Gln Ser Pro Ala Ser Leu Ile Val Ser Leu Gly
1               5                   10                  15

Gln Arg Ala Thr Ile Ser Cys Arg Ala Ser Lys Ser Val Asn Glu Tyr
            20                  25                  30

Gly Tyr Thr Tyr Met His Trp Tyr Gln Gln Lys Pro Gly Leu Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

<210> SEQ ID NO 584
<211> LENGTH: 126
<212> TYPE: PRT
<213> ORGANISM: Artificial Sequence;
<220> FEATURE:
<223> OTHER INFORMATION: Synthetic

<400> SEQUENCE: 584

Gln Ile Gln Leu Lys Glu Ser Gly Pro Ala Val Ile Lys Pro Ser Gln
```

```
                1               5                   10                  15
Ser Leu Ser Leu Thr Cys Ile Val Ser Gly Phe Ser Ile Thr Ser Ser
                20                  25                  30

Val Tyr Cys Trp Gln Trp Ile Arg Gln Pro Pro Gly Lys Gly Leu Glu
            35                  40                  45

Trp Met Gly Arg Ile Cys Tyr Asp Gly Ser Val Asp Tyr Ser Pro Ser
        50                  55                  60

Ile Thr Ser Arg Gly Thr Ile Ser Arg Asp Thr Ser Leu Asn Lys Val
65                  70                  75                  80

Phe Phe Gln Leu Ser Ser Val Thr Asn Glu Asp Thr Ala Met Tyr Tyr
                85                  90                  95

Cys Ser Arg Glu Asn His Ile Asp Tyr Tyr Asp Thr Tyr Pro Ser
            100                 105                 110

Phe Asp Val Trp Gly Ala Gly Thr Thr Val Thr Val Ser Ser
            115                 120                 125
```

<210> SEQ ID NO 585
<211> LENGTH: 15
<212> TYPE: PRT
<213> ORGANISM: Artificial Sequence;
<220> FEATURE:
<223> OTHER INFORMATION: Synthetic

<400> SEQUENCE: 585

```
Arg Ala Ser Lys Ser Val Asn Glu Tyr Gly Tyr Thr Tyr Met His
1               5                   10                  15
```

<210> SEQ ID NO 586
<211> LENGTH: 7
<212> TYPE: PRT
<213> ORGANISM: Artificial Sequence;
<220> FEATURE:
<223> OTHER INFORMATION: Synthetic

<400> SEQUENCE: 586

```
Leu Ala Ser Asn Leu Asp Ser
1               5
```

<210> SEQ ID NO 587
<211> LENGTH: 9
<212> TYPE: PRT
<213> ORGANISM: Artificial Sequence;
<220> FEATURE:
<223> OTHER INFORMATION: Synthetic

<400> SEQUENCE: 587

```
Gln His Ser Arg Glu Leu Pro Tyr Thr
1               5
```

<210> SEQ ID NO 588
<211> LENGTH: 12
<212> TYPE: PRT
<213> ORGANISM: Artificial Sequence;
<220> FEATURE:
<223> OTHER INFORMATION: Synthetic

<400> SEQUENCE: 588

```
Gly Phe Ser Ile Thr Ser Ser Val Tyr Cys Trp Gln
1               5                   10
```

<210> SEQ ID NO 589
<211> LENGTH: 16
<212> TYPE: PRT

<213> ORGANISM: Artificial Sequence;
<220> FEATURE:
<223> OTHER INFORMATION: Synthetic

<400> SEQUENCE: 589

Arg Ile Cys Tyr Asp Gly Ser Val Asp Tyr Ser Pro Ser Ile Thr Ser
1               5                   10                  15

<210> SEQ ID NO 590
<211> LENGTH: 16
<212> TYPE: PRT
<213> ORGANISM: Artificial Sequence;
<220> FEATURE:
<223> OTHER INFORMATION: Synthetic

<400> SEQUENCE: 590

Glu Asn His Ile Asp Tyr Tyr Asp Thr Thr Tyr Pro Ser Phe Asp Val
1               5                   10                  15

<210> SEQ ID NO 591
<211> LENGTH: 336
<212> TYPE: DNA
<213> ORGANISM: Artificial Sequence;
<220> FEATURE:
<223> OTHER INFORMATION: Synthetic

<400> SEQUENCE: 591
gacattgtgc tgacacagtc tcctgcttcc ttaattgtat ctctgggca gagggccacc      60 atctcgtgca gggccagcaa aagtgtcaat gaatatggct atacttatat gcactggtac     120
caacagaaac caggactgcc acccaaactc ctcatctatc ttgcatccaa tctagattct     180
ggggtccctg ccaggttcag tggcagtggg tctgggacag acttcaccct caacatccat     240
cctgtggagg aggaggatgc tgcaacctat tactgtcaac acagtaggga gcttccgtac     300
acgttcggag ggggaccaa gctggaaata aaacgg                                336

<210> SEQ ID NO 592
<211> LENGTH: 378
<212> TYPE: DNA
<213> ORGANISM: Artificial Sequence;
<220> FEATURE:
<223> OTHER INFORMATION: Synthetic

<400> SEQUENCE: 592
cagattcagc tgaaggagtc tggacctgct gtcatcaagc catcacagtc actgtctctc      60
acgtgcatag tctctggatt ctccatcaca agtagtgttt attgctggca gtggatccgc     120
cagcccccag gaaagggatt agagtggatg gacgcatct gttatgacgg ttcagttgac      180
tatagtccat ccatcacaag ccgcggcacc atctccagag acacatctct gaacaaagtc     240
tttttccagc tgagctctgt gacaaatgag gacacagcca tgtactactg ttccagggaa     300
aaccatattg attactacga tactacttat ccgtccttcg atgtctgggg cgcagggacc     360
acggtcaccg tctcctca                                                    378

<210> SEQ ID NO 593
<211> LENGTH: 19
<212> TYPE: PRT
<213> ORGANISM: Artificial Sequence;
<220> FEATURE:
<223> OTHER INFORMATION: Synthetic

<400> SEQUENCE: 593

Ser Gly Ser Gly Gly Trp Leu Leu Ser Pro Arg Gly Ser Arg Pro Ser

-continued

```
1               5                   10                  15

Trp Gly Pro

<210> SEQ ID NO 594
<211> LENGTH: 19
<212> TYPE: PRT
<213> ORGANISM: Artificial Sequence;
<220> FEATURE:
<223> OTHER INFORMATION: Synthetic

<400> SEQUENCE: 594

Ser Gly Ser Gly Leu Leu Ser Pro Arg Gly Ser Arg Pro Ser Trp Gly
1               5                   10                  15

Pro Thr Asp

<210> SEQ ID NO 595
<211> LENGTH: 19
<212> TYPE: PRT
<213> ORGANISM: Artificial Sequence;
<220> FEATURE:
<223> OTHER INFORMATION: Synthetic

<400> SEQUENCE: 595

Ser Gly Ser Gly Ser Pro Arg Gly Ser Arg Pro Ser Trp Gly Pro Thr
1               5                   10                  15

Asp Pro Arg

<210> SEQ ID NO 596
<211> LENGTH: 19
<212> TYPE: PRT
<213> ORGANISM: Artificial Sequence;
<220> FEATURE:
<223> OTHER INFORMATION: Synthetic

<400> SEQUENCE: 596

Ser Gly Ser Gly Arg Gly Ser Arg Pro Ser Trp Gly Pro Thr Asp Pro
1               5                   10                  15

Arg Arg Arg

<210> SEQ ID NO 597
<211> LENGTH: 19
<212> TYPE: PRT
<213> ORGANISM: Artificial Sequence;
<220> FEATURE:
<223> OTHER INFORMATION: Synthetic

<400> SEQUENCE: 597

Ser Gly Ser Gly Ser Arg Pro Ser Trp Gly Pro Thr Asp Pro Arg Arg
1               5                   10                  15

Arg Ser Arg

<210> SEQ ID NO 598
<211> LENGTH: 19
<212> TYPE: PRT
<213> ORGANISM: Artificial Sequence;
<220> FEATURE:
<223> OTHER INFORMATION: Synthetic

<400> SEQUENCE: 598

Ser Gly Ser Gly Pro Ser Trp Gly Pro Thr Asp Pro Arg Arg Arg Ser
1               5                   10                  15

Arg Asn Leu
```

<210> SEQ ID NO 599
<211> LENGTH: 19
<212> TYPE: PRT
<213> ORGANISM: Artificial Sequence;
<220> FEATURE:
<223> OTHER INFORMATION: Synthetic

<400> SEQUENCE: 599

Ser Gly Ser Gly Trp Gly Pro Thr Asp Pro Arg Arg Arg Ser Arg Asn
1               5                   10                  15

Leu Gly Lys

<210> SEQ ID NO 600
<211> LENGTH: 19
<212> TYPE: PRT
<213> ORGANISM: Artificial Sequence;
<220> FEATURE:
<223> OTHER INFORMATION: Synthetic

<400> SEQUENCE: 600

Ser Gly Ser Gly Pro Thr Asp Pro Arg Arg Arg Ser Arg Asn Leu Gly
1               5                   10                  15

Lys Val Ile

<210> SEQ ID NO 601
<211> LENGTH: 15
<212> TYPE: PRT
<213> ORGANISM: Artificial Sequence;
<220> FEATURE:
<223> OTHER INFORMATION: Synthetic

<400> SEQUENCE: 601

Gly Trp Leu Leu Ser Pro Arg Gly Ser Arg Pro Ser Trp Gly Pro
1               5                   10                  15

<210> SEQ ID NO 602
<211> LENGTH: 15
<212> TYPE: PRT
<213> ORGANISM: Artificial Sequence;
<220> FEATURE:
<223> OTHER INFORMATION: Synthetic

<400> SEQUENCE: 602

Leu Leu Ser Pro Arg Gly Ser Arg Pro Ser Trp Gly Pro Thr Asp
1               5                   10                  15

<210> SEQ ID NO 603
<211> LENGTH: 15
<212> TYPE: PRT
<213> ORGANISM: Artificial Sequence;
<220> FEATURE:
<223> OTHER INFORMATION: Synthetic

<400> SEQUENCE: 603

Ser Pro Arg Gly Ser Arg Pro Ser Trp Gly Pro Thr Asp Pro Arg
1               5                   10                  15

<210> SEQ ID NO 604
<211> LENGTH: 15
<212> TYPE: PRT
<213> ORGANISM: Artificial Sequence;
<220> FEATURE:
<223> OTHER INFORMATION: Synthetic

<400> SEQUENCE: 604

Arg Gly Ser Arg Pro Ser Trp Gly Pro Thr Asp Pro Arg Arg Arg
1               5                   10                  15

<210> SEQ ID NO 605
<211> LENGTH: 15
<212> TYPE: PRT
<213> ORGANISM: Artificial Sequence;
<220> FEATURE:
<223> OTHER INFORMATION: Synthetic

<400> SEQUENCE: 605

Ser Arg Pro Ser Trp Gly Pro Thr Asp Pro Arg Arg Arg Ser Arg
1               5                   10                  15

<210> SEQ ID NO 606
<211> LENGTH: 15
<212> TYPE: PRT
<213> ORGANISM: Artificial Sequence;
<220> FEATURE:
<223> OTHER INFORMATION: Synthetic

<400> SEQUENCE: 606

Ser Pro Arg Gly Ser Arg Pro Ser Trp Gly Pro Thr Asp Pro Arg
1               5                   10                  15

<210> SEQ ID NO 607
<211> LENGTH: 15
<212> TYPE: PRT
<213> ORGANISM: Artificial Sequence;
<220> FEATURE:
<223> OTHER INFORMATION: Synthetic

<400> SEQUENCE: 607

Arg Gly Ser Arg Pro Ser Trp Gly Pro Thr Asp Pro Arg Arg Arg
1               5                   10                  15

<210> SEQ ID NO 608
<211> LENGTH: 15
<212> TYPE: PRT
<213> ORGANISM: Artificial Sequence;
<220> FEATURE:
<223> OTHER INFORMATION: Synthetic

<400> SEQUENCE: 608

Ser Arg Pro Ser Trp Gly Pro Thr Asp Pro Arg Arg Arg Ser Arg
1               5                   10                  15

<210> SEQ ID NO 609
<211> LENGTH: 15
<212> TYPE: PRT
<213> ORGANISM: Artificial Sequence;
<220> FEATURE:
<223> OTHER INFORMATION: Synthetic

<400> SEQUENCE: 609

Pro Ser Trp Gly Pro Thr Asp Pro Arg Arg Arg Ser Arg Asn Leu
1               5                   10                  15

<210> SEQ ID NO 610
<211> LENGTH: 15
<212> TYPE: PRT
<213> ORGANISM: Artificial Sequence;
<220> FEATURE:
<223> OTHER INFORMATION: Synthetic

<400> SEQUENCE: 610

Trp Gly Pro Thr Asp Pro Arg Arg Arg Ser Arg Asn Leu Gly Lys

```
<210> SEQ ID NO 611
<211> LENGTH: 15
<212> TYPE: PRT
<213> ORGANISM: Artificial Sequence;
<220> FEATURE:
<223> OTHER INFORMATION: Synthetic

<400> SEQUENCE: 611

Pro Thr Asp Pro Arg Arg Arg Ser Arg Asn Leu Gly Lys Val Ile
1               5                   10                  15

<210> SEQ ID NO 612
<211> LENGTH: 23
<212> TYPE: PRT
<213> ORGANISM: Artificial Sequence;
<220> FEATURE:
<223> OTHER INFORMATION: Synthetic

<400> SEQUENCE: 612

Gly Ser Arg Pro Ser Trp Gly Pro Thr Asp Pro Arg His Arg Ser Arg
1               5                   10                  15

Asn Val Gly Lys Val Ile Asp
            20

<210> SEQ ID NO 613
<211> LENGTH: 23
<212> TYPE: PRT
<213> ORGANISM: Artificial Sequence;
<220> FEATURE:
<223> OTHER INFORMATION: Synthetic

<400> SEQUENCE: 613

Gly Ser Arg Pro Ser Trp Gly Pro Asn Asp Pro Arg His Arg Ser Arg
1               5                   10                  15

Asn Val Gly Lys Val Ile Asp
            20

<210> SEQ ID NO 614
<211> LENGTH: 23
<212> TYPE: PRT
<213> ORGANISM: Artificial Sequence;
<220> FEATURE:
<223> OTHER INFORMATION: Synthetic

<400> SEQUENCE: 614

Gly Ser Arg Pro Ser Trp Gly Pro Ser Asp Pro Arg His Arg Ser Arg
1               5                   10                  15

Asn Val Gly Lys Val Ile Asp
            20

<210> SEQ ID NO 615
<211> LENGTH: 11
<212> TYPE: PRT
<213> ORGANISM: Artificial Sequence;
<220> FEATURE:
<223> OTHER INFORMATION: Synthetic

<400> SEQUENCE: 615

Arg Gly Ser Arg Pro Ser Trp Gly Pro Thr Asp
1               5                   10

<210> SEQ ID NO 616
<211> LENGTH: 11
```

```
<212> TYPE: PRT
<213> ORGANISM: Artificial Sequence;
<220> FEATURE:
<223> OTHER INFORMATION: Synthetic

<400> SEQUENCE: 616

Arg Gly Ser Arg Pro Ser Trp Gly Pro Asn Asp
1               5                   10
```

DETECTION METHODS EMPLOYING HCV CORE LIPID AND DNA BINDING DOMAIN MONOCLONAL ANTIBODIES

CROSS-REFERENCE TO RELATED APPLICATIONS

The present application is a Continuation-In-Part of U.S. application Ser. No. 15/079,013, filed Mar. 23, 2016, which is a Divisional of U.S. application Ser. No. 14/138,991, filed Dec. 23, 2013, now U.S. Pat. No. 9,371,374, issued Jun. 21, 2016, which claims priority to U.S. Provisional Patent Application No. 61/783,529, filed Mar. 14, 2013, each of which are herein incorporated by reference in their entireties.

STATEMENT REGARDING JOINT RESEARCH AGREEMENT

The subject matter disclosed and claimed herein was made by or on behalf of the parties to a joint research agreement, Icahn School of Medicine at Mount Sinai and Abbott Laboratories, within the meaning of 35 U.S.C. § 100(h) and § 1.9(e). The joint research agreement was in effect on or before the date the claimed invention was made, and the claimed invention was made as a result of activities undertaken within the scope of the joint research agreement.

Immediately before the paragraph beginning on page 1, line 4, please insert the following heading:

FIELD OF THE INVENTION

The present disclosure provides detection methods employing HCV core lipid binding domain and DNA binding domain monoclonal antibodies or antibody fragments. In certain embodiments, the lipid binding domain monoclonal antibody or antibody fragment recognizes an epitope in amino acids 141 to 161 of HCV core protein and the DNA binding domain antibody or antibody fragment recognizes an epitope in amino acids 95-123 (e.g., in amino acids 99-117) of HCV core protein.

BACKGROUND OF THE INVENTION

According to WHO statistics, as many as 170 million people worldwide are infected by hepatitis C virus (HCV), a viral infection of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections is a combination of interferon and ribavirin drugs, however the treatment is not effective in all cases and the liver transplantation is indicated in hepatitis C-related end-stage liver disease. At present, there is no vaccine available to prevent HCV infection, therefore all precautions to avoid infection must be taken.

Thus, patient care, as well as the prevention of transmission of Hepatitis C Virus (HCV) by blood and blood products or by close personal contact requires extreme vigilance using sensitive detection assays. This creates a need for specific methods for screening and identifying carriers of HCV and HCV-contaminated blood or blood products. Serological determination of HCV exposure relies on the detection of HCV present in human blood plasma or sera. This can be accomplished by detection of distinct structural and non-structural proteins encoded by the virus.

The HCV virus is a (+) sense single-stranded enveloped RNA virus in the Hepacivirus genus of the Flaviviridae family. The viral genome is approximately 10 kb in length and encodes a 3011 amino acid polyprotein precursor. The HCV genome has a large single open reading frame (ORF) coding for a unique polyprotein. This polyprotein is co- and post-translationally processed by cellular and viral proteases into three structural proteins, i.e., core, E1 and E2 and at least six non-structural NS2, NS3, NS4A, NS4B, NS5A and NS5B proteins. (Choo et al., Science 244: 359-362 (1989)).

Following HCV exposure, the virus enters a susceptible hepatocyte and viral replication occurs. During an eclipse phase period of approximately 10 days, viral presence is not evident (i.e., viral RNA cannot be detected), serum transaminase levels are within normal limits, and no evidence exists of an immune response to HCV (Busch et al., Transfusion 40:143 (2000)). Typically, about 10 days following exposure, HCV RNA can be detected, often with viral loads between 100,000-120,000,000 HCV RNA copies per ml of serum. Typically several weeks later, an increase in ALT levels is observed, indicating inflammation of the liver; antibodies are detected an average of about 70 days after exposure.

Screening of blood for exposure to HCV, either by the detection of antibodies to HCV or by the detection of viral-specific molecules (e.g., HCV RNA or HCV core proteins) in serum/plasma is an integral and important part of patient care. Blood or blood products derived from individuals identified as having been exposed to HCV, by these tests, are removed from the blood supply and are not utilized for distribution to recipients of blood products (see, e.g., U.S. Pat. No. 6,172,189). These tests may also be utilized in the clinical setting to diagnose liver disease attributable to HCV infection.

Serologic antibody tests rely on the use of recombinant antigens or synthetic peptides, representing selected fragments of the viral polyprotein. The first generation anti-HCV screening tests were based on detection of antibodies directed against a recombinant protein (HCV genotype 1a) originating from sequences located in the nonstructural NS-4 protein (C100-3) (Choo et al., Science 244:359 (1989); Kuo et al., Science 244:362 (1989)). The first generation assays failed to detect antibodies in approximately 10% of individuals having chronic HCV infection and up to 10-30% of individuals presenting with acute HCV infection. The second generation anti-HCV assays have incorporated recombinant proteins from three different regions of the HCV genome (HCV genotype 1a), including amino acid sequences from the core, NS3, and NS4 protein (Mimms et al., Lancet 336:1590 (1990); Bresters et al., Vox Sang 62:213 (1992)), allowing a marked improvement over the first generation tests in identifying HCV infected blood donors (Aach et al., N Engl J Med 325:1325 (1991); Kleinman et al., Transfusion 32:805 (1992). The second-generation assays detect antibodies in close to 100% of chronic HCV cases (Hino K., Intervirology 37:77 (1994)) and in nearly 100% of the acute cases by 12 weeks post infection (Alter et al., N Engl J Med 327:1899 (1992); Bresters et al., Vox Sang 62:213 (1992)). The third generation test includes a recombinant protein expressing amino acid sequences from the NS5 region, as well as antigens from the core, NS3 and NS4. Some studies have indicated a slight improvement in sensitivity in comparing the third generation tests to second generation tests (Lee et al., Transfusion 35:845 (1995); Courouce et al. Transfusion 34:790-795 (1994)), but this improvement is largely attributed to changes in the NS3 protein rather than the inclusion of NS5 (Courouce et al., Lancet 343:853 (1994)).

In general, the second and third generation HCV antibody tests detect exposure to HCV about 70 days after exposure. Since HCV establishes persistent, and in many cases lifelong infection, the detection of antibodies to HCV represents a very efficient method for determining exposure to HCV. However, antibody testing alone will frequently fail to detect HCV infected individuals during the first 70 days after exposure.

It has been suggested that testing for HCV antigen detects exposure to HCV significantly earlier than antibody testing and represents an alternative to nucleic acid testing for detecting exposure to HCV during the pre-seroconversion period. The HCV antigen detection test is rapid, simple, may-not require sample extraction or other pretreatment, and is not as prone to handling errors (e.g., contamination) as may occur in the HCV RNA tests. Thus, HCV core antigen tests present a practical alternative to HCV RNA for screening blood donors or for monitoring antiviral therapy.

Existing HCV antigen tests rely on detecting the presence of the HCV core antigen in serum or plasma. HCV core protein is a structural protein of HCV comprising the first 191 amino acids of the polyprotein and that forms the internal viral coat encapsidating the genomic RNA. Two different types of serologic assays have been developed which permit detection of HCV core antigens in serum. One assay format detects HCV core antigens in subjects prior to seroconversion and is utilized in screening blood donors, while the other assay format detects core antigens only in hepatitis C patients, regardless of their HCV antibody status, and is utilized in clinical laboratories to diagnose exposure to HCV or to monitor antiviral therapy. The currently available core antigen detection assays all use antibodies against the DNA binding domain of HCV core which is located at amino acids 1-125 of the core protein. The core protein also contains a lipid binding domain that is located between amino acids 134-171. To date there have been no antigens described from that section of core protein and until now it has been assumed that core detection required antibodies against the DNA binding domain.

Thus, binding proteins that can readily detect HCV core antigen will markedly improve the available methods of detection of HCV exposure in a patient. Thus, there is a recognized need for new antibodies that can readily be employed in screening tests.

SUMMARY OF THE INVENTION

The present disclosure provides detection methods employing HCV core lipid binding domain and DNA binding domain monoclonal antibodies or antibody fragments. In certain embodiments, the lipid binding domain monoclonal antibody or antibody fragment recognizes an epitope in amino acids 141 to 161 of HCV core protein and the DNA binding domain antibody or antibody fragment recognizes an epitope in amino acids 95-123 (e.g., in amino acids 99-117) of HCV core protein. The DNA binding domain, may also be referred to as the RNA binding domain. Both DNA and RNA binding domain refer to amino acids 1-125 of the HCV core protein.

In some embodiments, provided herein are methods for the detection of HCV protein in a test sample comprising: (i) contacting a test sample suspected of containing HCV with a first antibody, or antigen-binding portion thereof, directed against an epitope in the DNA (or RNA) binding domain of an HCV core protein to form a complex between the first antibody, or the antigen-binding portion thereof, and the HCV core protein located within the test sample, wherein the epitope in the DNA binding domain is within amino acids 95-123 of full-length HCV core protein; (ii) contacting the complex formed in step (i) with a second antibody, or antigen-binding portion thereof, directed against an epitope in the lipid binding domain of HCV core protein, to form a complex between the second antibody, or the antigen-binding portion thereof, and the complex formed in step (i), wherein the epitope in the lipid binding domain is within amino acids 141-161 of full-length HCV core protein; and (iii) detecting the complex formed in step (ii).

In some embodiments, provided herein are methods for the detection of HCV protein in a test sample comprising: (i) contacting a test sample suspected of containing HCV with a first antibody, or antigen-binding portion thereof, directed against an epitope in the lipid binding domain of an HCV core protein, to form a complex between the first antibody, or the antigen-binding portion thereof, and the HCV core protein located within the test sample; wherein the epitope in the lipid binding domain is within amino acids 141-161 of full-length HCV core protein, (ii) contacting the complex formed in step (i) with a second antibody, or antigen-binding portion thereof, directed against an epitope in the DNA (or RNA) binding domain of HCV core protein to form a complex between the second antibody, or the antigen-binding portion thereof, and the complex formed in step (i), wherein the epitope in the DNA binding domain is within amino acids 95-123 of full-length HCV core protein; and (iii) detecting the complex formed in step (ii).

In other embodiments, provide herein are systems or compositions comprising: (i) a first antibody, or antigen-binding portion thereof, directed against an epitope in the DNA binding domain of HCV core antigen, wherein the epitope in the DNA binding domain is within amino acids 95-123 of full-length HCV core protein; and (ii) a second antibody, or antigen-binding portion thereof, directed against an epitope in the lipid binding domain of HCV core antigen, wherein the epitope in the lipid binding domain is within amino acids 141-161 of full-length HCV core antigen. In certain embodiments, the first and second antibodies, or fragments thereof, are in separate or the same container. In further embodiments, the systems further comprise a sample from a subject suspect of being infected with HCV.

In other embodiments, the first and/or second antibody, or the antigen-binding portion thereof, is detectably labeled with a label, and wherein the detecting the complex in step (iii) comprises detecting the label. In some embodiments, provide herein the HCV core protein in the complex is an HCV mini-core protein. In particular embodiments, the HCV core protein in the complex is a full-length HCV core protein. In additional embodiments, the epitope in the DNA binding domain is within amino acids 95-117 of full-length HCV core protein. In further embodiments, the epitope in the DNA binding domain is within amino acids 103-109 or 103-110 of full-length HCV core protein. In certain embodiments, the epitope in the DNA binding domain is within amino acids 99-123 of full-length HCV core protein. In some embodiments, the epitope in the DNA binding domain is within amino acids 109-113 of full-length HCV core protein.

In certain embodiments, the present invention provides a monoclonal antibody that is specifically immunoreactive with the lipid binding domain of HCV core antigen. More particularly, the HCV core antigen is amino acid residues 134-171 of HCV. In more particular embodiments, the antibody specifically binds at least one epitope formed by amino acid sequence MGYIPLVGAPLGGAARALAH-GVRVLEDGVNYATGNLPG (SEQ ID NO:578). In more specific embodiments, the antibody is immunoreactive with an epitope formed by amino acids 141-161, 134-154 and 151-171 of HCV core antigen.

Another aspect of the invention provides a monoclonal antibody that is specifically immunoreactive with the lipid binding domain of HCV core antigen, wherein said monoclonal antibody has a heavy chain variable domain selected from the group consisting of the antibodies listed in FIG. 1A, and a light chain variable domain selected from the group consisting of the antibodies listed in FIG. 1B.

It is contemplated that any of the antibodies described herein may be prepared as immunoassay reagents, more particularly, such reagents preferably are labeled with a detectable label.

In still other embodiments, immunoassay reagents of the invention comprise one or more of the antibodies disclosed herein being bound to a solid phase.

The immunoassay reagents comprising the antibodies of the invention may further comprise an additional antibody against an HCV antigen. For example, such an additional antibody is an additional anti-core antibody.

A further aspect of the invention is directed to an immunoassay for the detection of HCV in a test sample, said immunoassay comprising:

(i) contacting a test sample suspected of containing HCV with a first antibody directed against HCV core antigen to form a complex between said first antibody and antigen located within said test sample;

(ii) contacting said complex formed in step (i) with an antibody to a core lipid binding domain, to form a complex between said antibody to a core lipid binding domain and antigen in the complex formed in step (i) wherein said antibody to a core lipid binding domain is detectably labeled; and (iii) detecting the label of the complex formed in step (ii).

In more specific embodiments, the immunoassay may further be characterized in that the first antibody is directed to the DNA binding domain of HCV core antigen. In more particular embodiments the antibody employed in step (ii) is labeled with a fluorescent label. In exemplary embodiments, the label is acridinium.

In some embodiments, the immunoassay is one in which the antibody of step (i) is coated on solid phase. In specific preferred embodiments, the antibody of step (i) comprises an antibody that is distinct from the antibody of step (ii). Alternatively, the immunoassay is one in which the antibody of step (i) comprises an antibody that is the same as the antibody of step (ii).

Any of the immunoassays of the invention may be used on a test sample obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patient, the method optionally further comprises modifying the therapeutic/prophylactic treatment of the patient as needed to improve efficacy.

As will be described in further detail herein, it will be understood by those skilled in the art that any of the immunoassays of the invention may be readily adapted for use in an automated system or a semi-automated system.

BRIEF DESCRIPTION OF SEVERAL VIEWS OF THE DRAWINGS

FIG. 1A shows the heavy chain variable domains of preferred antibodies of the present invention. FIG. 1A discloses SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, and 100, respectively, in order of appearance.

FIG. 1B shows the light chain variable domains of preferred antibodies of the present invention. FIG. 1B discloses SEQ ID NOS: 302, 304, 306, 308, 310, 312, 314, 316, 318, 320, 322, 324, 324, 326, 328, 330, 332, 334, 336, 338, 340, 340, 342, 344, 346, 348, 350, 352, 354, 356, 358, 360, 362, 364, 366, 368, 370, 370, 370, 372, 374, 376, 376, 378, 380, 382, 384, 386, 388, 388, 388, respectively, in order of appearance.

FIGS. 2A and 2B show two representations of a clustering diagram derived from the alignments of FIG. 1A.

FIG. 8A shows the amino acid sequence of Neo4 antibody light chain variable region. This figure shows the light chain CDRs underlined, which include CDRL1 (RASKSVNEY-GYTYMH; SEQ ID NO:585), CDRL2 (LASNLDS; SEQ ID NO:586), and CDRL3 (QHSRELPYT, SEQ ID NO:587).

FIG. 8B shows the amino acid sequence of Neo4 antibody heavy chain variable region. This figure shows the heavy chain CDRs underlined, which include CDRH1 (GFSITSS-VYCWQ; SEQ ID NO:588), CDRH2 (RICYDGSVDYSP-SITS; SEQ ID NO:589), and CDRH3 (ENHIDYYDT-TYPSFDV; SEQ ID NO:590).

FIG. 9A shows the nucleic acid sequence encoding the light chain variable region of Neo4 (SEQ ID NO:591).

FIG. 9B shows the nucleic acid sequence encoding the heavy chain variable region of Neo4 (SEQ ID NO:592).

DETAILED DESCRIPTION OF THE INVENTION

Figure 2B:
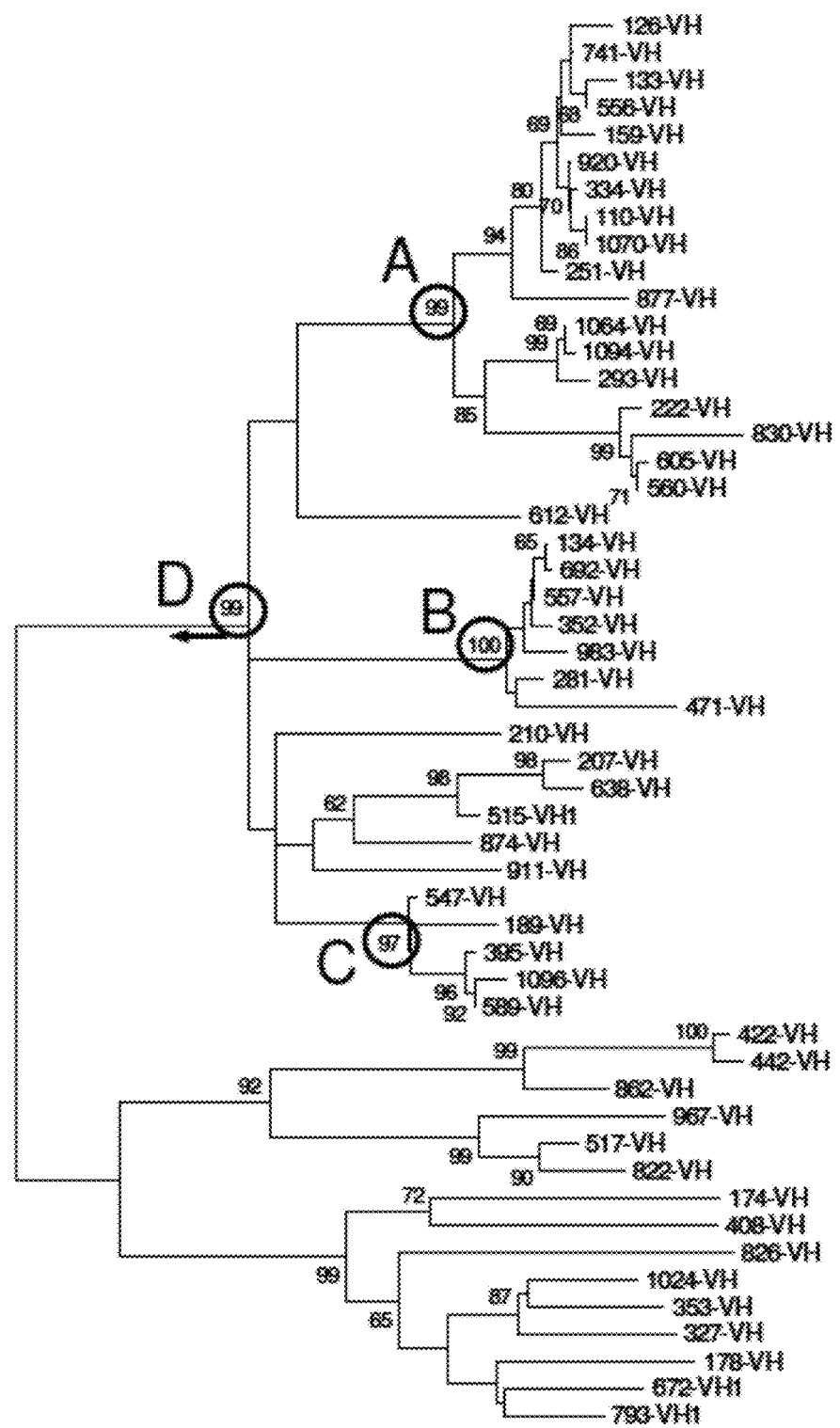
Figure 3:
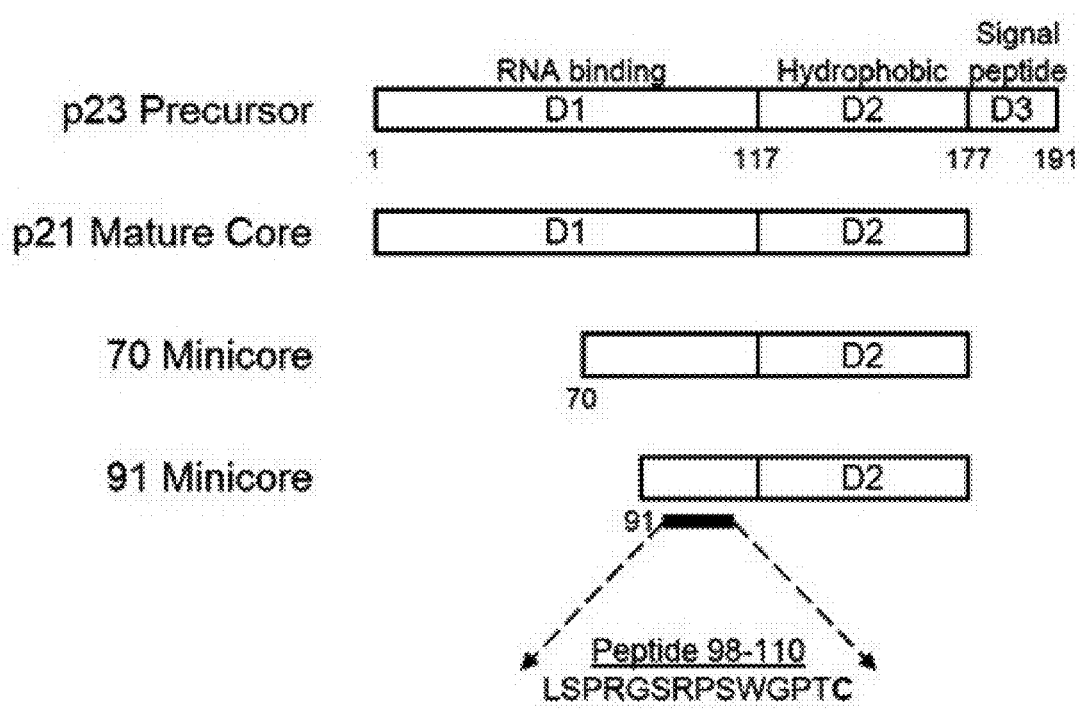
FIG. 3 shows the core proteins encoded by HCV, including the precursor p23, mature core p21, and N-terminally deleted 70 and 91 mini-cores. Both p21 mature core and minicore proteins contain the hydrophobic domain D2 which interacts with lipids. Minicores contain only part of domain D1, the RNA-binding domain (aka, the DNA binding domain). The location of an immunogen used in Example 14 (peptides 98-110; SEQ ID NO582) with respect to full length HCV core and mini-cores 70 and 91 is shown in this figure.

The present disclosure provides detection methods employing HCV core lipid binding domain and DNA binding domain monoclonal antibodies or antibody fragments. In certain embodiments, the lipid binding domain monoclonal antibody or antibody fragment recognizes an epitope in amino acids 141 to 161 of HCV core protein and the DNA binding domain antibody or antibody fragment recognizes an epitope in amino acids 95-123 (e.g., in amino acids 99-117) of HCV core protein.

In some embodiments, the present invention describes the development of monoclonal antibodies directed against the Hepatitis C Virus core antigen, specifically, the lipid binding domain of core antigen between amino acids 134-171. The immunogen used was a synthetic peptide and screening of hybridomas utilized both the immunogen peptide and a set of three overlapping smaller peptides within the 134-171 region. In addition, a recombinant core antigen representing amino acids 1-169 was used for screening to determine the efficacy of the identified monoclonal antibodies as reactive with HCV core protein. The antibodies are delineated by their reactivity to the antigen, the immunogen peptide, and smaller overlapping peptides comprising the immunogen. Binding kinetics of the antibodies to the immunogen peptide were determined by SPR (surface plasmon resonance) using a BIAcore 4000 instrument. Immunoreactivity to the recombinant core antigen was determined by standard ELISA.

In addition, to show that the monoclonal antibodies of the present invention were useful in analyzing the presence of core antigen, core antigen capture microtiter plate assays were performed by using monoclonal antibodies directed to epitopes within the DNA binding domain of HCV core (e.g. amino acids 1-125) as the capture reagent and the 134-171-directed antibodies of the present invention as detection reagents. These assays produced results to demonstrate the utility of the 134-171-directed antibodies of the invention for HCV core antigen detection immunoassays. This is the first demonstration of an antigen capture assay that independently targets two major domains of HCV core for capture and detection. Previously reported core antigen detection assays use antibodies that bind to epitopes within the DNA binding domain (e.g., amino acids 1-125).

To produce the antibodies of the present invention, mice were immunized with a synthetic peptide comprised of HCV core genotype 1 consensus sequence from amino acids 134-171 linked to BSA. More specifically, the immunogen had the sequence of:

```
                                       (SEQ ID NO: 578)
    MGYIPLVGAPLGGAARALAHGVRVLEDGVNYATGNLPG.
```

In addition, the binding of the monoclonal antibodies to three specific N-terminally biotinylated epitope regions also was characterized and is further discussed in the Examples. Specifically, the three overlapping epitopes were derived from the above region and had the sequences of:

```
    HCVc 134-154
                                       (SEQ ID NO: 573)
    MGYIPLVGAPLGGAARALAHG

HCVc 141-161
                                       (SEQ ID NO: 574)
    GAPLGGAARALAHGVRVLEDG

HCVc 151-171
                                       (SEQ ID NO: 575)
    LAHGVRVLEDGVNYATGNLPG
```

The immunogen was conjugated to BSA to produce the antibodies. In other embodiments, the immunogen was conjugated to TT and fibrils. The TT sequence is often used to provide a more robust immune response in mice. The sequence of the TT conjugate was:

```
                                       (SEQ ID NO: 577)
    Ac-Met-Gly-Tyr-Ile-Pro-Leu-Val-Gly-Ala-Pro-Leu-

Gly-Gly-Ala-Ala-Arg-Ala-Leu-Ala-His-Gly-Val-Arg-

Val-Leu-Glu-Asp-Gly-Val-Asn-Tyr-Ala-Thr-Gly-Asn-

Leu-Pro-Gly-Gln-Tyr-Ile-Lys-Ala-Asn-Ser-Lys-Phe-

Ile-Gly-Ile-Thr-Glu-Leu-NH2.
```

The sequence of the fibrils conjugate was:

```
                                       (SEQ ID NO: 579)
    Ac-Met-Gly-Tyr-Ile-Pro-Leu-Val-Gly-Ala-Pro-Leu-

Gly-Gly-Ala-Ala-Arg-Ala-Leu-Ala-His-Gly-Val-Arg-

Val-Leu-Glu-Asp-Gly-Val-Asn-Tyr-Ala-Thr-Gly-Asn-

Leu-Pro-Gly-Gln-Gln-Lys-Phe-Gln-Phe-Gln-Phe-Glu-

Gln-Gln-NH2.
```

B-lymphocytes were fused with a myeloma fusion partner to create hybridomas that were then screened for reactivity against the immunogen peptide, three overlapping peptides within the immunogen peptide sequence, and a recombinant HCV core antigen. Kinetic profiling using a Biacore 4000 allowed for identification of clusters of antibodies wherein the clusters are defined by their ability to bind to the immunogen peptide, or shorter peptides overlapping the 134-171 region. Combining these results with immunoreactivity, or lack thereof, for the recombinant antigen as determined by ELISA, allowed further delineation of the antibodies into groups with similar characteristics (specificities).

To briefly summarize the screening results discussed in further detail in the Examples, the greatest immune response was seen in mice immunized with the peptide linked to BSA. Additionally, the response from these mice was predominantly focused on the amino acid 141-161 region, although there was also some response to the amino acid 134-154 and 151-171 regions as well. With the HCV peptide linked to TT, an immune response was seen, however, this response was not as strong as with BSA. The response was spread over all 3 epitope regions. On the other hand, mice immunized using the amino acid 134-171 peptide linked to a peptide that would form fibril networks failed to show a significant immune response. The antibodies of the present invention are described in further detail in FIGS. 1A and 1B, and in the Examples.

The HCV core antigen used for these studies was expressed in *E. coli* and purified in a two-step process using IMAC followed by reverse-phase HPLC based on previously published methods (Boulant et al., J. Virol. (2005), 79(17):11353-11365).

In this manner a significant array of monoclonal antibodies that are specific for the lipid binding domain of HCV core have been produced. These monoclonal antibodies have utility in development of diagnostic assays for the detection of HCV core antigen in the serum and plasma of infected individuals. Prior to the present invention, there has been no reported generation of monoclonal antibodies to the multiple epitopes within the core amino acid 134-171 region that have shown binding activity to the HCV full length core peptide. The availability of the monoclonal antibodies of the present invention allows for the development of immunoassays for core antigen detection wherein two major domains of HCV core antigen are targeted. Previous core antigen assays described the use of monoclonals directed to epitopes within amino acid 1-125 (nucleic acid binding domain). Because the previously described monoclonal antibodies were only able to target the nucleic acid binding domain of HCV core, they were at best inefficient and often ineffective at detection of core protein fragments, breakdown products, or smaller core proteins derived by internal translation initiation. The present invention for the first time overcomes these inadequacies in the previous assays by providing specific monoclonal antibodies that can be used as reagents to more efficiently and rapidly detect HCV core present in a test sample.

More particularly, the antibodies described herein are reagents useful for detection of HCV core antigen and are useful reagents to facilitate investigation of the life cycle of HCV. As noted above, HCV encoded proteins are expressed in a concerted process in which ribosomes bind to the internal ribosome entry site (IRES) and initiate translation, leading to synthesis of the viral polyprotein, which is cleaved to produce the classical HCV proteins, p21 core, E1, E2, p'7, and the nonstructural proteins. None of the viral enzymes, including the viral polymerase, can be made without the initiation of translation in the core gene region. Because of this temporal relationship, it is believed that translation events in this region control the expression all HCV proteins. Hence, a complete understanding of the core gene and its gene products is essential to understanding the life cycle of the virus and may shed light on our understanding of mechanisms of virus pathogenicity. Recently, a new family of conserved viral proteins, referred to as minicores have been described (Eng et al., J Virol. 2009 April; 83(7): 3104-3114). These proteins are encoded in the same reading frame as the core gene but, are believed to be derived from internal translation initiation events rather than post-translational processing of the full-length core protein. One of the minicore proteins described is termed "91 minicore" named for the presumed initiator codon within core. It is hypothesized that "134 minicore" also exists, being derived from translation initiation at codon 134 which encodes a methionine in many HCV isolates. However, reagents are not available that allow detection of minicores that are, essentially, derived from the lipid binding domain. Such proteins may play an important role in HCV persistence.

Since the monoclonal antibodies were raised against a linear, synthetic peptide derived from HCV core 134-171, it is unknown whether they will bind to the native, complete core antigen or processed forms of HCV core that exist in infected individuals. However, provided that the monoclonal antibodies of the present invention are able at least to bind one or more epitopes presented by the linear HCV core region from amino acids 134-171, it is contemplated that such binding will be sufficient to render these monoclonal antibodies significantly useful in HCV detection assays. Some of the monoclonal antibodies of the present invention react with recombinant core antigen while others do not, suggesting that within the core amino acid 134-171 region, there are both linear and conformational epitopes. Antibodies recognizing either linear or conformational epitopes are very useful tools for the study of virus assembly within infected cells and the virus life cycle generally.

Finally, these reagents can also be used in immunoassays where it is desirable to determine the presence of only the lipid binding domain. Since little is known about circulating levels of minicores in infected individuals it is possible that they are present at much higher levels than core proteins containing the region of amino acids 1-125. In providing antibodies that detect HCV core peptides outside of the region of amino acids 1-125, the present invention provides HCV core antigen detection assays with much greater sensitivity than those currently available.

DEFINITIONS

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CHL CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG-3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g., cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.R5 and complement Clq, respectively. Neonatal Fc receptors (FcRn) are the critical components determining the circulating half-life of antibodies. At least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al. Nature; 264: 415-20; Thies et al 1999 J Mol Biol; 293: 67-79.). Mutation of cysteine residues within the hinge regions to prevent heavy chain-heavy chain disulfide bonds will destabilize dimerization of CH3 domains. Residues responsible for CH3 dimerization have been identified (Dall'Acqua 1998 Biochemistry 37: 9266-73.). Therefore, it is possible to generate a monovalent half-Ig. Interestingly, these monovalent half Ig molecules have been found in nature for both IgG and IgA subclasses (Seligman 1978 Ann Immunol 129: 855-70; Biewenga et al 1983 Clin Exp Immunol 51: 395-400). The stoichiometry of FcRn: Ig Fc region has been determined to be 2:1 (West et al. 2000 Biochemistry 39: 9698-708), and half Fc is sufficient for mediating FcRn binding (Kim et al 1994 Eur J Immunol; 24: 542-548.). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However the half Ig molecule may have certain advantage in tissue penetration due to its smaller size than that of a regular antibody. At least one amino acid residue may be replaced in the constant region of the binding protein of the present disclosure, for example the Fc region, such that the dimerization of the heavy chains is disrupted, resulting in half DVD Ig molecules. The anti-inflammatory activity of IgG is completely dependent on sialylation of the N-linked glycan of the IgG Fc fragment. The precise glycan requirements for anti-inflammatory activity has been determined, such that an appropriate IgG1 Fc fragment can be created, thereby generating a fully recombinant, sialylated IgG1 Fc with greatly enhanced potency (Anthony, R. M., et al. (2008) Science 320:373-376).

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. (See, e.g., Holliger, P., et al. (1993) Proc. Natl. Acad. Sci. USA 90:6444-6448; Poljak, R. J., et al. (1994) Structure 2:1121-1123). Such antibody binding portions are known in the art. (See, e.g., Kontermann and Dubel eds., Antibody Engineering (2001) Springer-Verlag. New York. 790 pp. (ISBN 3-540-41354-5)). In addition, single chain antibodies also include "linear antibodies" comprising a pair of tandem Fv segments (VH-CH1-VH-CH1) which, together with complementary light chain polypeptides, form a pair of antigen binding regions (Zapata et al., Protein Eng. 8(10): 1057-1062 (1995); and U.S. Pat. No. 5,641,870).

The term "multivalent binding protein" is used throughout this specification to denote a binding protein comprising two or more antigen binding sites. In one aspect, the multivalent binding protein is engineered to have three or more antigen binding sites, and is generally not a naturally occurring antibody. Dual variable domain (DVD) binding proteins comprise two or more antigen binding sites and are tetravalent or multivalent binding proteins. DVDs as described herein can be monospecific, i.e., capable of one antigen such as HCV core protein, or multispecific, i.e. capable of binding two or more antigens. DVD binding proteins comprising two heavy chain DVD polypeptides and two light chain DVD polypeptides are referred to as DVD-Ig, and are described for example in U.S. Pat. No. 7,612,181, the disclosure of which is herein incorporated by reference in its entirety. Each half of a DVD-Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

An "immunoglobulin constant domain" refers to a heavy or light chain constant domain. Human IgG heavy chain and light chain constant domain amino acid sequences are known in the art.

The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody", as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R. (1997) TIB Tech. 15:62-70; Azzazy H., and Highsmith W. E. (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see, Taylor, L. D., et al. (1992) Nucl. Acids Res. 20:6287-6295; Kellermann S-A. and Green L. L. (2002) Current Opinion in Biotechnology 13:593-597; Little M. et al. (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. Such recombinant human antibodies can be subjected to in vitro mutagenesis (or, when an animal transgenic for human Ig sequences is used, in vivo somatic mutagenesis) such that the amino acid sequences of the VH and VL regions of the recombinant antibodies are sequences that, while derived from and related to human germline VH and VL sequences, may not naturally exist within the human antibody germline repertoire in vivo.

An "affinity matured" antibody is an antibody with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. Affinity matured antibodies are produced by procedures known in the art. Marks et al. BidlTechnology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); Hawkins et al, J. Mol. Biol. 226:889-896 (1992) and selective mutation at selective mutagenesis positions, contact or hypermutation positions with an activity enhancing amino acid residue as described in U.S. Pat. No. 6,914,128 B1.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. In one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region. As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

As used herein, the term "neutralizing" refers to counteracting the biological activity of an antigen when a binding protein specifically binds the antigen. In one aspect, the neutralizing binding protein binds the cytokine and reduces its biologically activity by at least about 20%, 40%, 60%, 80%, 85% or more.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition structural definitions of epitopes (overlapping, similar, identical) are informative, but functional definitions are often more relevant as they encompass structural (binding) and functional (modulation, competition) parameters.

The term "surface plasmon resonance", as used herein, refers to an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J.). For further descriptions, see Jonsson, U., et al. (1993) Ann. Biol. Clin. 51:19-26; Jonsson, U., et al.

(1991) Biotechniques 11:620-627; Johnsson, B., et al. (1995) J. Mol. Recognit. 8:125-131; and Johnnson, B., et al. (1991) Anal. Biochem. 198:268-277.

The term "Kon", as used herein, is intended to refer to the on rate constant for association of a binding protein (e.g., an antibody) to the antigen to form the, e.g., antibody/antigen complex as is known in the art. The "Kon" also is known by the terms "association rate constant", or "ka", as used interchangeably herein. This value indicating the binding rate of an antibody to its target antigen or the rate of complex formation between an antibody and antigen.

The term "Koff", as used herein, is intended to refer to the off rate constant for dissociation, or "dissociation rate constant", of a binding protein (e.g., an antibody) from the, e.g., antibody/antigen complex as is known in the art. This value indicates the dissociation rate of an antibody from its target antigen or separation of Ab-Ag complex over time into free antibody and antigen.

The term "KD" as used herein, is intended to refer to the "equilibrium dissociation constant", and refers to the value obtained in a titration measurement at equilibrium, or by dividing the dissociation rate constant (koff) by the association rate constant (kon). The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

"Label" and "detectable label" mean a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In one aspect, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., 3H, 14C, 35S, 90Y, 99Tc, 111In, 125I, 131I, 177Lu, 166Ho, or 153Sm); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

The term "conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. In one aspect, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The terms "isolated polynucleotide" and "isolated nucleotide molecule" as used interchangeably herein mean a polynucleotide (e.g., of genomic, cDNA, or synthetic origin, or some combination thereof) that, is not associated with all or a portion of a polynucleotide with which the "isolated polynucleotide" or "isolated nucleotide molecule" is found in nature, or does not occur in nature as part of a larger sequence. An "isolated polynucleotide" or "isolated nucleotide molecule" may be operably linked to a polynucleotide that it is not linked to in nature.

The terms "regulate" and "modulate" as used interchangeably herein refer to a change or an alteration in the activity of a molecule of interest (e.g., the biological activity of a cytokine). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction. Correspondingly, the term "modulator," as used herein, is a compound capable of changing or altering an activity or function of a molecule of interest (e.g., the biological activity of a cytokine). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

"Patient" and "subject" may be used interchangeably herein to refer to an animal, such as a mammal, including a primate (for example, a human, a monkey, and a chimpanzee), a non-primate (for example, a cow, a pig, a camel, a llama, a horse, a goat, a rabbit, a sheep, a hamster, a guinea pig, a cat, a dog, a rat, a mouse, a whale), a bird (e.g., a duck or a goose), and a shark. Preferably, the patient or subject is a human, such as a human being treated or assessed for a disease, disorder or condition, a human at risk for a disease, disorder or condition, a human having a disease, disorder or condition, and/or human being treated for a disease, disorder or condition.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

"Component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide or other analyte as above, such as a composition comprising an analyte such as polypeptide, which is optionally immobilized on a solid support, such as by binding to an anti-analyte (e.g., anti-polypeptide) antibody. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to analyte (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

Monoclonal Antibodies

FIGS. 1A and 1B show the sequences of various antibodies that have been determined to be specific for HCV core antigen and more particularly, have been determined to be specific for the lipid binding domain of HCV core antigen. It has been found that these monoclonal antibodies are specifically immunoreactive with the lipid binding domain of HCV core antigen. More specifically, it is found that the antibodies of the present invention specifically bind at least one epitope formed by amino acid sequence MGYIPLVGA-PLGGAARALAHGVRVLED GVNYATGNLPG (SEQ ID NO:578). More particularly, the monoclonal antibodies at least are immunoreactive with an epitope formed by amino acids 141-161, 134-154 and 151-171 of HCV core antigen. Given the disclosure of these monoclonal antibodies, the present invention contemplates the uses thereof in specific immunoassays to facilitate a rapid and efficient detection of the presence of HCV in a test sample by determining the presence of HCV core antigen in such a test sample.

The anti-HCV core binding proteins, including monoclonal antibodies and any derivative (e.g., a fragment or variant) thereof that comprises the CDRs of the heavy and light chains of the monoclonal antibodies described herein (see FIGS. 1A and 1B) provided that such a derivative retains the property of binding specifically to HCV core protein lipid binding domain, can be used in immunoassays for diagnosing or prognosing hepatitis C virus infection in a mammal. As used throughout the present disclosure, "mammal" includes humans and non-human primates, as well as other animals. It will be understood that a target analyte in the immunoassays and related methods is the lipid domain of HCV core protein, and hence the target analyte is HCV core protein which would be present in the sample, such as for example, after HCV infection. Additionally, it should be understood that the immunoassay may detect two or more target analytes provided that at least one of the analytes is HCV core protein, the second or additional target analyte may be another core protein analyte (e.g., the DNA binding domain of HCV core protein) or may be an analyte that is not HCV core protein.

The nucleotide (DNA) sequences and deduced protein sequences encoding the heavy and light chain variable domains of anti-HCV core monoclonal antibodies were obtained by immunizing mice with a synthetic peptide comprised of HCV core genotype 1 consensus sequence from amino acids 134-171 and a tetanus toxoid (TT) peptide sequence. In some embodiments, the amino acid 134-171 sequence was conjugated to BSA. However, in other embodiments, the synthetic peptide also was conjugated to the TT sequence as this is often used to provide a more robust immune response in mice, by methods known to those skilled in the art such as those described in detail herein below and in, for example, Goding, J. W. 1983. Monoclonal Antibodies: Principles and Practice, Pladermic Press, Inc., NY, N.Y., pp. 56 97. Briefly, to produce a human-human hybridoma, a human lymphocyte donor is selected. A donor who is known as infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity. For monoclonal anti-HCV core antibodies, the antibodies must bind to HCV core protein and more specifically, the lipid binding domain of HCV core protein respectively. Cells producing antibodies of the desired specificity are selected. Other methods for obtaining monoclonal antibodies can be used, as known in the art. The Examples below describes how the anti-HCV core monoclonal antibodies were obtained and characterized following isolation of mRNA from hybridoma cells grown in cell culture. Deduced amino acid sequences of the heavy and light chain variable regions for the anti-HCV core monoclonal antibodies of the present invention are listed in FIG. 1A and FIG. 1B, respectively.

The deduced amino acid sequences of the heavy and the light chain domains were assigned SEQ ID NOs and the corresponding cDNAs sequences encoding the same are shown in the Sequence Table in Appendix A.

The cDNA sequences set forth in the Sequence Table represent exemplary embodiments of the disclosed cDNAs. Variations are contemplated in the cDNA sequences shown therein. Such variations include those that will result in a nucleic acid sequence that is capable of directing production of analogs of the corresponding protein shown in the Sequence Table. It will be understood that due to the degeneracy of the genetic code, many substitutions of nucleotides may be made that will lead to a DNA sequence that remains capable of directing production of the corresponding protein or its analogs. All such variant DNA sequences that are functionally equivalent to any of the sequences described herein, are encompassed by the present disclosure.

A variant of any of the binding proteins (as exemplified by monoclonal antibodies of the invention shown in FIGS. 1A and 1B) described herein means a protein (or polypeptide) that differs from a given protein (e.g., an anti-HCV core monoclonal antibody) in amino acid sequence by the addition (e.g., insertion), deletion, or conservative substitution of amino acids, but that retains the biological activity of the given protein. A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to IL-18. Use of "variant" herein is intended to encompass fragments of a variant unless otherwise contradicted by context.

The antibodies of the present invention or antigen binding fragments of those antibodies (e.g., fragments that comprise the heavy and light chain CDRs of the antibodies of the present invention) may also be produced by genetic engineering. For example, the technology for expression of both heavy and light chain genes in E. coli is the subject of the PCT patent applications; publication number WO 901443, WO901443, and WO 9014424 and in Huse et al., 1989 Science 246:1275 1281. The present disclosure also encompasses an isolated recombinant vector comprising a nucleic acid molecule as described herein, as well as a host cell comprising such a recombinant vector. A vector is a nucleic acid molecule, which may be a construct, capable of transporting another nucleic acid to which it has been linked. A vector may include any preferred or required operational elements. Preferred vectors are those for which the restriction sites have been described and which contain the operational elements needed for transcription of the nucleic acid sequence. Such operational elements include for example at least one suitable promoter, at least one operator, at least one leader sequence, at least one terminator codon, and any other DNA sequences necessary or preferred for appropriate transcription and subsequent translation of the nucleic acid sequence. Such vectors contain at least one origin of replication recognized by the host organism along with at least one selectable marker and at least one promoter sequence capable of initiating transcription of the nucleic acid sequence. A vector may be a plasmid into which additional DNA segments may be ligated. A vector may be a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as a plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Sequences that are operably linked are in a relationship permitting them to function in their intended manner. A control sequence operably linked to a coding sequence is ligated in such a way that expression of the coding sequence is achieved under conditions compatible with the control sequences. Operably linked sequences include both expression control sequences that are contiguous with the gene of interest and expression control sequences that act in trans or at a distance to control the gene of interest. Expression control sequences are polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. Control sequences include components whose presence is essential for expression and processing, and can also include additional components whose presence is advantageous, for example, leader sequences and fusion partner sequences.

A host cell may be transformed with a vector that introduces exogenous DNA into a host cell in order to render that cell one that recombinantly produces the antibodies of the present invention. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Transformed cells include stably transformed cells in which the inserted DNA is capable of replication either as an autonomously replicating plasmid or as part of the host chromosome, and cells which transiently express the inserted DNA or RNA for limited periods of time.

Suitable host organisms include for example a eukaryotic cell system such as but not limited to cell lines such as HeLa, MRC-5 or CV-1. Host organisms such as host cells are cultured under conditions appropriate for amplification of the vector and expression of the protein, as well known in the art. Expressed recombinant proteins may be detected by any of a number of methods also well known in the art.

Although the HCV detection aspects of the present invention merely need the antibodies to be monoclonal antibodies such that they specifically recognize HCV core antigen, it may in some embodiments be desirable to produce humanized versions of the antibodies of the present invention. "Humanized" antibodies and production thereof is well known to those of skill in the art. General reviews of "humanized" antibodies are provided by Morrison S., 1985 Science 229:1202 and by Oi et al., 1986 BioTechniques 4:214. Suitable "humanized" antibodies can be alternatively produced by CDR or CEA substitution (Jones et al., 1986 Nature 321:552; Verhoeyan et al., 1988 Science 239:1534; Biedler et al. 1988 J. Immunol. 141:4053, the entire disclosures of which are incorporated herein by reference).

In other embodiments, the monoclonal antibodies of the present invention may serve as useful starting materials for the production of engineered and derivatized binding proteins including dual variable domain immunoglobulin (DVD-Ig) binding proteins comprising one or more anti-HCV monoclonal antibodies as described herein. For example, DVD-Ig's with unique binding affinities for HCV core protein may be produced, as described for example in U.S. Pat. No. 7,612,181, the entire disclosure of which is hereby incorporated by reference. DVD-Ig binding proteins are capable of binding one or more targets. Preferably the binding protein comprises a polypeptide chain comprising VD1-(X1)n-VD2-C-(X2)n, wherein VD1 is a first variable domain, VD2 is a second variable domain, C is a constant domain, X1 represents an amino acid or polypeptide, X2 represents an Fc region and n is 0 or 1. The binding protein can be generated using various techniques.

In exemplary techniques, the DVD-Ig can be formed with four polypeptide chains which form four functional antigen binding sites. Thus, for example, the DVD-Ig is capable of binding HCV core protein. The binding protein can be capable of modulating a biological function of HCV core protein, or of neutralizing HCV core protein. Exemplary such binding proteins have at least one heavy chain variable domain comprising an amino acid sequence of at least 90% identity with one of the antibodies of the present invention and at least the corresponding light chain variable domain comprising an amino acid sequence having at least 90% identity with a sequence of that light chain variable domain.

The variable domains of a DVD binding protein can be obtained from parent antibodies, including polyclonal and monoclonal antibodies capable of binding antigens of interest. The monoclonal antibodies that specifically bind to HCV core protein described herein are suitable parent antibodies. Generally, antibodies used for the DVD binding protein may be naturally occurring or may be generated by recombinant technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those as described herein for preparing the anti-HCV core protein monoclonal antibodies, and those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Hybridomas are selected, cloned and further screened for desirable characteristics, including robust hybridoma growth, high antibody production and desirable antibody characteristics, as discussed in Example 1 below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art. In a preferred embodiment, the hybridomas are mouse hybridomas. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an antibody capable of binding a specific antigen.

Recombinant monoclonal antibodies are also generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) Proc. Natl. Acad. Sci. USA 93:7843-7848. In this method, single cells secreting antibodies of interest, e.g., lymphocytes derived from an immunized animal, are identified, and, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to the antigen of interest. The amplified immunoglobulin sequences further can be manipulated in vitro, such as by in vitro affinity maturation methods such as those described in PCT Publication WO 97/29131 and PCT Publication WO 00/56772.

Monoclonal antibodies are also produced by immunizing a non-human animal comprising some, or all, of the human immunoglobulin locus with an antigen of interest. In a preferred embodiment, the non-human animal is a XENOMOUSE® transgenic mouse, an engineered mouse strain that comprises large fragments of the human immunoglobulin loci and is deficient in mouse antibody production. See, e.g., Green et al. Nature Genetics 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE® transgenic mouse produces an adult-like human repertoire of fully human antibodies, and generates antigen-specific human Mabs. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics 15:146-156 (1997), Green and Jakobovits J. Exp. Med. 188:483-495 (1998), the disclosures of which are hereby incorporated by reference.

In vitro methods also can be used to make the parent antibodies, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, US patent application publication 20030186374, and PCT Publication No. WO 97/29131, the contents of each of which are incorporated herein by reference.

Parent antibodies can also be generated using various phage display methods known in the art. In phage display methods, functional antibody domains are displayed on the surface of phage particles that carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies as described herein include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of parent antibodies. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the parent antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the parent antibodies include those disclosed in Wittrup, et al. U.S. Pat. No. 6,699,658 incorporated herein by reference.

The monoclonal antibodies described herein can be further modified to generate CDR grafted and Humanized parent antibodies. CDR-grafted parent antibodies comprise heavy and light chain variable region sequences from a human antibody wherein one or more of the CDR regions of VH and/or VL are replaced with CDR sequences of murine antibodies capable of binding antigen of interest. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs has at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing such antibodies are known in the art (see EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352).

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.html; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immunology.html.www.immunologylink.com/; pathbox.wustl.edu/.about.hcenter/index.-html; www.biotech.ufledu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/aboutjraats/linksl.html; www.recab.uni-hd.de/immuno.bme.nwu.edu/; www.mrc-cpe.cam.ac.uk/imt-doc/pu-blic/INTRO.html; www.ibt.unam.mx/virV_-mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.ukfabout.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stataim.html; www.biosci.missouri.edu/smithgp/index.html; www.cryst.bioc.cam.ac.uk/.abo-ut.fmolina/Webpages/Pept/spottech.html; wwwjerini.de/fr roducts.htm; www.patents.ibm.con/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Parent monoclonal antibodies may be selected from various monoclonal antibodies capable of binding specific targets including, or in addition to, HCV proteins, as well known in the art.

Parent monoclonal antibodies may also be selected from various therapeutic antibodies approved for use, in clinical trials, or in development for clinical use, particularly those that may be applicable in treating symptoms of HCV infection, or in treating conditions or diseases that co-exist with HCV infection, such as cancer, including particularly hepatocellular carcinoma.

As noted throughout the present invention, it may be desirable to label the antibodies of the present invention. A labeled antibody (or a binding protein derived from one of the antibodies of the present invention) comprises the antibody, which is derivatized or linked to another functional molecule (e.g., another peptide or protein). For example, the monoclonal antibody can be derivatized by functionally linking it (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the binding protein with another molecule (such as a streptavidin core region or a polyhistidine tag).

Useful detectable agents with which monoclonal antibody may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. The antibody may also be derivatized with detectable enzymes, such as alkaline phosphatase, horseradish peroxidase, glucose oxidase and the like. When derivatized with a detectable enzyme, the detection is achieved by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A monoclonal antibody of the invention may also be derivatized with biotin, and detected through indirect measurement of avidin or streptavidin binding, or vice versa.

While the compositions of the present invention have demonstrated use in diagnostic applications for determining the presence of HCV core antigen in a test sample, it is contemplated that the compositions of the present invention also may serve a diagnostic or therapeutic purpose for in vivo administration to a mammal. Thus, in some embodiments, the present invention provides pharmaceutical and diagnostic compositions comprising one or more anti-HCV core binding proteins disclosed herein as an active ingredient. Pharmaceutical or diagnostic compositions may comprise any monoclonal antibody described herein, or any combination thereof, and a pharmaceutically acceptable carrier, diluent and/or excipient. Generally, the pharmaceutical and diagnostic compositions are prepared by combining the active ingredient with the carrier, diluent and/or excipient.

The compositions comprising binding proteins as described herein are for use in, but not limited to, diagnosing, detecting, or monitoring a disorder, but may also find use in preventing, treating, managing, or ameliorating of a disorder or one or more symptoms thereof, and/or in research. In a specific embodiment, a composition comprises one or more monoclonal antibodies of the present invention or a binding protein derived from one or more of the monoclonal antibodies of the present invention. In another embodiment, the composition comprises one or more monoclonal antibodies or binding proteins derived therefrom as described herein and one or more diagnostic, prophylactic or therapeutic agents other than monoclonal antibodies or binding proteins derived therefrom as described herein.

Immunoassays

Immunoassays according to the present disclosure include such techniques commonly recognized in the art, including for example radioimmunoassay, Western blot assay, immunofluorescent assay, enzyme immunoassay, chemiluminescent assay, immunohistochemical assay, immunoprecipitation and the like. Standard techniques known in the art for ELISA are well-known and described for example in Methods in Immunodiagnosis, 2nd Edition, Rose and Bigazzi, eds., John Wiley and Sons, 1980 and Campbell et al., Methods of Immunology, W. A. Benjamin, Inc., 1964, both of which are incorporated herein by reference Immunoassays may be a direct, indirect, competitive, or noncompetitive immunoassay as described in the art (Oellerich, M. 1984. J. Clin. Chem. Clin. BioChem 22:895 904). Biological samples appropriate for such detection assays include, but are not limited to blood, plasma, serum, liver, saliva, lymphocytes or other mononuclear cells.

In preferred embodiments, the antibodies described herein are used in immunoassays specific for the detection of HCV. Examples include, but are not limited to, sandwich immunoassay, radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds an analyte of interest such as HCV core (or a fragment thereof) is attached to the surface of a mass spectrometry probe, such as a pre-activated protein chip array. The analyte (or a fragment thereof) is then specifically captured on the biochip, and the captured analyte (or a fragment thereof) is detected by mass spectrometry. Alternatively, the analyte (or a fragment thereof) can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, is an example of a preferred immunoassay.

An immunoassay for determining the presence or amount of human hepatitis C virus in a sample may comprise, for example, combining an HCV core protein binding protein with the sample for a time sufficient for the binding protein to bind to any human hepatitis C virus that may be present in the sample, and determining the presence or amount of human hepatitis C virus present in the sample based on specific binding of the binding protein to the human hepatitis C virus core protein. The disclosure also encompasses an immunoassay device for detecting the presence or absence of human HCV in a sample, wherein the device comprises any of the antibodies described herein immobilized on a solid support. The anti-HCV core antibodies and any analogs thereof may be prepared in the form of a kit, alone, or in combinations with other reagents such as secondary antibodies, for use in immunoassays.

Methods well-known in the art for collecting, handling and processing urine, blood, serum and plasma, and other body fluids, are used in the practice of the present disclosure, for instance, when an anti-HCV core antibody of the present invention is employed as an immunodiagnostic reagent and/or in an analyte immunoassay kit. The test sample can comprise further moieties in addition to the HCV core antigen, including for example, antibodies, antigens, haptens, hormones, drugs, enzymes, receptors, proteins, peptides, polypeptides, oligonucleotides and/or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally may be performed (e.g., as part of a regimen on a commercial platform).

The pretreatment reagent can be any reagent appropriate for use with the immunoassay and kits of the present disclosure. The pretreatment optionally comprises: (a) one or more solvents (e.g., methanol and ethylene glycol) and optionally, salt, (b) one or more solvents and salt, and optionally, detergent, (c) detergent, or (d) detergent and salt. Pretreatment reagents are known in the art, and such pretreatment can be employed as has been previously described, e.g., as used for assays on Abbott TDx, AxSYM®, and ARCHITECT® analyzers (Abbott Laboratories, Abbott Park, as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay Comparison with TDx Monoclonal Whole Blood and EMIT Cyclosporine Assays, Clin. Chem. 45: 432-435 (1999)), and/or as commercially available. Additionally, pretreatment can be performed as described in U.S. Pat. No. 5,135,875, European Patent Pub. No. 0 471 293, U.S. Provisional Patent App. 60/878,017, filed Dec. 29, 2006, and U.S. Patent App. Pub. No. 2008/0020401 (incorporated by reference in its entirety for its teachings regarding pretreatment).

With use of a pretreatment reagent the assay is rendered more sensitive by disruption of preformed/preexisting immune complexes or viral particles in the test sample. In such a pretreated test sample, the anti-HCV core antibody in the sample is separated from the antigen and the remaining antigen in the sample is then tested for the presence of HCV core antigen using the monoclonal antibodies of the present invention. The HCV core antigen in the test sample is thus subjected to an antibody capture step to capture any HCV antigen present in the test sample.

In some other embodiments, use of the pretreatment does not require such a separation step. The entire mixture of test sample and pretreatment reagent are contacted with an antibody specific for the targeted antigen (in this case HCV core antigen, or more particularly, HCV core antigen lipid binding domain). The pretreatment reagent employed for such an assay typically is diluted in the pretreated test sample mixture, either before or during capture by the first antibody that is used to capture the HCV antigen. Despite such dilution, a certain amount of the pretreatment reagent may still be present in the test sample mixture during capture. The capture reagents may be an antibody of the present invention, alternatively, it may be another anti-HCV core antigen antibody or indeed it may be an antibody directed against a non-core protein antigen of HCV (e.g., an antibody against an envelope protein, E1, or E2 or other portion of HCV).

In one assay format, after the test sample is obtained from a subject, a first mixture is prepared. The mixture contains the test sample being assessed for the presence of a given antigen (e.g., in the present case, for the presence of HCV core antigen) and a first specific binding partner (typically an antibody that recognizes an HCV epitope), wherein the first specific binding partner and any HCV antigen contained in the test sample form a first antibody-antigen complex. The order in which the test sample and the first specific binding partner are added to form the mixture is not critical. The first specific binding partner may be immobilized on a solid phase, but in alternative embodiments, the first specific binding partner may be in a solution phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

The methods described are amenable for adaption to systems that utilize microparticle technology including in automated and semi-automated systems wherein the solid phase comprises a microparticle. Such systems include those described in pending U.S. patent application Ser. Nos. 425,651 and 425,643, which correspond to published EPO applications Nos. EP 0 425 633 and EP 0 424 634, respectively, which are incorporated herein by reference.

After the mixture containing the first specific binding partner-analyte complex is formed, any unbound analyte is removed from the complex using any technique known in the art. For example, the unbound analyte can be removed by washing. Desirably, however, the first specific binding partner is present in excess of any analyte present in the test sample in order to optimize maximal binding of the analyte present in the test sample by the first specific binding partner.

After removal of unbound analyte, a second specific binding partner is added to the mixture to form a first specific binding partner-analyte-second specific binding partner complex. The second specific binding partner is preferably an anti-analyte antibody that binds to an epitope on the analyte that differs from the epitope on analyte bound by the first specific binding partner. Simply by way of example, assuming that the assay is for detection of HCV core antigen, a first "capture" antibody is used that is specific for the DNA binding domain of HCV core antigen (alternatively, the first antibody is an anti HCV core antibody that is specific for the HCV core antigen lipid binding domain, such as the antibodies described herein), once this first capture antibody captures HCV core protein from the sample, a second anti-core antigen antibody that binds the lipid binding domain of HCV core antigen (where the first antibody bound the DNA binding domain, or alternatively, where the first antibody is first antibody is specific for the HCV core antigen lipid binding domain, the second antibody could be specific for the DNA binding domain of HCV core antigen). Preferably, in such embodiments, the second specific binding partner is labeled with or contains a detectable label as described above in order to facilitate detection of the (capture antibody-antigen-second antibody) complex.

Any suitable detectable label as is known in the art can be used. For example, the detectable label can be a radioactive label (such as $^3H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with a chemiluminescent agent such as an acridinium compound, detectably labeled first specific binding partner-analyte complexes form. Alternatively, if a second specific binding partner is used and the second specific binding partner is detectably labeled with a chemiluminescent agent such as an acridinium compound, detectably labeled first specific binding partner-analyte-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture (e.g., the source of the hydrogen peroxide being one or more buffers or other solutions that are known to contain hydrogen peroxide) before, simultaneously with, or after the addition of an above-described acridinium compound. Hydrogen peroxide can be generated in situ in a number of ways such as would be apparent to one skilled in the art.

Upon the simultaneous or subsequent addition of at least one basic solution to the sample, a detectable signal, namely, a chemiluminescent signal, indicative of the presence of analyte is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of analyte in the sample can be quantified. Specifically, the amount of analyte in the sample is proportional to the intensity of the signal generated. The amount of analyte present can be quantified by comparing the amount of light generated to a standard curve for analyte or by comparison to a reference standard. The standard curve can be generated using serial dilutions or solutions of known concentrations of analyte by mass spectroscopy, gravimetric methods, and other techniques known in the art. While the above is described with emphasis on use of an acridinium compound as the chemiluminescent agent, one of ordinary skill in the art can readily adapt this description for use of other chemiluminescent agents.

Analyte immunoassays generally can be conducted using any format known in the art, such as, but not limited to, a sandwich format. Specifically, in one immunoassay format, at least two antibodies are employed to capture and quantify analyte, such as human analyte, or a fragment thereof in a sample. More specifically, preferably, the at least two antibodies bind to different epitopes on an analyte (or a fragment thereof) forming an immune complex, which is referred to as a "sandwich." Generally, in the immunoassays one or more antibodies can be used to capture the analyte (or a fragment thereof) in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody," the "detection antibodies," the "conjugate," or the "conjugates"). Thus, in the context of a sandwich immunoassay format, an anti-HCV core antibody of the present invention can be used as a capture antibody, a detection antibody, or both. For example, one anti-HCV core antibody having a domain that can bind a first epitope (e.g., the lipid binding domain of HCV core antigen) on an analyte can be used as a capture antibody and/or another anti-HCV core antibody having a domain that can bind a second epitope (e.g., the DNA binding domain of HCV core antigen) can be used as a detection antibody, or vice versa. Alternatively, one antibody having a first domain that can bind an epitope on a HCV core antigen and a second antibody that binds an epitope on a different HCV antigen can be used as a capture antibody and/or a detection antibody to detect, and optionally quantify, two or more analytes.

Generally speaking, a sample being tested for (for example, suspected of containing) analyte can be contacted with at least one capture antibody (or antibodies) and at least one detection antibody (which can be a second detection antibody or a third detection antibody or even a successively numbered antibody, e.g., as where the capture and/or detection antibody comprise multiple antibodies) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a sample suspected of containing analyte (or a fragment thereof) is first brought into contact with at least one first capture antibody under conditions that allow the formation of a first antibody/analyte complex. If more than one capture antibody is used, a first capture antibody/analyte complex comprising two or more capture antibodies is formed. In a sandwich assay, the antibodies, i.e., preferably, the at least one capture antibody, are used in molar excess amounts of the maximum amount of analyte (or a fragment thereof) expected in the test sample. For example, from about 5 ug to about 1 mg of antibody per mL of buffer (e.g., microparticle coating buffer) can be used.

Competitive inhibition immunoassays, which are often used to measure small analytes because binding by only one antibody is required, comprise sequential and classic formats. In a sequential competitive inhibition immunoassay a capture antibody to an analyte of interest is coated onto a well of a microtiter plate or other solid support. When the sample containing the analyte of interest is added to the well, the analyte of interest binds to the capture antibody. After washing, a known amount of labeled (e.g., biotin or horseradish peroxidase (HRP)) analyte is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay an antibody to an analyte of interest is coated onto a solid support (e.g., a well of a microtiter plate). However, unlike the sequential competitive inhibition immunoassay, the sample and the labeled analyte are added to the well at the same time. Any analyte in the sample competes with labeled analyte for binding to the capture antibody. After washing, the signal generated by the labeled analyte is measured and is inversely proportional to the amount of analyte in the sample.

Optionally, prior to contacting the test sample with the at least one capture antibody (for example, the first capture antibody), the at least one capture antibody can be bound to a solid support, which facilitates the separation of the first antibody/analyte (or a fragment thereof) complex from the test sample. The substrate to which the capture antibody is bound can be any suitable solid support or solid phase that facilitates separation of the capture antibody-analyte complex from the sample.

Examples of solid phases or supports are well known to those of skill in the art and include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen or the antibody to the substrate results; alternatively, a chemical coupling agent or other means can be used to bind covalently the antibody to the substrate, provided that such binding does not interfere with the ability of the antibody to bind to analyte. Alternatively, the antibody can be bound with microparticles, which have been previously coated with streptavidin (e.g., DYNAL® Magnetic Beads, Invitrogen, Carlsbad, Calif.) or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the antibody. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture reagents, such as antibodies (or fragments thereof), each of which is specific for analyte(s) can be attached to solid phases in different physical or addressable locations (e.g., such as in a biochip configuration (see, e.g., U.S. Pat. No. 6,225,047; Int'l Patent App. Pub. No. WO 99/51773; U.S. Pat. No. 6,329,209; International Patent App. Pub. No. WO 00/56934, and U.S. Pat. No. 5,242,828). If the capture reagent is attached to a mass spectrometry probe as the solid support, the amount of analyte bound to the probe can be detected by laser desorption ionization mass spectrometry. Alternatively, a single column can be packed with different beads, which are derivatized with the one or more capture reagents, thereby capturing the analyte in a single place (see, antibody-derivatized, bead-based technologies, e.g., the xMAP technology of Luminex (Austin, Tex.)).

After the test sample being assayed for analyte (or a fragment thereof) is brought into contact with the at least one capture antibody (for example, the first capture antibody), the mixture is incubated in order to allow for the formation of a first antibody (or multiple antibody)-analyte (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/analyte complex, the complex is then contacted with at least one detection antibody under conditions which allow for the formation of a (first or multiple) capture antibody/analyte/second detection antibody complex). While captioned for clarity as the "second" antibody (e.g., second detection antibody), in fact, where multiple antibodies are used for capture and/or detection, the at least one detection antibody can be the second, third, fourth, etc. antibodies used in the immunoassay. If the capture antibody/analyte complex is contacted with more than one detection antibody, then a (first or multiple) capture antibody/analyte (or a fragment thereof)/(multiple) detection antibody complex is formed. As with the capture antibody (e.g., the first capture antibody), when the at least one (e.g., second and any subsequent) detection antibody is brought into contact with the capture antibody/analyte (or a fragment thereof) complex, a period of incubation under conditions similar to those described above is required for the formation of the (first or multiple) capture antibody/analyte/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antibody/analyte/(second or multiple) detection antibody complex. Any detectable label known in the art can be used (see discussion above).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9[N-tosyl-N-(3-carboxypropyl)]-10-(3-sulfopropyl)acridinium carboxamide) or SP SP-Acridinium Ester (i.e., N10-(3-sulfopropyl)-N-(3-sulfopropyl)-acridinium-9-carboxamide).

The (first or multiple) capture antibody/analyte/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support, it can be simultaneously contacted with the analyte-containing sample and the at least one second detection antibody to form a first (multiple) antibody/analyte/second (multiple) antibody complex, followed by removal of the fluid (test sample) from contact with the solid support. If the at least one first capture antibody is not bound to a solid support, then the (first or multiple) capture antibody/analyte/(second or multiple) detection antibody complex does not have to be removed from the test sample for quantification of the amount of the label.

After formation of the labeled capture antibody/analyte/detection antibody complex (e.g., the first capture antibody/analyte/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using appropriate means, such as a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of analyte or a fragment thereof in the test sample is determined by appropriate means, such as by use of a standard curve that has been generated using serial dilutions of analyte or a fragment thereof of known concentration. Other than using serial dilutions of analyte or a fragment thereof, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at about room temperature (i.e., at from about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

In view of the above, a method of determining the presence, amount, or concentration of HCV core (or a fragment thereof) in a test sample is provided. The method comprises assaying the test sample for an HCV core antigen (or a fragment thereof) by an assay (i) employing (i') at least one of an antibody, a fragment of an antibody that can bind to an analyte, a variant of an antibody that can bind to an analyte, a fragment of a variant of an antibody that can bind to an analyte, or a DVD-Ig (or a fragment, a variant, or a fragment of a variant thereof) that can bind to an HCV core antigen, and (ii') at least one detectable label and (ii) comprising comparing a signal generated by the detectable label as a direct or indirect indication of the presence, amount or concentration of the HCV core antigen (or a fragment thereof) in the test sample to a signal generated as a direct or indirect indication of the presence, amount or concentration of HCV core antigen (or a fragment thereof) in a control or calibrator. The calibrator is optionally part of a series of calibrators, in which each of the calibrators differs from the other calibrators by the concentration of analyte.

The method can comprise (i) contacting the test sample with at least one first specific binding partner for HCV core (or a fragment thereof) selected from the group consisting of an antibody of the present invention, a fragment of such an antibody that can bind to an HCV core antigen, a variant of an antibody that can bind to an HCV core antigen, a fragment of a variant of an antibody that can bind to an HCV core antigen, or a DVD-Ig (or a fragment, a variant, or a fragment of a variant thereof) that can bind to an HCV core antigen so as to form a first specific binding partner/HCV core antigen (or fragment thereof) complex, (ii) contacting the first specific binding partner/HCV core antigen (or fragment thereof) complex with at least one second specific binding partner for the HCV core antigen (or fragment thereof) selected from the group consisting of a detectably labeled anti-HCV core antibody, a detectably labeled fragment of an anti-HCV core antibody that can bind to HCV core antigen, a detectably labeled variant of an anti-HCV core antibody that can bind to HCV core antigen, a detectably labeled fragment of a variant of an anti-HCV core antibody that can bind to HCV core antigen, and a detectably labeled DVD-Ig (or a fragment, a variant, or a fragment of a variant thereof) so as to form a first specific binding partner/HCV core antigen (or fragment thereof)/second specific binding partner complex, and (iii) determining the presence, amount or concentration of HCV core antigen in the test sample by detecting or measuring the signal generated by the detectable label in the first specific binding partner/HCV core antigen (or fragment thereof)/second specific binding partner complex formed in (ii).

Alternatively, the method can comprise contacting the test sample with at least one first specific binding partner for HCV core (or a fragment thereof) selected from the group consisting of an antibody, a fragment of an antibody that can bind to an HCV core, a variant of an antibody that can bind to an HCV core, a fragment of a variant of an antibody that can bind to an HCV core, and a DVD-Ig (or a fragment, a variant, or a fragment of a variant thereof) and simultaneously or sequentially, in either order, contacting the test sample with at least one second specific binding partner, which can compete with HCV core (or a fragment thereof)

for binding to the at least one first specific binding partner and which is selected from the group consisting of a detectably labeled HCV core, a detectably labeled fragment of HCV core that can bind to the first specific binding partner, a detectably labeled variant of HCV core that can bind to the first specific binding partner, and a detectably labeled fragment of a variant of HCV core that can bind to the first specific binding partner. Any HCV core (or a fragment thereof) present in the test sample and the at least one second specific binding partner compete with each other to form a first specific binding partner/HCV core (or fragment thereof) complex and a first specific binding partner/second specific binding partner complex, respectively. The method further comprises determining the presence, amount or concentration of HCV core in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of HCV core in the test sample.

The above methods can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

With regard to the methods of assay (and kit therefor), it may be possible to employ commercially available anti-HCV core antibodies or methods for production of anti-HCV core as described in the literature. Commercial supplies of various antibodies include, but are not limited to, Santa Cruz Biotechnology Inc. (Santa Cruz, Calif.), GenWay Biotech, Inc. (San Diego, Calif.), and R&D Systems (RDS; Minneapolis, Minn.).

Generally, a predetermined level can be employed as a benchmark against which to assess results obtained upon assaying a test sample for HCV core or a fragment thereof, e.g., for detecting disease or risk of disease. Generally, in making such a comparison, the predetermined level is obtained by running a particular assay a sufficient number of times and under appropriate conditions such that a linkage or association of HCV core presence, amount or concentration with a particular stage or endpoint of a disease, disorder or condition or with particular clinical indicia can be made. Typically, the predetermined level is obtained with assays of reference subjects (or populations of subjects). The HCV core measured can include fragments thereof, degradation products thereof, and/or enzymatic cleavage products thereof.

In particular, with respect to a predetermined level as employed for monitoring HCV disease progression and/or treatment, the amount or concentration of analyte or a fragment thereof may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for HCV core antigen is defined in accordance with standard practice. Because the levels of HCV core in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable disease, for example, and a "normal" (sometimes termed "control") patient or population is/are one(s) that exhibit(s) no detectable disease, respectively, for example. Furthermore, given that HCV core is not routinely found at a high level in the majority of the human population, a "normal subject" can be considered an individual with no substantial detectable increased or elevated amount or concentration of HCV core, and a "normal" (sometimes termed "control") patient or population is/are one(s) that exhibit(s) no substantial detectable increased or elevated amount or concentration of HCV core. An "apparently normal subject" is one in which HCV core has not yet been or currently is being assessed. The level of an HCV core is said to be "elevated" when the HCV core is normally undetectable (e.g., the normal level is zero, or within a range of from about 25 to about 75 percentiles of normal populations), but is detected in a test sample, as well as when the HCV core is present in the test sample at a higher than normal level. Thus, inter alia, the disclosure provides a method of screening for a subject having, or at risk of having, a particular disease, disorder, or condition. The method of assay can also involve the assay of other markers and the like.

Accordingly, the methods described herein also can be used to determine whether or not a subject has or is at risk of developing a HCV disease, disorder or condition. Specifically, such a method can comprise the steps of:

(a) determining the concentration or amount in a test sample from a subject of HCV core (or a fragment thereof) (e.g., using the methods described herein, or methods known in the art); and (b) comparing the concentration or amount of HCV core (or a fragment thereof) determined in step (a) with a predetermined level, wherein, if the concentration or amount of HCV core determined in step (a) is favorable with respect to a predetermined level, then the subject is determined not to have or be at risk for a given disease, disorder or condition. However, if the concentration or amount of HCV core determined in step (a) is unfavorable with respect to the predetermined level, then the subject is determined to have or be at risk for a given disease, disorder or condition.

Additionally, provided herein is method of monitoring the progression of disease in a subject. Optimally the method comprising the steps of:

(a) determining the concentration or amount in a test sample from a subject of HCV core;

(b) determining the concentration or amount in a later test sample from the subject of HCV core; and (c) comparing the concentration or amount of HCV core as determined in step (b) with the concentration or amount of HCV core determined in step (a), wherein if the concentration or amount determined in step (b) is unchanged or is unfavorable when compared to the concentration or amount of HCV core determined in step (a), then the disease in the subject is determined to have continued, progressed or worsened. By comparison, if the concentration or amount of HCV core as determined in step (b) is favorable when compared to the concentration or amount of HCV core as determined in step (a), then the disease in the subject is determined to have discontinued, regressed or improved.

Optionally, the method further comprises comparing the concentration or amount of HCV core as determined in step (b), for example, with a predetermined level. Further, optionally the method comprises treating the subject with one or more pharmaceutical compositions for a period of time if the comparison shows that the concentration or amount of HCV core as determined in step (b), for example, is unfavorably altered with respect to the predetermined level.

In still other embodiments, any of the assays described herein for monitoring presence or levels of HCV core antigen can advantageously be combined with other assays that also determine HCV infection. For example, any of the HCV core determining methods of the invention may further comprise determining the level of another HCV antigen or HCV antibody directed to an antigen other than core protein, including but not limited to determining the presence of HCV Core, E1, E2, NS2, NS3, NS4a, NS4b and NS5.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of HCV core is determined (e.g., using the methods described herein or as known in the art). After the concentration or amount of HCV core is determined, optionally the concentration or amount of HCV core is then compared with a predetermined level. If the concentration or amount of HCV core as determined in the first test sample is lower than the predetermined level, then the subject is not treated with one or more pharmaceutical compositions. However, if the concentration or amount of HCV core as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of HCV core is determined in the second or subsequent test sample is determined (e.g., using the methods described herein or as known in the art). The concentration or amount of HCV core as determined in each of the second and subsequent test samples is then compared with the concentration or amount of HCV core as determined in the first test sample (e.g., the test sample that was originally optionally compared to the predetermined level). If the concentration or amount of HCV core as determined in step (c) is favorable when compared to the concentration or amount of HCV core as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of HCV core as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's HCV core level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally, the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from a given disease, disorder or condition will benefit from treatment. In particular, the disclosure relates to HCV core companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, a given disease, disorder or condition is a candidate for therapy. Generally, the subject is one who has experienced some symptom of a given disease, disorder or condition or who has actually been diagnosed as having, or being at risk for, a given disease, disorder or condition, and/or who demonstrates an unfavorable concentration or amount of HCV core or a fragment thereof, as described herein.

The method optionally comprises an assay as described herein, where HCV core is assessed before and following treatment of a subject with one or more pharmaceutical compositions (e.g., particularly with a pharmaceutical related to a mechanism of action involving HCV core), with immunosuppressive therapy, or by immunoabsorption therapy, or where HCV core is assessed following such treatment and the concentration or the amount of HCV core is compared against a predetermined level. An unfavorable concentration of amount of HCV core observed following treatment confirms that the subject will not benefit from receiving further or continued treatment, whereas a favorable concentration or amount of HCV core observed following treatment confirms that the subject will benefit from receiving further or continued treatment. This confirmation assists with management of clinical studies, and provision of improved patient care.

The method of assay also can be used to identify a compound that ameliorates a given disease, disorder or condition. For example, a cell that expresses HCV core can be contacted with a candidate compound. The level of expression of HCV core in the cell contacted with the compound can be compared to that in a control cell using the method of assay described herein.

In yet another detection method, each of the binding proteins as described herein can be employed in the detection of HCV antigens in fixed tissue sections, as well as fixed cells by immunohistochemical analysis.

In addition, these binding proteins can be bound to matrices similar to CNBr-activated Sepharose and used for the affinity purification of specific HCV proteins from cell cultures, or biological tissues such as blood and liver.

The monoclonal antibodies as described herein can also be used for the generation of chimeric antibodies for therapeutic use, or other similar applications. In addition, as discussed herein throughout the antibodies also could be used in the production of DVD-Ig molecules.

The monoclonal antibodies or fragments thereof can be provided individually to detect HCV core antigens. It is contemplated that combinations of the monoclonal antibodies (and fragments thereof) provided herein also may be used together as components in a mixture or "cocktail" of at least one anti-HCV core antibody as described herein with antibodies to other HCV regions, each having different binding specificities. Thus, this cocktail can include the monoclonal antibodies as described herein, which are directed to HCV core protein, and other monoclonal antibodies to other antigenic determinants of the HCV genome. Examples of other monoclonal antibodies useful for these contemplated cocktails include those to HCV C-100, HCV 33C, HCV CORE, HCV NS5 and/or HCV putative ENV, which are disclosed in, for example, U.S. Ser. No. 07/610,175 entitled MONOCLONAL ANTIBODIES TO HEPATITIS C VIRUS AND METHOD FOR USING SAME, U.S. Ser. No. 07/610,175 entitled MONOCLONAL ANTIBODIES TO HCV 33C PROTEINS AND METHODS FOR USING SAME, U.S. Ser. No. 07/648,475 entitled MONOCLONAL ANTIBODIES TO PUTATIVE HCV ENVELOPE REGION AND METHODS FOR USING SAME, U.S. Ser. No. 07/648,473 entitled MONOCLONAL ANTIBODIES TO HCV CORE PROTEINS AND METHODS FOR USING SAME and in co-filed patent application entitled MONOCLONAL ANTIBODIES TO HCV N55 PROTEIN AND METHODS FOR USING SAME, U.S. Ser. No. 07/748,563, all of which enjoy common ownership and are incorporated herein by reference. This cocktail of monoclonal antibodies as described herein would be used in the assay formats detailed herein in place of the monoclonal antibody to HCV core, and thus would be able to detect the HCV core and other HCV antigens.

The polyclonal antibody or fragment thereof which can be used in the assay formats should specifically bind to HCV core or other HCV proteins used in the assay, such as HCV C-100 protein, HCV 33C protein, HCV ENV, HCV E2/NS1 or HCV NS5 protein. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

As noted elsewhere herein throughout, the test samples which can be tested by the methods as described herein described herein include human and animal body fluids such as whole blood, serum, plasma, cerebrospinal fluid, urine, biological fluids such as cell culture supernatants, fixed tissue specimens and fixed ceil specimens.

The indicator reagent comprises a signal-generating compound (label) that is capable of generating a measurable signal detectable by external means conjugated (attached) to a specific binding member for HCV core. "Specific binding member" as used herein means a member of a specific binding pair. That is, two different molecules where one of the molecules through chemical or physical means specifically binds to the second molecule. In addition to being an antibody member of a specific binding pair for HCV core, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV core as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds such as acridinium, phenanthridinium and dioxetane compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The use of scanning probe microscopy (SPM) for immunoassays also is a technology to which the monoclonal antibodies as described herein are easily adaptable. In scanning probe microscopy, in particular in atomic force microscopy, the capture phase, for example, at least one of the monoclonal antibodies as described herein, is adhered to a solid phase and a scanning probe microscope is utilized to detect antigen/antibody complexes which may be present on the surface of the solid phase. The use of scanning tunnelling microscopy eliminates the need for labels that normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (the HCV core specific substance, which is the monoclonal antibody as described herein) is attached to a surface suitable for scanning. The attachment of the HCV core specific substance may be by adsorption to a test piece, which comprises a solid phase of a plastic or metal surface, following methods known to those of ordinary skill in the art. Or, covalent attachment of a specific binding partner (HCV core specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl) trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis(succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl]aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent application Ser. Nos. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present disclosure expresses a preference for the use of solid phases, it is contemplated that the monoclonal antibodies as described herein can be utilized in non-solid phase assay systems. These assay systems are known to those skilled in the art, and are considered to be within the scope of the disclosure.

It is contemplated that the reagent employed for the assay can be provided in the form of a kit with one or more containers such as vials or bottles, with each container containing a separate reagent such as a monoclonal antibody, or a cocktail of monoclonal antibodies, detection reagents and washing reagents employed in the assay.

The antibodies can also be used as a means of enhancing the immune response. The antibodies can be administered in amount similar to those used for other therapeutic administrations of antibody. For example, normal immune globulin is administered at 0.02 0.1 ml/lb body weight during the early incubation period of other viral diseases such as rabies, measles, and hepatitis B to interfere with viral entry into cells. Thus, antibodies reactive with the HCV core proteins can be passively administered alone or in conjunction with another anti-viral agent to a host infected with an HCV to enhance the immune response and/or the effectiveness of an antiviral drug.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

Kits

Also contemplated herein are kits for assaying a test sample for the presence, amount or concentration of HCV core protein (or a fragment thereof) in a test sample. Such a kit comprises at least one component for assaying the test sample for HCV core protein (or a fragment thereof) and instructions for assaying the test sample for the HCV core (or a fragment thereof). The at least one component for assaying the test sample for the HCV core (or a fragment thereof) can include a composition comprising an anti-HCV core protein monoclonal antibody or an anti-HCV core protein DVD-Ig (or a fragment, a variant, or a fragment of a variant thereof), which is optionally immobilized or capable of being immobilized on a solid phase.

The kit can comprise at least one component for assaying the test sample for HCV core protein by immunoassay, e.g., chemiluminescent microparticle immunoassay, and instructions for assaying the test sample for an HCV core by immunoassay, e.g., chemiluminescent microparticle immunoassay. For example, the kit can comprise at least one specific binding partner for an HCV core, such as an anti-HCV core, monoclonal/polyclonal antibody (or a fragment thereof that can bind to the HCV core, a variant thereof that can bind to the HCV core, or a fragment of a variant that can bind to the HCV core) or an anti-HCV core DVD-Ig (or a fragment, a variant, or a fragment of a variant thereof), either of which can be detectably labeled. Alternatively or additionally, the kit can comprise detectably labeled HCV core (or a fragment thereof that can bind to an anti-HCV core, monoclonal/polyclonal antibody or an anti-HCV core DVD-Ig (or a fragment, a variant, or a fragment of a variant thereof)), which can compete with any HCV core in a test sample for binding to an anti-HCV core, monoclonal/polyclonal antibody (or a fragment thereof that can bind to the HCV core, a variant thereof that can bind to the HCV core, or a fragment of a variant that can bind to the HCV core) or an anti-HCV core DVD-Ig (or a fragment, a variant, or a fragment of a variant thereof), either of which can be immobilized on a solid support. The kit can comprise a calibrator or control, e.g., isolated or purified HCV core. The kit can comprise at least one container (e.g., tube, microtiter plates or strips, which can be already coated with a first specific binding partner, for example) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions can be in paper form or computer-readable form, such as a disk, CD, DVD, or the like.

Any antibodies, such as an anti-HCV core antibody or an anti-HCV core DVD-Ig, or tracer can incorporate a detectable label as described herein, such as a fluorophore, a radioactive moiety, an enzyme, a biotin/avidin label, a chromophore, a chemiluminescent label, or the like, or the kit can include reagents for carrying out detectable labeling. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, enzyme substrates, detection reagents, and the like.

Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, a solution, and/or at least one basic solution. If desired, the kit can contain a solid phase, such as a magnetic particle, bead, test tube, microtiter plate, cuvette, membrane, scaffolding molecule, film, filter paper, disc or chip.

The kit (or components thereof), as well as the method of determining the presence, amount or concentration of an HCV core in a test sample by an assay, such as an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., an anti-HCV core, monoclonal/polyclonal antibody (or a fragment thereof, a variant thereof, or a fragment of a variant thereof) or an anti-HCV core DVD-Ig (or a fragment thereof, a variant thereof, or a fragment of a variant thereof) is attached; either way, sandwich formation and HCV core reactivity can be impacted), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format, such as an ELISA, may incubate a detection antibody, such as the conjugate reagent, for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Patent App. Pub. No. 2003/0170881, U.S. Patent App. Pub. No. 2004/0018577, U.S. Patent App. Pub. No. 2005/0054078, and U.S. Patent App. Pub. No. 2006/0160164, which are incorporated in their entireties by reference for their teachings regarding same.

In particular, with regard to the adaptation of an HCV core assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized anti-HCV core, monoclonal/polyclonal antibody (or a fragment thereof, a variant thereof, or a fragment of a variant thereof) or anti-HCV core DVD-Ig (or a fragment thereof, a variant thereof, or a fragment of a variant thereof), are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising a specific binding partner for an HCV core, such as an anti-HCV core, monoclonal/polyclonal antibody (or a fragment thereof, a variant thereof, or a fragment of a variant thereof that can bind the HCV core) or an anti-HCV core DVD-Ig (or a fragment thereof, a variant thereof, or a fragment of a variant thereof that can bind the HCV core), either of which can be detectably labeled. Within the fluid pouch of the cartridge is an aqueous reagent that includes p-aminophenol phosphate.

In operation, a sample suspected of containing an HCV core is added to the holding chamber of the test cartridge, and the cartridge is inserted into the I-STAT® reader. After the specific binding partner for an HCV core has dissolved into the sample, a pump element within the cartridge forces the sample into a conduit containing the chip. Here it is oscillated to promote formation of the sandwich. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of HCV core in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-Stat cartridge format, using a nucleic acid sequence linked to the signal antibody as a signal amplifier.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Animal Immunizations

Female CAF1/J and RBF/DnJ mice (both from The Jackson Laboratory, Bar Harbor, Me.) were immunized on weeks 0, 4 and 10 with 50 μg of an HCV core peptide corresponding to amino acids (all numbering per HCV-1) 134-171 covalently linked to BSA (ALRZ-8 immunogen).

HCV core peptide-BSA was prepared by AnaSpec, Inc. (Fremont, Calif.). The immunogen peptide was emulsified in Complete or Incomplete Adjulite Freund's Adjuvant (Pacific Immunology, Ramona, Calif.). Complete Freund's adjuvant was used for the primary immunization and Incomplete Freund's adjuvant for the second and third immunizations. Each inoculum was prepared by first diluting the HCV peptide-BSA to the appropriate concentration in sterile saline (0.9% sodium chloride), adding an equal volume of adjuvant and then mixing by passing back and forth between two syringes via a 3-way stopcock until a thick, stable emulsion was formed. Sera samples were taken 10-14 days following the 3rd immunization. On the $4^{th}$ and 3' days prior to B cell harvest, RBF/DnJ mice #306 and 315 were administered 50 μg peptide-BSA diluted in sterile saline. This inoculum was delivered into the body cavity near the spleen.

ALRZ-8 immunogen (SEQ ID NO: 576)
Ac-MGYIPLVGAPLGGAARALAHGVRVLEDGVNYATGNLPGC-BSA.

Example 2

Screening of Mouse Sera for Antigen Immunoreactivity

Mouse sera samples collected 7-10 days after their final immunization were first tested in a 96-well micro titer enzyme immunoassay (EIA) for reactivity to each of three synthetic (Anaspec, Inc.) carboxy-terminal biotinylated HCV core peptides. The peptides used for screening were derived from the immunogen sequence described in Example 1 and had the following designations and sequences: Peptide 1 (all numbering per HCV-1), amino acids 134-151: MGYIPLVGAPLGGAARALAHG (SEQ ID NO:573); Peptide 2, amino acids 141-161: GAPLG-GAARALAHGVRVLEDG (SEQ ID NO:574), Peptide 3, amino acids 151-171, LAHGVRVLEDGVNYATGNLPG (SEQ ID NO:575). Assay plates (NUNC Corporation, Naperville, Ill.) were coated with 100 μL/well of sheep anti-mouse IgG Fc specific antibody (Jackson ImmunoResearch, West Grove, Pa.) diluted to 2 μg/mL in phosphate-buffered saline (PBS). Plates were incubated at 37 deg C. for about 2 hours and then at about 21 deg C. for about 2 hours. The capture antibody was then removed and 200 μL/well of blocking solution (3% w/v [weight/volume] bovine serum albumin (BSA) and 0.5% v/v [volume/volume] polysorbate-20 diluted in PBS added. The plates were incubated for about 30 minutes and then washed with distilled water. Next, serial dilutions (in block solution) of the mouse sera or a positive control were added to the assay plates (100 μL/well), incubated for between 2 and 20 hours and then washed with dH$_2$O. Next, 100 μL/well of normal serum solution (NSS; block solution containing 2% v/v normal mouse serum) was added for additional blocking. This solution helps to prevent non-specific binding in the assay well. The plates were incubated for about 30 minutes and then washed with dH$_2$O. Subsequently, 100 μL/well of a 224 nM solution of each peptide was added to the assay wells for a brief incubation, after which the plates were washed with dH$_2$O (sera samples were tested for reactivity to individual peptides, rather than a mixture of all three). Next, 100 μL/well horse radish peroxidase labeled streptavidin (Jackson ImmunoResearch) diluted to 200 ng/mL in blocking solution was added, allowed to incubate for about 30 minutes and then the plates washed; o-phenylenediamine substrate (OPD) was used as the chromagen to generate signal, and the reaction was quenched using 1 N sulfuric acid. Signal was read at a wavelength of 492 nm.

Example 3

Screening of Mouse Sera for Relative Affinity

Relative affinity testing was completed for each sera sample—peptide combination for which a strong signal was seen in the previous assay. To determine the relative affinity of each serum sample for the individual core peptides, samples were tested for reactivity to limiting concentrations of each biotin labeled peptide. The assay format was identical to that described above, except that instead of preparing serial dilutions of mouse sera test samples, each sample was prepared at a single dilution, in blocking solution. Additionally, the individual peptides were tested at varying concentrations, beginning with a 500 nM solution in blocking solution followed by ten log 2 dilutions, also in blocking solution. Binding curves were generate and used to determine relative affinity for each sera sample. Based on these results, RBF/DnJ mice #306 and 315 were chosen for B cell fusion.

Example 4

Mouse Splenocyte Fusion

On the day of fusion, the mice were euthanized and their splenocytes were harvested and placed into Iscoves Modified Dulbeccos Medium (IMDM) supplemented with Pen Strep (Invitrogen Corporation). A cell fusion was performed as described by Kohler and Milstein (Nature 1975; 256:495-7). Each mouse spleen was placed into a petri dish containing IMDM. The splenocytes were perfused out of each spleen using a syringe containing IMDM and a cell scraper. All splenocytes from mouse #306 and 315 were isolated and pooled in a 50 ml centrifuge tube, then counted using a hemocytometer with trypan blue dye exclusion to determine viability. Approximately $8.0 \times 10^8$ total cells at 89% viability were recovered from these spleens. Approximately $7.6 \times 10^6$ cells/ml were estimated to be B-cells based on their physical appearance under the microscope. Approximately 5 mL of this cell suspension was used for a first fusion experiment (fusion 208A), and the remaining cells were processed using magnetic activated cell sorting (MACS) and a Pan B-cell isolation kit (Miltenyi Biotech) to enrich the cell population for B-cells and deplete other cell types. Approximately $6.7 \times 10^8$ total cells were incubated with the Pan B-cell biotin labeled antibody cocktail followed by the anti-biotin micobeads per manufacturer's instructions. The cell suspension/microbead mixture was washed by centrifugation and passed over a Miltenyi Biotech LS column contained within a magnetic field. B-cells flow freely through the column and other cell types are retained in the column. The columns were washed 3 times with PBS containing 2% FBS to wash out all B-cells. The B-cell suspension was centrifuged and the pellet was resuspended in IMDM, and then counted using a hemocytometer. Approximately $1.4 \times 10^8$ B-cells were recovered from the enrichment procedure. Approximately $7.0 \times 10^7$ B-cells from that suspension were used for a second fusion experiment (fusion 208B) and the remaining B-cells were cryopreserved for later usage.

The unenriched splenocytes from the spleens (~$3.8 \times 10^7$ B-cells for fusion 208A) and the enriched B-cell pool (~$7.0 \times 10^7$ B-cells for fusion 208B) were washed by centrifugation in separate tubes and the cell pellets were resuspended in IMDM. These splenocytes were mixed with an equal number of NS/0 myeloma cells and centrifuged into a pellet. The fusion was accomplished by exposing the splenocytes and NS/0 cells to 50% Polyethylene glycol (PEG) (American Type Culture Collection—Molecular Weight 1300-1600) in HSFM. One mL of the PEG solution was added to each cell pellet over 30 seconds, followed by one additional minute of incubation. The PEG and cell pellet was diluted by slowly adding 30 mL of IMDM over 30 seconds. The fused cells were then removed from suspension by centrifugation and decanting the supernatant. The cell pellet from each fusion (208A and 208B) was re-suspended into ~250 mL of IMDM supplemented with ~10% FBS (Hyclone Laboratories), HAT (Hypoxanthine, Aminopterin, Thymidine) (Sigma Laboratories), HT Supplement (Invitrogen Corporation), BM Condimed H1 (Roche Applied Science), Cholesterol and L-Glutamine (Invitrogen Corporation) in order to select for hybridomas. The fused cells were seeded into T162 culture flasks containing the HAT medium and cultured in bulk for approximately 48 hours at 37° C. with 5% $CO_2$. Following 48 hours of HAT selection, the bulk culture was centrifuged and the pellet was re-suspended into semi-solid tissue culture medium. The semi-solid tissue culture medium consisted of a 50% mixture of 2×IMDM (Invitrogen) with Clone Matrix (Molecular Devices) supplemented with 10% FBS, HT Supplement, Penn/Strep, L-Glutamine, and anti-mouse IgG-FITC Clone Detect (Molecular Devices). The semi-solid culture plates were allowed to incubate for 7-10 days before colony selection on the ClonepixFL (Molecular Devices). A colony grown in the semi-solid medium was considered a clone because the single cell initiating it had not been allowed to move and mix with other cells during growth, but all cell lines of interest will be subcloned at a later date to ensure clonality. An immunoprecipitation reaction occurs between the antibody being produced by the colony and the goat anti-mouse IgG Fc-FITC that fluoresces. The brighter the fluorescence signal observed, the more antibody being produced. Colonies were analyzed for fluorescence on the ClonepixFL and the ones with the brightest fluorescent signal were selected for automated transfer to 96 well tissue culture plates containing IMDM supplemented with 10% FBS, HT supplement, cholesterol, L-Glutamine, and Pen Strep. The 96 well tissue culture plates were allowed to grow for 3 to 7 days at 37° C. prior to supernatant screening for antibody production.

Example 5

Hybridoma Screening and Selection Using Peptides

Cell supernatant samples were analyzed for anti-HCV antibodies by EIA. Sheep anti-mouse IgG Fc (Jackson Immunoresearch) was coated on 96 well micro-titer EIA plates at 1 µg/mL. After the capture reagent had been coated on the solid phase, remaining solution was removed and the plates were blocked using 3% BSA in PBS. The wells were washed with distilled water and cell supernatants were added to the blocked plates and allowed to incubate at room temperature for at least one hour. The anti-mouse IgG Fc captures the anti-HCV mouse antibody from the supernatant. Following the incubation, the plates were washed using distilled water. A 3% normal mouse serum in BSA block solution was added to all wells and incubated at room temperature for 30 minutes to block any unbound sheep anti-mouse IgG Fc capture sites coated on the plate. The wells were washed with distilled water and a mixture of the biotinylated HCV peptides described in Example 2 (i.e. corresponding to amino acids 134-154, 141-161, and 151-171 of HCV-1), each at 100 ng/mL, was added and incubated for 30 minutes at room temperature. Following this incubation, the biotinylated antigens were washed from the plates using distilled water and streptavidin-HRPO (Jackson Immunoresearch) diluted to approximately 200 ng/mL was added to the plates and allowed to incubate for 30 minutes. The plates were washed with distilled water and o-phenylenediamine substrate was used as the chromogen to generate signal. Plates were read at 492 nm and the results were analyzed. Wells were considered positive if they had an EIA signal at least 3 times greater than background. Positive wells were expanded to 24 well plates in IMDM supplemented with 10% FBS, HT supplement, cholesterol, and L-Glutamine.

Following 5-14 days of growth, the 24 well cultures were evaluated by EIA in the same manner as previously described, except the supernatant samples were titrated against each of the biotinylated HCV core peptides individually and BSA to identify clones that might bind non-specifically to the peptides or the blocking protein. The 24 well cultures generating signal at least 5 times greater than the average BSA background value of 0.08 OD units with at least one of the screening peptides were considered positive and selected for further evaluation. Values are listed in Table 1.

TABLE 1

| Clone # | Reactivity to HCV bt-134-154 | Reactivity to HCV bt-141-161 | Reactivity to HCV bt-151-171 | BSA (Pep) |
|---|---|---|---|---|
| HCV 208A-1006 | 0.15 | 3.56 | 0.07 | 0.08 |
| HCV 208A-1007 | 0.07 | 3.53 | 0.08 | 0.07 |
| HCV 208A-1015 | 0.07 | 0.42 | 0.11 | 0.08 |
| HCV 208A-1022 | 0.08 | 1.63 | 0.08 | 0.09 |
| HCV 208A-1032 | 0.12 | 3.73 | 0.09 | 0.08 |
| HCV 208A-1064 | 0.10 | 3.50 | 0.12 | 0.07 |
| HCV 208A-1081 | 0.06 | 3.52 | 0.06 | 0.05 |
| HCV 208A-110 | 0.07 | 2.88 | 0.11 | 0.06 |
| HCV 208A-122 | 0.06 | 2.65 | 0.09 | 0.06 |
| HCV 208A-126 | 0.20 | 2.08 | 0.10 | 0.10 |
| HCV 208A-133 | 0.10 | 3.68 | 0.13 | 0.06 |
| HCV 208A-134 | 2.06 | 0.08 | 0.06 | 0.07 |
| HCV 208A-147 | 0.67 | 0.07 | 0.06 | 0.20 |

TABLE 1-continued

| Clone # | Reactivity to HCV bt-134-154 | Reactivity to HCV bt-141-161 | Reactivity to HCV bt-151-171 | BSA (Pep) |
|---|---|---|---|---|
| HCV 208A-152 | 0.08 | 3.55 | 0.09 | 0.07 |
| HCV 208A-158 | 0.10 | 2.70 | 0.09 | 0.07 |
| HCV 208A-159 | 0.15 | 3.77 | 0.19 | 0.08 |
| HCV 208A-160 | 0.11 | 3.28 | 0.09 | 0.09 |
| HCV 208A-194 | 0.07 | 0.20 | 0.06 | 0.07 |
| HCV 208A-207 | 1.24 | 0.17 | 0.08 | 0.07 |
| HCV 208A-208 | 0.09 | 3.22 | 0.29 | 0.10 |
| HCV 208A-210 | 0.06 | 1.15 | 0.05 | 0.06 |
| HCV 208A-222 | 0.06 | 2.70 | 0.08 | 0.07 |
| HCV 208A-227 | 0.08 | 0.24 | 0.43 | 0.07 |
| HCV 208A-230 | 0.08 | 0.42 | 0.07 | 0.07 |
| HCV 208A-264 | 0.05 | 0.07 | 0.37 | 0.09 |
| HCV 208A-286 | 0.11 | 2.62 | 0.11 | 0.06 |
| HCV 208A-293 | 0.08 | 2.42 | 0.11 | 0.07 |
| HCV 208A-312 | 0.22 | 3.70 | 0.06 | 0.06 |
| HCV 208A-334 | 0.05 | 3.07 | 0.05 | 0.05 |
| HCV 208A-352 | 1.08 | 0.07 | 0.06 | 0.07 |
| HCV 208A-367 | 0.08 | 1.79 | 0.10 | 0.08 |
| HCV 208A-381 | 0.07 | 3.69 | 0.12 | 0.08 |
| HCV 208A-382 | 0.10 | 0.07 | 0.43 | 0.08 |
| HCV 208A-393 | 0.06 | 1.04 | 0.06 | 0.05 |
| HCV 208A-422 | 0.05 | 0.84 | 0.10 | 0.07 |
| HCV 208A-427 | 0.20 | 3.82 | 0.11 | 0.11 |
| HCV 208A-442 | 0.08 | 3.04 | 0.06 | 0.06 |
| HCV 208A-460 | 0.09 | 2.69 | 0.10 | 0.07 |
| HCV 208A-470 | 0.08 | 0.10 | 0.08 | 0.08 |
| HCV 208A-489 | 0.06 | 3.11 | 0.07 | 0.06 |
| HCV 208A-493 | 0.09 | 3.60 | 0.07 | 0.07 |
| HCV 208A-557 | 0.05 | 2.41 | 0.06 | 0.05 |
| HCV 208A-558 | 0.12 | 0.95 | 0.14 | 0.10 |
| HCV 208A-562 | 0.21 | 3.71 | 0.12 | 0.09 |
| HCV 208A-575 | 0.07 | 1.55 | 0.13 | 0.12 |
| HCV 208A-576 | 0.08 | 3.05 | 0.09 | 0.06 |
| HCV 208A-584 | 0.89 | 0.10 | 0.06 | 0.08 |
| HCV 208A-603 | 0.07 | 1.35 | 0.09 | 0.07 |
| HCV 208A-604 | 0.05 | 2.27 | 0.06 | 0.05 |
| HCV 208A-605 | 0.22 | 3.71 | 0.16 | 0.11 |
| HCV 208A-638 | 0.07 | 2.96 | 0.09 | 0.06 |
| HCV 208A-641 | 0.10 | 0.93 | 0.11 | 0.09 |
| HCV 208A-658 | 0.06 | 1.10 | 0.08 | 0.20 |
| HCV 208A-692 | 3.67 | 0.38 | 0.07 | 0.06 |
| HCV 208A-695 | 0.08 | 3.82 | 0.11 | 0.07 |
| HCV 208A-719 | 0.07 | 3.60 | 0.09 | 0.06 |
| HCV 208A-736 | 3.24 | 0.12 | 0.06 | 0.07 |
| HCV 208A-741 | 1.20 | 3.37 | 0.06 | 0.07 |
| HCV 208A-744 | 0.12 | 3.88 | 0.10 | 0.08 |
| HCV 208A-759 | 0.16 | 3.95 | 0.14 | 0.08 |
| HCV 208A-768 | 0.11 | 3.28 | 0.09 | 0.09 |
| HCV 208A-774 | 0.14 | 3.53 | 0.12 | 0.07 |
| HCV 208A-793 | 0.07 | 2.96 | 0.10 | 0.07 |
| HCV 208A-807 | 0.79 | 0.07 | 0.06 | 0.06 |
| HCV 208A-826 | 3.28 | 0.11 | 0.11 | 0.10 |
| HCV 208A-828 | 0.07 | 3.35 | 0.10 | 0.07 |
| HCV 208A-830 | 0.07 | 2.88 | 0.08 | 0.06 |
| HCV 208A-850 | 0.07 | 3.49 | 0.10 | 0.06 |
| HCV 208A-863 | 0.07 | 4.00 | 0.08 | 0.06 |
| HCV 208A-874 | 0.05 | 0.73 | 0.06 | 0.05 |
| HCV 208A-877 | 0.06 | 1.21 | 0.05 | 0.06 |
| HCV 208A-879 | 0.09 | 0.17 | 0.79 | 0.19 |
| HCV 208A-920 | 0.17 | 4.00 | 0.08 | 0.08 |
| HCV 208A-926 | 0.06 | 3.32 | 0.07 | 0.09 |
| HCV 208A-938 | 0.09 | 3.49 | 0.09 | 0.10 |
| HCV 208A-939 | 3.33 | 0.17 | 0.05 | 0.05 |
| HCV 208A-967 | 0.52 | 0.73 | 0.18 | 0.07 |
| HCV 208A-982 | 0.08 | 3.40 | 0.06 | 0.07 |
| HCV 208A-983 | 3.03 | 0.40 | 0.05 | 0.05 |
| HCV 208B-1024 | 0.08 | 0.75 | 0.15 | 0.10 |
| HCV 208B-1029 | 0.07 | 0.51 | 0.10 | 0.06 |
| HCV 208B-1043 | 0.16 | 0.12 | 3.88 | 0.07 |
| HCV 208B-1070 | 0.07 | 3.50 | 0.05 | 0.05 |
| HCV 208B-1072 | 0.09 | 2.28 | 0.09 | 0.12 |
| HCV 208B-109 | 0.08 | 3.46 | 0.11 | 0.07 |
| HCV 208B-1094 | 0.12 | 3.28 | 0.13 | 0.10 |
| HCV 208B-1096 | 0.34 | 0.13 | 3.56 | 0.08 |
| HCV 208B-131 | 0.13 | 0.18 | 3.89 | 0.10 |
| HCV 208B-141 | 1.66 | 0.09 | 0.06 | 0.06 |
| HCV 208B-174 | 0.08 | 1.26 | 0.07 | 0.08 |
| HCV 208B-178 | 0.10 | 0.07 | 1.69 | 0.07 |
| HCV 208B-181 | 0.12 | 2.44 | 0.07 | 0.06 |
| HCV 208B-183 | 0.31 | 0.14 | 0.09 | 0.11 |
| HCV 208B-189 | 0.55 | 0.15 | 3.95 | 0.09 |
| HCV 208B-207 | 0.19 | 0.09 | 0.50 | 0.07 |
| HCV 208B-214 | 0.16 | 0.07 | 0.60 | 0.06 |
| HCV 208B-230 | 0.41 | 0.12 | 0.08 | 0.08 |
| HCV 208B-251 | 0.11 | 2.35 | 0.41 | 0.10 |
| HCV 208B-281 | 1.48 | 0.16 | 0.12 | 0.07 |
| HCV 208B-309 | 0.11 | 2.34 | 0.09 | 0.09 |
| HCV 208B-319 | 0.17 | 3.43 | 0.13 | 0.13 |
| HCV 208B-327 | 0.07 | 0.05 | 0.49 | 0.05 |
| HCV 208B-348 | 0.07 | 0.20 | 0.07 | 0.07 |
| HCV 208B-353 | 0.07 | 2.47 | 0.07 | 0.07 |
| HCV 208B-395 | 0.54 | 0.13 | 3.69 | 0.11 |
| HCV 208B-408 | 0.81 | 0.20 | 0.16 | 0.06 |
| HCV 208B-409 | 0.09 | 3.21 | 0.14 | 0.07 |
| HCV 208B-446 | 0.06 | 2.50 | 0.08 | 0.06 |
| HCV 208B-457 | 0.75 | 0.66 | 0.24 | 0.17 |
| HCV 208B-471 | 1.62 | 0.11 | 0.08 | 0.10 |
| HCV 208B-488 | 0.08 | 0.07 | 0.30 | 0.08 |
| HCV 208B-515 | 0.51 | 0.13 | 0.06 | 0.06 |
| HCV 208B-517 | 0.10 | 0.41 | 0.70 | 0.11 |
| HCV 208B-547 | 0.12 | 0.08 | 2.90 | 0.08 |
| HCV 208B-556 | 0.13 | 3.07 | 0.18 | 0.08 |
| HCV 208B-560 | 0.11 | 3.90 | 0.14 | 0.07 |
| HCV 208B-589 | 0.27 | 0.10 | 2.85 | 0.12 |
| HCV 208B-591 | 0.08 | 3.10 | 0.07 | 0.07 |
| HCV 208B-602 | 0.20 | 1.87 | 0.20 | 0.07 |
| HCV 208B-608 | 0.19 | 0.37 | 0.13 | 0.07 |
| HCV 208B-612 | 3.05 | 3.04 | 0.15 | 0.08 |
| HCV 208B-616 | 0.10 | 0.71 | 0.11 | 0.09 |
| HCV 208B-617 | 0.45 | 0.51 | 0.13 | 0.10 |
| HCV 208B-646 | 0.15 | 3.94 | 0.18 | 0.08 |
| HCV 208B-652 | 0.21 | 0.55 | 0.10 | 0.09 |
| HCV 208B-672 | 0.08 | 2.79 | 0.10 | 0.08 |
| HCV 208B-739 | 1.13 | 0.11 | 0.07 | 0.08 |
| HCV 208B-742 | 0.08 | 0.44 | 0.07 | 0.09 |
| HCV 208B-750 | 0.10 | 3.41 | 0.12 | 0.09 |
| HCV 208B-762 | 0.07 | 0.65 | 0.05 | 0.05 |
| HCV 208B-765 | 0.10 | 0.64 | 0.16 | 0.08 |
| HCV 208B-778 | 0.11 | 0.06 | 0.23 | 0.06 |
| HCV 208B-780 | 0.07 | 1.02 | 0.17 | 0.10 |
| HCV 208B-788 | 0.09 | 0.49 | 0.10 | 0.16 |
| HCV 208B-793 | 0.09 | 0.72 | 0.09 | 0.13 |
| HCV 208B-796 | 0.07 | 3.03 | 0.07 | 0.09 |
| HCV 208B-822 | 0.08 | 1.35 | 0.07 | 0.05 |
| HCV 208B-826 | 0.53 | 1.35 | 0.08 | 0.07 |
| HCV 208B-853 | 0.09 | 0.74 | 0.12 | 0.13 |
| HCV 208B-860 | 0.12 | 0.73 | 0.12 | 0.07 |
| HCV 208B-862 | 0.21 | 3.28 | 0.10 | 0.09 |
| HCV 208B-894 | 0.07 | 0.09 | 0.48 | 0.07 |
| HCV 208B-909 | 0.09 | 3.11 | 0.11 | 0.07 |
| HCV 208B-911 | 0.09 | 0.09 | 0.71 | 0.10 |
| HCV 208B-922 | 0.93 | 0.11 | 0.11 | 0.09 |
| HCV 208B-952 | 0.07 | 0.64 | 0.07 | 0.09 |
| HCV 208B-954 | 0.06 | 3.43 | 0.06 | 0.06 |
| HCV 208B-956 | 0.10 | 0.85 | 0.05 | 0.05 |
| HCV 208B-960 | 0.09 | 3.38 | 0.11 | 0.08 |
| HCV 208B-982 | 0.20 | 1.10 | 0.13 | 0.09 |

Example 6

Cloning and Expression of Recombinant HCV Core1-169

The nucleotide sequence encoding amino acids 1-169 of HCV-1 was codon optimized for *E. coli* expression and cloned into a modified pET32a vector wherein the sequence encoding a thioredoxin fusion protein was eliminated and replaced with Methionine (M). In addition, a carboxy-terminal hexahistidine tag (SEQ ID NO:580) was included immediately after codon 169 of HCV core to facilitate purification via immobilized metal affinity chromatography (IMAC). *E. coli* BL21(DE3) cells were transformed with purified plasmid DNA and a clone harboring the plasmid pET-HCVCore1-169 identified. The protein expressed therefrom was designated as HCV Core1-169.

Protein expression was achieved by culturing the pET-HCVCore1-169-transformed *E. coli* BL21(DE3) cells in terrific broth (TB) medium. Cells were grown in a fermentor to an OD600 nm of 10 and then induced with 1 mM IPTG and grown at 37° C. for approximately three hours until an OD600 nm of approximately 20 was obtained. Cells were harvested by centrifugation and lysed by sonication in 25 mM Tris-HCl buffer (pH 7.4) containing 150 mM NaCl, 1 mM DTT, 5 mM $MgCl_2$, lysozyme and benzonase. The lysate was clarified by centrifugation and the insoluble fraction was dissolved in 25 mM Tris-HCl buffer (pH 7.4) containing 150 mM NaCl, 6 M urea, 1.0% n-dodecyl-β-D-maltoside, 1 mM DTT, and 5 mM $MgCl_2$. The dissolved lysate was again clarified by centrifugation and the soluble fraction was loaded onto a HisTrap Fast Flow column (GE Healthcare). The column was then washed with 25 column volumes of 25 mM Tris-HCl buffer (pH 7.4) containing 150 mM NaCl, 1 mM DTT, 5 mM $MgCl_2$, 6 M urea, 0.1% n-dodecyl-β-D-maltoside, and 10 mM imidazole. Elution was done using the same buffer and a linear gradient of imidazole (0-500 mM). Eluted fractions containing the desired protein of interest (determined by SDS-PAGE) were pooled and dialyzed against 25 mM Tris-HCl buffer (pH 7.4) containing 150 mM NaCl, 1 mM DTT, 5 mM $MgCl_2$, with and without 6 M urea and 0.1% n-dodecyl-β-D-maltoside.

HCV Core1-169 Nucleotide Sequence
(SEQ ID NO: 571)
Atgtctaccaacccgaaaccgcagaaaaaaaacaaacgtaacaccaaccg tcgtccgcaggacgttaaattcccgggtggtggtcagatcgttggtggtg tttacctgctgccgcgtcgtggtccgcgtctgggtgttcgtgctacgcgt aaaacctctgaacgttctcagccgcgtgggcgtcgtcagccgatcccgaa agctcgtcgtccggaaggtcgtacctgggctcagccgggttacccgtggc cgctgtacggtaacgaaggttgcggttgggctggttggctgctgtctccg cgtggatctcgtccgtcttggggtccgaccgacccgcgtcgtcgttctcg taaccttggtaaagttatcgataccctgacctgcggtttcgctgacctga tgggttacataccgctggttggagctccgctgggtggtgctgctcgtgct ctggcgcatggcgtgcgtgttctggaagatggcgtcaactatgccaccgg taatctg HCV Core1-169 Amino Acid Sequence
(SEQ ID NO: 572)
Mstnpkpqkknkrntnrrpqdvkfpgggqivggyyllprrgprlgvratr ktsersqprgrrqpipkarrpegrtwaqpgypwplygnegcgwagwllsp rgsrpswgptdprrrsrnlgkvidtltcgfadlmgyiplvgaplggaara lahgvrvledgvnyatgnl.

Example 7

Hybridoma Screening Using Core Antigen

The 24 well cultures were then evaluated by EIA for their ability bind HCV core1-169 (as described in Example 6) coated directly onto microtiter plates (solid phase assay). HCV core1-169 was coated onto 96 well micro-titer EIA plates at 1 μg/mL. After the capture reagent had been coated on the solid phase, the solution was removed and the plates were blocked using 3% BSA in PBS. The wells were washed with distilled water and 5 fold serial dilutions of the cell culture supernatants were added and allowed to incubate at room temperature for at least one hour. The plates were washed with distilled water and a HRP labeled goat anti-mouse IgG FC antibody diluted at approximately 200 ng/ml in BSA block solution was added to the plates and allowed to incubate for 30 minutes at room temperature. The plates were washed with distilled water and o-phenylenediamine substrate was used as the chromagen to generate signal. Plates were read at 492 nm and the results were analyzed.

Antibodies with BSA background reactivity greater than or equal to the core 1-169 reactivity value were considered negative and not used in calculating the average BSA background value. For the remainder of antibodies to be considered positive for core 1-169, they had to have an EIA signal of, at least, 0.50 OD units, or at least 5 times greater than the average BSA background signal of 0.10 OD units. Values are listed in Table 2.

TABLE 2

| Clone # | Solid Phase HCV Core OD (A492) | BSA OD (A492) |
|---|---|---|
| HCV 208A-1006 | 0.75 | 0.09 |
| HCV 208A-1007 | 0.39 | 0.06 |
| HCV 208A-1015 | 0.16 | 0.08 |
| HCV 208A-1022 | 0.09 | 0.07 |
| HCV 208A-1032 | 1.27 | 0.08 |
| HCV 208A-1064 | 0.94 | 0.08 |
| HCV 208A-1081 | 1.25 | 0.06 |
| HCV 208A-110 | 1.60 | 0.08 |
| HCV 208A-122 | 1.36 | 0.06 |
| HCV 208A-126 | 0.69 | 0.24 |
| HCV 208A-133 | 1.73 | 0.07 |
| HCV 208A-134 | 0.10 | 0.07 |
| HCV 208A-147 | 0.08 | 0.10 |
| HCV 208A-152 | 1.31 | 0.07 |
| HCV 208A-158 | 1.16 | 0.06 |
| HCV 208A-159 | 0.57 | 0.35 |
| HCV 208A-160 | 1.65 | 0.08 |
| HCV 208A-194 | 0.08 | 0.07 |
| HCV 208A-207 | 0.11 | 0.06 |
| HCV 208A-208 | 0.77 | 0.28 |
| HCV 208A-210 | 0.87 | 0.06 |
| HCV 208A-222 | 1.06 | 0.07 |
| HCV 208A-227 | 0.06 | 0.08 |
| HCV 208A-230 | 0.08 | 0.06 |
| HCV 208A-264 | 0.09 | 0.07 |
| HCV 208A-286 | 1.20 | 0.08 |
| HCV 208A-293 | 1.41 | 0.07 |
| HCV 208A-312 | 1.39 | 0.07 |
| HCV 208A-334 | 1.28 | 0.09 |
| HCV 208A-352 | 0.10 | 0.08 |
| HCV 208A-367 | 0.88 | 0.07 |
| HCV 208A-381 | 1.43 | 0.13 |
| HCV 208A-382 | 0.08 | 0.07 |
| HCV 208A-393 | 0.24 | 0.07 |
| HCV 208A-422 | 1.68 | 1.10 |
| HCV 208A-427 | 0.62 | 0.11 |
| HCV 208A-442 | 1.61 | 0.06 |
| HCV 208A-460 | 1.68 | 0.07 |
| HCV 208A-470 | 0.08 | 0.07 |
| HCV 208A-489 | 1.37 | 0.07 |
| HCV 208A-493 | 1.58 | 0.06 |
| HCV 208A-557 | 1.40 | 0.07 |
| HCV 208A-558 | 0.40 | 0.25 |
| HCV 208A-562 | 1.29 | 0.07 |
| HCV 208A-575 | 0.12 | 0.06 |
| HCV 208A-576 | 1.13 | 0.06 |
| HCV 208A-584 | 0.07 | 0.06 |
| HCV 208A-603 | 0.25 | 0.07 |
| HCV 208A-604 | 1.27 | 0.06 |
| HCV 208A-605 | 0.55 | 0.06 |
| HCV 208A-638 | 1.07 | 0.06 |

TABLE 2-continued

| Clone # | Solid Phase HCV Core OD (A492) | BSA OD (A492) |
|---|---|---|
| HCV 208A-641 | 0.20 | 0.07 |
| HCV 208A-658 | 0.83 | 0.07 |
| HCV 208A-692 | 0.07 | 0.06 |
| HCV 208A-695 | 0.61 | 0.17 |
| HCV 208A-719 | 1.12 | 0.06 |
| HCV 208A-736 | 0.07 | 0.07 |
| HCV 208A-741 | 1.20 | 0.06 |
| HCV 208A-744 | 1.57 | 0.07 |
| HCV 208A-759 | 0.36 | 0.22 |
| HCV 208A-768 | 1.12 | 0.07 |
| HCV 208A-774 | 1.41 | 0.06 |
| HCV 208A-793 | 1.24 | 0.06 |
| HCV 208A-807 | 0.14 | 0.10 |
| HCV 208A-826 | 0.09 | 0.06 |
| HCV 208A-828 | 1.49 | 0.07 |
| HCV 208A-830 | 1.16 | 0.06 |
| HCV 208A-850 | 1.18 | 0.06 |
| HCV 208A-863 | 1.55 | 0.07 |
| HCV 208A-874 | 0.45 | 0.06 |
| HCV 208A-877 | 0.90 | 0.07 |
| HCV 208A-879 | 0.32 | 0.30 |
| HCV 208A-920 | 1.14 | 0.07 |
| HCV 208A-926 | 1.14 | 0.09 |
| HCV 208A-938 | 0.83 | 0.13 |
| HCV 208A-939 | 0.07 | 0.06 |
| HCV 208A-967 | 1.08 | 1.30 |
| HCV 208A-982 | 1.25 | 0.07 |
| HCV 208A-983 | 0.12 | 0.06 |
| HCV 208B-1024 | 0.60 | 0.40 |
| HCV 208B-1029 | 0.07 | 0.07 |
| HCV 208B-1043 | 0.86 | 0.15 |
| HCV 208B-1070 | 1.24 | 0.08 |
| HCV 208B-1072 | 0.89 | 0.07 |
| HCV 208B-109 | 0.62 | 0.15 |
| HCV 208B-1094 | 0.90 | 0.17 |
| HCV 208B-1096 | 0.49 | 0.15 |
| HCV 208B-131 | 0.74 | 0.06 |
| HCV 208B-141 | 0.07 | 0.08 |
| HCV 208B-174 | 0.15 | 0.06 |
| HCV 208B-178 | 0.89 | 0.07 |
| HCV 208B-181 | 0.47 | 0.07 |
| HCV 208B-183 | 0.84 | 0.85 |
| HCV 208B-189 | 0.49 | 0.11 |
| HCV 208B-207 | 0.06 | 0.08 |
| HCV 208B-214 | 0.09 | 0.06 |
| HCV 208B-230 | 0.08 | 0.09 |
| HCV 208B-251 | 0.79 | 0.08 |
| HCV 208B-281 | 0.09 | 0.07 |
| HCV 208B-309 | 0.77 | 0.07 |
| HCV 208B-319 | 0.50 | 0.11 |
| HCV 208B-327 | 0.14 | 0.08 |
| HCV 208B-348 | 0.90 | 0.67 |
| HCV 208B-353 | 0.30 | 0.06 |
| HCV 208B-395 | 0.50 | 0.12 |
| HCV 208B-408 | 0.09 | 0.08 |
| HCV 208B-409 | 0.52 | 0.13 |
| HCV 208B-446 | 0.78 | 0.24 |
| HCV 208B-457 | 0.13 | 0.11 |
| HCV 208B-471 | 0.24 | 0.12 |
| HCV 208B-488 | 0.34 | 0.07 |
| HCV 208B-515 | 0.06 | 0.07 |
| HCV 208B-517 | 0.79 | 0.07 |
| HCV 208B-547 | 0.46 | 0.13 |
| HCV 208B-556 | 0.74 | 0.36 |
| HCV 208B-560 | 1.07 | 0.07 |
| HCV 208B-589 | 0.68 | 0.17 |
| HCV 208B-591 | 0.72 | 0.08 |
| HCV 208B-602 | 0.14 | 0.06 |
| HCV 208B-608 | 0.07 | 0.06 |
| HCV 208B-612 | 0.18 | 0.06 |
| HCV 208B-616 | 0.19 | 0.15 |
| HCV 208B-617 | 0.93 | 1.21 |
| HCV 208B-646 | 1.24 | 0.07 |
| HCV 208B-652 | 0.10 | 0.07 |
| HCV 208B-672 | 1.77 | 0.79 |
| HCV 208B-739 | 0.19 | 0.17 |
| HCV 208B-742 | 0.29 | 0.08 |
| HCV 208B-750 | 0.98 | 0.07 |
| HCV 208B-762 | 1.62 | 1.49 |
| HCV 208B-765 | 0.15 | 0.12 |
| HCV 208B-778 | 0.10 | 0.08 |
| HCV 208B-780 | 1.05 | 0.97 |
| HCV 208B-788 | 0.21 | 0.21 |
| HCV 208B-793 | 0.85 | 0.42 |
| HCV 208B-796 | 0.49 | 0.14 |
| HCV 208B-822 | 0.22 | 0.06 |
| HCV 208B-826 | 0.65 | 0.08 |
| HCV 208B-853 | 0.10 | 0.06 |
| HCV 208B-860 | 0.12 | 0.08 |
| HCV 208B-862 | 0.49 | 0.12 |
| HCV 208B-894 | 0.07 | 0.07 |
| HCV 208B-909 | 0.66 | 0.23 |
| HCV 208B-911 | 1.18 | 1.17 |
| HCV 208B-922 | 0.07 | 0.08 |
| HCV 208B-952 | 0.16 | 0.07 |
| HCV 208B-954 | 1.10 | 0.07 |
| HCV 208B-956 | 0.12 | 0.07 |
| HCV 208B-960 | 1.16 | 0.09 |
| HCV 208B-982 | 0.46 | 0.08 |

Example 8

Hybridoma Screening Via Core Antigen Capture Assay

The cell lines that were identified as positive at the 24 well stage by peptide-based EIA (Example 5) or HCV Core1-169 solid phase immunoassay (Example 7) were expanded for cryopreservation, followed by generation of high-density spent-cell supernatant. The high density exhausted supernatant from fusion 208A and 208B cell lines were tested for their ability to detect HCV Core1-169 captured from solution by a monoclonal antibody (14-153-229, U.S. Pat. No. 7,858,752) directed against an epitope within the nucleic acid binding domain of HCV Core (e.g. amino acids 1-125), also known as Domain 1. An anti-domain 1 monoclonal antibody was coated on the solid phase of 96 well micro-titer EIA plates at 1 ug/mL. After the capture reagent had been coated on the solid phase, it was removed and the plates were blocked for 30 minutes at room temperature using a 5×PBS buffer containing 2% fish gelatin, 0.5% Tween20, and 0.1% n-Dodecyl-N,N-Dimethylamine-N-Oxide (Affymetrix). The plates were washed with distilled water and a 50 ng/ml solution of Core1-169 antigen diluted in the fish gelatin/detergent solution was added to all wells and allowed to incubate for at least 30 minutes at room temperature. The wells were washed with distilled water and cell supernatants were titrated down the blocked plates and allowed to incubate at room temperature for at least 30 minutes at room temperature. The plates were washed with distilled water and a HRP labeled goat anti-mouse IgG FC antibody diluted to approximately 200 ng/ml in BSA block solution was added to the plates and allowed to incubate for 30 minutes at room temperature. The plates were washed with distilled water and o-phenylenediamine substrate was used as the chromagen to generate signal. Plates were read at 492 nm and the results were analyzed. Antibodies were considered positive for Core1-169 if they had EIA signal of, at least, 0.50 OD units, or at least 5 times greater than the average BSA background signal of 0.10 OD units. Values are listed in Table 3.

TABLE 3

| Clone # | Captured HCV Core OD (A492) | BSA OD (A492) |
|---|---|---|
| HCV 208A-1006 | 0.97 | 0.10 |
| HCV 208A-1007 | 1.25 | 0.13 |
| HCV 208A-1015 | 0.15 | 0.14 |
| HCV 208A-1022 | 0.33 | 0.22 |
| HCV 208A-1032 | 1.53 | 0.08 |
| HCV 208A-1064 | 1.57 | 0.09 |
| HCV 208A-1081 | 1.95 | 0.09 |
| HCV 208A-110 | 1.87 | 0.07 |
| HCV 208A-122 | 2.10 | 0.07 |
| HCV 208A-126 | 1.20 | 0.07 |
| HCV 208A-133 | 1.46 | 0.08 |
| HCV 208A-134 | 0.13 | 0.09 |
| HCV 208A-147 | 0.14 | 0.08 |
| HCV 208A-152 | 1.60 | 0.06 |
| HCV 208A-158 | 1.84 | 0.08 |
| HCV 208A-159 | 1.29 | 0.08 |
| HCV 208A-160 | 1.54 | 0.08 |
| HCV 208A-194 | 0.14 | 0.14 |
| HCV 208A-207 | 0.41 | 0.09 |
| HCV 208A-208 | 1.77 | 0.07 |
| HCV 208A-210 | 0.87 | 0.08 |
| HCV 208A-222 | 2.07 | 0.08 |
| HCV 208A-227 | 0.09 | 0.08 |
| HCV 208A-230 | 0.07 | 0.08 |
| HCV 208A-264 | 0.09 | 0.08 |
| HCV 208A-286 | 2.06 | 0.14 |
| HCV 208A-293 | 2.31 | 0.07 |
| HCV 208A-312 | 2.07 | 0.08 |
| HCV 208A-334 | 1.90 | 0.10 |
| HCV 208A-352 | 0.53 | 0.08 |
| HCV 208A-367 | 1.41 | 0.08 |
| HCV 208A-381 | 2.18 | 0.07 |
| HCV 208A-382 | 0.11 | 0.08 |
| HCV 208A-393 | 0.07 | 0.09 |
| HCV 208A-422 | 0.18 | 0.11 |
| HCV 208A-427 | 1.84 | 0.08 |
| HCV 208A-442 | 0.36 | 0.14 |
| HCV 208A-460 | 1.50 | 0.08 |
| HCV 208A-470 | 0.09 | 0.09 |
| HCV 208A-489 | 1.46 | 0.07 |
| HCV 208A-493 | 1.44 | 0.08 |
| HCV 208A-557 | 2.39 | 0.08 |
| HCV 208A-558 | 0.23 | 0.18 |
| HCV 208A-562 | 2.15 | 0.07 |
| HCV 208A-575 | 0.30 | 0.10 |
| HCV 208A-576 | 1.44 | 0.07 |
| HCV 208A-584 | 1.10 | 1.20 |
| HCV 208A-603 | 1.55 | 0.09 |
| HCV 208A-604 | 1.75 | 0.07 |
| HCV 208A-605 | 2.21 | 0.08 |
| HCV 208A-638 | 2.24 | 0.08 |
| HCV 208A-641 | 0.11 | 0.10 |
| HCV 208A-658 | 0.91 | 0.08 |
| HCV 208A-692 | 0.57 | 0.09 |
| HCV 208A-695 | 1.77 | 0.09 |
| HCV 208A-719 | 1.68 | 0.08 |
| HCV 208A-736 | 0.32 | 0.10 |
| HCV 208A-741 | 1.90 | 0.08 |
| HCV 208A-744 | 1.62 | 0.10 |
| HCV 208A-759 | 0.63 | 0.08 |
| HCV 208A-768 | 2.29 | 0.08 |
| HCV 208A-774 | 1.91 | 0.09 |
| HCV 208A-793 | 1.19 | 0.08 |
| HCV 208A-807 | 0.09 | 0.08 |
| HCV 208A-826 | 0.17 | 0.08 |
| HCV 208A-828 | 1.55 | 0.08 |
| HCV 208A-830 | 2.09 | 0.08 |
| HCV 208A-850 | 1.50 | 0.09 |
| HCV 208A-863 | 1.88 | 0.08 |
| HCV 208A-874 | 0.18 | 0.10 |
| HCV 208A-877 | 1.25 | 0.08 |
| HCV 208A-879 | 0.15 | 0.11 |
| HCV 208A-920 | 1.82 | 0.08 |
| HCV 208A-926 | 1.83 | 0.08 |
| HCV 208A-938 | 1.66 | 0.08 |
| HCV 208A-939 | 0.31 | 0.09 |
| HCV 208A-967 | 0.18 | 0.15 |
| HCV 208A-982 | 1.44 | 0.09 |
| HCV 208A-983 | 0.64 | 0.09 |
| HCV 208B-1024 | 0.31 | 0.12 |
| HCV 208B-1029 | 0.14 | 0.15 |
| HCV 208B-1043 | 1.21 | 0.07 |
| HCV 208B-1070 | 1.25 | 0.08 |
| HCV 208B-1072 | 1.45 | 0.08 |
| HCV 208B-109 | 1.28 | 0.10 |
| HCV 208B-1094 | 1.51 | 0.08 |
| HCV 208B-1096 | 1.75 | 0.07 |
| HCV 208B-131 | 1.52 | 0.08 |
| HCV 208B-141 | 0.17 | 0.11 |
| HCV 208B-174 | 0.75 | 0.09 |
| HCV 208B-178 | 1.09 | 0.08 |
| HCV 208B-181 | 1.65 | 0.07 |
| HCV 208B-183 | 0.11 | 0.10 |
| HCV 208B-189 | 1.81 | 0.12 |
| HCV 208B-207 | 0.07 | 0.08 |
| HCV 208B-214 | 0.08 | 0.08 |
| HCV 208B-230 | 0.13 | 0.09 |
| HCV 208B-251 | 1.39 | 0.10 |
| HCV 208B-281 | 0.11 | 0.12 |
| HCV 208B-309 | 1.23 | 0.08 |
| HCV 208B-319 | 1.45 | 0.08 |
| HCV 208B-327 | 0.11 | 0.09 |
| HCV 208B-348 | 0.21 | 0.23 |
| HCV 208B-353 | 0.91 | 0.10 |
| HCV 208B-395 | 1.95 | 0.08 |
| HCV 208B-408 | 0.09 | 0.10 |
| HCV 208B-409 | 1.34 | 0.10 |
| HCV 208B-446 | 1.08 | 0.08 |
| HCV 208B-457 | 0.09 | 0.07 |
| HCV 208B-471 | 0.35 | 0.08 |
| HCV 208B-488 | 0.10 | 0.08 |
| HCV 208B-515 | 0.08 | 0.08 |
| HCV 208B-517 | 0.97 | 0.12 |
| HCV 208B-547 | 1.62 | 0.07 |
| HCV 208B-556 | 1.35 | 0.18 |
| HCV 208B-560 | 1.30 | 0.07 |
| HCV 208B-589 | 1.29 | 0.08 |
| HCV 208B-591 | 1.66 | 0.08 |
| HCV 208B-602 | 0.24 | 0.07 |
| HCV 208B-608 | 0.09 | 0.08 |
| HCV 208B-612 | 1.20 | 0.08 |
| HCV 208B-616 | 0.09 | 0.08 |
| HCV 208B-617 | 0.07 | 0.08 |
| HCV 208B-646 | 1.29 | 0.08 |
| HCV 208B-652 | 0.10 | 0.09 |
| HCV 208B-672 | 0.99 | 0.08 |
| HCV 208B-739 | 0.88 | 0.09 |
| HCV 208B-742 | 0.12 | 0.08 |
| HCV 208B-750 | 1.53 | 0.08 |
| HCV 208B-762 | 0.28 | 0.21 |
| HCV 208B-765 | 0.36 | 0.44 |
| HCV 208B-778 | 0.08 | 0.07 |
| HCV 208B-780 | 0.10 | 0.08 |
| HCV 208B-788 | 0.09 | 0.07 |
| HCV 208B-793 | 0.17 | 0.20 |
| HCV 208B-796 | 1.19 | 0.09 |
| HCV 208B-822 | 0.12 | 0.11 |
| HCV 208B-826 | 0.72 | 0.41 |
| HCV 208B-853 | 0.08 | 0.09 |
| HCV 208B-860 | 0.09 | 0.09 |
| HCV 208B-862 | 1.07 | 0.07 |
| HCV 208B-894 | 0.09 | 0.09 |
| HCV 208B-909 | 0.39 | 0.10 |
| HCV 208B-911 | 0.14 | 0.17 |
| HCV 208B-922 | 0.08 | 0.08 |
| HCV 208B-952 | 0.09 | 0.08 |
| HCV 208B-954 | 1.53 | 0.07 |
| HCV 208B-956 | 0.14 | 0.12 |
| HCV 208B-960 | 1.19 | 0.08 |
| HCV 208B-982 | 0.99 | 0.08 |

Example 9

Determination of Anti-HCV Core Antibody Binding Kinetics

The affinities/kinetics of the anti-HCV core peptide 134-171 monoclonal antibodies were determined using a Biacore 4000 instrument (GE Healthcare Bio-Sciences AB, Uppsala, Sweden). First, after pre-treating a CM5 Series S biosensor chip (GE Healthcare) with duplicate injections of 100 mM HCl, 50 mM NaOH, and 0.1% SDS, a rabbit anti-mouse IgG Capture Biosensor was created by amine-coupling rabbit anti-mouse IgG antibody (GE Healthcare, Piscataway, N.J.) on Spots 1, 2, 4, and 5 in all four flow cells of the biosensor chip via EDC/NHS/ethanolamine chemistry provided in an Amine Coupling Kit (GE Healthcare). Clarified anti-HCV Core antibody exhausted hybridoma supernatants and HCV Core peptide were diluted into a filtered buffer composed of 10×HBS-EP+ buffer (GE Healthcare; hereinafter "running buffer") diluted 10-fold into distilled $H_2O$, supplemented with 0.1% BSA and 0.1% CM-Dextran, and 0.2 µm filtered. Each HCV Core antibody supernatant was diluted 1:1 with running buffer and 0.2 µm filtered again. A 53 amino acid custom peptide (ALRZ-9 peptide, Anaspec, Fremont, Calif.) was chemically synthesized to contain HCV Core residues 134-171 and a carboxy-terminal tetanus toxoid (TT) immunogenic T-cell epitope peptide (Eur. J. Immunol. (1989), 19:2237-2242) with the terminal amino and carboxy groups acetylated and amidated, respectively. The lyophilized HCV core 134-171-tetanus toxoid synthetic peptide immunogen was diluted in distilled water to a stock concentration of 0.7 or 1 mg/mL and further diluted into running buffer to concentrations of either 0.457 to 3,000 nM or 0.412 to 2,700 nM, both using a 3-fold dilution series. All antigen solutions were 0.2 µm filtered prior to use.

The HCV Core 134-171-TT peptide procedure was as follows: 10 µL of HCV Core antibody was separately injected over Spots 1 and 5 in all four flow cells at 10 µL/minute. After all the spots contained captured antibody, the flow rate was increased to 30 µL/minute and the biosensor was equilibrated at this new flow rate for 2 minutes; then, a 3 minute injection (90 µL) of HCV Core peptide followed by 4 minutes of running buffer. All biosensor surfaces were regenerated with one 30 µL injection of 10 mM glycine, pH 1.7 (GE Healthcare), at a flow rate of 10 µL/minute. All concentrations were tested in duplicate. The binding kinetics (association and dissociation) were monitored via sensorgrams during antigen injection followed by running buffer. The sensorgrams were double-referenced and fit to a 1:1 binding model using Biacore 4000 Evaluation software (GE Healthcare Bio-Sciences AB) to determine association and dissociation rates, as well as overall $K_D$. Kinetic and affinity values are listed in Table 4. If values are not present, then either binding kinetics could not be determined or the antibody did not interact with the HCV Core 134-171-TT peptide in this assay.

ALRZ-9 peptide (SEQ ID NO: 577)

Ac-MGYIPLVGAPLGGAARALAHGVRVLEDGVNYATGNLPGQYIKANSK
FIGITEL-NH2

TABLE 4

| | Binding Interactions with HCV Core 134-171-TT Peptide | | |
|---|---|---|---|
| Clone # | ka (1/Ms) | kd (1/s) | KD (M) |
| HCV 208A-1006 | 1.8E+06 | 6.2E−04 | 3.5E−10 |
| HCV 208A-1007 | 1.8E+06 | 7.4E−04 | 4.1E−10 |
| HCV 208A-1022 | 1.6E+05 | 2.5E−03 | 1.6E−08 |
| HCV 208A-1032 | 1.2E+06 | 5.5E−04 | 4.5E−10 |
| HCV 208A-1064 | 1.6E+06 | 3.4E−04 | 2.1E−10 |
| HCV 208A-1081 | 1.3E+06 | 5.7E−04 | 4.5E−10 |
| HCV 208A-110 | 1.7E+06 | 5.5E−04 | 3.3E−10 |
| HCV 208A-122 | 1.8E+06 | 2.1E−04 | 1.2E−10 |
| HCV 208A-133 | 1.2E+06 | 5.0E−04 | 4.1E−10 |
| HCV 208A-134 | 1.8E+04 | 3.8E−05 | 2.1E−09 |
| HCV 208A-152 | 7.7E+05 | 4.0E−04 | 5.2E−10 |
| HCV 208A-158 | 1.3E+06 | 4.4E−04 | 3.3E−10 |
| HCV 208A-159 | 1.4E+06 | 6.5E−04 | 4.5E−10 |
| HCV 208A-160 | 1.6E+06 | 6.1E−04 | 3.8E−10 |
| HCV 208A-207 | 3.1E+05 | <1E−05 | <3.2E−11 |
| HCV 208A-208 | 1.6E+06 | 5.4E−04 | 3.4E−10 |
| HCV 208A-222 | 1.1E+06 | 3.5E−04 | 3.1E−10 |
| HCV 208A-286 | 2.0E+06 | 2.5E−04 | 1.2E−10 |
| HCV 208A-293 | 2.1E+06 | 2.3E−04 | 1.1E−10 |
| HCV 208A-312 | 2.1E+06 | 2.6E−04 | 1.3E−10 |
| HCV 208A-334 | 1.7E+06 | 5.7E−04 | 3.4E−10 |
| HCV 208A-352 | 1.0E+05 | 5.4E−05 | 5.2E−10 |
| HCV 208A-367 | 1.5E+06 | 5.9E−04 | 3.9E−10 |
| HCV 208A-381 | 2.0E+06 | 2.7E−04 | 1.3E−10 |
| HCV 208A-427 | 1.2E+06 | 5.6E−04 | 4.5E−10 |
| HCV 208A-460 | 1.3E+06 | 5.6E−04 | 4.4E−10 |
| HCV 208A-489 | 1.3E+06 | 6.6E−04 | 4.9E−10 |
| HCV 208A-493 | 1.4E+06 | 5.7E−04 | 4.1E−10 |
| HCV 208A-557 | 2.4E+06 | 2.1E−04 | 9.1E−11 |
| HCV 208A-562 | 1.7E+06 | 6.6E−04 | 4.0E−10 |
| HCV 208A-576 | 1.2E+06 | 5.8E−04 | 4.9E−10 |
| HCV 208A-603 | 1.5E+06 | 5.6E−04 | 3.9E−10 |
| HCV 208A-604 | 1.3E+06 | 5.8E−04 | 4.5E−10 |
| HCV 208A-605 | 8.7E+05 | 3.7E−04 | 4.3E−10 |
| HCV 208A-638 | 2.7E+06 | 5.3E−04 | 2.0E−10 |
| HCV 208A-695 | 2.0E+06 | 7.1E−04 | 3.5E−10 |
| HCV 208A-719 | 1.9E+06 | 5.7E−04 | 3.0E−10 |
| HCV 208A-736 | 2.2E+04 | 1.7E−05 | 7.6E−10 |
| HCV 208A-741 | 1.7E+06 | 6.9E−04 | 4.1E−10 |
| HCV 208A-744 | 1.3E+06 | 6.0E−04 | 4.5E−10 |
| HCV 208A-768 | 1.1E+06 | 3.6E−04 | 3.3E−10 |
| HCV 208A-774 | 1.3E+06 | 5.9E−04 | 4.5E−10 |
| HCV 208A-793 | 1.8E+06 | 6.6E−04 | 3.7E−10 |
| HCV 208A-826 | 1.8E+04 | 7.4E−05 | 4.2E−09 |
| HCV 208A-828 | 1.4E+06 | 5.7E−04 | 4.2E−10 |
| HCV 208A-830 | 3.4E+06 | 5.4E−04 | 1.6E−10 |
| HCV 208A-850 | 1.6E+06 | 6.0E−04 | 3.9E−10 |
| HCV 208A-863 | 1.3E+06 | 6.1E−04 | 4.6E−10 |
| HCV 208A-877 | 1.1E+06 | 2.4E−03 | 2.2E−09 |
| HCV 208A-920 | 1.5E+06 | 5.6E−04 | 3.9E−10 |
| HCV 208A-926 | 1.7E+06 | 5.6E−04 | 3.3E−10 |
| HCV 208A-938 | 1.6E+06 | 5.2E−04 | 3.2E−10 |
| HCV 208A-939 | 2.5E+04 | 2.2E−04 | 9.0E−09 |
| HCV 208A-982 | 1.3E+06 | 6.2E−04 | 4.9E−10 |
| HCV 208A-983 | 9.7E+04 | 4.6E−05 | 4.6E−10 |
| HCV 208B-1024 | 1.0E+06 | 1.4E−02 | 1.5E−08 |
| HCV 208B-1043 | 1.1E+06 | 6.0E−04 | 5.4E−10 |
| HCV 208B-1070 | 1.6E+06 | 5.2E−04 | 3.2E−10 |
| HCV 208B-1072 | 1.3E+06 | 5.5E−04 | 4.2E−10 |
| HCV 208B-109 | 1.4E+06 | 5.1E−04 | 3.7E−10 |
| HCV 208B-1094 | 1.5E+06 | 2.5E−04 | 1.6E−10 |
| HCV 208B-1096 | 1.3E+06 | 6.0E−04 | 4.6E−10 |
| HCV 208B-131 | 1.3E+06 | 1.7E−03 | 1.3E−09 |
| HCV 208B-141 | 3.1E+04 | 1.6E−04 | 5.3E−09 |
| HCV 208B-174 | 7.6E+05 | 1.8E−04 | 2.5E−10 |
| HCV 208B-181 | 2.0E+06 | 3.6E−04 | 1.8E−10 |
| HCV 208B-189 | 8.8E+05 | 1.5E−04 | 1.7E−10 |
| HCV 208B-251 | 1.1E+06 | 6.5E−04 | 5.8E−10 |
| HCV 208B-281 | 2.2E+03 | 2.5E−04 | 9.6E−08 |
| HCV 208B-309 | 1.2E+06 | 6.8E−04 | 5.7E−10 |
| HCV 208B-319 | 2.2E+06 | 2.8E−04 | 1.3E−10 |
| HCV 208B-395 | 1.3E+06 | 4.7E−04 | 3.6E−10 |
| HCV 208B-409 | 1.9E+06 | 2.8E−04 | 1.5E−10 |
| HCV 208B-446 | 2.1E+06 | 2.8E−04 | 1.4E−10 |
| HCV 208B-471 | 2.2E+05 | 5.5E−05 | 2.5E−10 |

TABLE 4-continued

| | Binding Interactions with HCV Core 134-171-TT Peptide | | |
|---|---|---|---|
| Clone # | ka (1/Ms) | kd (1/s) | KD (M) |
| HCV 208B-547 | 1.6E+06 | 4.9E−03 | 3.2E−09 |
| HCV 208B-556 | 1.5E+06 | 6.0E−04 | 4.0E−10 |
| HCV 208B-560 | 1.1E+06 | 2.6E−04 | 2.3E−10 |
| HCV 208B-589 | 9.6E+05 | 6.1E−04 | 6.3E−10 |
| HCV 208B-591 | 2.2E+06 | 2.0E−04 | 9.3E−11 |
| HCV 208B-612 | 1.8E+05 | 6.5E−05 | 3.5E−10 |
| HCV 208B-646 | 1.8E+06 | 6.0E−04 | 3.4E−10 |
| HCV 208B-672 | 2.2E+06 | 3.4E−04 | 1.6E−10 |
| HCV 208B-739 | 2.8E+05 | 5.5E−05 | 2.0E−10 |
| HCV 208B-750 | 2.0E+06 | 2.6E−04 | 1.3E−10 |
| HCV 208B-796 | 1.5E+06 | 6.8E−04 | 4.6E−10 |
| HCV 208B-862 | 1.4E+06 | 1.0E−04 | 7.0E−11 |
| HCV 208B-954 | 1.6E+06 | 5.5E−04 | 3.4E−10 |
| HCV 208B-960 | 1.6E+06 | 5.6E−04 | 3.5E−10 |
| HCV 208B-982 | 2.2E+06 | 8.0E−04 | 3.5E−10 |

Example 10

BIACore Antibody Binding Pair Analysis with Nucleic Acid Binding Domain mAbs

The ability of the anti-HCV core peptide 134-171 monoclonal antibodies to form antibody binding pairs with anti-HCV Core C11-3, C11-7, C11-9, and C11-14 (U.S. Pat. No. 6,727,092; Morota, et al, J. Virol. Meth., 2009, 157:8-14) antibodies and recombinant HCV Core1-169 antigen was determined using a Biacore 4000 instrument (GE Healthcare Bio-Sciences AB). First, after pre-treating a CM5 Series S biosensor chip (GE Healthcare) with duplicate injections of 100 mM HCl, 50 mM NaOH, and 0.1% SDS, a rabbit anti-mouse IgG Capture Biosensor was created by amine-coupling rabbit anti-mouse IgG antibody (GE Healthcare, Piscataway, N.J.) on Spots 1, 2, 4, and 5 in all four flow cells of the biosensor chip via EDC/NHS/ethanolamine chemistry provided in an Amine Coupling Kit (GE Healthcare).

Clarified anti-HCV Core (peptide aa 134-171) antibody exhausted hybridoma supernatants, recombinant HCV Core1-169 antigen, 3 different purified mouse monoclonal IgG representing isotypes IgG1, IgG2a, and IgG2b non-reactive to HCV Core used as blocking reagents, and anti-HCV Core C11-3, C11-7, C11-9, and C11-14 mAbs were diluted into a filtered running buffer (hereinafter "running buffer") composed of 10×PBS buffer (GE Healthcare) diluted 5-fold into distilled H$_2$O, supplemented with 3 mM EDTA, 0.1% BSA, 0.1% CM-Dextran, 0.1% n-Dodecyl-N,N-Dimethylamine-N-Oxide, an extra 500 mM NaCl, and 0.2 µm filtered. Each HCV Core antibody supernatant was diluted 1:1, the recombinant HCV Core1-169 antigen was diluted to 500 nM per the calculated dimer molecular weight (39,453 Da), the anti-HCV Core C11-3, C11-7, C11-9, and C11-14 purified monoclonal antibodies were individually diluted to 20 µg/mL, and the 3 mouse IgG blocking reagents were all diluted as a pool with each isotype having a concentration of at least 100 µg/mL in running buffer. All dilutions were 0.2 µm filtered prior to use.

The HCV Core antibody-antigen-antibody sandwich procedure was as follows. 20 µL of the HCV Core C11 antibodies were injected over Spots 1 and 5 in all four flow cells at 10 µL/minute: C11-3 in flow cell 1, C11-7 in flow cell 2, C11-9 in flow cell 3, and c11-14 in flow cell 4. The flow rate was increased to 30 µl/minute and the remaining available anti-mouse IgG binding sites on the biosensor were blocked with the mouse IgG1, IgG2a, and IgG2b isotype pool by injecting 60 µL over Spots 1 and 2 and then 60 µL over Spots 4 and 5 in all flow cells. 60 µL of HCV Core1-169 antigen was injected over Spot 1 and then another 60 µL over Spot 5 in all flow cells. 60 µL of one HCV Core antibody diluted supernatant was inject over Spots 1 and 2 over all flow cells and another diluted supernatant over Spots 4 and 5 in all flow cells. The flow rate was decreased 10 µl/minute and all biosensor surfaces were regenerated with one 30 µL injection of 10 mM glycine, pH 1.7 (GE Healthcare).

Using the Biacore 4000 Evaluation Epitope Mapping software module (GE Healthcare Bio-Sciences AB), the binding response for each C11 antibody, antigen, and HCV Core antibody supernatant was determined after each injection and used to calculate an expected response reference value using the dimeric antigen and antibody (150,000 Da) molecular weights. An expected percent binding value was determined using individual samples versus the reference value. Any expected percent binding values that were greater than 5.0 were considered positive for the ability to form an antibody sandwich with the recombinant HCV Core1-169 antigen. Expected percent values are listed in Table 5.

TABLE 5

| Secondary Conjugate Antibody Anti-HCV Core 134-171 antibodies | Primary Capture Antibody Anti-HCV Core antibody | | | |
|---|---|---|---|---|
| | C11-3 | C11-7 | C11-9 | C11-14 |
| HCV 208A-1006 | 2.4 | 3.1 | ≤1.0 | 2.5 |
| HCV 208A-1007 | 4.4 | 6.1 | 2.7 | 4.2 |
| HCV 208A-1015 | ≤1.0 | ≤1.0 | ≤1.0 | ≤1.0 |
| HCV 208A-1022 | ≤1.0 | 1.3 | ≤1.0 | ≤1.0 |
| HCV 208A-1032 | 19.5 | 26.7 | 15.7 | 21.8 |
| HCV 208A-1064 | 16.3 | 19.6 | 10.5 | 16.3 |
| HCV 208A-1081 | 19.0 | 25.9 | 14.9 | 20.8 |
| HCV 208A-110 | 15.7 | 21.1 | 9.4 | 14.8 |
| HCV 208A-122 | 17.3 | 19.7 | 9.6 | 14.8 |
| HCV 208A-126 | 1.2 | 2.0 | ≤1.0 | 1.3 |
| HCV 208A-133 | 9.8 | 13.9 | 5.8 | 9.3 |
| HCV 208A-134 | ≤1.0 | ≤1.0 | ≤1.0 | ≤1.0 |
| HCV 208A-147 | ≤1.0 | ≤1.0 | ≤1.0 | ≤1.0 |
| HCV 208A-152 | 10.0 | 12.5 | 6.9 | 9.8 |
| HCV 208A-158 | 14.0 | 16.5 | 7.8 | 12.4 |
| HCV 208A-159 | 4.6 | 7.0 | 3.3 | 5.5 |
| HCV 208A-160 | 15.5 | 20.9 | 8.7 | 13.8 |
| HCV 208A-194 | ≤1.0 | ≤1.0 | ≤1.0 | ≤1.0 |
| HCV 208A-207 | ≤1.0 | ≤1.0 | ≤1.0 | ≤1.0 |
| HCV 208A-208 | 2.6 | 3.2 | ≤1.0 | 2.5 |
| HCV 208A-210 | 1.2 | 1.6 | ≤1.0 | ≤1.0 |
| HCV 208A-222 | 15.6 | 18.8 | 10.7 | 15.0 |
| HCV 208A-227 | ≤1.0 | 1.1 | ≤1.0 | ≤1.0 |
| HCV 208A-230 | ≤1.0 | ≤1.0 | ≤1.0 | ≤1.0 |
| HCV 208A-264 | ≤1.0 | 1.1 | ≤1.0 | ≤1.0 |
| HCV 208A-286 | 18.9 | 22.1 | 13.0 | 18.5 |
| HCV 208A-293 | 17.9 | 20.9 | 11.0 | 16.4 |
| HCV 208A-312 | 16.3 | 19.7 | 11.8 | 16.4 |
| HCV 208A-334 | 17.2 | 20.6 | 10.3 | 15.9 |
| HCV 208A-352 | ≤1.0 | ≤1.0 | ≤1.0 | ≤1.0 |
| HCV 208A-367 | 9.7 | 14.5 | 6.1 | 9.3 |
| HCV 208A-381 | 17.2 | 20.3 | 12.3 | 17.4 |
| HCV 208A-382 | ≤1.0 | 1.5 | ≤1.0 | ≤1.0 |
| HCV 208A-393 | ≤1.0 | ≤1.0 | ≤1.0 | ≤1.0 |
| HCV 208A-422 | ≤1.0 | ≤1.0 | ≤1.0 | ≤1.0 |
| HCV 208A-427 | 15.5 | 22.1 | 11.7 | 16.5 |
| HCV 208A-442 | ≤1.0 | 1.6 | ≤1.0 | ≤1.0 |
| HCV 208A-460 | 17.5 | 24.3 | 12.9 | 18.3 |
| HCV 208A-470 | ≤1.0 | ≤1.0 | ≤1.0 | ≤1.0 |
| HCV 208A-489 | 15.9 | 21.9 | 11.5 | 16.6 |
| HCV 208A-493 | 12.6 | 17.7 | 7.8 | 12.2 |
| HCV 208A-557 | 17.7 | 21.4 | 13.3 | 17.6 |
| HCV 208A-558 | ≤1.0 | 1.1 | ≤1.0 | ≤1.0 |
| HCV 208A-562 | 13.8 | 17.1 | 9.5 | 14.8 |
| HCV 208A-575 | ≤1.0 | ≤1.0 | ≤1.0 | ≤1.0 |

TABLE 5-continued

| Secondary Conjugate Antibody Anti-HCV Core 134-171 antibodies | Primary Capture Antibody Anti-HCV Core antibody | | | |
|---|---|---|---|---|
| | C11-3 | C11-7 | C11-9 | C11-14 |
| HCV 208A-576 | 12.6 | 16.9 | 9.1 | 13.3 |
| HCV 208A-584 | ≤1.0 | 1.6 | ≤1.0 | ≤1.0 |
| HCV 208A-603 | 6.7 | 9.1 | 4.0 | 6.8 |
| HCV 208A-604 | 15.4 | 20.8 | 9.8 | 14.8 |
| HCV 208A-605 | 15.9 | 19.3 | 11.9 | 15.8 |
| HCV 208A-638 | 14.1 | 16.9 | 9.2 | 13.3 |
| HCV 208A-641 | ≤1.0 | ≤1.0 | ≤1.0 | ≤1.0 |
| HCV 208A-658 | 1.8 | 2.5 | ≤1.0 | ≤1.0 |
| HCV 208A-692 | ≤1.0 | ≤1.0 | ≤1.0 | ≤1.0 |
| HCV 208A-695 | 14.2 | 20.4 | 9.5 | 15.0 |
| HCV 208A-719 | 7.5 | 10.0 | 4.9 | 8.0 |
| HCV 208A-736 | ≤1.0 | ≤1.0 | ≤1.0 | ≤1.0 |
| HCV 208A-741 | 19.4 | 22.7 | 14.2 | 21.2 |
| HCV 208A-744 | 16.7 | 22.5 | 10.5 | 16.1 |
| HCV 208A-759 | ≤1.0 | ≤1.0 | ≤1.0 | ≤1.0 |
| HCV 208A-768 | 12.7 | 17.1 | 8.8 | 12.6 |
| HCV 208A-774 | 18.5 | 24.5 | 13.4 | 19.3 |
| HCV 208A-793 | 3.8 | 6.2 | 2.5 | 3.9 |
| HCV 208A-807 | ≤1.0 | ≤1.0 | ≤1.0 | ≤1.0 |
| HCV 208A-826 | ≤1.0 | 1.3 | ≤1.0 | ≤1.0 |
| HCV 208A-828 | 14.8 | 20.7 | 10.9 | 16.5 |
| HCV 208A-830 | 11.9 | 14.7 | 7.9 | 11.7 |
| HCV 208A-850 | 7.3 | 9.7 | 4.4 | 7.5 |
| HCV 208A-863 | 18.0 | 24.9 | 12.1 | 18.0 |
| HCV 208A-874 | ≤1.0 | ≤1.0 | ≤1.0 | ≤1.0 |
| HCV 208A-877 | 9.4 | 12.1 | 5.9 | 10.7 |
| HCV 208A-879 | ≤1.0 | ≤1.0 | ≤1.0 | ≤1.0 |
| HCV 208A-920 | 19.3 | 22.9 | 13.2 | 19.1 |
| HCV 208A-926 | 19.3 | 26.3 | 14.7 | 21.1 |
| HCV 208A-938 | 14.1 | 21.0 | 10.4 | 15.5 |
| HCV 208A-939 | ≤1.0 | ≤1.0 | ≤1.0 | ≤1.0 |
| HCV 208A-967 | ≤1.0 | ≤1.0 | ≤1.0 | ≤1.0 |
| HCV 208A-982 | 19.2 | 26.3 | 15.0 | 20.6 |
| HCV 208A-983 | ≤1.0 | ≤1.0 | ≤1.0 | ≤1.0 |
| HCV 208B-1024 | 10.9 | 14.3 | 7.1 | 12.2 |
| HCV 208B-1029 | ≤1.0 | ≤1.0 | ≤1.0 | ≤1.0 |
| HCV 208B-1043 | 17.4 | 20.7 | 12.0 | 17.9 |
| HCV 208B-1070 | 22.0 | 28.6 | 17.7 | 25.3 |
| HCV 208B-1072 | 25.0 | 30.2 | 19.3 | 27.4 |
| HCV 208B-109 | 12.5 | 16.0 | 8.6 | 13.3 |
| HCV 208B-1094 | 24.4 | 28.4 | 19.8 | 27.8 |
| HCV 208B-1096 | 15.1 | 16.9 | 11.4 | 16.3 |
| HCV 208B-131 | 11.4 | 12.4 | 6.8 | 11.6 |
| HCV 208B-141 | ≤1.0 | ≤1.0 | ≤1.0 | ≤1.0 |
| HCV 208B-174 | 1.6 | 1.5 | ≤1.0 | 1.6 |
| HCV 208B-178 | ≤1.0 | 1.7 | ≤1.0 | ≤1.0 |
| HCV 208B-181 | 7.4 | 10.0 | 5.4 | 8.1 |
| HCV 208B-183 | ≤1.0 | ≤1.0 | ≤1.0 | ≤1.0 |
| HCV 208B-189 | 2.3 | 2.9 | ≤1.0 | 2.7 |
| HCV 208B-207 | ≤1.0 | ≤1.0 | ≤1.0 | ≤1.0 |
| HCV 208B-214 | ≤1.0 | ≤1.0 | ≤1.0 | ≤1.0 |
| HCV 208B-230 | ≤1.0 | ≤1.0 | ≤1.0 | ≤1.0 |
| HCV 208B-251 | 16.6 | 20.1 | 12.3 | 18.2 |
| HCV 208B-281 | ≤1.0 | ≤1.0 | ≤1.0 | ≤1.0 |
| HCV 208B-309 | 13.6 | 17.5 | 10.2 | 15.5 |
| HCV 208B-319 | 6.0 | 8.5 | 4.2 | 6.3 |
| HCV 208B-327 | ≤1.0 | ≤1.0 | ≤1.0 | ≤1.0 |
| HCV 208B-348 | ≤1.0 | 1.5 | ≤1.0 | ≤1.0 |
| HCV 208B-353 | 1.9 | 2.6 | ≤1.0 | 2.4 |
| HCV 208B-395 | 7.6 | 9.4 | 5.2 | 7.8 |
| HCV 208B-408 | ≤1.0 | ≤1.0 | ≤1.0 | ≤1.0 |
| HCV 208B-409 | 1.8 | 2.7 | ≤1.0 | 2.0 |
| HCV 208B-446 | 10.0 | 12.2 | 7.8 | 10.3 |
| HCV 208B-457 | ≤1.0 | ≤1.0 | ≤1.0 | ≤1.0 |
| HCV 208B-471 | ≤1.0 | ≤1.0 | ≤1.0 | ≤1.0 |
| HCV 208B-488 | ≤1.0 | ≤1.0 | ≤1.0 | ≤1.0 |
| HCV 208B-515 | ≤1.0 | ≤1.0 | ≤1.0 | ≤1.0 |
| HCV 208B-517 | ≤1.0 | ≤1.0 | ≤1.0 | ≤1.0 |
| HCV 208B-547 | 7.2 | 8.3 | 4.9 | 8.2 |
| HCV 208B-556 | 11.5 | 15.3 | 8.3 | 12.7 |
| HCV 208B-560 | 10.6 | 15.5 | 8.3 | 12.0 |
| HCV 208B-589 | 9.4 | 11.7 | 6.7 | 9.9 |
| HCV 208B-591 | 19.1 | 23.0 | 15.1 | 21.7 |
| HCV 208B-602 | 1.3 | 1.8 | ≤1.0 | ≤1.0 |
| HCV 208B-608 | ≤1.0 | ≤1.0 | ≤1.0 | ≤1.0 |
| HCV 208B-612 | 3.8 | 4.4 | ≤1.0 | 3.1 |
| HCV 208B-616 | ≤1.0 | ≤1.0 | ≤1.0 | ≤1.0 |
| HCV 208B-617 | ≤1.0 | ≤1.0 | ≤1.0 | ≤1.0 |
| HCV 208B-646 | 22.0 | 30.2 | 17.8 | 25.6 |
| HCV 208B-652 | ≤1.0 | 1.3 | ≤1.0 | ≤1.0 |
| HCV 208B-672 | 2.6 | 2.8 | ≤1.0 | 2.7 |
| HCV 208B-739 | ≤1.0 | ≤1.0 | ≤1.0 | ≤1.0 |
| HCV 208B-742 | ≤1.0 | ≤1.0 | ≤1.0 | ≤1.0 |
| HCV 208B-750 | 22.8 | 27.3 | 17.2 | 24.1 |
| HCV 208B-762 | ≤1.0 | ≤1.0 | ≤1.0 | ≤1.0 |
| HCV 208B-765 | ≤1.0 | ≤1.0 | ≤1.0 | ≤1.0 |
| HCV 208B-778 | ≤1.0 | ≤1.0 | ≤1.0 | ≤1.0 |
| HCV 208B-780 | ≤1.0 | ≤1.0 | ≤1.0 | ≤1.0 |
| HCV 208B-788 | ≤1.0 | ≤1.0 | ≤1.0 | ≤1.0 |
| HCV 208B-793 | ≤1.0 | ≤1.0 | ≤1.0 | ≤1.0 |
| HCV 208B-796 | 20.2 | 27.7 | 17.3 | 25.2 |
| HCV 208B-822 | ≤1.0 | ≤1.0 | ≤1.0 | ≤1.0 |
| HCV 208B-826 | ≤1.0 | ≤1.0 | ≤1.0 | ≤1.0 |
| HCV 208B-853 | ≤1.0 | ≤1.0 | ≤1.0 | ≤1.0 |
| HCV 208B-860 | ≤1.0 | ≤1.0 | ≤1.0 | ≤1.0 |
| HCV 208B-862 | 11.2 | 15.2 | 8.9 | 12.6 |
| HCV 208B-894 | ≤1.0 | ≤1.0 | ≤1.0 | ≤1.0 |
| HCV 208B-909 | 1.6 | 2.5 | ≤1.0 | ≤1.0 |
| HCV 208B-911 | ≤1.0 | ≤1.0 | ≤1.0 | ≤1.0 |
| HCV 208B-922 | ≤1.0 | ≤1.0 | ≤1.0 | ≤1.0 |
| HCV 208B-952 | ≤1.0 | ≤1.0 | ≤1.0 | ≤1.0 |
| HCV 208B-954 | 23.9 | 32.7 | 18.4 | 26.0 |
| HCV 208B-956 | ≤1.0 | ≤1.0 | ≤1.0 | ≤1.0 |
| HCV 208B-960 | 21.0 | 28.1 | 15.8 | 22.9 |
| HCV 208B-982 | 4.5 | 5.4 | ≤1.0 | 4.9 |

Example 11

Immunoglobulin Purification and Labeling

Anti-HCV core hybridomas were expanded in Hybridoma Serum Free Medium (Invitrogen Corporation) supplemented with L-glutamine and 10% Ultra Low IgG FBS (Invitrogen Corporation) and seeded into roller bottles at approximately $0.5 \times 10E^5$ cells/mL. The cultures were incubated at 37° C. while rotating at approximately 1 revolution per minute for 10-14 days, or until a terminal end culture was obtained. The terminal roller bottle supernatant was harvested and clarified with a 0.45 micron filter. The clarified supernatant was diluted with an equal volume of 1.5 M glycine, 3M NaCl buffer, pH 8.9, then loaded onto a pre-equilibrated 5 ml Protein A column using the AKTA automated purification system (Amersham/Pharmacia/GE). The column was then washed with approximately 5 column volumes of binding buffer and when a stable baseline is achieved, the mAb was eluted with 0.1 M sodium citrate buffer, pH 2.8. The IgG was then transferred to a desalting column and exchanges into PBS, pH 7.2-7.4, and then further dialyzed in PBS pH 7.2-7.4, using 10,000 molecular weight cut-off dialysis membrane (Pierce Chemical). Selected antibodies were biotinylated by using Sulfo-NHS-LC-Biotin (Pierce) at a 20-fold molar excess and incubated for 30 minutes at room temperature. Unbound biotin was removed through dialysis in PBS pH 7.2-7.4. All biotinylated monoclonals were tested by EIA to confirm successful labeling.

Example 12

HCV Core Antigen Capture Assays

Purified anti-HCV core134-171 monoclonal antibodies were evaluated for their ability to form binding pairs with themselves and two other domain 1 monoclonal antibodies using HCV core1-169 recombinant antigen in an EIA format. Anti-HCV Domain 1 monoclonal antibodies, C11-7 and C11-9, and anti-HCV core134-171 monoclonals were coated onto microtiter plates at approximately 1000 ng/ml and allowed to incubate overnight at 2-8 degrees C. After the capture reagent had been coated on the solid phase, the plates were blocked using a 5×PBS buffer containing 2% fish gelatin, 0.5 Tween 20, and 0.1% n-dodecyl-N,N-dimethylamine-N-oxide. The wells were washed with distilled water and purified core 1-169 antigen was added to the blocked plates in serial dilutions from 50 to 0.78 ng/ml diluted in fish gelatin block, and then allowed to incubate at room temperature for approximately 30 minutes. The wells were washed with distilled water and biotin labeled anti-HCV core monoclonals were added to the plates at concentrations ranging from 100 to 5000 ng/ml, and then incubated for 30 minutes at room temperature. The plates were washed with distilled water and streptavidin-HRPO diluted to approximately 200 ng/mL was added to the plates and allowed to incubate for 30 minutes at room temperature. The plates were washed with distilled water and o-phenylenediamine substrate was used as the chromagen to generate signal and the optical density at 492 nm was measured.

Table 6 summarizes the assay signal (OD492 nm) for each antibody pair combination using 25 ng/ml of core1-169 antigen, which indicates whether or not each binding pair is capable of forming a sandwich. An OD492 value of at least 3× greater than the value generated by a negative control (NC) monoclonal antibody as a capture or conjugate reagent are considered positive for core antigen detection.

Example 13

Sequences of Anti-Core 134-171 Variable Domains

A subset of the anti-HCV core 134-171 hybridomas were selected for determination of variable heavy (VH) and variable light (VL) chain nucleotide and deduced amino acid sequences. Total RNA was extracted from the hybridoma cells using Trizol (Invitrogen) or Tri-Reagent (Sigma) according to the manufacturer's recommendations. The heavy chain and light chain cDNA was generated from the extracted total RNA using Superscript III (Life Technologies) and oligo dT primers following standard protocols. The 5' RACE (rapid amplification of cDNA ends) protocol was used to amplify the variable heavy and light chain cDNA sequences using a dC anchor primer (5'-AAGCAGTGG-TATCAACGCAGAGTACCCCCCCCCCCCCCCCC-3'; SEQ ID NO:581) and a generic primer specific to the constant region of the mouse heavy or light chain (Novogen). Amplicons were cloned into a commercially available vector (pCR2.1-TOPO cloning kit, Invitrogen) per the manufacturer's directions and transformed into TOP10 *E. coli*. At least eight colonies were selected for PCR amplification of cloned variable domain sequences using M13 forward and reverse primers. Amplicons were treated with ExoSap (Affymetrix) prior to sequencing using M13 forward primer and BigDye Terminator v3.1 cycle sequencing kit (Applied Biosystems, Foster City, Calif.). Sequences were obtained using ABI3130xl automated sequencer and assembled and analyzed using Vector NTI software (Invitrogen).

Deduced amino acid sequences were aligned using ClustalW (Higgins et al., Nucleic Acids Res. 22:4673-4680, 1994) as implemented in the MEGA5 software package (Tamura et al., Molecular Biology and Evolution 28: 2731-2739, 2011). MEGA5 software was used to determine groupings or clusters of related heavy chain amino acid sequences from the alignments and phylogenetic tree con-

TABLE 6

|  | 208A-110 (aa 141-161) | 208A-692 (aa 134-154) | 208A-293 (aa 141-161) | 208A-557 (aa 141-161) | 208A-207-271 (aa 134-154) | 208B-741 (aa 134-154 & 141-161) |
|---|---|---|---|---|---|---|
| 208A-110-Bt | 0.18 | 0.14 | 0.20 | 0.17 | 0.17 | 0.20 |
| 208A-692-Bt | 0.54 | 0.35 | 0.51 | 0.53 | 0.39 | 0.44 |
| 208A-293-Bt | 0.52 | 0.34 | 0.49 | 0.52 | 0.39 | 0.50 |
| 208A-557-Bt | 0.44 | 0.13 | 0.41 | 0.32 | 0.18 | 0.38 |
| 208A-207-271-Bt | 0.38 | 0.42 | 0.42 | 0.82 | 0.36 | 0.30 |
| 208B-741-Bt | 0.42 | 0.32 | 0.42 | 0.40 | 0.33 | 0.36 |
| 208B-1096-Bt | 0.19 | 0.15 | 0.24 | 0.17 | 0.18 | 0.23 |
| 208B-395-334-Bt | 0.21 | 0.15 | 0.26 | 0.21 | 0.20 | 0.21 |
| 208B-612-226-Bt | 0.26 | 0.18 | 0.28 | 0.23 | 0.24 | 0.23 |
| NC mAb-Bt | 0.16 | 0.15 | 0.23 | 0.18 | 0.17 | 0.18 |
| C11-7-Bt | 1.78 | 0.18 | 1.55 | 0.64 | 0.22 | 1.76 |
| C11-9-Bt | 2.59 | 0.58 | 1.84 | 1.18 | 0.44 | 2.32 |

|  | 208B-1096 (aa 151-171) | 208B-395-334 (aa 151-171) | 208B-612-226 (aa 134-154 & 141-161) | NC capture mAb | C11-7 (aa 115-121) | C11-9 (aa 29-37) |
|---|---|---|---|---|---|---|
| 208A-110-Bt | 0.21 | 0.22 | 0.20 | 0.15 | 0.18 | 0.13 |
| 208A-692-Bt | 0.38 | 0.44 | 0.37 | 0.40 | 2.92 | 2.66 |
| 208A-293-Bt | 0.41 | 0.44 | 0.37 | 0.37 | 2.87 | 2.60 |
| 208A-557-Bt | 0.35 | 0.28 | 0.25 | 0.18 | 0.22 | 0.14 |
| 208A-207-271-Bt | 0.33 | 0.37 | 0.33 | 0.37 | 2.47 | 2.20 |
| 208B-741-Bt | 0.52 | 0.34 | 0.29 | 0.29 | 2.36 | 2.13 |
| 208B-1096-Bt | 0.26 | 0.20 | 0.24 | 0.17 | 1.06 | 0.33 |
| 208B-395-334-Bt | 0.23 | 0.23 | 0.26 | 0.20 | 0.89 | 0.32 |
| 208B-612-226-Bt | 0.70 | 0.83 | 0.23 | 0.21 | 1.52 | 0.64 |
| NC mAb-Bt | 0.21 | 0.22 | 0.22 | 0.18 | 0.17 | 0.14 |
| C11-7-Bt | 0.45 | 0.46 | 0.53 | 0.22 | 0.23 | 1.04 |
| C11-9-Bt | 0.82 | 0.95 | 0.63 | 0.62 | 1.91 | 2.75 | struction using the Neighbor Joining method with complete deletion of sequence gaps in the alignment. Tree topology, and hence clusters or groups therein, was examined for reliability by using a bootstrap test from 1000 replicates. As a general rule, if the bootstrap value for a given interior branch is 95% or higher, then the topology at that branch is considered "correct" (Nei and Kumar, Molecular Evolution and Phylogenetics, 2000; Oxford University Press, New York). Analysis of heavy chain variable domain sequences from 52 anti-HCV core 134-171 monoclonals revealed the existence of 4 main groups with bootstrap values>95%. Antibodies comprising three of these groups exhibited specificity for binding to one of each of the peptides used for screening, i.e. Group B with peptide 1 (134-154), Group A with peptide 2 (141-161), and Group C with peptide 3 (151-171). FIG. 2 provides two representations of the tree topology.

Example 14

Generating the Neo4 Antibody

Six peptides from the HCV core region (genotype 1b) were synthesized. The HCV core amino acid (aa) positions covered by each peptide are as follows: peptide 1, 98-110; peptide 2, 104-113; peptide 3, 104-121; peptide 4, 110-124; peptide 5, 101-112, and peptide 6, 153-165. Balb/C mice were each immunized with a combination of 2 different peptides; peptides 1 with 6; peptides 2 with 3; peptides 4 with 5; and peptides 1 with 5. All of the peptides were conjugated to keyhole limpet hemocyanin (KLH) at their C-terminus through an added cysteine residue. Mice were boosted four times. Spleens were collected for 2 independent fusions using the PEG 1500 chemical method. The Myeloma fusion partner used was SP2/0. Subcloning began after fusion screening. 150 cells were plated onto a 96 well plate which usually nets about 1 cell per well. Three rounds of subcloning were performed. Media used for the growth of cells from stable clones was Iscove's Modified Dulbecco's Medium (IMDM) with 10% FBS. Supernatants were analyzed by ELISA using the above core peptides. Hybridoma supernatants and ascites generated from ELISA-positive clones were then screened by western blot for their ability to detect minicores. One hybridoma clone (Neo4) was identified that gave an exceptionally strong signal at detecting minicore and p21 core proteins. The isotype of this antibody was determined to be IgG1. Antibodies were subsequently purified with Protein G sepharose and used for the detection of minicores.

Study Population. Hepatologists and other providers at the Icahn School of Medicine at Mount Sinai recruited patients with a HCV viral load of 10 million IU/mL or above. Written informed consent was obtained and up to 16 mL of blood were collected, and serum was prepared. Data on age, sex, HCV genotype, viral load, and other medical conditions were extracted from medical records. The study was conducted in compliance with the Icahn School Blood was obtained from four patients with high-titer HCV and two non-infected volunteers (Table 7). All four HCV-infected patients were male and had a HCV viral load over 10 million IU/mL. Patients with a high HCV viral load were selected for this study because they were expected to have relatively high blood levels of HCV proteins, enabling the development of methods for detection.

TABLE 7

Clinical characteristics of patients

| Patient ID | HCV Viral Load (IU/mL) | HCV Genotype | Age (years) | Sex | Other |
|---|---|---|---|---|---|
| P1 | $7.46 \times 10^7$ | 1b | 49 | M | HIV co-infected |
| P2 | $2.91 \times 10^7$ | 1b | 63 | M | 5 years post kidney transplant |
| P3 | $1.23 \times 10^7$ | 1a | 67 | M | — |
| P4 | $>1 \times 10^{8*}$ | 1a | 60 | M | 1 year post liver transplant and B cell lymphoma |
| N1 | — | — | 55 | M | Healthy control |
| N2 | — | — | 65 | F | Healthy control |

*Value was above the upper limit of detection of the assay

Figure 4:
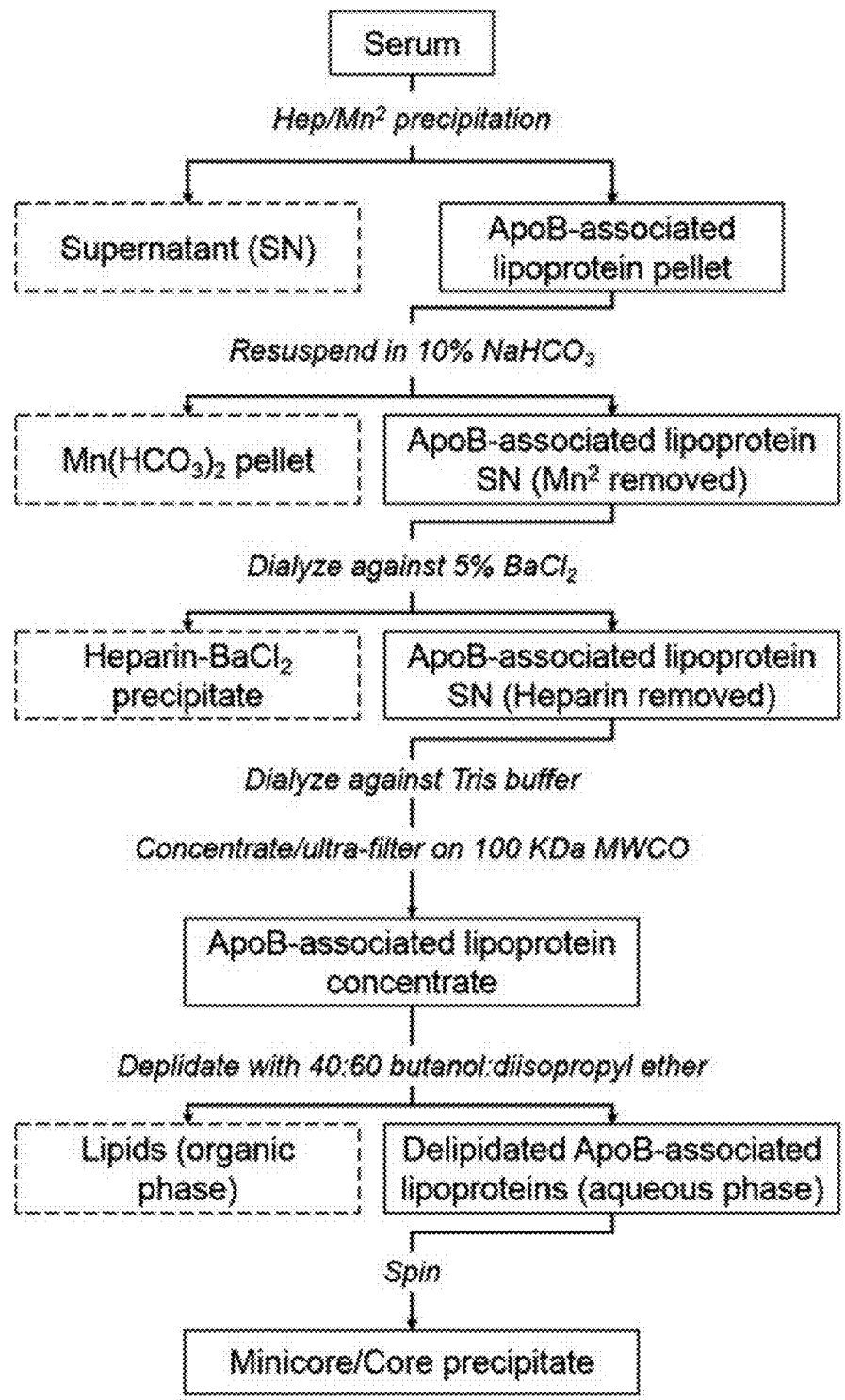
FIG. 4 shows a flow diagram of an exemplary purification scheme for isolating HCV core and HCV minicores.
Figures 5A, 5B:
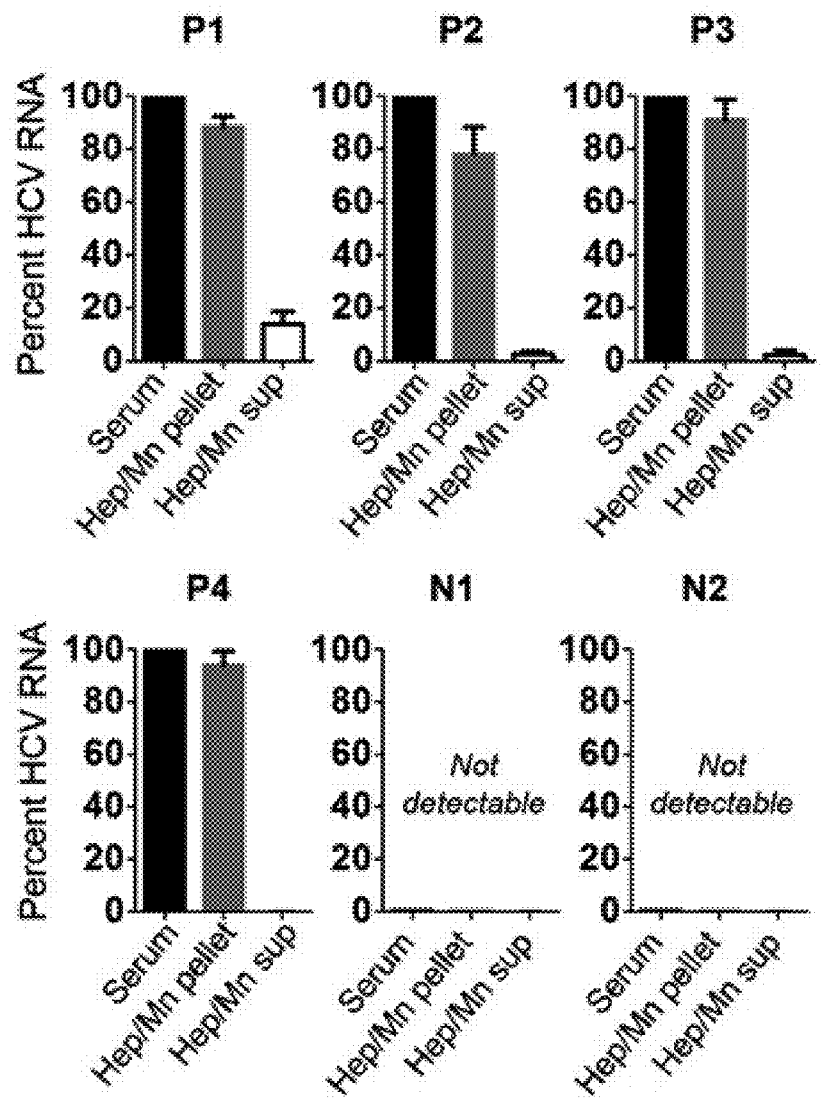
FIGS. 5A and 5B show results from Example 14 where it was shown that HCV RNA is enriched in the heparin/$Mn^{+2}$ pellet fraction in the four HCV patients (P1-P4), but not in two normal controls (N1-N2).

Isolation and Characterization of Minicores and p21 Core in Blood. The general procedure for isolating minicore and mature p21 core protein from patient blood is shown in FIG. 4. An equal volume of 50 mM Tris (pH 7.3) and 150 mM NaCl was added to 3.5 mL of serum and passed through a 0.45 μm syringe filter to remove aggregates. ApoB-associated lipoproteins were then precipitated by mixing an equal volume of heparin/Mn$^{+2}$ solution containing 60 mM Tris (pH 7.3), 110 mM MnCl$_2$.4H$_2$O, 154 mM NaCl, and 400 USP/mL heparin. Solution was incubated for 1 h on ice in the dark. The precipitate was recovered by centrifugation at 3,000×g (30 min; 4° C.) and washed with gentle resuspension three times with 3.5 mL of an ice-cold solution containing 50 mM Tris (pH 7.3), 55 mM MnCl$_2$.4H$_2$O, 154 mM NaCl, and 200 USP units/mL heparin. Heparin/Mn$^{+2}$ was then removed: Manganese was removed from the heparin/Mn$^2$ pellet by resuspension in 2.0 or 2.5 mL of 10% NaHCO$_3$, which precipitates an insoluble Mn(HCO$_3$)$_2$ that is removed by centrifugation at 1,500×g (15 min; 4° C.). Heparin was removed by dialyzing 3 times (in 24 h) with one liter of 5% BaCl$_2$ in 20 mM Tris (pH 7) in a Slide-A-Lyzer Cassette G2 (Thermo Scientific) with a 20,000 MWCO. The supernatant was collected from the dialysis unit and the heparin-BaCl$_2$ insoluble complex was removed by centrifugation at 1,500×g (15 min; 4° C.). Excess BaCl$_2$ was removed from the supernatant by dialyzing 3 times (in 24 h; 4° C.) with one liter of TNE buffer consisting of 20 mM Tris (pH 7.0), 0.15 M NaCl and 1 mM EDTA. The supernatant was collected from the dialysis unit and stored at −80° C. After thawing, the supernatant was concentrated using a 15 mL Amicon Ultra centrifugal filtration unit with a 100 kDa MWCO (Millipore) (3,200×g; 90 min; 4° C.). Concentrated volumes ranged between 130 μL and 210 μL. Finally, samples were delipidated to allow for loading onto a Western blot gel. Samples were delipidated using an extraction method previously described for whole serum and plasma which partitions proteins into an aqueous phase and lipids into an organic phase using a 2× mixture of butanol and diisopropyl ether (butanol:DIPE at 40:60; v/v) (see, Cham et al., J Lipid Res 1976; 17:176-81, herein incorporated by reference). The original protocol was modified by using only a 1× volume of the 40:60 butanol:DIPE mixture to our sample rather than a 2× volume. It was found that the 2× volume can greatly dehydrate the aqueous phase. Also, instead of extracting by end-over-end tube rotation of the samples for 30 minutes, the samples were just briefly vortexed. The lipid-containing organic and protein-containing aqueous phases were separated by centrifugation at 400×g (2 min; 25° C.). The lower aqueous phase was immediately collected, placed on ice for 1 h, and then stored at −80° C. Incubation of the protein-containing aqueous phase on ice for 1 h followed by freeze-thawing led to the formation of a precipitate that was pelleted by gentle centrifugation at 1,000×g (30 sec; 4° C.). The pellet was solubilized in a solution containing 8 M Urea and 1% SDS, sonicated, adjusted with NuPage sample buffer, heated and loaded onto NuPAGE gels. This pellet contained core and minicore proteins. These proteins were not detected in the supernatant. After electrophoresis, gels were processed for western analysis. Protease inhibitors, Complete-EDTA free (Roche) and 1 mM phenylmethylsulfonyl fluoride (PMSF) were used throughout the purification procedure.

HCV-Infected Cell Culture Lysate. Huh-7.5 cells infected with a Con1/JFH chimeric HCV were were lysed directly in culture dishes after three washes with Dulbecco's phosphate buffered saline with 2×LDS NuPage sample buffer (Life Technologies) containing 4% lithium dodecyl sulfate and 10% 2-mercaptoethanol.

Western Blot Analysis. Samples were electrophoresed in 10% NuPAGE Bis-Tris gels (Life Technologies) and the proteins were transferred to 0.2 uM pore size, polyvinylidene difluoride (PVDF) membranes. Antibodies targeting the C-terminal portion of p21 core and used to detect minicores were a combination of Neo4 monoclonal antibody at a concentration of 2 ug/ml mixed with mAb1 (C11-3) at 1 ug/ml, that we previously described (see, Eng et al., J Virol 2009; 83:3104-14, herein incorporated by reference). Antibody targeting the N-terminal portion of core is C11-10 (Abbott Labs, epitope 32-36).

Quantification of HCV RNA. QIAamp Viral RNA mini kit (Qiagen) was used to purify RNA from serum, Hep/Mn$^{+2}$ pellet and supernatant. For the heparin/Mn$^{+2}$ pellet and supernatatant, heparin was removed from the purified RNAs by treating with heparinase I (Sigma) (Johnson et al., Biotechniques 2003; 35:1140-2, 1144, herein incorporated by reference). Reverse transcription (RT) of RNA was performed using SuperScript III First-Strand Synthesis (Invitrogen) and random hexamers. RT-reaction products were then used for quantitative-PCR (q-PCR) using the LightCycler 480 SYBR Green I Master kit and the LightCycler 480 instrument (Roche).

Figure 6:
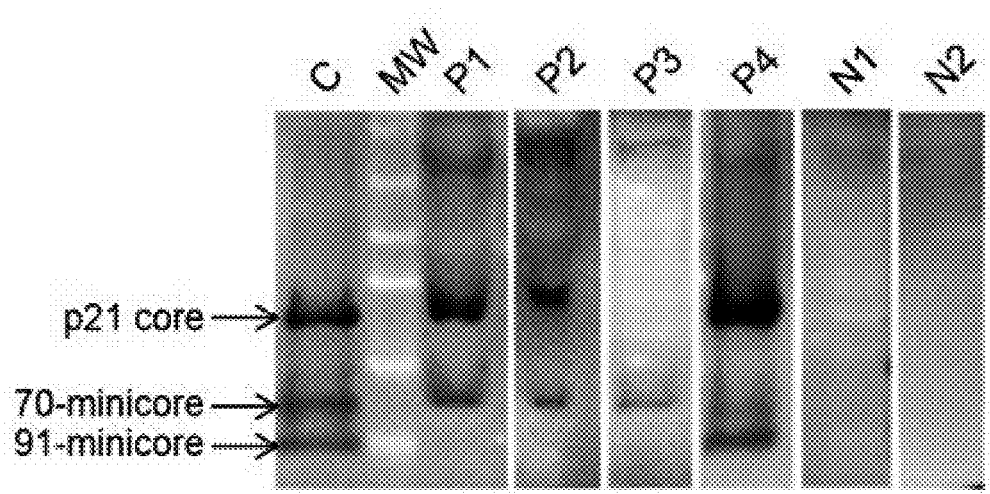
FIG. 6 shows results from Example 14, where minicores are detected by western blot in four HCV patients (lanes P1-P4) and not in two normal controls (lanes N1, N2). Cell culture supernatant of infected cells serves as a positive control (lane C).
Figure 7:
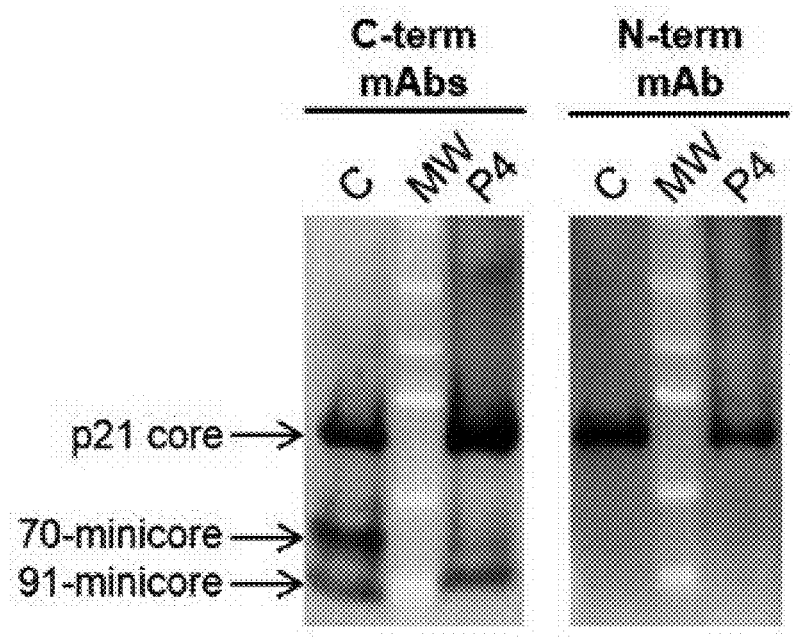
FIG. 7 shows results of Example 14, where duplicate Western blots of sample P4 were probed with antibodies directed either to the C-term or N-term portion of the core protein confirms the identity of mini-cores.

Minicores were present in the blood of all four patients (FIG. 6). The relative amounts of p21 core, 70 minicore and 91 minicore varied from patient to patient. Patient samples P1, P2, and P4 had prominent p21 core bands. Interestingly, P1, P2, and P4 were immune compromised as a result of HIV infection or immunosuppressive drugs, while P3 had no known immunological deficiency (Table 7). P1, P2, and P3 had prominent 70 minicore bands, and P4 had a prominent 91 minicore band. A cell culture lysate of HCV-infected Huh-7.5 cells provided molecular weight markers of the core protein isoforms (FIGS. 6 and 7, lanes C). To confirm the identity of the core isoform bands, duplicate Western blots of sample P4 were probed with antibodies specific for either the N- or the C-terminal portion of the core protein (FIG. 7), allowing detection of p21 core only (N-term) or p21 plus the 70 and 91 minicores (C-term).

This study provides direct evidence that HCV-expressed non-classical proteins (minicores) are present in blood during natural infections in addition to the conventional proteins. Minicores were detected in all four high HCV viral load patients. The presence of relatively large quantities of minicores in blood suggests that they enhance viral transmission and/or pathogenesis/persistence.

Example 15

Neo4 Antibody Sequencing

This example describes how the nucleotide and deduced amino acid sequences of the light and heavy chain variable domains of the Neo4 monoclonal antibody were determined. Total cellular RNA was extracted from the anti-HCV core Neo4 hybridoma cells using Trizol (Tri-ZOL, Invitrogen) per manufacturer's recommendations. To sequence the variable domains, cDNA was generated from the extracted RNA using Superscript III (Life Technologies) and an oligo-dT primer (Novagen). Amplification of the respective immunoglobulin variable sequences was performed by 5'RACE PCR using a dC-anchor primer and a murine consensus heavy or light chain primer. Purified products were cloned into pCR™2.1-TOPO® (Life Technologies) which was then used to transform *E. coli*. For sequence analysis, variable heavy and variable light chain fragments from multiple *E. coli* colonies were PCR amplified using M13 forward and reverse primers. Sequencing was performed using the BigDye Terminator v3.1 cycle sequencing kit (Applied Biosystems) on the ABI 3130x1 Genetic Analyzer. At least 5 heavy or light chain clones were viewed, analyzed, and annotated using Vector NTI Advance (Life Technologies) to create the consensus nucleotide sequences. FIG. 8 shows the amino acid sequence of the light chain variable region (FIG. 8A, SEQ ID NO:583) and the heavy chain variable region (FIG. 8B, SEQ ID NO:584) of Neo4. The CDRs were identified by visual inspection of the deduced amino acid sequences relative to the locations of conserved features within the respective domains (see, Kabat et al., (1987) Sequences of Proteins of Immunological Interest, 4th ed., U. S. Govt. Printing Office No. 165-492, Bethesda, Md.). FIG. 8A shows the light chain CDRs underlined, which include CDRL1 (RASKSVNEYGYTYMH; SEQ ID NO:585), CDRL2 (LASNLDS; SEQ ID NO:586), and CDRL3 (QHSRELPYT, SEQ ID NO:587). FIG. 8B shows the heavy chain CDRs underlined, which include CDRH1 (GFSITSSVYCWQ; SEQ ID NO:588), CDRH2 (RICYDGSVDYSPSITS; SEQ ID NO:589), and CDRH3 (ENHIDYYDTTYPSFDV; SEQ ID NO:590). FIG. 9A shows the nucleic acid sequence encoding the light chain variable region of Neo4 (SEQ ID NO:591), and FIG. 9B shows the nucleic acid sequence encoding the heavy chain variable region of Neo4 (SEQ ID NO:592).

Example 16

Neo4 and CLL-3 (ABT-4) Antibody Epitope Mapping

Purified Neo4 and C11-3 (ABT-4) monoclonal IgG samples were analyzed for reactivity to overlapping HCV core antigen peptides by EIA. Biotin-(SGSG)-15 mer HCV core-amide peptides were synthesized that overlapped by two amino acids and encompassed the entire length of HCV core protein amino acids 1-191 (Mimotopes). Each of the 89 synthesized peptides was coated in an individual micro-titer well as indicated on the peptide plate key (Table 8) as shown. The coated plates were kept dry in a sealed foil pouch and stored at <10 degrees C. until ready for use. A peptide coated plate for each test antibody was blocked using 3% BSA in PBS with 0.5% Tween 20. The blocked plates were washed with distilled water and a 2 ug/mL solution of purified IgG from each test sample diluted in BSA block solution was added to each peptide coated well of the blocked plate and allowed to incubate at room temperature for at least one hour. Following incubation the plates were washed with distilled water. A 200 ng/mL solution of peroxidase labeled F(ab')2 fragment goat anti-mouse IgG Fc fragment specific (Jackson Immunoresearch) in BSA block solution was added to all wells and incubated at room temperature for 30 minutes. The plates were washed with distilled water and o-phenylenediamine substrate was used as the chromagen to generate signal. Plates were read at 492 nm and the results were analyzed. Wells were considered positive if they had an EIA signal at least 3 times greater than background. The reactivity of ABT-4 to the peptides is shown with shading in Table 9, while the reactivity of the Neo4 antibody to the peptides is shown with shading in Table 10. As shown in these tables, the ABT-4 mAb reacts with peptide numbers 48-53 while the Neo4 reacts with peptide numbers 50-55.

TABLE 8

Peptide Plate Key

| | 1 | 2 | 3 | 4 | 5 | 6 | 7 | 8 | 9 | 10 | 11 | 12 |
|---|---|---|---|---|---|---|---|---|---|---|---|---|
| A | 1 | 9 | 17 | 25 | 33 | 41 | 49 | 57 | 65 | 73 | 81 | 89 |
| B | 2 | 10 | 18 | 26 | 34 | 42 | 50 | 58 | 66 | 74 | 82 | Blank |
| C | 3 | 11 | 19 | 27 | 35 | 43 | 51 | 59 | 67 | 75 | 83 | Blank |
| D | 4 | 12 | 20 | 28 | 36 | 44 | 52 | 60 | 68 | 76 | 84 | Blank |
| E | 5 | 13 | 21 | 29 | 37 | 45 | 53 | 61 | 69 | 77 | 85 | Blank |
| F | 6 | 14 | 22 | 30 | 38 | 46 | 54 | 62 | 70 | 78 | 86 | Blank |
| G | 7 | 15 | 23 | 31 | 39 | 47 | 55 | 63 | 71 | 79 | 87 | Blank |
| H | 8 | 16 | 24 | 32 | 40 | 48 | 56 | 64 | 72 | 80 | 88 | Blank |

TABLE 9

HCV ABT-4

| | 1 | 2 | 3 | 4 | 5 | 6 | 7 | 8 | 9 | 10 | 11 | 12 |
|---|---|---|---|---|---|---|---|---|---|---|---|---|
| A | 0.05 | 0.06 | 0.07 | 0.06 | 0.07 | 0.07 | 0.97 | 0.07 | 0.07 | 0.07 | 0.07 | 0.07 |
| B | 0.06 | 0.06 | 0.06 | 0.06 | 0.06 | 0.07 | 0.97 | 0.07 | 0.07 | 0.07 | 0.07 | 0.07 |
| C | 0.06 | 0.07 | 0.06 | 0.06 | 0.06 | 0.06 | 1.00 | 0.07 | 0.07 | 0.07 | 0.07 | 0.07 |
| D | 0.06 | 0.07 | 0.06 | 0.06 | 0.06 | 0.07 | 0.96 | 0.07 | 0.06 | 0.06 | 0.06 | 0.06 |
| E | 0.05 | 0.06 | 0.06 | 0.06 | 0.06 | 0.07 | 0.36 | 0.06 | 0.06 | 0.06 | 0.06 | 0.06 |
| F | 0.07 | 0.06 | 0.06 | 0.06 | 0.06 | 0.07 | 0.08 | 0.06 | 0.06 | 0.06 | 0.06 | 0.06 |
| G | 0.06 | 0.06 | 0.06 | 0.06 | 0.06 | 0.07 | 0.06 | 0.06 | 0.06 | 0.06 | 0.07 | 0.06 |
| H | 0.06 | 0.06 | 0.07 | 0.07 | 0.08 | 0.81 | 0.07 | 0.07 | 0.08 | 0.07 | 0.09 | 0.07 |

TABLE 10

HCV Neo4

| | 1 | 2 | 3 | 4 | 5 | 6 | 7 | 8 | 9 | 10 | 11 | 12 |
|---|---|---|---|---|---|---|---|---|---|---|---|---|
| A | 0.06 | 0.05 | 0.04 | 0.04 | 0.05 | 0.04 | 0.05 | 0.05 | 0.04 | 0.04 | 0.04 | 0.05 |
| B | 0.06 | 0.05 | 0.05 | 0.04 | 0.04 | 0.04 | 1.03 | 0.05 | 0.05 | 0.05 | 0.04 | 0.05 |
| C | 0.05 | 0.05 | 0.05 | 0.04 | 0.04 | 0.05 | 0.96 | 0.05 | 0.05 | 0.10 | 0.05 | 0.05 |
| D | 0.06 | 0.07 | 0.05 | 0.04 | 0.05 | 0.05 | 0.93 | 0.06 | 0.04 | 0.05 | 0.05 | 0.05 |
| E | 0.05 | 0.05 | 0.05 | 0.04 | 0.04 | 0.04 | 0.96 | 0.05 | 0.05 | 0.05 | 0.05 | 0.04 |
| F | 0.06 | 0.06 | 0.07 | 0.05 | 0.05 | 0.06 | 1.01 | 0.05 | 0.04 | 0.06 | 0.05 | 0.05 |
| G | 0.07 | 0.06 | 0.05 | 0.05 | 0.05 | 0.05 | 0.97 | 0.04 | 0.05 | 0.05 | 0.05 | 0.04 |
| H | 0.06 | 0.06 | 0.05 | 0.06 | 0.05 | 0.04 | 0.04 | 0.04 | 0.04 | 0.05 | 0.05 | 0.05 |

A summary of the peptide reactivity of ABT-4 (C11-3) and Neo4 is provided in Table 11 below.

TABLE 11

Peptide Reactivity Summary

| | | | | HCV Core monoclonal antibody | |
|---|---|---|---|---|---|
| HCV Core Peptide # | HCV Core Peptide Sequence | SEQ ID NO | HCV Core Region | ABT-4 OD (A492 nm) | Neo4 OD (A492 nm) |
| 48 | SGSGGWLLSPRGSRPSWGP | 593 | aa 95-109 | 0.95 | 0.04 |
| 49 | SGSGLLSPRGSRPSWGPTD | 594 | aa 97-111 | 1.03 | 0.05 |
| 50 | SGSGSPRGSRPSWGPTDPR | 595 | aa 99-113 | 1.03 | 1.03 |
| 51 | SGSGRGSRPSWGPTDPRRR | 596 | aa 101-115 | 1.01 | 0.96 |
| 52 | SGSGSRPSWGPTDPRRRSR | 597 | aa 103-117 | 1.01 | 0.93 |
| 53 | SGSGPSWGPTDPRRRSRNL | 598 | aa 105-119 | 0.36 | 0.96 |

TABLE 11-continued

Peptide Reactivity Summary

| HCV Core Peptide # | HCV Core Peptide Sequence | SEQ ID NO | HCV Core Region | HCV Core monoclonal antibody | |
|---|---|---|---|---|---|
| | | | | ABT-4 OD (A492 nm) | Neo4 OD (A492 nm) |
| 54 | SGSGWGPTDPRRRSRNLGK | 599 | aa 107-121 | 0.08 | 1.01 |
| 55 | SGSGPTDPRRRSRNLGKVI | 600 | aa 109-123 | 0.08 | 0.97 |

Shown in Table 12 below, are the reactive HCV core peptides aligned, with the minimal overlap shaded. For Abt-4, the reactive sequence is shown to span from amino acid 95 to amino acid 117 of the core peptide sequence, with the minimum reactive sequence spanning from amino acid 103 to amino acid 109. For Neo4, the reactive sequence is shown to span from amino acid 99 to amino acid 123 of the core peptide sequence, with the minimum reactive sequence spanning from amino acid 109 to amino acid 113.

TABLE 12

| Abt4 (C11-3) | | Neo4 | |
|---|---|---|---|
| GWLLSPRGSRPSWGP | (SEQ ID NO: 601) | SPRGSRPSWGPTDPR | (SEQ ID NO: 606) |
| LLSPRGSRPSWGPTD | (SEQ ID NO: 602) | RGSRPSWGPTDPRRR | (SEQ ID NO: 607) |
| SPRGSRPSWGPTDPR | (SEQ ID NO: 603) | SRPSWGPTDPRRRSR | (SEQ ID NO: 608) |
| RGSRPSWGPTDPRRR | (SEQ ID NO: 604) | PSWGPTDPRRRSRNLR | (SEQ ID NO: 609) |
| SRPSWGPTDPRRRSR | (SEQ ID NO: 605) | WGPTDPRRRSRNLGK | (SEQ ID NO: 610) |
| | | PTDPRRRSRNLGKVI | (SEQ ID NO: 611) |

Example 17

HCV Core Peptide Reactivity of Anti-Core Monoclonal Antibodies

Assay wells were coated with sheep anti-mouse IgG Fc specific antibody and incubated overnight. The coating solution was then removed; the wells blocked using BSA/tween in PBS and then washed with dH2O. Serially diluted antibody (in block) test samples (Neo4 antibody and Abt-4 antibody) were then added, the plates incubated for at least 1 hour and then washed. Next, biotin labeled peptides (diluted to 500 ng/mL in block) were added, the plates incubated for 10 minutes while shaking at 700 rpm and then washed. Peroxidase conjugated streptavidin (diluted to 200 ng/mL in block) was then added to all assay wells, incubated for 20 minutes while shaking at 700 rpm and then washed. Finally, color was developed using OPD and signal quenched using 1N H2SO4. Signal was read at 492 nm. Data are tabulated and summarized in Table 13 below.

TABLE 13

| | normal mouse serum sera dil (1:X) | | | | | | | | | | | |
|---|---|---|---|---|---|---|---|---|---|---|---|---|
| bt-pep | 500 | 1,000 | 2,000 | 4,000 | 8,000 | 16,000 | 32,000 | 64,000 | 128,000 | 256,000 | 512,000 | 1.1 MM |
| WT1STHV | 0.0625 | 0.0552 | 0.0511 | 0.053 | 0.0537 | 0.06 | 0.0635 | 0.0628 | 0.067 | 0.0675 | 0.0743 | 0.0585 |
| Mut1T110N | 0.2575 | 0.0516 | 0.0617 | 0.0501 | 0.057 | 0.0626 | 0.0667 | 0.0702 | 0.0651 | 0.0677 | 0.0759 | 0.0631 |
| Mut6T110S | 0.2025 | 0.0545 | 0.0531 | 0.0505 | 0.0523 | 0.0611 | 0.0591 | 0.0631 | 0.069 | 0.0674 | 0.065 | 0.0621 |
| C113WT | 0.0603 | 0.056 | 0.0534 | 0.0532 | 0.0589 | 0.0537 | 0.0644 | 0.0623 | 0.066 | 0.066 | 0.0708 | 0.0586 |
| C113T109N | 0.0619 | 0.051 | 0.0534 | 0.0536 | 0.0607 | 0.0714 | 0.0751 | 0.0674 | 0.068 | 0.0629 | 0.0931 | 0.0726 |
| 92-133 | 0.0636 | 0.0521 | 0.0603 | 0.0533 | 0.0756 | 0.1009 | 0.0822 | 0.0656 | 0.0668 | 0.0615 | 0.0715 | 0.0691 |
| blank | 0.0563 | 0.0488 | 0.0538 | 0.0486 | 0.0508 | 0.0549 | 0.0679 | 0.0596 | 0.0631 | 0.065 | 0.0772 | 0.0783 |
| blank | 0.0691 | 0.0503 | 0.048 | 0.0494 | 0.0543 | 0.0534 | 0.0694 | 0.0584 | 0.0622 | 0.0654 | 0.0637 | 0.0772 |

| | HCV C11-3 ng/mL Ab | | | | | | | | | | | |
|---|---|---|---|---|---|---|---|---|---|---|---|---|
| bt-pep | 2000 | 1000 | 500 | 250 | 125 | 62.5 | 31.25 | 15.625 | 7.813 | 3.906 | 1.953 | 0.977 |
| WT1STHV | 2.1334 | 2.0583 | 2.1436 | 1.8662 | 2.038 | 2.098 | 1.8905 | 1.5079 | 1.1164 | 0.6026 | 0.3531 | 0.1881 |
| Mut1T110N | 0.0915 | 0.0721 | 0.0765 | 0.0857 | 0.1268 | 0.1549 | 0.1066 | 0.1103 | 0.0966 | 0.079 | 0.0854 | 0.0755 |
| Mut6T110S | 1.7329 | 2.1499 | 2.237 | 1.8305 | 2.0224 | 2.1105 | 1.5367 | 0.8075 | 0.3435 | 0.2271 | 0.0964 | 0.1005 |
| C113WT | 1.821 | 2.3479 | 2.3525 | 1.8679 | 2.3715 | 2.1987 | 1.758 | 1.0506 | 0.6131 | 0.2717 | 0.1721 | 0.1029 |
| C113T109N | 0.0707 | 0.0806 | 0.0882 | 0.0963 | 0.1475 | 0.2015 | 0.1599 | 0.1161 | 0.1192 | 0.0833 | 0.1143 | 0.1041 |

TABLE 13-continued

| | | | | | | | | | | | | |
|---|---|---|---|---|---|---|---|---|---|---|---|---|
| 92-133 | 1.4473 | 1.8692 | 1.9517 | 1.6777 | 1.8343 | 1.9204 | 1.5476 | 1.0138 | 0.5623 | 0.1832 | 0.1342 | 0.1163 |
| blank | 0.0657 | 0.071 | 0.0995 | 0.0639 | 0.0736 | 0.0987 | 0.1178 | 0.1047 | 0.101 | 0.0831 | 0.0937 | 0.0959 |
| blank | 0.0743 | 0.0711 | 0.0655 | 0.0644 | 0.0791 | 0.1032 | 0.1452 | 0.0979 | 0.1179 | 0.0856 | 0.0763 | 0.142 |

| | HCV Neo4 ng/mL Ab | | | | | | | | | | | |
|---|---|---|---|---|---|---|---|---|---|---|---|---|
| bt-pep | 2000 | 1000 | 500 | 250 | 125 | 62.5 | 31.25 | 15.625 | 7.813 | 3.906 | 1.953 | 0.977 |
| WT1STHV | 1.8978 | 2.0033 | 1.9126 | 1.9886 | 1.9279 | 1.8543 | 1.6701 | 1.4209 | 1.0414 | 0.6691 | 0.4092 | 0.2204 |
| Mut1T110N | 0.0882 | 0.0678 | 0.065 | 0.089 | 0.2042 | 0.1391 | 0.0938 | 0.0771 | 0.0729 | 0.0719 | 0.0728 | 0.0619 |
| Mut6T110S | 1.1667 | 1.165 | 1.1716 | 1.1549 | 1.2728 | 1.1072 | 0.4805 | 0.2502 | 0.1316 | 0.0847 | 0.0717 | 0.0644 |
| C113WT | 0.0766 | 0.2219 | 0.0561 | 0.0607 | 0.0599 | 0.0626 | 0.0622 | 0.0697 | 0.0731 | 0.0694 | 0.0765 | 0.0584 |
| C113T109N | 0.059 | 0.0591 | 0.0803 | 0.1105 | 0.0858 | 0.1106 | 0.0815 | 0.0736 | 0.0751 | 0.0717 | 0.0853 | 0.0784 |
| 92-133 | 1.3067 | 1.4138 | 1.4754 | 1.4019 | 1.3064 | 1.4726 | 1.1055 | 0.8058 | 0.45 | 0.2166 | 0.1293 | 0.0978 |
| blank | 0.0643 | 0.0581 | 0.0663 | 0.0538 | 0.0534 | 0.0641 | 0.0689 | 0.0674 | 0.0696 | 0.0728 | 0.093 | 0.0715 |
| blank | 0.0676 | 0.0515 | 0.051 | 0.0526 | 0.0512 | 0.0642 | 0.0723 | 0.0687 | 0.0708 | 0.0687 | 0.0715 | 0.0767 |

Sequences of HCV core peptides are shown below where # denotes position 110 of the HCV core protein sequence.

```
                         #
WT1STHV     GSRPSWGPTDPRHRSRNVGKVID   (SEQ ID NO: 612)
MUT1T110N   GSRPSWGPNDPRHRSRNVGKVID   (SEQ ID NO: 613)
MUT6T110S   GSRPSWGPSDPRHRSRNVGKVID   (SEQ ID NO: 614)
C113WT      RGSRPSWGPTD               (SEQ ID NO: 615)
C113T110N   RGSRPSWGPND               (SEQ ID NO: 616)
```

Differences in sequence relative to genotype 1 at position 110 are highlighted. Reactivity of C11-3 (Abt4) and Neo4 at the 15.6 ng/mL dilution are summarized below in Table 14.

TABLE 14

| | HCV C11-3 | HCV Neo4 |
|---|---|---|
| bt-pep | 15.6 ng/mL | 15.6 ng/mL |
| WT1STHV | 1.5079 | 1.4209 |
| Mut1T110N | 0.1103 | 0.0771 |
| Mut6T110S | 0.8075 | 0.2502 |
| C113WT | 1.0506 | 0.0697 |
| C113T109N | 0.1161 | 0.0736 |
| 92-133 | 1.0138 | 0.8058 |
| blank | 0.1047 | 0.0674 |
| blank | 0.0979 | 0.0687 |

Both Neo4 and C11-3 (Abt-4) are sensitive to the T110N mutation common among non-genotype 1 and 2 isolates. However, Neo4 appears to more susceptible to the T110S mutation compared to Abt4. Neo4 does not bind to peptides terminating at position 111 indicating that the Neo4 epitope involves HCV core sequences downstream of position 111.

This is consistent with the epitope mapping using the core peptide library wherein the Neo4 and Abt4 epitopes overlap but the Neo4 epitope is shifted downstream (C-terminally) relative to Abt 4 by about 3-4 amino acids.

Example 18

Monoclonal Antibodies Neo4 and 750 Used in Combination Enhance the Detection of HCV Core and 91-Minicore Proteins Core and 91-minicore proteins were expressed in 293T cells by transfecting plasmids which encode the respective proteins. The core and minicore plasmid constructs also contained the 5' two-thirds of the HCV E1 gene which normally follows the core gene in the HCV genome. Core protein sequences are cleaved away from E1 protein by cellular signal peptidase and signal peptide peptidase to yield the mature core or minicore proteins. The 91-minicore construct begins with a start codon at codon 91 of the core gene. HCV sequences in both constructs were codon-optimized for enhanced expression. Cell extracts were prepared 48 hours post-transfection using a 2× lithium dodecyl sulfate (LDS) gel loading buffer followed by sonication. Extracts were diluted with 1×LDS loading buffer and were run on 10% Bis-Tris NuPage gels. Proteins were transferred to 0.2 uM pore size polyvinylidene difluoride (PVDF) membranes for Western blot analysis. The HCV core epitopes targeted by Neo4 and 208A-750 monoclonal antibodies (aa98-110 and aa141-161, respectively as immunogens) are downstream of amino acid 91 and are thus capable of detecting both core and 91-minicore. The concentration of each antibody used in the Western blot analysis was at 2 µg/ml.

Figure 10:
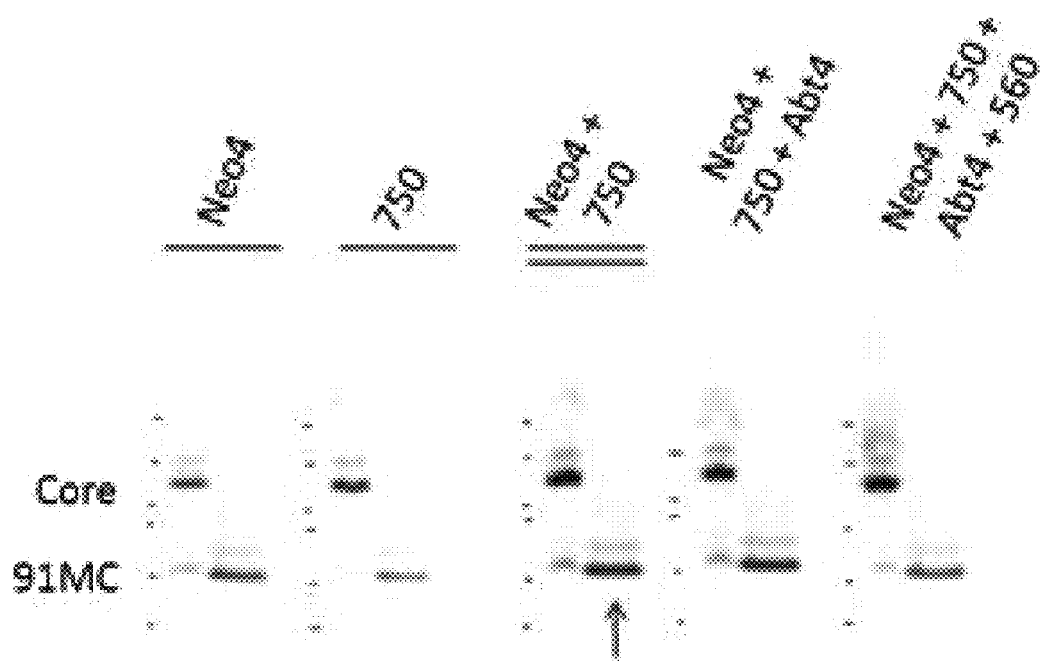
FIG. 10 shows results from Example 18, which demonstrated that when antibodies Neo4 and 208B-750 are used in combination, the signal intensity for core and 91-minicore are enhanced as compared to when the antibodies are used individually.

As shown in FIG. 10, when antibodies Neo4 and 208B-750 are used in combination, the signal intensity for core and 91-minicore are enhanced as compared to when the antibodies are used individually.

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-1064H | 1 | GAGGTCCAGCTGCAACAGTCTGGACCTGAGTT GGTGAAGCCTGGGGCCTCAGTGAAGATATCTT GCAAGACTTCTGGATACACTTTCACTGAATAC GCCATGCACTGGATGAAGCAGAGCCATGGAAA GAGCCTTGAGTGGATTGGAGGTATCAATCCTA CTAATGGTGATACAATCTACAACCAGAAGTTC AAGGACAAGGCCAAATTGACTGTAGACAGGTC CTCCAGCACAGCCTACATGGAGCTCCGCAGCC | 2 | 208A-1064H | EVQLQQSGPELVKPGASVKISCK TSGYTFTEYAMHWMKQSHGKSLE WIGGINPTNGDTIYNQKFKDKAK LTVDRSSSTAYMELRSLTSDDSA LFYCARRELDYFASWGQGTTLTV SS |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| | | TGACATCTGACGATTCTGCATTATTTTATTGT GCAAGACGGGAACTGGACTACTTTGCCTCCTG GGGCCAAGGCACCACTCTCACAGTCTCCTCA | | | |
| 208B-1094H | 3 | GAGGTCCAGCTGCAACAGTCTGGACCTGAGCT GGTGAAGCCTGGGGCCTCAGTGAAGATATCCT GCAAGACTTCTGGATACACTTTCACTGAATAC GCCATGCACTGGATGAAGCAGAGCCATGGAAA GAGCCTTGAGTGGATTGGCGGTATCAATCCTA CTAATGGTGATACAATCTACAACCAGAGGTTC AAGGACAAGGCCAAATTGACTGTAGACAGGTC CTCCAGCACAGCCTACATGGAGCTCCGCAGCC TGACATCTGACGATTCTGCATTATTTTATTGT GCAAGACGGGAACTGGACTACTTTGCCTCCTG GGGCCAAGGCACCACTCTCACAGTCTCCTCA | 4 | 208B-1094H | EVQLQQSGPELVKPGASVKISCK TSGYTFTEYAMHWMKQSHGKSLE WIGGINPTNGDTIYNQRFKDKAK LTVDRSSSTAYMELRSLTSDDSA LFYCARRELDYFASWGQGTTLTV SS |
| 208A-293H | 5 | GAGGTCCAGCTGCAACAGTCTGGACCTGAACT GGTGAAGCCTGGGGCCTCAGTGAAGATATCCT GTAAGGCTTCGGGATTCACTTTCACTGAATAC GCCATGCACTGGATGAAACAGAGCCATGGAAA GAGCCTTGAGTGGATTGGAGGTATCAATCCTA CTAACGGTGATGCAATCTACAACCAGAAGTTC AAGGACAAGGCCAAGTTGACTGTAGACAGGTC CTCCAGCACAGCCTACATGGAGCTCCGCAGCC TGACATCTGACGATTCTGCATTATTTTATTGT GCAAGACGGGAACTGGACTACTTTCCCTCCTG GGGCCAAGGCACCACTCTCACAGTCTCCTCA | 6 | 208A-293H | EVQLQQSGPELVKPGASVKISCK ASGFTFTEYAMHWMKQSHGKSLE WIGGINPTNGDAIYNQFKDKAK LTVDRSSSTAYMELRSLTSDDSA LFYCARRELDYFPSWGQGTTLTV SS |
| 208A-222H | 7 | GAGGTCCAGCTGCAACAGTCTGGACCTGAACT GGAAAAGCCTGGGGCTTCAGTGAGGATATCCT GCAAGACTTCTGGATACACATTCACTGAATAC GCCATGCACTGGGTGAAGCAGAGCCATGGAAA GAGCCTTGAGTGGATTGGAGGTATTAATCCTA ACAATGGCAATGCTATCTACAACCAGATATTC AAGGACAAGGCCACACTGACTGTGGACAGGTC CTCCAGCACAGCCTACATGGGCCTCCGCAGCC TGACATTCGGGGATTCTGGAGTCTACTTCTGT GTAAGACGACAACTGGACTACTTTGACTATTG GGGCCAGGGCGCCTCTCTCACAGTCTCCTCA | 8 | 208A-222H | EVQLQQSGPELEKPGASVRISCK TSGYTFTEYAMHWVKQSHGKSLE WIGGINPNNGNAIYNQIFKDKAT LTVDRSSSTAYMGLRSLTFGDSG VYFCVRRQLDYFDYWGQGASLTV SS |
| 208A-605H | 9 | GAGGTCCAGCTGCAACAGTCTGGACCTGAGCT GGAAAAGCCTGGGGCTTCAGTGAAGATATCCT GCAAGACTTCTGGATACACATTCACTGAATAC GCCATACACTGGGTGAAGCAGAGCCATGGAAT GAGCCTTGAGTGGATTGGAGGTATTAATCCTA GCAATGGCAATGCTATCTACAACCAAATATTC AAGGACAAGGCCACACTGACTGTGGACAGGTC CTCCAGCACAGCCTACATGGGCCTCCGCAGCC TGACATTTGGGGATTCTGGAGTCTACTTCTGT GTAAGACGACAACTGGACTTCTTTGACTATTG GGGCCAGGGCGCCTCTCTCACAGTCTCCTCA | 10 | 208A-605H | EVQLQQSGPELEKPGASVKISCK TSGYTFTEYAIHWVKQSHGMSLE WIGGINPSNGNAIYNQIFKDKAT LTVDRSSSTAYMGLRSLTFGDSG VYFCVRRQLDFFDYWGQGASLTV SS |
| 208B-560H | 11 | GAGGTCCAGCTGCAACAGTCTGGACCTGAGCT GGAAAAGCCTGGGGCTTCAGTGAAGATATCCT GCAAGACTTCTGGATACACATTCACTGAATAC GCCATGCACTGGGTGAAGCAGAGCCATGGAAT GAGCCTTGAGTGGATTGGAGGTATTAATCCTA GCAATGGCAATGCTATCTACAACCAGATATTC AAGGACAAGGCCACACTGACTGTGGACAGGTC CTCCAGCACAGCCTACATGGGCCTCCGCAGCC TGACATTTGGGGATTCTGGAGTCTACTTCTGT GTAAGACGACAACTGGACTTCTTTGACTATTG GGGCCAGGGCGCCTCTCTCACAGTCTCCTCA | 12 | 208B-560H | EVQLQQSGPELEKPGASVKISCK TSGYTFTEYAMHWVKQSHGMSLE WIGGINPSNGNAIYNQIFKDKAT LTVDRSSSTAYMGLRSLTFGDSG VYFCVRRQLDFFDYWGQGASLTV SS |
| 208A-830H | 13 | GAGGTCCGGCTGCAGCAGCCTGGACCTGAGGT GGAAAAGCCTGGGGCTTCAGTGAAGATATCCT GCAAGACTTCTGGATACACATTCACTGAATAC GCCATCCACTGGGTGAAACAGAGCCATGGAGA GAGCCTTGAGTGGATTGGAGGTATTAATCCTA GCAATGGCGATCCTATCTATAACCAGATATTC AAGGACAAGGCCACACTGACTGTGGACAGGTC CTCCAACACAGCCTACATGGGCCTCCGCAGCC TGACAGTTGGGGATTCTGGAGTCTACTTCTGT | 14 | 208A-830H | EVRLQQPGPEVEKPGASVKISCK TSGYTFTEYAIHWVKQSHGESLE WIGGINPSNGDPIYNQIFKDKAT LTVDRSSNTAYMGLRSLTVGDSG VYFCVRRQLDYFDFWGQGASLTV SS |

| APPENDIX A-DESCRIPTION OF SEQUENCES | | | | | |
|---|---|---|---|---|---|
| mAb Clone | SEQ ID | Nucleic Acid Seq | SEQ ID | mAb Clone | Amino Acid Seq |
| | | GTTAGACGACAACTGGACTACTTTGACTTTTG GGGCCAGGGCGCCTCTCTCACAGTCTCCTCA | | | |
| 208A-134H | 15 | CAGGGTCAGATGCAGCAGTCTGGAGCTGAACT GGCGAAGCCTGGGGCTTCAGTGAAGCTGTCCT GCAAGACTTCTGGCTTCACCTTCAGCAGTAGT TATATAAGTTGGTTGAAGCAAAAGCCTGGACA GAGTCTTGAGTGGATTGCATGGATTTATGCTG GAACTGGTAATACTAACTATAATCAGAAGTTC ACAGACAAGGCCCAACTGACTGTAGACACATC CTCCAGTACAGCCTACATGCAACTCAGCAGCC TGACAACTGAGGACTCTGCCATCTATTACTGT GCGATAAGTGGGACGGGATTTACTTACTGGGG CCAAGGGACTCTGGTCACTGTCTCTGCAACA | 16 | 208A-134H | QGQMQQSGAELAKPGASVKLSCK TSGFTFSSSYISWLKQKPGQSLE WIAWIYAGTGNTNYNQKFTDKAQ LTVDTSSSTAYMQLSSLTTEDSA IIYYCAISGTGFTYWGQGTLVTVS A |
| 208A-692H | 17 | CAGGGTCAGATGCAGCAGTCTGGAGCTGAACT GGTGAAGCCTGGGGCTTCAGTGAAGCTGTCCT GCAAGACTTCTGGCTTCACCTTCAGCAGTAGT TATATAAGTTGGTTGAAGCAAAAGCCTGGACA GAGTCTTGAGTGGATTGCATGGATTTATGCTG GAACTGGTAATACTAACTATAATCAGAAGTTC ACAGACAAGGCCCAACTGACTGTAGACACATC CTCCAGTACAGCCTACATGCAACTCAGCAGCC TGACAACTGAGGACTCTGCCATCTATTACTGT GCGATAAGTGGGACGGGATTTACTTACTGGGG CCAAGGGACTCTGGTCACTGTCTCTGCAACA | 18 | 208A-692H | QGQMQQSGAELAKPGASVKLSCK TSGFTFSSSYISWLKQKPGQSLE WIAWIFAGTGNTNYNQKFTDKAQ LTVDTSSSTAYMQLSSLTTEDSA IIYYCAISGTGFTYWGQGTLVTVS A |
| 208A-557H | 19 | CAGGGTCAGATGCAGCAGTCTGGAGCTGAGCT GGCGAAGCCTGGGGCTTCAGTGAAACTGTCCT GCAAGACTTCTGGCTTCACCTTCAGCAGTAGT TATATAAGTTGGTTGAAGCAAAAGCCTGGACA GAGTCTTGAGTGGATTGCATGGATTTTTGCTG GAACTGGTAATACTAATTATAATCAGAAGTTC ACAGACAAGGCCCAACTGACTGTAGACACATC CTCCAGTACAGCCTACATGCAACTCAGCAGCC TGACAACTGAGGACTCTGCCATCTATTACTGT GCGATAAGTGGGACGGGATTTACTTACTGGGG CCAAGGGACTCTGGTCACTGTCTCTGCA | 20 | 208A-557H | QGQMQQSGAELVKPGASVKLSCK TSGFTFSSSYISWLKQKPGQSLE WIAWIYAGTGNTNYNQKFTDKAQ LTVDTSSSTAYMQLSSLTTEDSA IIYYCAISGTGFTYWGQGTLVTVS A |
| 208A-352H | 21 | CAGGGTCAGATGCAGCAGTCTGGAGCTGAGCT GGTGAAGCCTGGGGCTTCAGTGAAGCTGTCCT GCAAGACTTCTGGCTTCACCTTCAGCAGTAGT TTTATAAGTTGGTTGAAGCAAAAGCCTGGACA GAGTCTTGAGTGGATTGCATGGATTTATGCTG GAACTGGAAATACTAACTATAATCAGAAGTTC ACAGACAAGGCCCAACTGACTGTAGACACATC CTCCAGCACAGCCTACATGCAATTCAGCAGCC TGACGACTGAGGACTCTGCCATCTATTACTGT GCGATAAGTGGGACGGGGTTTACTTACTGGGG CCAAGGGACTCTGGTCACTGTCTCTGCA | 22 | 208A-352H | QGQMQQSGAELVKPGASVKLSCK TSGFTFSSSFISWLKQKPGQSLE WIAWIYAGTGNTNYNQKFTDKAQ LTVDTSSSTAYMQFSSLTTEDSA IIYYCAISGTGFTYWGQGTLVTVS A |
| 208A-983H | 23 | CAGGGTCAGATGCAGCAGTCTGGAGCTGAGCT GGTGAAGCCTGGGGCTTCAGTGAAGCTGTCCT GCAAGACTTCTGGCTTCACCTTCAGCAGTAGT TATTTTAGTTGGTTGAAGCAAAAGCCTGGACA GAGTCTTGAGTGGATTGCATGGATTTATGCTG GAACTGGTAATACTATCTATAATCAGAAGTTC ACAGACAAGGCCCAACTGACTGTAGACACAGC CTCCAGCACAGCCTTCATGCAACTCAGCAGCC TGACAATTGAGGACTCTGCCATCTACTACTGT GCGATAAGTGGGACGGGGTTTACTTACTGGGG CCAAGGGACTCTGGTCACTGTCTCTGCAACA | 24 | 208A-983H | QGQMQQSGAELVKPGASVKLSCK TSGFTFSSSYFSWLKQKPGQSLE WIAWIYAGTGNTIYNQKFTDKAQ LTVDTSSTAFMQLSSLTIEDSA IIYYCAISGTGFTYWGQGTLVTVS A |
| 208B-281H | 25 | CAGGGTCAGCTGCAGCAGTCTGGAGCTGAGCT GGTGAAGCCTGGGGCTTCAGTGAAGCTGTCCT GCAAGACTTCTGCTTCACCTTCAGCAGTAGT TATATAAGTTGGTTGAAGCAAAGGCCTGGACA GAGTCTTGAGTGGATTGCATGGATTTATGCTG GAACTGGTGGTACTAACTATAATCAGAAGTTC ACAGACAAGGCCCAACTGACTGTAGACACATC CTCCAGCACAGCCTACATGCAATTCAGCAGCC TGACAACTGAGGACTCTGCCATCTATTACTGT GCGATAAGTGGGACGGGGTTATTTACTGGGG CCAAGGGACTCTGGTCACTGTCTCTGCA | 26 | 208B-281H | QGQLQQSGAELVKPGASVKLSCK TSGFTFSSSYISWLKQRPGQSLE WIAWIYAGTGGTNYNQKFTDKAQ LTVDTSSSTAYMQFSSLTTEDSA IITYCAISGTGFIYWGQGTLVTVS A |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208B-471H | 27 | CAGGGTCAGTTGCAGCAGTCTGGACCAGTACT GGTGAAGCCTGGGGCTTCAGAAATACTATACT GCAAGACTTCTGGCTTCACCTTCAGCAGTACC TATATAAGTTGGTTGAAGCAAAAGCCTGGACA GAGTCTTGAGTGGATTGCTGGATTTATGCTG GAACTGGTGCTACTAATTATAATCAGAAGTTC ACAGGCAAGGCCCAACTGACTGTAGACGCTTC CTCCAACACAGCCTACATGCACTTCAGCGGCC TGACACCTGAGGACTCTGCCATCTATTACTGT GCAATTTCTGGGGCGGGGGTTTACTGGGGCCA AGGGACTCTGGTCACTGTCTCTGCA | 28 | 208B-471H | QGQLQQSGPVLVKPGASEILYCK TSGFTFSSTYISWLKQKPGQSLE WIAWIYAGTGATNYNQKFTGKAQ LTVDASSNTAYMHFSGLTPEDSA IYYCAISGAGVYWGQGTLVTVSA |
| 208A-207H | 29 | CAGGGCCAACTGCAGCAGCCTGGGGCTGAGTT TGTGAAGCCTGGGGCTTCACTGAAGCTGTCCT GCAGGGCTTCTGGCTACACCTTCACCAGCTAC TGGATACACTGGGTGAAGCAGAGGCCTGGACA AGGCCTTGAGTGGATTGGAGAAATTGATCCTT CTGACAGTTATATTAACCAGAATCAAAAGTTC AGGGGCAAGGCCACATTGACTGTGGACAAATC CTCCAGCACAGCCTACATGGAACTCAGCGGCC TGACATCTGAAGACTCTGCGGTCTATTACTGT GCAAGACATTACTACGGTGTTCTTGACTCCTG GGGCCAAGGTACCACTCTCACAGTCTCCTCAA CA | 30 | 208A-207H | QGQLQQPGAEFVKPGASLKLSCR ASGYTFTSYWIHWVKQRPGQGLE WIGEIDPSDSYINQNQKFRGKAT LTVDKSSTAYMELSGLTSEDSA VYYCARHYYGVLDSWGQGTTLTV SS |
| 208A-638H | 31 | CAGGGCCAACTGCAGCAGCCTGGGGCTGAGTT TGTGAAGCCTGGGGCTTCACTGAAGCTGTCCT GCAGGGCTTCTGGCTACACCTTCACCAGCTAC TGGATTCACTGGGTGAAGCAGAGGCCTGGACA AGGCCTTGAGTGGATCGGAGAAGTTGATCCTT CTGACAGTTATATTAACCAGAATGAAAAGTTC AGGGGCAAGGCCACATTGACTGTGGACAAATC CTCCAGCACAGCCTACATGCAGCTCGGCAGCC TGACATCTGAAGACTCTGCGGTCTATTACTGT GCAAGACATTACTACGGTGTTCTTGACTCCTG GGGCCAAGGCACCGCTCTCACAGTCTCCTCA | 32 | 208A-638H | QGQLQQPGAEFVKPGASLKLSCR ASGYTFTSYWIHWVKQRPGQGLE WIGEVDPSDSYINQNEKFRGKAT LTVDKSSSTAYMQLGSLTSEDSA VYYCARHYYGVLDSWGQGTALTV SS |
| 208B-515H | 33 | CAGGTCCAACTGCAGCAGCCTGGGGCTGAACT TGTGAAGCCTGGGGCTTCACTGAAGCTGTCCT GCAGGGCCTCTGGCTACACCTTCACCAGCTAC TGGATTCACTGGGTGAAGCAGAGGCCTGGACA AGGCCTTGAGTGGATCGGAGAGATTGATCCTT CTGATAGTTATACTAACTACAATCAAAAGTTC AAGGGCAAGGCCACATTGACTGTAGACAAATC CTCCAGGGCAGCCTACATGCAGCTCAGCAGCC TGACATCTGAGGACTCTGCGGTCTATTACTGT GCAAGACATTACTACGGTGTCTTTGACTCCTG GGGCCAAGGCACCAAACTCACAGTCTCCTCA | 34 | 208B-515H | QVQLQQPGAELVKPGASLKLSCR ASGYTFTSYWIHWVKQRPGQGLE WIGEIDPSDSYTNYNQKFKGKAT LTVDKSSRAAYMQLSSLTSEDSA VYYCARHYYGVFDSWGQGTKLTV SS |
| 208A-874H | 35 | CAGGTCCAACTGCAGCAGCCTGGGGCTGAGCT TGTGAAGCCTGGGGCTTCAGTGAAGCTGTCCT GCAAGGCTTCTGGCTACACCCTCAGTAGCTAT TGGATGCACTGGGTGAAGCAGAGGCCTGGACA AGGCCTTGAGTGGATCGGAGAGATTCATCCTT CTGATAGTTATACTAGCTACAATCAAAAGTTC AAGGACAAGGCCACATTGACTGTAGACAAATC CTCCAGCACAGCCTACATGCAGCTCAGCAGCC TGACATCTGAGGACTCTGCAGTCTATTACTGT GCAAGGGGGGCTACATAGGTACGACGAGTT TGCTTACTGGGGCCAAGGGACTCTGGTCACTG TCTCTGCA | 36 | 208A-874H | QVQLQQPGAELVKPGASVKLSCK ASGYTLSSYWMHWVKQRPGQGLE WIGEIHPSDSYTSYNQKFKDKAT LTVDKSSSTAYMQLSSLTSEDSA VYYCARGGYYRYDEFAYWGQGTL VTVSA |
| 208B-911H | 37 | CAGGTCCATCTGCAGCAGCCTGGGGCTGAGCT GGTGAGGCCTGGGGTTTCAGTGAAGCTGTCCT GCAAGGCTTCTGGCTACACCTTCACCACCTAC TCGATAAACTGGATGAAGCAGAGGCCTGGACA AGGCCTTGAGTGGATCGGAAATATTTATCCT CTACCAGTCATACTAACTACAATCAAAAGTTC AGGGACAAGGCCACAATGACTGTAGACAAATC CTCCAGCACAGCCTACATGCAGCTCAGCAGCC CGACATCTGAGGACTCTGCGGTCTATTATTGT ACAATAAATGCCTATTCTATGGACTACTGGGG TCAAGGAACCTCAGTCACCGTCTCCTCA | 38 | 208B-911H | QVHLQQPGAELVRPGVSVKLSCK ASGYTFTTYSINWMKQRPGQGLE WIGNIYPSTSHTNYNQKFRDKAT MTVDKSSSTAYMQLSSPTSEDSA VYYCTINAYSMDYWGQGTSVTVS S |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208B-1096H | 39 | CAGGTCCAGCTTCAGCAGTCTGGGGCTGGACTGGCAAAACCTGGGGCCTCAGTGAAGATGTCCTGCAAGGCTTCTGGCTACACCTTTACTGCCAACAAGATGCACTGGGCAAAACAGCGGCCTGGACAGGGTCTGGAATGGATTGGATACATTGATCCTAGCTCTGGTTATACTGAATACAATCATAAGATCCAGTACAAGGCCACTTTGACTGCAGACACATCCTCCAGCACAGCCTACATGCAACTGAGCACCCTAACATTTGAAGACTCTGCAGTCTATTACTGTACAAATTTTGCTTACTGGGGCCAAGGGACTCTGGTCACTGTCTCAGCAACA | 40 | 208B-1096H | QVQLQQSGAGLAKPGASVKMSCKASGYTFTANKMHWAKQRPGQGLEWIGYIDPSSGYTEYNHKIQYKATLTADTSSSTAYMQLSTLTFEDSAVYYCTNFAYWGQGTLVTVSA |
| 208B-589H | 41 | CAGGTCCAGCTTCAGCAGTCTGGGGCTGGACTGGCAAAACCTGGGGCCTCAGTGAAGATGTCCTGCAAGGCTTCTGGCTACACCTTTACTGCCAACAAGATGCACTGGGCAAAACAGCGGCCTGGACAGGGTCTGGAATGGATTGGATACATTGATCCTAGCTCTGGTTATACTGAATACAATCATAAGATCCAGGACAAGGCCACATTGACTGCAGACACATCCTCCAGCACAGCCTACATGCAACTGAGCAGCCTAACATTTGAAGACTCTGCAGTCTATTACTGTACAAATTTTGCTTACTGGGGCCAAGGGACTCTGGTCACTGTCTCAGCA | 42 | 208B-589H | QVQLQQSGAGLAKPGASVKMSCKASGYTFTANKMHWAKQRPGQGLEWIGYIDPSSGYTEYNHKIQDKATLTADTSSSTAYMQLSSLTFEDSAVYYCTNFAYWGQGTLVTVSA |
| 208B-395H | 43 | CAGGTCCAGCTTCAGCAGTCTGGGGCTGGACTGGCAAAACCTGGGGCCTCAGTGAAGATGTCCTGCAAGGCTTCTGGCTATACCTTTACTGCCAACAAGATGCACTGGACAAAACAGCGGCCTGGACAGGGTCTGGAATGGATTGGATACATTGATCCTAGCTCTGGTTATACTCAATACAATCATAAGATCCAGGACAAGGCCACATTGACTGCAGACACATCCTCCAGCACAGCCTACATGCAACTGAGCAGCCTAACATTTGAAGACTCTGCAGTCTATTACTGTACAAATTTTGCTTACTGGGGCCAAGGGACTCTGGTCACTGTCTCAGCA | 44 | 208B-395H | QVQLQQSGAGLAKPGASVKMSCKASGYTFTANKMHWTKQRPGQGLEWIGYIDPSSGYTQYNHKIQDKATLTADTSSSTAYMQLSSLTFEDSAVYYCTNFAYWGQGTLVTVSA |
| 208B-189H | 45 | CAGGTCCACCTTCAGCAGTCTGGGGCTGAACTGGCCAAACCTGGGGCCTCAGTGCAGATGTCCTGCAAGGCTTCTGGCTACACCTTTACTGCCAACAAGATGCACTGGGCAAGACAGCGGCCTAGACAGGGTCTGGAATGGATTGGATACATTGATCCTGCCTCTGGCTATACTGAATACAATCAGAAGATCAAGGACAGGGCCACATTGACTGCAGACAAATCCTCCAGCACAGCCTACATGCAACTGAGCAGCCTGACATCTGAGGACTCTGCAGTCTATTACTGTACAAATTTTGCTTACTGGGGCCAAGGGACTCTGGTCACTGTCTCTACAACA | 46 | 208B-189H | QVHLQQSGAELAKPGASVQMSCKASGYTFTANKMHWARQRPRQGLEWIGYIDPASGYTEYNQKIKDRATLTADKSSSTAYMQLSSLTSEDSAVYYCTNFAYWGQGTLVTVST |
| 208B-547H | 47 | CAGGTCCAGCTTCAGCAGTCTGGGGCTGAACTGGCAAAACCTGGGGCCTCAGTGAAGATGTCCTGCAAGGCTTCTGGCTACACCTTTACTAGCAACAAGATGCACTGGGCAAAACAGCGGCCTGGACAGGGTCTGGAATGGATTGGATACATTGATCCTAGCTCTGGTTATACTGAATACAATCAGAAGATCAAGGACAAGGCCACATTGACTGCAGACAAATCCTCCAGCACAGCCTACATGCAACTGAGCAGCCTGACATCTGAGGACTCTGCAGTCTATTACTGTACAAATTTTGCTTACTGGGGCCAAGGGACTCTGGTCACTGTCTCTGCAACA | 48 | 208B-547H | QVQLQQSGAELAKPGASVKMSCKASGYTFTSNKMHWAKQRPGQGLEWIGYIDPSSGYTEYNQKIKDKATLTADKSSSTAYMQLSSLTSEDSAVYYCTNFAYWGQGTLVTVSA |
| 208A-210H | 49 | CAGGTCCAGTTGCAGCAGTCTGGACCTGAGTTGGTGAAGCCTGGGGCTTCAATGAGGATATCCTGCAAGGCTTCTGGCTACACCTTCACAAGCTACTATGTACACTGGATAAAGCAGAGGCCTGGACAGGGACTTGAGTGGATTGGATGTATTTATCCTGGAGATGTTAATACTGACTATAATGAGAAGTTCAAGGGCAAGGCCACGCTGACTGCAGACAAATCCTCCAGCACAGCCTACATGCAGGTCAGCACCCTGACCTCTGAGGACTCTGCGATCTATTTCTGTGTCCTTTATTACTACGGTAGTTTTGCTTACTGGGGCCAAGGGACTCTGGTCACTGTCTCTGCA | 50 | 208A-210H | QVQLQQSGPELVKPGASMRISCKASGYTFTSYYVHWIKQRPGQGLEWIGCIYPGDVNTDYNEKFKGKATLTADKSSSTAYMQVSTLTSEDSAIYFCVLYYYGSFAYWGQGTLVTVSA |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-422H | 51 | GATGTACAGCTTCAGGAGTCAGGACCTGGCCT<br>CGTGAATCCTTCTCAGTCTCTGTCTCTCACCT<br>GCTCTGTCACTGGCTACTCCATCACCAGTGGT<br>TATTACTGGATCTGGATCCAGCAGTCTCCAGG<br>AAACAAACTGGAATGGATGGGCTACATAAAGT<br>ACGACGGTGGCAATAACTACAGCCCATCTCTC<br>AAAAATCGAATCTCCATCGCTCGTGACACATC<br>TAAGAACCAGTGTTTCCTGAAGTTGAATTCTG<br>TGACTATTGAGGACACAGCTACATATTACTGT<br>ACAAGAGGGTCGGACTCCTTTGACTACTGGGG<br>CCAAGGCACCACTCTCACAGTCTCCTCA | 52 | 208A-422H | DVQLQESGPGLVNPSQSLSLTCS<br>VTGYSITSGYYWIWIQQSPGNKL<br>EWMGYIKYDGGNNYSPSLKNRIS<br>IARDTSKNQCFLKLNSVTIEDTA<br>TYYCTRGSDSFDYWGQGTTLTVS<br>S |
| 208A-442H | 53 | GATGTACAGCTTCAGGAGTCAGGACCTGGCCT<br>CGTGAATCCTTCTCAGTCTCTGTCTCTCACCT<br>GCTCTGTCACTGGCTACTCCATCACCAGTGGT<br>TATTACTGGATCTGGATCCGGCAGTTTCCAGG<br>AAACAAACTGGAATGGATGGGCTACATAAAGT<br>ACGACGGTGGCAATAACTACAGCCCATCTCTC<br>AAAAATCGAATCTCCATCGCTCGTGACACATC<br>TAAGAACCAGTTTTTCCTGAAGTTGAATTCTG<br>TGACTATTGAGGACACAGCTACATATTACTGT<br>ACAAGAGGGTCGGACTCCTTTGACTACTGGGG<br>CCAAGGCACCACTCTCACAGTCTCCTCA | 54 | 208A-442H | DVQLQESGPGLVNPSQSLSLTCS<br>VTGYSITSGYYWIWIRQFPGNKL<br>EWMGYIKYDGGNNYSPSLKNRIS<br>IARDTSKNQFFLKLNSVTIEDTA<br>TYYCTRGSDSFDYWGQGTTLTVS<br>S |
| 208B-862H | 55 | GATGTGCAGCTTCAGGAGTCGGGACCTGGCCT<br>GGTGAAACCTTCTCAGTCTCTGTCCCTCACCT<br>GCACTGTCACTGGCTACTCAATCACCAGTGAT<br>TATGCCTGGAACTGGATCCGGCAGTTTCCTGG<br>AAACAAACTGGAGTGGATGGGCTACATAAGCT<br>ACAGTGGTACCACTGTCTACAGCCCATCTCTC<br>AAAAGTCGAATCTCCATCACTCGGGACACATC<br>CAAAAACCAGTTCTTCCTGCAATTGAATTCTG<br>TGACTATTGAGGACTCAGCCACGTATTATTGT<br>GGGGGTAATTACTGGGGCCAAGGGACTCTGGT<br>CACTGTCTCTGCA | 56 | 208B-862H | DVQLQESGPGLVKPSQSLSLTCT<br>VTGYSITSDYAWNWIRQFPGNKL<br>EWMGYISYSGTTVYSPSLKSRIS<br>ITRDTSKNQFFLQLNSVTIEDSA<br>TYYCGGNYWGQGTLVTVSA |
| 208A-967H | 57 | CAGGTGCAGCTGGAGGAGTCAGGACCTGGCCT<br>GGTGGCGCCCTCACAGAGCCTGTCCATCACTT<br>GCACTGTCTCTGGATTTTCATTAACCAGCTAT<br>GGTGTATACACTGGGTTCGCCAGCCTCCAGGAAA<br>GGGTCTGGAGTGGCTGGGAGTAATATGGGCTG<br>TTGGAAGTATAAATTATAATTCGGCTCTCATG<br>TCCAGACTGAGCATCAGCAAGGACAACTCCAA<br>GAGCCAAGTTTTCTTAAAAATGAACAGTCTAC<br>GAACTGATGACACAGCCATGTACTACTGTGCC<br>AGAGATCGGACTACGGCTACCCCCTTCTTTGA<br>CTACTGGGGCCAAGGCACCACTCTCACAGTCT<br>CCTCATCCAAAACA | 58 | 208A-967H | QVQLEESGPGLVAPSQSLSITCT<br>VSGFSLTSYGVHWVRQPPGKGLE<br>WLGVIWAVGSINYNSALMSRLSI<br>SKDNSKSQVFLKMNSLRTDDTAM<br>YYCARDRTTATPFFDYWGQGTTL<br>TVSS |
| 208B-517H | 59 | CAGGTGCAGCTGAAGCAGTCAGGACCTGGCCT<br>AGTGCAGCCCTCACAGAGCCTGTCCATCACCT<br>GCACAGTCTCTGGTTTCTCATTAATTACCCAT<br>GGTGTACACTGGGTTCGCCAGTCTCCAGGAAA<br>GGGTCTGGAGTGGCTGGGAGTGATATGGAGTG<br>GTGGAAGCACAGACTATAATGCAGCTTTCATA<br>TCCAGACTGAGCATCAGCAAGGACACCTCCAA<br>GAGCCAAGTTTTCTTAAAAATGAGCAGTCTGC<br>AAGCTGATGACACAGCCATATACTACTGTGCC<br>AGAAATGGGGGGCTACGGCCTTTGACTACTG<br>GGGCCAAGGCACCACTCTCACAGTCTCCTCA | 60 | 208B-517H | QVQLKQSGPGLVQPSQSLSITCT<br>VSGFSLITHGVHWVRQSPGKGLE<br>WLGVIWSGGSTDYNAAFISRLSI<br>SKDTSKSQVFLKMSSLQADDTAI<br>YYCARNGGATAFDYWGQGTTLTV<br>SS |
| 208B-822H | 61 | CAGGTACAGCTGAAGCAGTCAGGACCTGGCCT<br>AGTGCAGCCCTCACAGAGCCTGTCCATCACCT<br>GCACAGTCTCTGGTTTCTCATTAATTACCTAT<br>GGTGTACACTGGGTTCGCCAGTCTCCAGGAAA<br>GGGTCTGGAGTGGCTGGGAGTGATATGGGGTG<br>GTGGAAGCACAGGCTATAATGCAGCTTTCGTA<br>TCCAGACTGAACATCACCAAGGACAACTCCAA<br>GAGCCAAGTTTTCTTTAAAAATGAACAGTCTGC<br>AACCTGATGACACAGCCATATACTACTGTGCC<br>AGAAATGGAGGGGCTACGGTCTTTGACTACTG<br>GGGCCAAGGCACCACTCTCACAGTCTCCTCA | 62 | 208B-822H | QVQLKQSGPGLVQPSQSLSITCT<br>VSGFSLITYGVHWVRQSPGKGLE<br>WLGVIWGGGSTGYNAAFVSRLNI<br>TKDNSKQVFFKMNSLQPDDTAI<br>YYCARNGGATVFDYWGQGTTLTV<br>SS |

| mAb Clone | SEQ ID | Nucleic Acid Seq | SEQ ID | mAb Clone | Amino Acid Seq |
|---|---|---|---|---|---|
| 208B-1024H | 63 | GAGGTGCAGCTGGTGGAGTCTGGGGGAGACTTAGTGAAGCCTGGAGGGTCCCTGAAACTCTCCTGTGCAGCCTCTGGATTCACTTTCAGTAACTATGGCATGTCTTGGGTTCGCCAGACTCCAGACAAGAGGCTGGAGTGGGTCGCAACCATTAGTAGTGGTGGTAGTTATAGCTACTATCCAGACAGTGTAAAGGGGCGGTTCACCATCTCCAGAGACAATGCCAAGAACATCCTGTACCTGCAAATGAGCAGTCTGAAGTCTGAGGACACAGCCATGTATTACTGTGCAAGTCTCTACTACGGCTACGGGGACTACTGGGGCCAAGGCACCGCTTTCACAGTCTCCTCA | 64 | 208B-1024H | EVQLVESGGDLVKPGGSLKLSCAASGFTFSNYGMSWVRQTPDKRLEWVATISSGGSYSYYPDSVKGRFTISRDNAKNILYLQMSSLKSEDTAMYYCASLYYGYGDYWGQGTAFTVSS |
| 208B-327H | 65 | GAAGTGCAGCTGGTGGAGTCTGGGGGAGGCTTGGTGAAGCCTGGAGGGTCCCTGAAACTCTCCTGTGCAGCCTCTGGATTCACTTTCAGTGACTCTTATATGTATTGGGTTCGCCAGACTCCGGACCAGAGGCTGGAGTGGGTCGCAACCATTAGTGATGGTGGTAGTTACACCTTCTATCCAGACAGTGTGAAGGGACGATTCACCATCTCCAGAGACAATGCCCAGAACAACCTGTACCTGCAAATGAGCAGTCTGAAGTCTGAGGACACAGCCATGTATTACTGTGCATCCCCCCATGCTGGCTACTTCGGCTGGTTTGCTTACTGGGGCCAGGGACTCTGGTCACTGTCTCTGCA | 66 | 208B-327H | EVQLVESGGGLVKPGGSLKLSCAASGFTFSDSYMYWVRQTPDQRLEWVATISDGGSYTFYPDSVKGRFTISRDNAQNNLYLQMSSLKSEDTAMYYCASPHAGYFGWFAYWGRGTLVTVSA |
| 208B-353H | 67 | GAGGTGCAGCTGGTGGAGTCTGGGGGAGACTTAGTGAAGCCTGGAGGGTCCCTGAAACTCTCCTGTGCAGCCTCTGGATTCACTTTCAATCACTATGGCATGTCTTGGGTTCGCCAGCCTCCAGACAAGAGACTGGAGTGGGTCGCAACCATTAGTAGTGGTGGTGGTTACACCTACTATCCAGACAGTGTGAAGGGGCGCTTCACCATCTCCAGAGACAATGCCAAGGACACCCTGTCCCTGCAAATGAGCAGTCTGAGGTCTGGGGACACAGCCGTGTATTACTGTGCAAGCCTATACGGTAGCCTGTTTGCTTACTGGGGCCAAGGGACTCTGGTCACTGTCTCTGCA | 68 | 208B-353H | EVQLVESGGDLVKPGGSLKLSCAASGFTFNHYGMSWVRQPPDKRLEWVATISSGGGYTYYPDSVKGRFTISRDNAKDTLSLQMSSLRSGDTAVYYCASLYGSLFAYWGQGTLVTVSA |
| 208B-178H | 69 | GACGTGAAGCTCGTGGAGTCTGGGGGAGGCTTAGTGAAGCTTGGAGGGTCCCTGAAACTCTCCTGTGCAGCCTCTGGATTCACTTTCAGTAGCTATTACATGTCTTGGGTTCGCCAGACTCCAGAGAAGAGGCTGGAGTTGGTCGCAGCCATTAATAGTAATGGTGGTAGCACCTACTATCCAGACACTGTGAAGGGCCGATTCACCATCTCCAGAGACAATGCCAAGAACACCCTGTACCTGCAAATGAGCAGTCTGAAGTCTGAGGACACAGCCTTGTATTACTGTGCAAGACATGGGGGACTGGGACGTAGGGACTGGTACTTCGATGTCTGGGGCGCAGGGACCACGGTCACCGTCTCCTCA | 70 | 208B-178H | DVKLVESGGGLVKLGGSLKLSCAASGFTFSSYYMSWVRQTPEKRLLVAAINSNGGSYYPDTVKGRFTISRDNAKNTLYLQMSSLKSEDTALYYCARHGGLGRRDWYFDVWGAGTTVTVSS |
| 208B-672H | 71 | GAAGTGAAACTGGTGGAGTCTGGGGGAAGTTTAGTCAGCCTGGAGGGTCCCTGAAACTCTCCTGCGCAGCCTCTGGATTCAATTTCAATACCTATGCCATGTCTTGGGTTCGCCAGACTCCAGAGAAGAGGCTGGAGTGGGTCGCATACATTAGTAATGGTGGTGGTAACACCTACTATGTAGACACTGTAAAGGGCCGATTCACCATCTCCAGAGACAATGCCAAGAACACCCTGTACCTGCGAATGAGCAGTCTGAAGTCTGAGGACACGGCCATGTATTACTGTGCAAGACATGGGCTCTACTGGGCTATTCTATGGACTACTGGGGTCAAGGAACCTCAGTCACCGTCTCCTCA | 72 | 208B-672H | EVKLVESGGSLVQPGGSLKLSCAASGFNFNTYAMSWVRQTPEKRLEWVAYISNGGGNTYYVDTVKGRFTISRDNAKNTLYLRMSSLKSEDTAMYYCARHGLYWGYSMDYWGQGTSVTVSS |
| 208B-793H | 73 | GAAGTGAAGCTGGTGGAGTCTGGGGGAGGTTTAGTGCAGCCAGGAGGGTCCCTGAAACTCTCCTGTGCAGCCTCTGGATTCACTTTCAGTAGCTATGCCATGTCTTGGGTTCGCCAGACTCCAGAGAGGAGGCTGGAGTGGGTCACATACATTAGTAATGGTGGTAGCACCTACTATTCAGACACTGTAAAGGGCCGATTCACCTTCTCCAGAGACAATGCCAAGAACACCCTGTACCTGCAAATGAGCAGTCTGAAGTCTGAGGACACGGCCATGTATTACTGTGCAAGACATGGACTGGGAAGGACAGGGTTTGC | 74 | 208B-793H | EVKLVESGGGLVQPGGSLKLSCAASGFTFSSYAMSWVRQTPERRLEWVTYISNGGSTYYSDTVKGRFFSRDNAKNTLYLQMSSLKSEDTAMYYCARHGLRTGFASWGQGTLVTVSA |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| | | TTCCTGGGGCCAAGGGACTCTGGTCACTGTCT CTGCA | | | |
| 208B-826H | 75 | GATGTGCAGCTGGTGGAGTCTGGGGGAGGCCT AGTGCAGGCTGGAGGGTCCCGGAAACTCTCCT GTGCAGCCTCTGGATTCCCTTTCAGTTCCTTT GGAATGCACTGGGTTCGTCAGGCTCCAGAGAA GGGGCTGGAGTGGGTCGCCTCCATTAGTAGTC GCACTAGTAAGATCTACTATGCAGACAACCTG AAGGGCCGATTCACCATCTCCAGAGACAATCC CAAGAACACCCTGTTCCTGCAAATGACCAGTC TTGGATCTGAGGACACGGCCATGTATTACTGT GTAAGATCCGTCTTTGGTAATTCTTACTGGTT TTTCGATGTCTGGGGCGCAGGGACCACGGTCA CCGTCTCCTCA | 76 | 208B-826H | DVQLVESGGGLVQAGGSRKLSCA ASGFPFSSFGMHWVRQAPEKGLE WVASISSRTSKIYYADNLKGRFT ISRDNPKNTLFLQMTSLGSEDTA MYYCVRSVFGNSYWFFDVWGAGT TVTVSS |
| 208B-174H | 77 | GAAGTGAAGCTTGAGGAGTCTGGAGGAGGCTT GGTACAACCTGGGGGATCCATGAAACTCTCCT GTGTAGCCTCTGGATTTTCTTTCAGTAGCTAC TGGATGTCTTGGGTCCGCCAGTCTCCAGAGAA GGGGCTTGACTGGGTTGCTGAAATTAGATTGA GATCTGATAATTATGCAACCCATTATGCGGAG TCTGTGAAGGGAGGTTCACCATCTCAAGAGA TGATTCCATAAGTCGTCTCTACCTGCAAATGA ACACCCTTAAGAGCTGAAGACACTGGAATTTAT TACTGTACATGGATGACGTACTGGGGCCAAGG GACTCTGGTCACTGTCTCTGCAACA | 78 | 208B-174H | EVKLEESGGGLVQPGGSMKLSCV ASGFSFSSYWMSWVRQSPEKGLD WVAEIRLRSDNYATHYAESVKGR FTISRDDSISRLYLQMNTLRAED TGIYYCTWMTYWGQGTLVTVSA |
| 208B-408H | 79 | GAGGTGAAGCTGGTGGAGTCTGGAGGAGGCTT GGTACAGCCTGGGGGTTCTCTGAGACTCTCCT GTGCAAGTTCTGGGTTCACCTTCACTGATTAC TACATGAGCTGGGTCCGCCAGCCTCCAGGAAA GGCACTTGAGTGGTTGGGTTTTATTAGAAACA AGCTTATGGTTACACGACCGAGTTCAGTGCA TCTGTGAACGGTCGGTTCACCATCTCCAGAGA TGATTCCAAAGCGTCCCCTATCTTCAAATGA ACACCCTGAGAGCTGAGGACAGTGCCACTTAT TACTGTGCGAGAGTCCTCTACTATGATTACGG GGGATTTGCTTACTGGGGCCAAGGGACTCTGG TCACTGTCTCTACA | 80 | 208B-408H | EVKLVESGGGLVQPGGSLRLSCA SSGFTFTDYYMSWVRQPPGKALE WLGFIRNKAYGYTTEFSASVNGR FTISRDDSQSVPYLQMNTLRAED SATYYCARVLYYDYGGFAYWGQG TLVTVST |
| 208B-612H | 81 | GAGGTCCAGCTGCAGCAGTCTGGACCTGAGCT GGTAAAGCCTGGGGCTTCAGTGAAGATGTCCT GTAAGGCTTCCGGATACAGATTCACTAGCTAT GTTATGCACTGGGTGAGGCAGAAGCCTGGACA GGGCCTTGAGTGGATTGGATATATTGATCCTC ACAATGATGATCAAAATACAGTGAGAAGTTC AGAGGTAAGGCCACACTGACTTCAGACAAGTC CTCCACCACAGCCTACATGGAGCTCAGCAGCC TGACCTCTGAGGACTCTGCGGTCTATTACTGT GTGAGATATTCTTACGACAGGGATTACAGTCC TATGGACTACTGGGGTCAAGGAACCTCAGTCA CCGTCTCCTCA | 82 | 208B-612H | EVQLQQSGPELVKPGASVKMSCK ASGYRFTSYVMHWVRQKPGQGLE WIGYIDPHND-- DTKYSEKFRGKATLTSDKSSTTA YMELSSLTSEDSAVYYCVRYSYD RDYSPMDYWGQGTSVTVSS |
| 208A-877H | 83 | CAGCTGCAACAGTCTGGACCTGAGCTGGTGAA GCCTGGGGCTTCAGTGAAAATTCCTGCAAGA CTTCTGGATACACATTCACTGAAAACGCCATG CACTGGGTGAAGCAGAGGCGTGGAAAGAGCCT TGAGTGGATTGGAGGTGTTAATCCTAACAATG GTGATACTGTCTACACCCAGAAGTTCAAGGGC AAGGCCACATTGACTGTAGCCAAGTCTTCCAG CACAGCCTACATGGAGCTCCGCACCATGACAT GTGAGGAATCTACAGTGTATTACTGTGCAAGC CGGGAACCGGACTTCTTTGACTACTGGGGCCA AGGCTCCTCTGTCACAGTCTCCTCA | 84 | 208A-877H | QLQQSGPELVKPGASVKISCKTS GYTFTENAMHWVKQSRGKSLEWI GGVNPNNGDTVYTQKFKGKATLT VAKSSSTAYMELRTMTCEESTVY YCASREPDFFDYWGQGSSVTVSS |
| 208B-251H | 85 | CAGCTGCAACAGTCTGGACCTGTACTGGTGAA GCCTGGGGCTTCAGTGAAAATTCCTGCAAGA CTTCTGGATACACATTCACTGAAAACGCCATG CACTGGGTGAAGCAGAGCCATGGAAAGAGCCT TGAGTGGATTGGAGGTGTTAATCCTAACAATG GTGATACTATCTACAACCAGAAGTTCAAGGGC AAGGCCACATTGACTGTAGACAAGTCCTCCAG CACAGCCTTCATGGAGCTCCGCAGCCTGACAT | 86 | 208B-251H | QLQQSGPVLVKPGASVKISCKTS GYTFTENAMHWVKQSHGKSLEWI GGVNPNNGDTIYNQKFKGKATLT VDKSSSTAFMELRSLTSEESPVY FCVRRELDFFDYWGQGTSVTVSS |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| | | CTGAAGAATCCCCAGTCTATTTCTGTGTAAGA CGGGAACTGGACTTCTTTGACTACTGGGGCCA AGGCACCTCTGTCACAGTCTCCTCA | | | |
| 208A-110H 208B-1070H | 87 | CAGCTGCAACAGTCTGGCCCTGTCCTGGTGAA GTCTGGGACTTCAGTTAAAATTTCCTGCAAGA CTTCTGGATACACATTCACTGAAAACGCCATG CACTGGGTGAAACAGAGCCATGGACAGAGCCT TGAGTGGATTGGAGGTGTTAATCCTAACAATG GTGATACTATCTTCAACCAGAAGTTCAAGGGC AAGGCCACATTGACTGTAGACAAGTCCTCCAG CACAGCCTTCATGGAGCTCCGCAGCCTGACAT CTGAAGAATCCACAGTCTATTACTGTGTAAGA CGGGAACTGGACTTCTTTGACTACTGGGGTCA AGGCACCTCTGTCACAGTCTCCTCA | 88 | 208A-110H 208B-1070H | QLQQSGPVLVKSGTSVKISCKTS GYTFTENAMHWVKQSHGQSLEWI GGVNPNNGDTIFNQKFKGKATLT VDKSSSTAFMELRSLTSEESTVY YCVRRELDFFDYWGQGTSVTVSS |
| 208A-334H 208A-920H | 89 | CAGCTGCAACAGTCTGGCCCTGTCCTGGTGAA GCCTGGGACTTCAGTGAAAATTTCCTGCAAGA CTTCTGGATACACATTCACTGAAAACGCCATG CACTGGGTGAAACAGAGCCATGGAAAGAGCCT TGAGTGGATTGGAGGTGTTAATCCTAACAATG GTGATACTATCTTCAACCAGAAGTTCAAGGGC AAGGCCACATTGACTGTAGACAAGTCCTCCAG CACAGCCTTCATGGAGCTCCGCAGCCTGACAT CTGAAGAATCCACAGTCTATTACTGTGTAAGA CGGGAACTGGACTTCTTTGACTACTGGGGCCA AGGCACCTCTGTCACAGTCTCCTCA | 90 | 208A-334H 208A-920H | QLQQSGPVLVKPGTSVKISCKTS GYTFTENAMHWVKQSHGKSLEWI GGVNPNNGDTIFNQKFKGKATLT VDKSSSTAFMELRSLTSEESTVY YCVRRELDFFDYWGQGTSVTVSS |
| 208A-159H | 91 | CAGCTGCAACAGTCTGGACCTGCCCAGGTGAA GCCTGGGGCTTCAGTGATGATTTCCTGCAAGA CTTCTGGATACACATTCACTGAAAACGCCATG CACTGGGTGAAACAGAGCCATGGAAAGAGCCT TGAGTGGATTGGAGGTGTTAATCCTAACAATG GTGATACTATTTTCAACCAGAAGTTCAAGGAC AAGGCCGCATTGACTGTAGACAAGTCCTCCAG CACAGCCTTCATGGAGCTCCGCAGCCTGACAT CTGAGGAGTCCACAGTCTATTACTGTGTAAGA CGGGAATTGGACTTCTTTGACTACTGGGGCCA AGGCACCTCTGTCACAGTCTCCTCA | 92 | 208A-159H | QLQQSGPAQVKPGASVMISCKTS GYTFTENAMHWVKQSHGKSLEWI GGVNPNNGDTIFNQKFKDKAALT VDKSSSTAFMELRSLTSEESTVY YCVRRELDFFDYWGQGTSVTVSS |
| 208A-126H | 93 | CAGCTGCAACAGTCTGGACCTGTCCTGGTGAA GCCTGGGCTTCAGTGATGATTTCCTGCAAGA CTTCTGGATACACATTCACTGAAAACGCCATG CACTGGGTGAAACAGAGCCATGGAAAGAGCCT TGAGTGGATTGGAGGTGTTAATCCTAACAATG GTGATACTATTTTCAACCAGAAGTTCAAGGGC AAGGCCACATTGACTGTAGACAAGTCCTCCAA CACAGCCTTCACGGAGCTCCGCAGCCTGCCAT CTGAAGAATCCACAGTCTATTACTGTGTTAGA CGGGGATTGGACTTCTTTGACTACTGGGGCCA AGGCACCTCTGTCACAGTCTCCTCA | 94 | 208A-126H | QLQQSGPVLVKPGASVMISCKTS GYTFTENAMHWVKQSHGKSLEWI GGVNPNNGDTIFNQKFKGKATLT VDKSSNTAFTELRSLPSEESTVY YCVRRGLDFFDYWGQGTSVTVSS |
| 208A-133H | 95 | CAGCTGCAACAGTCTGGCCCTGTCCTGGTGGG GCCTGGGGCTTCAGTGATGATTTCCTGCAAGA CTTCTGGATACACATTCACTGAAAACGCCATG CACTGGGTGGAACAGAGCCATGGAAAGAGCCT TGAGTGGATTGGAGGTGTTAATCCTAACAATG GTGATACTATTTTCAACCAGAAGTTCAAGGGC AAGGCCACATTGACTGTAGACAAGTCCTCCAG CACAGCCTTCATGGAGTTCCGCAGCCTGACAT CTGAAGAATCCACAGTCTATTACTGTGTAAGA CGGGAATTGGACTTCTTTGACTACTGGGGCCA AGGCACCTCTGTCACAGTCTCCTCA | 96 | 208A-133H | QLQQSGPVLVGPGASVMISCKTS GYTFTENAMHWVEQSHGKSLEWI GGVNPNNGDTIFNQKFKGKATLT VDKSSSTAFMEFRSLTSEESTVY YCVRRELDFFDYWGQGTSVTVSS |
| 208B-556H | 97 | CAGCTGCAACAGTCTGGACCTGTCCTGGTGAA GCCTGGGGCTTCAGTGATGATTTCCTGCAAGA CTTCTGGATACACATTCACTGAAAACGCCATG CACTGGGTGAAACAGAGCCATGGAAAGAGCCT TGAGTGGATTGGAGGTGTTAATCCTAACAATG GTGATACTATTTTCAACCAGAAGTTCAAGGGC AAGGCCACATTGACTGTAGACAAGTCCTCCAG CACAGCCTTCATGGAGTTCCGCAGCCTGACAT CTGAAGAATCCACAGTCTATTACTGTGTAAGA | 98 | 208B-556H | QLQQSGPVLVKPGASVMISCKTS GYTFTENAMHWVKQSHGKSLEWI GGVNPNNGDTIFNQKFKGKATLT VDKSSSTAFMEFRSLTSEESTVY YCVRRELDFFDYWGQGTSVTVSS |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| | | CGGGAATTGGACTTCTTTGACTACTGGGGCCA AGGCACCTCTGTCACAGTCTCCTCAACA | | | |
| 208A-741H | 99 | CAGCTGCAACAGTCTGGACCTGTCCTGGTGAA GCCTGGGGCTTCAGTGATGATTTCCTGCAAGA CTTCTGGATACACATTCACTGAAAACGCCATG CACTGGGTGAAACAGAGCCATGGAAAGAGCCT TGAGTGGATTGGAGGTGTTAATCCTAACAATG GTGATACTATTTTCAACCAGAAGTTCAAGGGC AAGGCCACATTGACTGTAGACAAGTCCTCCAG CACAGCCTTCATGGAGCTCCGCAGCCTGACAT CTGAAGAATCCACAGTCTATTACTGTGTAAGA CGGGAATTGGACTTCTTTGACTACTGGGGCCA AGGCACCTCTGTCACAGTCTCCTCA | 100 | 208A-741H | QLQQSGPVLVKPGASVMISCKTS GYTFTENAMHWVKQSHGKSLEWI GGVNPNNGDTIFNQKFKGKATLT VDKSSSTAFMELRSLTSEESTVY YCVRRELDFFDYWGQGTSVTVSS |
| 208A-1064 CDR H1<br>208B-1094 CDR H1<br>208A-293 CDR H1<br>208A-222 CDR H1<br>208B-560 CDR H1 | 101 | GAATACGCCATGCAC | 102 | 208A-1064 CDR H1<br>208B-1094 CDR H1<br>208A-293 CDR H1<br>208A-222 CDR H1<br>208B-560 CDR H1 | EYAMH |
| 208A-605 CDR H1<br>208A-830 CDR H1 | 103 | GAATACGCCATACAC | 104 | 208A-605 CDR H1<br>208A-830 CDR H1 | EYAIH |
| 208A-134 CDR H1<br>208A-692 CDR H1<br>208A-557 CDR H1<br>208B-281 CDR H1 | 105 | AGTAGTTATATAAGT | 106 | 208A-134 CDR H1<br>208A-692 CDR H1<br>208A-557 CDR H1<br>208B-281 CDR H1 | SSYIS |
| 208A-352 CDR H1 | 107 | AGTAGTTTTATAAGT | 108 | 208A-352 CDR H1 | SSFIS |
| 208A-983 CDR H1 | 109 | AGTAGTTATTTTAGT | 110 | 208A-983 CDR H1 | SSYFS |
| 208B-471 CDR H1 | 111 | AGCAGTACCTATATAAGT | 112 | 208B-471 CDR H1 | STYIS |
| 208A-207 CDR H1<br>208A-638 CDR H1<br>208B-515 CDR H1 | 113 | AGCTACTGGATACAC | 114 | 208A-207 CDR H1<br>208A-638 CDR H1<br>208B-515 CDR H1 | SYWIH |
| 208A-874 CDR H1 | 115 | AGCTATTGGATGCAC | 116 | 208A-874 CDR H1 | SYWMH |
| 208B-911 CDR H1 | 117 | CCTACTCGATAAAC | 118 | 208B-911 CDR H1 | TYSIN |
| 208B-1096 CDR H1<br>208B-589 CDR H1<br>208B-395 CDR H1<br>208B-189 CDR H1 | 119 | GCCAACAAGATGCAC | 120 | 208B-1096 CDR H1<br>208B-589 CDR H1<br>208B-395 CDR H1<br>208B-189 CDR H1 | ANKMH |
| 208B-547 CDR H1 | 121 | AGCAACAAGATGCAC | 122 | 208B-547 CDR H1 | SNKMH |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-210 CDR H1 | 123 | AGCTACTATGTACAC | 124 | 208A-210 CDR H1 | SYYVH |
| 208A-422 CDR H1<br>208A-442 CDR H1 | 125 | AGTGGTTATTACTGGATC | 126 | 208A-422 CDR H1<br>208A-442 CDR H1 | SGYYWI |
| 208B-862 CDR H1 | 127 | AGTGATTATGCCTGGAAC | 128 | 208B-862 CDR H1 | SDYAWN |
| 208A-967 CDR H1 | 129 | AGCTATGGTGTACAC | 130 | 208A-967 CDR H1 | SYGVH |
| 208B-517 CDR H1 | 131 | ACCCATGGTGTACAC | 132 | 208B-517 CDR H1 | THGVH |
| 208B-822 CDR H1 | 133 | ACCTATGGTGTACAC | 134 | 208B-822 CDR H1 | TYGVH |
| 208B-1024 CDR H1 | 135 | AACTATGGCATGTCT | 136 | 208B-1024 CDR H1 | NYGMS |
| 208B-327 CDR H1 | 137 | GACTCTTATATGTAT | 138 | 208B-327 CDR H1 | DSYMY |
| 208B-353 CDR H1 | 139 | CACTATGGCATGTCT | 140 | 208B-353 CDR H1 | HYGMS |
| 208B-178 CDR H1 | 141 | AGCTATTACATGTCT | 142 | 208B-178 CDR H1 | SYYMS |
| 208B-672 CDR H1 | 143 | ACCTATGCCATGTCT | 144 | 208B-672 CDR H1 | TYAMS |
| 208B-793 CDR H1 | 145 | AGCTATGCCATGTCT | 146 | 208B-793 CDR H1 | SYAMS |
| 208B-826 CDR H1 | 147 | TCCTTTGGAATGCAC | 148 | 208B-826 CDR H1 | SFGMH |
| 208B-174 CDR H1 | 149 | AGCTACTGGATGTCT | 150 | 208B-174 CDR H1 | SYWMS |
| 208B-408 CDR H1 | 151 | GATTACTACATGAGC | 152 | 208B-408 CDR H1 | DYYMS |
| 208B-612 CDR H1 | 153 | AGCTATGTTATGCAC | 154 | 208B-612 CDR H1 | SYVMH |
| 208A-877 CDR H1<br>208B-251 CDR H1<br>208A-110 CDR H1<br>208B-1070 CDR H1<br>208A-334 CDR H1<br>208A-920 CDR H1<br>208A-159 CDR H1<br>208A-126 CDR H1<br>208A-133 CDR H1<br>208B-556 CDR H1<br>208A-741 CDR H1 | 155 | GAAAACGCCATGCAC | 156 | 208A-877 CDR H1<br>208B-251 CD H1<br>208A-110 CDR H1<br>208B-1070 CDR H1<br>208A-334 CDR H1<br>208A-920 CDR H1<br>208A-159 CDR H1<br>208A-126 CDR H1<br>208A-133 CDR H1<br>208B-556 CDR H1<br>208A-741 CDR H1 | ENAMH |

-continued

| mAb Clone | SEQ ID | Nucleic Acid Seq | SEQ ID | mAb Clone | Amino Acid Seq |
|---|---|---|---|---|---|
| 208A-1064 CDR H2 208A-293 CDR H2 | 157 | GGTATCAATCCTACTAATGGTGATACAATCTA CAACCAGAAGTTCAAGGAC | 158 | 208A-1064 CDR H2 208A-293 CDR H2 | GINPTNGDTIYNQKFKD |
| 208B-1094 CDR H2 | 159 | GGTATCAATCCTACTAATGGTGATACAATCTA CAACCAGAGGTTCAAGGAC | 160 | 208B-1094 CDR H2 | GINPTNGDTIYNQRFKD |
| 208A-222 CDR H2 | 161 | GGTATTAATCCTAACAATGGCAATGCTATCTA CAACCAGATATTCAAGGAC | 162 | 208A-222 CDR H2 | GINPNNGNAIYNQIFKD |
| 208A-605 CDR H2 208B-560 CDR H2 | 163 | GGTATTAATCCTAGCAATGGCAATGCTATCTA CAACCAAATATTCAAGGAC | 164 | 208A-605 CDR H2 208B-560 CDR H2 | GINPSNGNAIYNQIFKD |
| 208A-830 CDR H2 | 165 | GGTATTAATCCTAGCAATGGCGATCCTATCTA TAACCAGATATTCAAGGAC | 166 | 208A-830 CDR H2 | GINPSNGDPIYNQIFKD |
| 208A-134 CDR H2 208A-557 CDR H2 208A-352 CDR H2 | 167 | TGGATTTATGCTGGAACTGGTAATACTAACTA TAATCAGAAGTTCACAGAC | 168 | 208A-134 CDR H2 208A-557 CDR H2 208A-352 CDR H2 | WIYAGTGNTNYNQKFTD |
| 208A-692 CDR H2 | 169 | TGGATTTTTGCTGGAACTGGTAATACTAATTA TAATCAGAAGTTCACAGAC | 170 | 208A-692 CDR H2 | WIFAGTGNTNYNQKFTD |
| 208A-983 CDR H2 | 171 | TGGATTTATGCTGGAACTGGTAATACTATCTA TAATCAGAAGTTCACAGAC | 172 | 208A-983 CDR H2 | WIYAGTGNTIYNQKFTD |
| 208B-281 CDR H2 | 173 | TGGATTTATGCTGGAACTGGTGGTACTAACTA TAATCAGAAGTTCACAGAC | 174 | 208B-281 CDR H2 | WIYAGTGGTNYNQKFTD |
| 208B-471 CDR H2 | 175 | TGGATTTATGCTGGAACTGGTGCTACTAATTA TAATCAGAAGTTCACAGGC | 176 | 208B-471 CDR H2 | WIYAGTGATNYNQKFTG |
| 208A-207 CDR H2 | 177 | GAAATTGATCCTTCTGACAGTTATATTAACCA GAATCAAAAGTTCAGGGGC | 178 | 208A-207 CDR H2 | EIDPSDSYINQNKFRG |
| 208A-638 CDR H2 | 179 | GAAGTTGATCCTTCTGACAGTTATATTAACCA GAATGAAAAGTTCAGGGGC | 180 | 208A-638 CDR H2 | EVDPSDSYINQNEKFRG |
| 208B-515 CDR H2 | 181 | GAGATTGATCCTTCTGATAGTTATACTAACTA CAATCAAAAGTTCAAGGGC | 182 | 208B-515 CDR H2 | EIDPSDSYTNYNQKFKG |
| 208A-874 CDR H2 | 183 | GAGATTCATCCTTCTGATAGTTATACTAGCTA CAATCAAAAGTTCAAGGAC | 184 | 208A-874 CDR H2 | EIHPSDSYTSYNQKFKD |
| 208B-911 CDR H2 | 185 | AATATTTATCCTTCTACCAGTCATACTAACTA CAATCAAAAGTTCAGGGAC | 186 | 208B-911 CDR H2 | NIYPSTSHTNYNQKFRD |
| 208B-1096 CDR H2 | 187 | TACATTGATCCTAGCTCTGGTTATACTGAATA CAATCATAAGATCCAGTAC | 188 | 208B-1096 CDR H2 | YIDPSSGYTEYNHKIQY |
| 208B-589 CDR H2 | 189 | TACATTGATCCTAGCTCTGGTTATACTGAATA CAATCATAAGATCCAGGAC | 190 | 208B-589 CDR H2 | YIDPSSGYTEYNHKIQD |
| 208B-395 CDR H2 | 191 | TACATTGATCCTAGCTCTGGTTATACTCAATA CAATCATAAGATCCAGGAC | 192 | 208B-395 CDR H2 | YIDPSSGYTQYNHKIQD |
| 208B-189 CDR H2 | 193 | TACATTGATCCTGCCTCTGGCTATACTGAATA CAATCAGAAGATCAAGGAC | 194 | 208B-189 CDR H2 | YIDPASGYTEYNQKIKD |
| 208B-547 CDR H2 | 195 | TACATTGATCCTAGCTCTGGTTATACTGAATA CAATCAGAAGATCAAGGAC | 196 | 208B-547 CDR H2 | YIDPSSGYTEYNQKIKD |
| 208A-210 CDR H2 | 197 | TGTATTTATCCTGGAGATGTTAATACTGACTA TAATGAGAAGTTCAAGGGC | 198 | 208A-210 CDR H2 | CIYPGDVNTDYNEKFKG |
| 208A-422 CDR H2 | 199 | TACATAAAGTACGACGGTGGCAATAACTACAG CCCATCTCTCAAAAAT | 200 | 208A-422 CDR H2 | YIKYDGGNNYSPSLKN |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-442 CDR H2 | | | | 208A-442 CDR H2 | |
| 208B-862 CDR H2 | 201 | TACATAAGCTACAGTGGTACCACTGTCTACAG CCCATCTCTCAAAAGT | 202 | 208B-862 CDR H2 | YISYSGTTVYSPSLKS |
| 208A-967 CDR H2 | 203 | GTAATATGGGCTGTTGGAAGTATAAATTATAA TTCGGCTCTCATGTCC | 204 | 208A-967 CDR H2 | VIWAVGSINYNSALMS |
| 208B-517 CDR H2 | 205 | GTGATATGGAGTGGTGGAAGCACAGACTATAA TGCAGCTTTCATATCC | 206 | 208B-517 CDR H2 | VIWSGGSTDYNAAFIS |
| 208B-822 CDR H2 | 207 | GTGATATGGGGTGGTGGAAGCACAGGCTATAA TGCAGCTTTCGTATCC | 208 | 208B-822 CDR H2 | VIWGGGSTGYNAAFVS |
| 208B-1024 CDR H2 | 209 | ACCATTAGTAGTGGTGGTAGTTATAGCTACTA TCCAGACAGTGTAAAGGGG | 210 | 208B-1024 CDR H2 | TISSGGSYSYYPDSVKG |
| 208B-327 CDR H2 | 211 | ACCATTAGTGATGGTGGTAGTTACACCTTCTA TCCAGACAGTGTGAAGGGA | 212 | 208B-327 CDR H2 | TISDGGSYTFYPDSVKG |
| 208B-353 CDR H2 | 213 | ACCATTAGTAGTGGTGGTGGTTACACCTACTA TCCAGACAGTGTGAAGGGG | 214 | 208B-353 CDR H2 | TISSGGGYTYYPDSVKG |
| 208B-178 CDR H2 | 215 | GCCATTAATAGTAATGGTGGTAGCACCTACTA TCCAGACACTGTGAAGGGC | 216 | 208B-178 CDR H2 | AINSNGGSTYYPDTVKG |
| 208B-672 CDR H2 | 217 | TACATTAGTAATGGTGGTGGTAACACCTACTA TGTAGACACTGTAAAGGGC | 218 | 208B-672 CDR H2 | YISNGGGNTYYVDTVKG |
| 208B-793 CDR H2 | 219 | TACATTAGTAATGGTGGTGGTAGCACCTACTA TTCAGACACTGTAAAGGGC | 220 | 208B-793 CDR H2 | YISNGGGSTYYSDTVKG |
| 208B-826 CDR H2 | 221 | TCCATTAGTAGTCGCACTAGTAAGATCTACTA TGCAGACAACCTGAAGGGC | 222 | 208B-826 CDR H2 | SISSRTSKIYYADNLKG |
| 208B-174 CDR H2 | 223 | GAAATTAGATTGAGATCTGATAATTATGCAAC CCATTATGCGGAGTCTGTGAAAGGG | 224 | 208B-174 CDR H2 | EIRLRSDNYATHYAESVKG |
| 208B-408 CDR H2 | 225 | TTTATTAGAAACAAAGCTTATGGTTACACGAC CGAGTTCAGTGCATCTGTGAACGGT | 226 | 208B-408 CDR H2 | FIRNKAYGYTTEFSASVNG |
| 208B-612 CDR H2 | 227 | TATATTGATCCTCACAATGATGATACAAAATA CAGTGAGAAGTTCAGAGGT | 228 | 208B-612 CDR H2 | YIDPHNDDTKYSEKFRG |
| 208A-877 CDR H2 | 229 | GGTGTTAATCCTAACAATGGTGATACTGTCTA CACCCAGAAGTTCAAGGGC | 230 | 208A-877 CDR H2 | GVNPNNGDTVYTQKFKG |
| 208B-251 CDR H2 | 231 | GGTGTTAATCCTAACAATGGTGATACTATCTA CAACCAGAAGTTCAAGGGC | 232 | 208B-251 CDR H2 | GVNPNNGDTIYNQKFKG |
| 208A-110 CDR H2 208B-1070 CDR H2 208A-334 CDR H2 208A-920 CDR H2 208A-126 CDR H2 208A-133 CDR H2 208B-556 CDR H2 208A-741 CDR H2 | 233 | GGTGTTAATCCTAACAATGGTGATACTATCTT CAACCAGAAGTTCAAGGGC | 234 | 208A-110 CDR H2 208B-1070 CDR H2 208A-334 CDR H2 208A-920 CDR H2 208A-126 CDR H2 208A-133 CDR H2 208B-556 CDR H2 208A-741 CDR H2 | GVNPNNGDTIFNQKFKG |
| 208A-159 CDR H2 | 235 | GGTGTTAATCCTAACAATGGTGATACTATTTT CAACCAGAAGTTCAAGGAC | 236 | 208A-159 CDR H2 | GVNPNNGDTIFNQKFKD |
| 208A-1064 CDR H3 | 237 | CGGGAACTGGACTACTTTGCCTCC | 238 | 208A-1064 CDR H3 | RELDYFAS |

| APPENDIX A-DESCRIPTION OF SEQUENCES | | | | | |
|---|---|---|---|---|---|
| mAb Clone | SEQ ID | Nucleic Acid Seq | SEQ ID | mAb Clone | Amino Acid Seq |
| 208B-1094 CDR H3 | | | | 208B-1094 CDR H3 | |
| 208A-293 CDR H3 | 239 | CGGGAACTGGACTACTTTCCCTCC | 240 | 208A-293 CDR H3 | RELDYFPS |
| 208A-222 CDR H3 | 241 | CGACAACTGGACTACTTTGACTAT | 242 | 208A-222 CDR H3 | RQLDYFDY |
| 208A-605 CDR H3 208B-560 CDR H3 | 243 | CGACAACTGGACTTCTTTGACTAT | 244 | 208A-605 CDR H3 208B-560 CDR H3 | RQLDFFDY |
| 208A-830 CDR H3 | 245 | CGACAACTGGACTACTTTGACTTT | 246 | 208A-830 CDR H3 | RQLDYFDF |
| 208A-134 CDR H3 208A-692 CDR H3 208A-557 CDR H3 208A-352 CDR H3 208A-983 CDR H3 | 247 | AGTGGGACGGGGTTTACTTAC | 248 | 208A-134 CDR H3 208A-692 CDR H3 208A-557 CDR H3 208A-352 CDR H3 208A-983 CDR H3 | SGTGFTY |
| 208B-281 CDR H3 | 249 | AGTGGGACGGGGTTTATTTAC | 250 | 208B-281 CDR H3 | SGTGFIY |
| 208B-471 CDR H3 | 251 | TCTGGGGCGGGGGTTTAC | 252 | 208B-471 CDR H3 | SGAGVY |
| 208A-207 CDR H3 208A-638 CDR H3 | 253 | CATTACTACGGTGTTCTTGACTCC | 254 | 208A-207 CDR H3 208A-638 CDR H3 | HYYGVLDS |
| 208B-515 CDR H3 | 255 | CATTACTACGGTGTCTTTGACTCC | 256 | 208B-515 CDR H3 | HYYGVFDS |
| 208A-874 CDR H3 | 257 | GGGGGCTACTATAGGTACGACGAGTTTGCTTAC | 258 | 208A-874 CDR H3 | GGYYRYDEFAY |
| 208B-911 CDR H3 | 259 | AATGCCTATTCTATGGACTAC | 260 | 208B-911 CDR H3 | NAYSMDY |
| 208B-1096 CDR H3 208B-589 CDR H3 208B-395 CDR H3 208B-189 CDR H3 208B-547 CDR H3 | 261 | TTTGCTTAC | 262 | 208B-1096 CDR H3 208B-589 CDR H3 208B-395 CDR H3 208B-189 CDR H3 208B-547 CDR H3 | FAY |
| 208A-210 CDR H3 | 263 | TATTACTACGGTAGTTTTGCTTAC | 264 | 208A-210 CDR H3 | YYYGSFAY |
| 208A-422 CDR H3 208A-442 CDR H3 | 265 | GGGTCGGACTCCTTTGACTAC | 266 | 208A-422 CDR H3 208A-442 CDR H3 | GSDSFDY |
| 208B-862 CDR H3 | 267 | AATTAC | 268 | 208B-862 CDR H3 | NY |
| 208A-967 CDR H3 | 269 | GATCGGACTACGGCTACCCCCTTCTTTGACTAC | 270 | 208A-967 CDR H3 | DRTTATPFFDY |

| mAb Clone | SEQ ID | Nucleic Acid Seq | SEQ ID | mAb Clone | Amino Acid Seq |
|---|---|---|---|---|---|
| 208B-517 CDR H3 | 271 | AATGGGGGGGCTACGGCCTTTGACTAC | 272 | 208B-517 CDR H3 | NGGATAFDY |
| 208B-822 CDR H | 273 | AATGGAGGGGCTACGGTCTTTGACTAC | 274 | 208B-822 CDR H | NGGATVFDY |
| 208B-1024 CDR H3 | 275 | CTCTACTACGGCTACGGGGACTAC | 276 | 208B-1024 CDR H3 | LYYGYGDY |
| 208B-327 CDR H3 | 277 | CCCCATGCTGGCTACTTCGGCTGGTTTGCTTAC | 278 | 208B-327 CDR H3 | PHAGYFGWFAY |
| 208B-353 CDR H3 | 279 | CTATACGGTAGCCTGTTTGCTTAC | 280 | 208B-353 CDR H3 | LYGSLFAY |
| 208B-178 CDR H3 | 281 | CATGGGGGACTGGGACGTAGGGACTGGTACTTCGATGTC | 282 | 208B-178 CDR H3 | HGGLGRRDWYFDV |
| 208B-672 CDR H3 | 283 | CATGGGCTCTACTGGGGCTATTCTATGGACTAC | 284 | 208B-672 CDR H3 | HGLYWGYSMDY |
| 208B-793 CDR H3 | 285 | CATGGACTGGGAAGGACAGGGTTTGCTTCC | 286 | 208B-793 CDR H3 | HGLGRTGFAS |
| 208B-826 CDR H3 | 287 | TCCGTCTTTGGTAATTCTTAC | 288 | 208B-826 CDR H3 | SVFGNSYWFFDV |
| 208B-174 CDR H3 | 289 | ATGACGTAC | 290 | 208B-174 CDR H3 | MTY |
| 208B-408 CDR H3 | 291 | GTCCTCTACTATGATTACGGGGATTTGCTTAC | 292 | 208B-408 CDR H3 | VLYYDYGGFAY |
| 208B-612 CDR H3 | 293 | TATTCTTACGACAGGGATTACAGTCCTATGGACTAC | 294 | 208B-612 CDR H3 | YSYDRDYSPMDY |
| 208A-877 CDR H3 | 295 | CGGGAACCGGACTTCTTTGACTAC | 296 | 208A-877 CDR H3 | REPDFFDY |
| 208B-251 CDR H3 208A-110 CDR H3 208B-1070 CDR H3 208A-334 CDR H3 208A-920 CDR H3 208A-159 CDR H3 208A-133 CDR H3 208B-556 CDR H3 208A-741 CDR H3 | 297 | CGGGAATTGGACTTCTTTGACTAC | 298 | 208B-251 CDR H3 208A-110 CDR H3 208B-1070 CDR H3 208A-334 CDR H3 208A-920 CDR H3 208A-159 CDR H3 208A-133 CDR H3 208B-556 CDR H3 208A-741 CDR H3 | RELDFFDY |
| 208A-126 CDR H3 | 299 | CGGGGATTGGACTTCTTTGACTAC | 300 | 208A-126 CDR H3 | RGLDFFDY |
| 208A-1064L | 301 | GACATTGTGCTGACACAGTCTCCTGCTTCCTTAATTGTTTCTCTGGGGCAGACGGCCACCATCTCATGCAGGGCCAGCCAAAGTGTCAGTACATCTAGGTTTAGTTATCTGCACTGGATCCAACAGAAACCAGGGCAGCCACCCAAACTCCTCATCAAGTATGCATCCAACCTTGAATCTGGGGTCCCTGTCAGGTTCAGTGGCAGTGGGTCTGGGACAGACTTCACCCTCAACATCCATCCTGTGGAGGAGGAGATACTGCAACATATTTCTGTCAGCACAGTTGGGAGTTTCCATTCACGTTCGGCTCGGGGACAAAGTTGAAAATAAAACGGGCTGATGCTGC | 302 | 208A-1064L | DIVLTQSPASLIVSLGQTATISCRASQSVSTSRFSYLHWIQQKPGQPPKLLIKYASNLESGVPVRFSGSGSGTDFTLNIHPVEEEDTATYFCQHSWEFPFTFGSGTKLKIKR |

-continued

| mAb Clone | SEQ ID | Nucleic Acid Seq | SEQ ID | mAb Clone | Amino Acid Seq |
|---|---|---|---|---|---|
| 208B-1094L | 303 | GACATTGTGCTGACACAGTCTCCTGCTTCCTT AATTGTTTCTCTGGGGCAGACGGCCACCATCT CATGCAGGGCCAGCCAAAGTCTCAGTACATCT AGGTTTAGCTATGTGCACTGGATCCAACAGAA ACCAGGGCAGCCACCCAAACTCCTCATCAAGT ATGCATCCAACCTTGAATCTGGGGTCCCTGTC AGGTTCAGTGGCAGTGGGTCTGGGACAGACTT CACCCTCAACATCCATCCTGTGGAGGAGGAGG ATACTGCAACATATTTCTGTCAGCACAGTTGG GAGTTTCCATTCACGTTCGGCTCGGGGACAAA GTTGAAAATAAAACGGGCTGATGCTGC | 304 | 208B-1094L | DIVLTQSPASLIVSLGQTATISC RASQSLSTSRFSYVHWIQQKPGQ PPKLLIKYASNLESGVPVRFSGS GSGTDFTLNIHPVEEEDTATYFC QHSWEFPFTFGSGTKLKIKR |
| 208A-293L | 305 | GACATTGTGCTGACACAGTCTCCTGCTTCCTT AATTGTATCTCTGGGGCAGAGGGCCACCATCT CATGTAGGGCCAGCCAAAGTGTCAGTACATCC AGGTTTAGTTATGTGCACTGGATCCAACAGAA ACCAGGGCAGCCACCCAAACTCCTCATCAAGT ATGCATCCAACCTTGAATCTGGGGTCCCTGTC AGGTTCAGTGGCAGTGGGTCTGGGACAGACTT CATCCTCAACATCCATCCTGTGGAGGAGGAGG ATACTGCAACATATTTCTGTCAGCACAGTTGG GAGTTTCCATTCACGTTCGGCTCGGGGACAAA GTTGGAAATAAAACGGGCTGATGCTGC | 306 | 208A-293L | DIVLTQSPASLIVSLGQRATISC RASQSVSTSRFSYVHWIQQKPGQ PPKLLIKYASNLESGVPVRFSGS GSGTDFILNIHPVEEEDTATYFC QHSWEFPFTFGSGTKLEIKR |
| 208A-134L | 307 | GAAGTTTTGATGACCCAAAGTCCACTCTCCCT GCCTGTCAGTCTTGGAGATCAGGCCTCCATCT CTTGCAGATCTAGTCAGAGCCTTGAACATACT AATGGAAACACCTATTTAGAGTGGTTCCTGCA GAGACCAGGCCAGCCTCCAAAGCTCCTGATCT ACAAAGTTTCCAGCCGATTTTCTGGGGTCCCA GACAGGTTCAGTGGCAGTGGATCAGGGACAGA TTTCACACTCAAGATCAGCAGAGTGGAGGCTG AGGATCTGGGAGTTTATTACTGTTTTCAAGGT TCACATGTTCCATTCACGTTCGGCTCGGGGAC AAAGTTGGCAATAAAACGGGCTGATGCTGC | 308 | 208A-134L | EVLMTQSPLSLPVSLGDQASISC RSSQSLEHTNGNTYLEWFLQRPG QPPKLLIYKVSSRFSGVPDRFSG SGSGTDFTLKISRVEAEDLGVYY CFQGSHVPFTFGSGTKLAIKR |
| 208A-692L | 309 | GAAGTTTTGATGACCCAAAGTCCACTCTCCCT GCCTGTCAGTCTTGGAGATCAGGCCTCCATCT CTTGCAGATCTAGTCAGAGCCTTGAACATAGT AATGGAAACACCTATTTAGAGTGGTTCCTGCA GAGACCAGGCCAGCCTCCAAAGCTCCTGATCT ACAAAGTTTCCAGCCGATTTTCTGGGGTCCCA GACAGGTTCAGTGGCAGTGGATCAGGGACAGA TTTCACACTCAAGATCAGCAGAGTGGAGGCTG AGGATCTGGGAGTTTATTACTGTTTTCAAGGT TCACATGTTCCATTCACGTTCGGCTCGGGGAC AAAGTTGGCAATAAAACGGGCTGATGCTGC | 310 | 208A-692L | EVLMTQSPLSLPVSLGDQASISC RSSQSLEHSNGNTYLEWFLQRPG QPPKLLIYKVSSRFSGVPDRFSG SGSGTDFTLKISRVEAEDLGVYY CFQGSHVPFTFGSGTKLAIKR |
| 208A-352L | 311 | GATGTTTTGATGGCCCAAACTCCACTCTCCCT GCCTGTCACCCTTGGAGATCAAGCCTCCATCT CTTGCAGATCTAGTCAGAGCCTTGTACATAGT AATGGAAACACCTATTTAGAGTGGTTCCTGCA GAAACCAGGCCAGTCTCCAAAGCTCCTGATCT ACAACGTTTCCAACCGATTTTCTGGGGTCCCA GACAGGTTCAGTGGCAGTGGATCAGGGACAGA TTTCACACTCAAGATCAGCAGAGTGGAGGCTG AGGATCTGGGAGTTTATTACTGCTTTCAAGGT TCACATGTTCCACTCACGTTCGGCTCGGGGAC AAAGTTGGAAATAAAACGGGCTGATGCTGC | 312 | 208A-352L | DVLMAQTPLSLPVTLGDQASISC RSSQSLVHSNGNTYLEWFLQKPG QSPKLLIYNVSNRFSGVPDRFSG SGSGTDFTLKISRVEAEDLGVYY CFQGSHVPLTFGSGTKLEIKR |
| 208A-983L | 313 | GATGTTTTGATGACCCAAACTCCACTCTCCCT GCCTGTCAATCTTGGAGATCAGGCCTCCATCT CTTGCAGATCTAGTCAGAGCCTTCTACATAGT AATGGAAACACCTATTTAGAGTGGTTCCTGCA GAAACCAGGCCAGTCTCCAAAGCTCCTGATCT ACAATGTTTCCAACCGATTTTCTGGGGTCCCA GACAGGTTCAGTGGCAGTGGATCAGGGACAGA TTTCACACTCAAGATCAGCAGAGTGGAGGCTG AGGATCTGGGAGTTTATTACTGCTTTCAAGGT TCACATGTTCCATTCACGTTCGGCTCGGGGAC AAAGTTGGCAATAAAACGGGCTGATGCTGC | 314 | 208A-983L | DVLMTQTPLSLPVNLGDQASISC RSSQSLLHSNGNTYLEWFLQKPG QSPKLLIYNVSNRFSGVPDRFSG SGSGTDFTLKISRVEAEDLGVYY CFQGSHVPFTFGSGTKLAIKR |
| 208B-281L | 315 | GATGTTTTGATGACCCAAACTCCACTCTCCCT GCCTGTCAGTCTTGGAGATCAAGCCTCCATCT | 316 | 208B-281L | DVLMTQTPLSLPVSLGDQASISC RSSQSLVHNNGNTYLEWFLQKPG |

| mAb Clone | SEQ ID | Nucleic Acid Seq | SEQ ID | mAb Clone | Amino Acid Seq |
|---|---|---|---|---|---|
| | | CTTGCAGATCTAGTCAGAGCCTTGTACATAAT<br>AATGGAAACACCTATTTAGAATGGTTCCTGCA<br>GAAACCAGGCCAGTCTCCAAAGCTCCTGATCT<br>ACAAAGTTTCCAACCGATTTTCTGGGGTCCCA<br>GACAGGTTCAGTGGCAGTGGATCAGGGACAGA<br>TTTCACACTCAAGATCAGCAGAGTGGAGGCTG<br>AGGATCTGGGAGTTTATTACTGCTTTCAAGGT<br>TCACATGTTCCATTCACGTTCGGCTCGGGGAC<br>AAAGTTGGAAATAAAACGGGCTGATGCTGC | | | QSPKLLIYKVSNRFSGVPDRFSG<br>SGSGTDFTLKISRVEAEDLGVYY<br>CFQGSHVPFTFGSGTKLEIKR |
| 208B-1024L | 317 | GATGTTTTGATGACCCAAACTCCACTCTCCCT<br>GCCTGTCAGTCTTGGAGATCAAGCCTCCATCT<br>CTTGCAGATCTAGTCAGAGCATTGTACACAGT<br>AATGGAAACACCTATTTAGAGTGGTACCTGCA<br>GAAACTAGGCCAGTCTCCAAAGCTCCTGATCT<br>ACAGAGTTTCCAACCGATTTTCTGGGGTCCCA<br>GACAGGTTCAGTGGCAGTGGATCAGGGACAGA<br>TTTCACACTCAAGATCAGCAGAGTGGAGGCTG<br>AGGATCTGGGAGTTTATTACTGCTTTCAAGGT<br>TCACATGTTCCGTGGACGTTCGGTGGAGGCAC<br>CAAGCTGGAAATCAAACGGGCTGATGCTGC | 318 | 208B-1024L | DVLMTQTPLSLPVSLGDQASISC<br>RSSQSIVHSNGNTYLEWYLQKLG<br>QSPKLLIYRVSNRFSGVPDRFSG<br>SGSGTDFTLKISRVEAEDLGVYY<br>CFQGSHVPWTFGGGTKLEIKR |
| 208B-471L | 319 | GATGTTGTGATGACCCAAACTCCACTCTCCCT<br>GCCTGTCAGTCTTGGAGATCAAGCCTCCATCT<br>CTTGCAGATCTAGTCAGAGCCTTCTACATAGT<br>AATGGAAACACCTATTTAGAATGGTACCTGCA<br>GAAACCTGGCCAGTCTCCAAACCTCCTGATCT<br>ACAATGTTTCCAACCGATTTTCTGGGGTCCCA<br>GACAGGTTCAGTGGCAGTGGATCAGGGACAGA<br>TTTCGCACTCAAGATCAGCAGAGTGGGGGCTG<br>AGGATCTGGGAGTTTATTACTGCTTTCAAGGT<br>TCACATGTTCCGCTCACGTTCGGTGCTGGGAC<br>CAAGCTGGAGCTGAAACGGGCTGATGCTGC | 320 | 208B-471L | DVVMTQTPLSLPVSLGDQASISC<br>RSSQSLLHSNGNTYLEWYLQKPG<br>QSPNLLIYNVSNRFSGVPDRFSG<br>SGSGTDFALKISRVGAEDLGVYY<br>CFQGSHVPLTFGAGTKLELKR |
| 208B-862L | 321 | GATGTTGTGCTGACCCAAACTCCACTCTCCCT<br>GCCTCTCAGTCTTGGAGATCAGGCCTCCATCT<br>CTTGCAGATCTAGTCAGACCCTTCTACACAGT<br>GATGGAGACACCTATTTACATTGGTACCTGCA<br>GAAGCCAGGCCAGTCTCCAAAGCTCCTGATCT<br>ACAAACTTTCCAACCGATTTTCTGGGGTCCCA<br>GACAGGTTCAGTGGCAGTGGATCAGGGACAGA<br>TTTCACACTCAAGATCAGCAGAGTGGAGGCTG<br>AGGATCTGGGAGTTTATTTCTGCTCTCAAAGT<br>ACACATGTTCCGTACACGTTCGGAGGGGGGAC<br>CAAGCTGGAAATAAAACGGGCTGATGCTGC | 322 | 208B-862L | DVVLTQTPLSLPFSFGNKASIFC<br>KFSQTLLHRDGNPFLLWYLQKPG<br>QSPKLLIYKLSNRFFGVPKRFRG<br>RGSGTNFPLKISKGEAEDLGVFF<br>CSQSTHVPYTFGGGTKLEIKR |
| 208B-589L<br>208B-1096L | 323 | GATATTGTGATGACCCAGACTCCACTCACTTT<br>GTCGGTTACCATTGGACAACCAGCTTCCATCT<br>CTTGCAAGTCAAGTCAGAGCCTCTTATTTACT<br>AATGGAAAAACCTATTTAAATTGGTTTTTACA<br>GAGGCCAGGCCAGTCTCCAAAACGCCTAATCT<br>ATCTGCTGTCTAAATTGGACTCTGGAGTCCCT<br>GACAGGTTCAGTGGCAGTGGATCAGGGACAGA<br>TTTCACACTGAAAATCAGCAGAGTGGAGGCTG<br>AGGATTTGGGAGTTTATTACTGCTTGCAGAGT<br>ACATATTTTCCTCTCACGTTCGGTGCTGGGAC<br>CAAGCTGGAGCTGAAACGGGCTGATGCTGC | 324 | 208B-589L<br>208B-1096L | DIVMTQTPLTLSVTIGQPASISC<br>KSSQSLLFTNGKTYLNWFLQRPG<br>QSPKRLIYLLSKLDSGVPDRFSG<br>SGSGTDFTLKISRVEAEDLGVYY<br>CLQSTYFPLTFGAGTKLELKR |
| 208B-189L | 325 | GATGTTGTGATGACCCAGACTCCACTCACTTT<br>GTCGGTTACCATTGGACAACCAGCTTCCATCT<br>CTTGCAAGTCAAGTCAGAGCCTCTTATATACT<br>AATGGAAAGACCTATTTGAATTGGTTATTACA<br>GAGGCCAGGCCAGTCTCCAAAACGCCTAATCT<br>ATCTGGTGTCAAAATTGGACTCTGGAGTCCCT<br>GACAGGTTCAGTGGCAGTGGATCAGGGACAGA<br>TTTCACACTGAAAATCAGCAGAGTGGAGGCTG<br>AGGATTTGGGAGTTTATTACTGCTTGCAGAGT<br>ATACATTTTCCGTACACGTTCGGAGGGGGGAC<br>CAAGCTGGACATAAAACGGGCTGATGCTGC | 326 | 208B-189L | DVVMTQTPLTLSVTIGQPASISC<br>KSSQSLLYTNGKTYLNWLLQRPG<br>QSPKRLIYLVSKLDSGVPDRFSG<br>SGSGTDFTLKISRVEAEDLGVYY<br>CLQSIHFPYTFGGGTKLDIKR |
| 208B-327L | 327 | GATATTGTGATGACGCAGGCTGCATTCTCCAA<br>TCCAGTCACTCCTGGAACATCAGTTTCCATCT<br>CCTGCAGGTCTAGTAAGAGTCTCCTACATAGT<br>AATGGCATCACTTATTTGTATTGGTATCTGCA | 328 | 208B-327L | DIVMTQAAFSNPVTPGTSVSISC<br>RSSKSLLHSNGITYLYWYLQKPG<br>QSPQLLIYQMSKIASGVPDRFRS<br>SGSGTDFTLRISRVEAADVGVYY |

| mAb Clone | SEQ ID | Nucleic Acid Seq | SEQ ID | mAb Clone | Amino Acid Seq |
|---|---|---|---|---|---|
| | | GAAGCCAGGCCAGTCTCCTCAGCTCCTGATTT ATCAGATGTCCAAGATTGCCTCAGGAGTCCCA GACAGGTTCAGGAGCAGTGGGTCAGGAACTGA TTTCACACTGAGAATCAGCAGAGTGGAGGCTG CGGATGTGGGTGTTTATTACTGTGCTCAAAAT CTAGAACTTCCGTGGACGTTCGGTGGAGGCAC CAAGCTGGAAATCAAACGGGCTGATGCTGC | | | CAQNLELPWTFGGGTKLEIKR |
| 208A-874L | 329 | GACATTGTGATGACCCAGTCTCACAAATTCAT GTCCACATCAATAGGAGACAGGGTCAGCATCA CCTGCAAGGCCAGTCAGAATGTGAGTCCTGCT GTAGCCTGGTATCAACAGAAACCAGGACAATC TCCTAAACTACTGATTTACTCGGCATCCTCCC GATACACTGGAGTCCCTGATCGCTTCACTGGC AGTGGATCTGGGACGGCTTTCACTTTCACCAT CAGCAGTGTGCAGGCTGAAGACCTGGCAGTTT ATTTCTGTCAGCAACATTTTAGTACTCCGTGG ACGTTCGGTGGAGGCACCATGCTGGAAATCAA ACGGGCTGATGCTGC | 330 | 208A-874L | DIVMTQSHKFMSTSIGDRVSITC KASQNVSPAVAWYQQKPGQSPKL LIYSASSRYTGVPDRFTGSGSGT AFTFTISSVQAEDLAVYFCQQHF STPWTFGGGTMLEIKR |
| 208B-353L | 331 | GACATTGTGATGACCCAGTCTCAAAAATTCAT GTCCACAACAGTTGGGGACAGGGTCAGAGTCA CCTGCAAGGCCAGTCAGAATGTGGGTACTGCT GTAGCCTGGTATCAACAGAAACCAGGACAATC TCCTAAACTACTGATTTACTCAGCATCCAATC GGTACACTGGAGTCCCTGATCGCTTCACAGGC AGTGGATCTGGGACAGATTTCACTCTCACCAT TACCAATATGCAGTCTGAAGACCTGGCAGATT ATTTCTGTCAGCAATATAGCACCTATCCTCTC ACGTTCGGCTCGGGGGCAAAGTTGGAAATAAA ACGGGCTGATGCTGC | 332 | 208B-353L | DIVMTQSQKFMSTTVGDRVRVTC KASQNVGTAVAWYQQKPGQSPKL LIYSASNRYTGVPDRFTGSGSGT DFTLTITNMQSEDLADYFCQQYS TYPLTFGSGAKLEIKR |
| 208B-793L | 333 | GACATTGTGATGACCCAGTCTCACAAATTCAT GTCCACATCAGTAGGAGACAGGGTCAGCATCA CCTGCAAGGCCAGTCAGGATGTGGGTACTGCT GTAGCCTGGTATCAACAGAAACCAGGACAATC TCCTAAACTACTGATTTACTGGGCATCCACCC GGCACACTGGAGTCCCTGATCGCTTCACAGGC AGTGGATCTGGGACAGATTTCACTCTCACCAT TAGCAATGTGCAGTCTGAAGACTTGGCAGATT ATTTCTGTCAGCAATATAGCAACTATCTCACG TTCGGTGCTGGGACCAAGCTGGAGGTGAAACG GGCTGATGCTGC | 334 | 208B-793L | DIVMTQSHKFMSTSVGDRVSITC KASQDVGTAVAWYQQKPGQSPKL LIYWASTRHTGVPDRFTGSGSGT DFTLTISNVQSEDLADYFCQQYS NYLTFGAGTKLEVKR |
| 208B-672L | 335 | GACATCCAGATGACCCAGTCTCCATCCTCCTT ATCTGCCTCTCTGGGCGAAAGAGTCAGTCTCA CTTGTCGGGCAAGTCAGGACATTGGTGGTAGC ATAAAACTGGCTTCAGCAGGAACCAGATGGAAC TATTAAACGCCTGATCTACGCCACATCCAGTT TAGATTCTGGTGTCCCCAAAAGGTTCAGTGGC AGTAGGTCTGGGTCAGATTATTCTCTCACCAT CAGCAGCCTTGAGTCTGAAGATTTTGTAGACT ATTACTGTCTACAATATGCTAGTTCTCCTCCG ACGTTCGGTGGAGGCACCAAACTGGAAATCAA ACGGGCTGATGCTGC | 336 | 208B-672L | DIQMTQSPSSLSASLGERVSLTC RASQDIGGSINWLQQEPDGTIKR LIYATSSLDSGVPKRFSGSRSGS DYSLTISSLESEDFVDYYCLQYA SSPPTFGGGTKLEIKR |
| 208B-408L | 337 | GACATCCAGATGACTCAGTCTCCAGCCTCCCT ATCTGCATCTGTGGGAGAACTGTCACCATCA CATGTCGAGCAAGTGGGAATATTCACACTTAT TTAGCATGGTATCAGCAGAAACAGGGAAAATC TCCTCAGCTCCTGGTCTACAATGCAAACACCT TGGCAGATGGTGTGCCATCAAGGTTCAGTGGC AGTGGATCAGGAACACAATTTTCTCTCAAGAT CAACAGTCTGCAGCCTGACGATTTTGGGAGTT ATTACTGTCAACATTTTTGGAGTGCTCCGTGG ACGTTCGGTGGAGGCACCCAGCTGGAAATCAA ACGGGCTGATGCTGC | 338 | 208B-408L | DIQMTQSPASLSASVGETVTITC RASGNIHTYLAWYQQKQGKSPQL LVYNANTLADGVPSRFSGSGSGT QFSLKINSLQPDDFGSYYCQHFW SAPWTFGGGTQLEIKR |
| 208A-207L 208B-826L | 339 | GATATTGTGTTAACTCAGTCTCCAGCCACCCT GTCTGTGACTCCAGGAGATAGAGTCAGTCTTT CCTGCAGGGCCAGTCAAAGAATTTACAACTAC CTACACTGGTATCAACAAAAATCACATGAGTC TCCAAGGCTTCTCACCAAGTATGCTTCCCAGT CCATCTCTGGGATCCCCTCCAGGTTCAGTGGC | 340 | 208A-207L 208B-826L | DIVLTQSPATLSVTPGDRVSLSC RASQRIYNYLHWYQQKSHESPRL LTKYASQSISGIPSRFSGSGSGT DFILTINSVETEDFGMYFCQQSN SWPLTFGAGTKLELRR |

| APPENDIX A-DESCRIPTION OF SEQUENCES | | | | | |
|---|---|---|---|---|---|
| mAb Clone | SEQ ID | Nucleic Acid Seq | SEQ ID | mAb Clone | Amino Acid Seq |
| | | AGTGGCTCAGGGACAGATTTCATTCTCACTAT CAACAGTGTGGAGACTGAAGATTTTGGAATGT ATTTCTGTCAACAGAGTAACAGCTGGCCTCTC ACGTTCGGTGCTGGGACCAAGCTGGAGCTGAG ACGGGCTGATGCTGC | | | |
| 208B-395L | 341 | GATATTGTGTTAACTCAGTCTCCAGCCACCCT GTCTGTGACTCCAGGAGATAGAGTCAGTCTTT CCTGCAGGGCCAGTCAAAGAATTTACAACTAC CTACACTGGTATCAACAAAAATCACATGAGTC TCCAAGGCTTCTCATCAAGTATGCTTCCCAGT CCATCTCTGGGATCCCCTCCAGGTTCAGTGGC AGTGGCTCAGGGACAGATTTCATTCTCACTAT CAACAGTGTGGAGACTGAAGATTTTGGAATGT ATTTCTGTCAACAGAGTAACAGCTGGCCTCTC ACGTTCGGTGCTGGGACCAAGCTGGAGCTGAG ACGGGCTGATGCTGC | 342 | 208B-395L | DIVLTQSPATLSVTPGDRVSLSC RASQRIYNYLHWYQQKSHESPRL LIKYASQSISGIPSRFSGSGSGT DFILTINSVETEDFGMYFCQQSN SWPLTFGAGTKLELRR |
| 208B-517L | 343 | GACATTGTGATGACTCAGTCTCCAGCCACCCT GTCTGTGACTCCAGGAGATAGAGTCTCTCTTT CCTGCAGGGCCAGTCAGAGTATTAGCGACTAC TTACACTGGTATCAACAAAAATCACATGAGTC TCCAAGGCTTCTCATCAAATATGCTTCCCAAT CCATCTCTGGGATCCCCTCCAGGTTCCGTGGC AGTGGATCAGGGTCACATTTCACTCTCAGTAT CAACAGTGTGGAACCTGAAGATGTTGGAGTGT ATTACTGTCAAAATGGTCACAGTTTTCCGTGG ACGTTCGGTGGAGGCACCAAGCTGGAAATCAA ACGGGCTGATGCTGC | 344 | 208B-517L | DIVMTQSPATLSVTPGDRVSLSC RASQSISDYLHWYQQKSHESPRL LIKYASQSISGIPSRFRGSGSGS HFTLSINSVEPEDVGVYYCQNGH SFPWTFGGGTKLEIKR |
| 208B-822L | 345 | GACATTGTGATGACTCAGTCTCCAGCCACCCT GTCTGTGACTCCAGGAGATAGAGTCTCTCTTT CCTGCAGGGCCAGCCAGTCAGTATTAGCGACTAC TTACACTGGTATCAACAAAAATCGCATGAGTC TCCAAGGCTTCTCATCAAATATGCTTCCCAAT CCATCTCTGGGATCCCCTCCAGGTTCAGTGGC AGTGGATCAGGGTCACATTTCACTCTCAGTAT CAACAGTGTGGAACCTGAAGATGTTGGAGTGT ATTACTGTCAAAATGGTCACAGTTTTCCGTGG ACGTTCGGTGGAGGCACCAAGCTGGAAATCAA ACGGGCTGATGCTGC | 346 | 208B-822L | DIVMTQSPATLSVTPGDRVSLSC RASQTISDYLHWYQQKSHESPRL LIKYASQSISGIPSRFSGSGSGS HFTLSINSVEPEDVGVYYCQNGH SFPWTFGGGTKLEIKR |
| 208A-210L | 347 | GAGATTGTGCTCACTCAGTCTCCAGCCATCAC AGCTGCATCTCTGGGGCAAAACGTCACCATCA CCTGCAGAGCCAGCTCAAGTGTAAGTTACATG CATTGGTACCGGCAGAAGTCCGGCACCTCCCC CCAACTATGGATTTATGAGATATCCAGACGGG CTTCTGGAGTCCCAGCTCGCTTCCGTGCCAGT GGGTCTGGGACCTCTTATTCTCTCACAATCAG CAGCATGGAGGCTGAAGATGCTGCCATTTATT ACTGCCAGCAGTGGAATTATCCTCTCACGTTC GGTGCTGGGACCAAGCTGGAGGTGAAACGGGC TGATGCTGC | 348 | 208A-210L | EIVLTQSPAITAASLGQNVTITC RASSSVSYMHWYRQKSGTSPQLW IYEISRRASGVPARFRASGSGTS YSLTISSMEAEDAAIYYCQQWNY PLTFGAGTKLEVKR |
| 208B-547L | 349 | GAAGTTGTGCTCACTCAGTCTCCAGCCATCAC AGCTGCATCTCTGGGGCAAAAGGTCACCATCA CCTGCAGAGCCAGCTCAAGTGTAAGTTACATG CACTGGTACCGGCAGAAGTCAGGCACCTCCCC CCAGCCATGGATTTATGAAATATCCACACTGG CTTCTGGAGTCCCAACTCGCTTCCGTGCCAGT GGGTCTGGGACCTCTTATTCTCTCACAATCAG CAGCATGGAGGCTGAAGATGCTGCCATTTATT ACTGCCAGCAGTGGAATTATCCTCTCACGTTC GGTGCTGGGACCAAGCTGGAACTGAAACGGGC TGATGCTGC | 350 | 208B-547L | EVVLTQSPAITAASLGQKVTITC RASSSVSYMHWYRQKSGTSPQPW IYEISTLASGVPTRFRASGSGTS YSLTISSMEAEDAAIYYCQQWNY PLTFGAGTKLELKR |
| 208A-638L | 351 | CAAATTGTTCTCACCCAGTCTCCAACAATCAT GTCTGCATCTCTAGGGGAACGGGTCACCATGA CCTGCACTGCCAGCTCAAGTGTGAGTTCCAGT TACTTGCACTGGTTCCAGCAGAAGCCAGGATC CTCCCCCAAACTCTGGATTTATAGCACATCCA ACCTGGCTTCTGGAGTCCCACCTCGCTTCAGT GGCAGTGGGTCTGGGACCTCTTACTCTCTCTC AATCAGCAGCGTGGAGGCTGAAGATGTTGCCA | 352 | 208A-638L | QIVLTQSPTIMSASLGERVTMTC TASSSVSSSYLHWFQQKPGSSPK LWIYSTSNLASGVPPRFSGSGSG TSYSLSISSVEAEDVATYYCLQF HRSPWTFGGGAKLEIKR |

| | | -continued | | | |
|---|---|---|---|---|---|
| APPENDIX A-DESCRIPTION OF SEQUENCES | | | | | |
| mAb Clone | SEQ ID | Nucleic Acid Seq | SEQ ID | mAb Clone | Amino Acid Seq |
| | | CTTATTACTGCCTCCAGTTTCATCGTTCCCG TGGACGTTCGGTGGAGGCGCCAAGTTGGAAAT CAAACGGGCTGATGCTGC | | | |
| 208B-515L | 353 | CAAATTGTTTTCACCCAGTATCCAGCAATAAT GTCTGCATCTCTAGGGGAACGGGTCACCATGA CCTGCACAGCCAGCTCAAGTGTAACTTCCAGT TACTTGCACTGGTTCCAGCAGAAGCCAGGATC CTCCCCCAAACTCTGGATTTATAGCACGTCCA ACCCGGGTTCTGGAGTCCCAGCTCGCTTCAGT GGCAGAGGATCTGGGACCTCTTACTCTCTCTC AATCAGCAGCATGGAGGCTGAAGATGCTGCCA CTTATTACTGCCTCCAGTTTCATCGTTCCCG TGGACGTTCGGTGGAGGCACCAAGCTGGAAAT CAGACGGGCTGATGCTGC | 354 | 208B-515L | QIVFTQYPAIMSASLGERVTMTC TASSSVTSSYLHWFQQKPGSSPK LWIYSTSNPGSGVPARFSGRGSG TSYSLSISSMEAEDAATYYCLQF HRSPWTFGGGTKLEIRR |
| 208A-877L | 355 | CAAATTGTTCTCACCCAGTCTCCAGCAATCAT GTCTGTATCTCCAGGGGAGAAGGTCTCCATGA CCTGCAGTGCCAGCTCAAGTGTCACTTACATG CACTGGTATCAGCAGAAGTCAGGCACCTCCCC CAAAAGATGGATTTATGACACATCCGAGCTGG CTTCTGGAGTCCCTGCTCGCTTCAGTGGCAGT GGGTCTGGGACCACTTACTCTCTCACAATCAG CAGCATGGAGGCTGAAGATGCTGCCACTTATT ACTGCCAGCAGTGGAGTAATAAACCGCTCACG TTCGGTGCTGGGACCAAGCTGGAGCTGAAACG GGCTGATGCTGC | 356 | 208A-877L | QIVLTQSPAIMSVSPGEKVSMTC SASSSVTYMHWYQQKSGTSPKRW IYDTSELASGVPARFSGSGSGTT YSLTISSMEAEDAATYYCQQWSN KPLTFGAGTKLELKR |
| 208B-174L | 357 | CAAAATGTTCTCACCCAGTCTCCAGCAATCAT GTCTGCATCTCCAGGGGAGAAGGTCACCATGT CCTGCAGTGCCAGCTCAAGTGTCACTTACATG TTCTGGTACCAGCTGAAGCCAGAATCCTCCCC CAGACTCCTGATTTATGACACATCCAATTTGG CTTCTGGCGTCCCTGTTCGCTTCAGTGGCAGT GGGTCTGGGACCTCTTACTCTCTCACAATCAG CCGTATGGAGGCTGAAGATGCTGCCACTTATT ACTGCCAGGAGTGGAGTAGTTACCCACTCACG TTCGGTGCTGGGACCAAGCTGGACCTGAAACG GGCTGATGCTGC | 358 | 208B-174L | QNVLTQSPAIMSASPGEKVTMSC SASSSVTYMFWYQLKPESSPRLL IYDTSNLASGVPVRFSGSGSGTS YSLTISRMEAEDAATYYCQEWSS YPLTFGAGTKLDLKR |
| 208B-612L | 359 | CAAATTGTTCTCACCCAGTCTCCAACACTCAT GTCTGCATCGCCAGGAGAAAAGGTCACCATGA CCTGCAGTGCCAGCTCAACTGTGACTTACATT TACTGGTACCAACAGAAGCCCGGCTCCTCCCC CAGACTCTGGATGTATGACACATTCAACCTGG TTTCTGGAGTCCCTGCTCGCTTCAGTGGCAGT AGGTCTGGGACCTCTTATTTTCTCACAATCAG TAGCATGGAGGGTGAAGATGCTGCCACTTATT ACTGCCAACAGTACAGTGATTCCCGTACACG TTCGGAGGGGGGACCAAGCTGGAGATAAAACG GGCTGATGCTGC | 360 | 208B-612L | QIVLTQSPTLMSASPGEKVTMTC SASSTVTYIYWYQQKPGSSPRLW MYDTFNLVSGVPARFSGSRSGTS YPLTISSMEGEDAATYYCQQYSD SPYTFGGGTKLEIKR |
| 208B-911L | 361 | CAAATTGTTCTCACCCAGTCTCCAGAGATCAT GTCTGCATCTCCAGGGGAGAAGGTCACCATAA CCTGCAGTGCCAGCTCAAGTGTAAGTTTCATG TATTGGTTCCAGCAGAAGCCAGGCACTTCTCC CAAACTCTGGATTTATATCACATCCAACCTGG CTTCTGGAGTCCCTACTCGCTTCAGTGGCAGT GGATCTGGGACCTCTTACTCTCTCACAATCAG CCGAATGGAGGCTGAAGATGCTGCCACTTATT ACTGCCAGCAAAGGAGTAGTTTCCCGTACACG TTCGGAGGGGGGACCAAACTGGAAATGAAACG GGCTGATGCTGC | 362 | 208B-911L | QIVLTQSPEIMSASPGEKVTITC SASSSVSFMYWFQQKPGTSPKLW IYITSNLASGVPTRFSGSGSGTS YSLTISRMEAEDAATYYCQQRSS FPYTFGGGTKLEMKR |
| 208A-422L 208A-442L | 363 | GACATTGTGCTGACCCAATCTCCAGCTTCTTT GGCTGTGTCTCTAGGGCAGAGGGCCATCATCT CCTGCAAGGCCAGCCAAAGTGTCAGTTTTGCT GGTACTAATTTAATGCACTGGTACCAACAGAA ACCAGGACAGCAACCCAAACTCCTCATCTATC GTGCATCCAACCTAGAAACTGGGGTTCCTACC AGGTTTAGTGGCAGTGGGTCTAGGACAGACTT CACCCTCAATATCCATCCTGTGGAGGAAGATG ATGCTGCAACCTATTACTGTCAGCAAAGTAGG | 364 | 208A-422L 208A-442L | DIVLTQSPASLAVSLGQRAIISC KASQSVSFAGTNLMHWYQQKPGQ QPKLLIYRASNLETGVPTRFSGS GSRTDFTLNIHPVEEDAATYYC QQSREYYTFGGGTKLEIKR |

| mAb Clone | SEQ ID | Nucleic Acid Seq | SEQ ID | mAb Clone | Amino Acid Seq |
|---|---|---|---|---|---|
| | | GAATATTACACGTTCGGAGGGGGGACCAAGCT GGAAATAAAACGGGCTGATGCTGC | | | |
| 208A-967L | 365 | GACATTGTGCTGACCCAATCTCCAGCTTCTTT GGCTGGGTCTCTAGGGAAAAGGGCCCCCATCT CCTGCAAAGCCAGCGAAAGTGTCAATTTTTTT GGTACTAATTTAATACACTGGTACCAACAAAA ACCAGGACAGCCCCCCAAACTCCTCATCTATC ATGCATCCAACCTAAAAACTGGAGTCCCTGCC AGGTTCAGGGGCAGGGGTCTAAAACAAACTT CCCCCTCCCCATTGATCCTGTGGAGGAAAATG ATGTTGCAATCTATTACTGTCTGCAAAATAGG AAAATTCCTCTCACGTTCGGGGTTGGGACCAA GCTGGAGCTGAAACGGGCTGATGCTGC | 366 | 208A-967L | DIVLTQSPASLAGSLGKRAPISC KASESVNEFGTNLIHWYQQKPGQ PPKLLIYHASNLKTGVPARFRGR GSKTNFPLPIDPVEENDVAIYYC LQNRKIPLTFGVGTKLELKR |
| 208B-178L | 367 | GACATTGTGCTGACCCAATCTCCAGCTTCTTT GGCTGTGTCTCTAGGGCAGAGGGCCACCATCT CCTGCAGAGCCAGCGAAAGTGTTGATAATTAT GGCATTAGTTTTATGCACTGGTACCAGCAGAA ACCAGGACAGCCACCCAAACTCCTCATCTATC GTGCATCCAACCTAGAATCTGGGATCCCTGCC AGGTTCAGTGGCAGTGGGTCTAGGACAGACTT CACCCTCACCATTAATCCTGTGGAGACTGATG ATGTTGCAACCTATTACTGTCAGCAAAGTAAT AAGGATCCATTCACGTTCGGCTCGGGGGCAAA GTTGGAAATAAAACGGGCTGATGCTGC | 368 | 208B-178L | DIVLTQSPASLAVSLGQRATISC RASESVDNYGISFMHWYQQKPGQ PPKLLIYRASNLESGIPARFSGS GSRTDFTLTINPVETDDVATYYC QQSNKDPFTFGSGAKLEIKR |
| 208A-222L 208A-605L 208B-560L | 369 | GACATTGTGGTGACACAGTCTCCTGCTTCCTT AGCTGTATCTCTGGGGCAGAGGGCCACCATCT CATGCAGGGCCAGCCAAAGTGTCAGTACATCT AGATATAGTTATCTGCACTGGTACCAACAGAA ACCAGGACAACCTCCCAAACTCCTCATCAAGT ATGCATCCAACCTAGAATCTGGGTCCCTGCC AGGTTCAGTGGCAGTGGGTCTGGGACAGACTT CACCCTCAATATCCATCCTGTGGGGAGGAGG ATACTGCAACATATTACTGTCAGCACAGTTGG GAGTTTCCATTCACGTTCGGCTCGGGGACAAA GTTGGAAATAAAACGGGCTGATGCTGC | 370 | 208A-222L 208A-605L 208B-560L | DIVVTQSPASLAVSLGQRATISC RASQSVSTSRYSYLHWYQQKPGQ PPKLLIKYASNLESGVPARFSGS GSGTDFTLNIHPVEEDTATYYC QHSWEFPPFTFGSGTKLEIKR |
| 208A-830L | 371 | GACATTGTACTGACACAGTCTCCTGCTTCCTT AGCTGTATCTCTGGGGCAGAGGGCCACCATCT CATGCAGGTCCAGCCAAAGTGTCAGTACATCT AGATATAGTTATTTGCACTGGTACCAACAGAA ACCAGGACAACCTCCCAAACTCCTCATCAAGT ATGCATCCAACCTAGAATCTGGGGTCCCTGCC AGGTTCAGTGGCAGTGGGTCTGGGACAGACTT CACCCTCAACATCCATCCTGTGGGGAGGAGG ATCCTGCAACATATTACTGTCAGCACAGTTGG GAGTTTCCATTCACGTTCGGCTCGGGGACAAA GTTGGAAATAAAACGGGCTGATGCTGC | 372 | 208A-830L | DIVLTQSPASLAVSLGQRATISC RSSQSVSTSRYSYLHWYQQKPGQ PPKLLIKYASNLESGVPARFSGS GSGTDFTLNIHPVEEDPATYYC QHSWEFPPFTFGSGTKLEIKR |
| 208A-557L | 373 | GACATTGCCCTGACACAGTCTCCTGCTTCGTT AGCTGTATCTCTGGGGCAGAGGGCCACCATCT CATGCAGGGCCAGCCAAAGTGTCAGTACATCT AGGTATAGTTATATGCACTGGTACCAACAGAA ACCAGGACAACCACCCGAACTCCTCATCAAGT ATGCATCCAACCTAGAATCTGGGGTCCCTGCC AGGTTCAGTGGCAGTGGGTCTGGGACAGACTT CACCCTCAACATCCATCCTGTGGGGAGGAGG ATACTGCAACATATTACTGTCAGCACAGTTGG GATTTTCCATTCACGTTCGGCTCGGGGACAAA GTTGGAAATAAAACGGGCTGATGCTGC | 374 | 208A-557L | DIALTQSPASLAVSLGQRATISC RASQSVSTSRYSYMHWYQQKPGQ PPELLIKYASNLESGVPARFSGS GSGTDFTLNIHPVEEDTATYYC QHSWDFPPFTFGSGTKLEIKR |
| 208A-133L 208B-556L | 375 | GACATTGTGCTGACACAGTCTCCTGCTTCCTT AGCTGTTTCTCTGGGGCAGAGGGCCACCATCT CATGCAGGGCCAGCCAAAGTGTCAGTACATCT AGGTATAGCTACATGCACTGGTACCAACAGAA ACCAGGACAGCCACCCAAACTCCTCATCAAGT ATGCATCCAACCTAGAATCTGGGTCCCTGCC AGGTTCAGTGGCAGTGGGTCTGGGACAGACTT CACCCTCAACATCCATCCTGTGGCGGAGGAGG ATACTGCAACATATTACTGTCAGCACAGTTGG GAGTTTCCATTCACGTTCGGCTCGGGGACAAA GTTGGAAATAAAACGGGCTGATGCTGC | 376 | 208A-133L 208B-556L | DIVLTQSPASLAVSLGQRATISC RASQSVSTSRYSYMHWYQQKPGQ PPKLLIKYASNLESGVPARFSGS GSGTDFTLNIHPVAEEDTATYYC QHSWEFPPFTFGSGTKLEIKR |

| mAb Clone | SEQ ID | Nucleic Acid Seq | SEQ ID | mAb Clone | Amino Acid Seq |
|---|---|---|---|---|---|
| 208B-1070L | 377 | GACATTGTGCTGACACAGTCTCTTGCTTCCTT AGCTGTTTCTCTGGGGCAGAGGGCCACCATCT CATGCAGGGCCAGCCAAAGTGTCAGTACATCT AGGTATAGTTATATGCACTGGTACCAACAGAA ACCAGGACAGCCACCCAAACTCCTCATCAAGT ATGCATCCAACCTTGAATGTGGGGTCCGTGCC AGGTTCAGTGGCAGTGGGTGTGGGACAGACTT CACCCTCAACATCCATCCTGTGGAGGAGGAGG ATACTGCAGCATATTACTGTCAGCACAGTTGG GAGTTTCCATTCACGTTCGGCTCGGGGACAAA ATTGGAAATAAAACGGGCTGATGCTGC | 378 | 208B-1070L | DIVLTQSLASLAVSLGQRATISC RASQSVSTSRYSYMHWYQQKPGQ PPKLLIKYASNLECGVRARFSGS GCGTDFTLNIHPVEEEDTAAYYC QHSWEFPFTFGSGTKLEIKR |
| 208A-159L | 379 | GACATTGTACTGACACAGTCTCCTGCTTCCTT AGCTGTTTCTCTGGGGCAGAGGGCCACCATCT CCTGCAGGGCCAGCCAAAGTGTCAGTACATCT AGGTATAGTTATGTGCACTGGTATCAACAGAA ACCAGGACAGCCACCCAAACTCCTCATCAAGT ATGCAGCCAACCTAGAATCTGGGGTCCCTGCC AGGTTCAGTGGCAGTGGGTCTGGGACAGACTT CACCCTCAACATCCATCCTGTGGCGGAGGAGG ATGCTGCAGCATATTACTGTCAGCACAGTTGG GAGTTTCCATTCACGTTCGGCTCGGGGACAAA GTTGGAAATAAAACGGGCTGATGCTGC | 380 | 208A-159L | DIVLTQSPASLAVSLGQRATISC RASQSVSTSRYSYVHWYQQKPGQ PPKLLIKYAANLESGVPARFSGS GSGTDFTLNIHPVAEEDAAYYC QHSWEFPFTFGSGTKLEIKR |
| 208A-741L | 381 | GACATTGTGCTGACACAGTCTCCTGCTTCCTT AGCTGTTTCTCTGGGGCAGAGGACCACCATCT CATGCGGGGCCAGCCAAAGTGTCAGTACATCT AGGTTTAGTTATATGCACTGGTACCAACAGAA ACCAGGACAGCCACCCAAACTCCTCATCAAGT ATGCATCCAACCTAGAATCTGGGGTCCCTGCC AGGTTCAGTGGCAGTGGGTCTGGGACAGACTT CACCCTCAACATCCATCCTGTGGCGGAGGAGG ATACTGCAGCATATTACTGTCAGCACAGTTGG GAGTTTCCATTCACGTTCGGCTCGGGGACAAA GTTGGAAATAAAACGGGCTGATGCTGC | 382 | 208A-741L | DIVLTQSPASLAVSLGQRTTISC GASQSVSTSRFSYMHWYQQKPGQ PPKLLIKYASNLESGVPARFSGS GSGTDFTLNIHPVAEEDTAAYYC QHSWEFPFTFGSGTKLEIKR |
| 208A-334L | 383 | GACATTGTGCTGACACAGTCTCCTGCTTCCTT AGCTGTTTCTCTGGGGCAGAGGGCCACCATCT CATGCAGGGCCAGCCAAAGTGTCAGTACATCT AGGTATAGTTATATGCACTGGTACCAACAGAA ACCAGGACAGCCACCCAAACTCCTCATCAAGT ATGCATCCAACCTAGAATCTGGGGTCCCTGCC AGGTTCAGTGGCAGTGGGTCTGGGACAGACTT CACCCTCAACATCCATCCTGTGGCGGAGGAGG ATACTGCAGCATATTACTGTCAGCACAGTTGG GGGTTTCCATTCACGTTCGGCTCGGGGACAAA GTTGGAAATAAAGCGGGCTGATGCTGC | 384 | 208A-334L | DIVLTQSPASLAVSLGQRATISC RASQSVSTSRYSYMHWYQQKPGQ PPKLLIKYASNLESGVPARFSGS GSGTDFTLNIHPVAEEDAAYYC QHSWGFPFTFGSGTKLEIKR |
| 208B-251L | 385 | GACATTGTGCTGACACAGTCTCCTGCTTCCTT AGCTGTATCTTTGGGAAAAAAGGCCACCATCT CATGCAGGGCCAGCCAAAGTGTCAGTACATCT AGGTATAGTTATATGCACTGGTACCAACAGAA ACCAGGACACCCACCCAAACTCCTCATCAAAT ATGCATCCAACCTAGAATCTGGGGTCCCTGCC AGGTTCAGTGGCAGTGGGTCTGGGACAGACTT CACCCTCAACATCCATCCTGTGGCGGAGGAGG ATACTGCAGCATATTACTGTCAGCACAGTTGG GAGTTTCCATTCACGTTCGGCTCGGGGACAAA GTTGGAAATAAAACGGGCTGATGCTGC | 386 | 208B-251L | DIVLTQSPASLAVSLGKKATISC RASQSVSTSRYSYMHWYQQKPGH PPKLLIKYASNLESGVPARFSGS GSGTDFTLNIHPVAEEDTAAYYC QHSWEFPFTFGSGTKLEIKR |
| 208A-110L 208A-126 208A-920L | 387 | GACATTGTGCTGACACAGTCTCCTGCTTCCTT AGCTGTTTCTCTGGGGCAGAGGGCCACCATCT CATGCAGGGCCAGCCAAAGTGTCAGTACATCT AGGTATAGTTATATGCACTGGTACCAACAGAA ACCAGGACAGCCACCCAAACTCCTCATCAAGT ATGCATCCAACCTTGAATCTGGGGTCCCTGCC AGGTTCAGTGGCAGTGGGTCTGGGACAGACTT CACCCTCAACATCCATCCTGTGGCGGAGGAGG ATACTGCAGCATATTACTGTCAGCACAGTTGG GAGTTTCCATTCACGTTCGGCTCGGGGACAAA ATTGGAAATAAAACGGGCTGATGCTGC | 388 | 208A-110L 208A-126 208A-920L | DIVLTQSPASLAVSLGQRATISC RASQSVSTSRYSYMHWYQQKPGQ PPKLLIKYASNLESGVPARFSGS GSGTDFTLNIHPVAEEDTAAYYC QHSWEFPFTFGSGTKLEIKR |

| APPENDIX A-DESCRIPTION OF SEQUENCES | | | | | |
|---|---|---|---|---|---|
| mAb Clone | SEQ ID | Nucleic Acid Seq | SEQ ID | mAb Clone | Amino Acid Seq |
| 208A-692CDRL1 | 389 | AGATCTAGTCAGAGCCTTGAACATAGTAATGGAAACACCTATTTAGAG | 390 | 208A-692CDRL1 | RSSQSLEHSNGNTYLE |
| 208A-352CDRL1 | 391 | AGATCTAGTCAGAGCCTTGTACATAGTAATGGAAACACCTATTTAGAG | 392 | 208A-352CDRL1 | RSSQSLVHSNGNTYLE |
| 208A-983CDRL1 208B-471CDRL1 | 393 | AGATCTAGTCAGAGCCTTGTACATAGTAATGGAAACACCTATTTAGAG | 394 | 208A-983CDRL1 208B-471CDRL1 | RSSQSLLHSNGNTYLE |
| 208B-1024CDRL1 | 395 | AGATCTAGTCAGAGCATTGTACACAGTAATGGAAACACCTATTTAGAG | 396 | 208B-1024CDRL1 | RSSQSIVHSNGNTYLE |
| 208A-134CDRL1 | 397 | AGATCTAGTCAGAGCCTTGAACATACTAATGGAAACACCTATTTAGAG | 398 | 208A-134CDRL1 | RSSQSLEHTNGNTYLE |
| 208B-281CDRL1 | 399 | AGATCTAGTCAGAGCCTTGTACATAATAATGGAAACACCTATTTAGAA | 400 | 208B-281CDRL1 | RSSQSLVHNNGNTYLE |
| 208B-327CDRL1 | 401 | AGGTCTAGTAAGAGTCTCCTACATAGTAATGGCATCACTTATTTGTAT | 402 | 208B-327CDRL1 | RSSKSLLHSNGITYLY |
| 208B-862CDRL1 | 403 | AGATCTAGTCAGACCCTTCTACACAGTGATGGAGACACCTATTTACAT | 404 | 208B-862CDRL1 | KFSQTLLHRDGNPFLL |
| 208B-589CDRL1 208B-1096CDRL1 | 405 | AAGTCAAGTCAGAGCCTCTTATTTACTAATGGAAAAACCTATTTAAAT | 406 | 208B-589CDRL1 208B-1096CDRL1 | KSSQSLLFTNGKTYLN |
| 208B-189CDRL1 | 407 | AAGTCAAGTCAGAGCCTCTTATATACTAATGGAAAGACCTATTTGAAT | 408 | 208B-189CDRL1 | KSSQSLLYTNGKTYLN |
| 208A-874CDRL1 | 409 | AAGGCCAGTCAGAATGTGAGTCCTGCTGTAGCC | 410 | 208A-874CDRL1 | KASQNVSPAVA |
| 208B-353CDRL1 | 411 | AAGGCCAGTCAGAATGTGGGTACTGCTGTAGCC | 412 | 208B-353CDRL1 | KASQNVGTAVA |
| 208B-793CDRL1 | 413 | AAGGCCAGTCAGGATGTGGGTACTGCTGTAGCC | 414 | 208B-793CDRL1 | KASQDVGTAVA |
| 208B-672CDRL1 | 415 | CGGGCAAGTCAGGACATTGGTGGTAGCATAAAC | 416 | 208B-672CDRL1 | RASQDIGGSIN |
| 208B-408CDRL1 | 417 | CGAGCAAGTGGGAATATTCACACTTATTTAGCA | 418 | 208B-408CDRL1 | RASGNIHTYLA |
| 208A-207CDRL1 208B-826CDRL1 208B-395CDRL1 | 419 | AGGGCCAGTCAAAGAATTTACAACTACCTACAC | 420 | 208A-207CDRL1 208B-826CDRL1 208B-395CDRL1 | RASQRIYNYLH |
| 208B-517CDRL1 | 421 | AGGGCCAGCCAGAGTATTAGCGACTACTTACAC | 422 | 208B-517CDRL1 | RASQSISDYLH |
| 208B-822CDRL1 | 423 | AGGGCCAGCCAGACTATTAGCGACTACTTACAC | 424 | 208B-822CDRL1 | RASQTISDYLH |
| 208A-210CDRL1 | 425 | AGAGCCAGCTCAAGTGTAAGTTACATGCAT | 426 | 208A-210CDRL1 | RASSSVSYMH |
| 208B-547CDRL1 | 427 | AGAGCCAGCTCAAGTGTAAGTTACATGCAT | 428 | 208B-547CDRL1 | RASSSVSYMH |
| 208A-638CDRL1 | 429 | ACTGCCAGCTCAAGTGTGAGTTCCAGTTACTTGCAC | 430 | 208A-638CDRL1 | TASSSVSSSYLH |
| 208B-515CDRL1 | 431 | ACAGCCAGCTCAAGTGTAACTTCCAGTTACTTGCAC | 432 | 208B-515CDRL1 | TASSSVTSSYLH |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-877CDRL1 | 433 | AGTGCCAGCTCAAGTGTCACTTACATGCAC | 434 | 208A-877CDRL1 | SASSSVTYMH |
| 208B-174CDRL1 | 435 | AGTGCCAGCTCAAGTGTCACTTACATGTTC | 436 | 208B-174CDRL1 | SASSSVTYMF |
| 208B-612CDRL1 | 437 | AGTGCCAGCTCAACTGTGACTTACATTTAC | 438 | 208B-612CDRL1 | SASSTVTYIY |
| 208B-911CDRL1 | 439 | AGTGCCAGCTCAAGTGTAAGTTTCATGTAT | 440 | 208B-911CDRL1 | SASSSVSFMY |
| 208A-422CDRL1 208A-442CDRL1 | 441 | AAGGCCAGCCAAAGTGTCAGTTTTGCTGGTACTAATTTAATGCAC | 442 | 208A-422CDRL1 208A-442CDRL1 | KASQSVSFAGTNLMH |
| 208A-967CDRL1 | 443 | AAAGCCAGCGAAAGTGTCAATTTTTTTGGTACTAATTTAATACAC | 444 | 208A-967CDRL1 | KASESVNFFGTNLIH |
| 208B-178CDRL1 | 445 | AGAGCCAGCGAAAGTGTTGATAATTATGGCATTAGTTTTATGCAC | 446 | 208B-178CDRL1 | RASESVDNYGISFMH |
| 208A-222CDRL1 208A-605CDRL1 208B-560CDRL1 | 447 | AGGGCCAGCCAAAGTGTCAGTACATCTAGATATAGTTATCTGCAC | 448 | 208A-222CDRL1 208A-605CDRL1 208B-560CDRL1 | RASQSVSTSRYSYLH |
| 208A-557CDRL1 208A-133CDRL1 208B-556CDRL1 208B-1070CDRL1 208B-251CDRL1 208A-110CDRL1 208A-126CDRL1 208A-920CDRL1 208A-334CDRL1 | 449 | AGGGCCAGCCAAAGTGTCAGTACATCTAGGTATAGTTATATGCAC | 450 | 208A-557CDRL1 208A-133CDRL1 208B-556CDRL1 208B-1070CDRL1 208B-251CDRL1 208A-110CDRL1 208A-126CDRL1 208A-920CDRL1 208A-334CDRL1 | RASQSVSTSRYSYMH |
| 208A-741CDRL1 | 451 | GGGGCCAGCCAAAGTGTCAGTACATCTAGGTTTAGTTATATGCAC | 452 | 208A-741CDRL1 | GASQSVSTSRFSYMH |
| 208A-830CDRL1 | 453 | AGGTCCAGCCAAAGTGTCAGTACATCTAGATATAGTTATTTGCAC | 454 | 208A-830CDRL1 | RSSQSVSTSRYSYLH |
| 208A-1064CDRL1 | 455 | AGGGCCAGCCAAAGTGTCAGTACATCTAGGTTTAGTTATCTGCAC | 456 | 208A-1064CDRL1 | RASQSVSTSRFSYLH |
| 208A-159CDRL1 | 457 | AGGGCCAGCCAAAGTGTCAGTACATCTAGGTATAGTTATGTGCACTGG | 458 | 208A-159CDRL1 | RASQSVSTSRYSYVH |
| 208A-293CDRL1 | 459 | AGGGCCAGCCAAAGTGTCAGTACATCCAGGTTTAGTTATGTGCAC | 460 | 208A-293CDRL1 | RASQSVSTSRFSYVH |
| 208B-1094CDRL1 | 461 | AGGGCCAGCCAAAGTCTCAGTACATCTAGGTTTAGCTATGTGCAC | 462 | 208B-1094CDRL1 | RASQSLSTSRFSYVH |
| 208A-692CDRL2 208A-134CDRL2 | 463 | AAAGTTTCCAGCCGATTTTCT | 464 | 208A-692CDRL2 208A-134CDRL2 | KVSSRFS |

APPENDIX A-DESCRIPTION OF SEQUENCES -continued

| mAb Clone | SEQ ID | Nucleic Acid Seq | SEQ ID | mAb Clone | Amino Acid Seq |
|---|---|---|---|---|---|
| 208B-281CDRL2 | 465 | AAAGTTTCCAACCGATTTTCT | 466 | 208B-281CDRL2 | KVSNRFS |
| 208B-862CDRL2 | 467 | AAACTTTCCAACCGATTTTCT | 468 | 208B-862CDRL2 | KLSNRFF |
| 208A-352CDRL2<br>208A-983CDRL2<br>208B-471CDRL2 | 469 | AATGTTTCCAACCGATTTTCT | 470 | 208A-352CDRL2<br>208A-983CDRL2<br>208B-471CDRL2 | NVSNRFS |
| 208B-1024CDRL2 | 471 | AGAGTTTCCAACCGATTTTCT | 472 | 208B-1024CDRL2 | RVSNRFS |
| 208B-327CDRL2 | 473 | CAGATGTCCAAGATTGCCTCA | 474 | 208B-327CDRL2 | QMSKIAS |
| 208B-589CDRL2<br>208B-1096CDRL2 | 475 | CTGCTGTCTAAATTGGACTCT | 476 | 208B-589CDRL2<br>208B-1096CDRL2 | LLSKLDS |
| 208B-189CDRL2 | 477 | CTGGTGTCAAAATTGGACTCT | 478 | 208B-189CDRL2 | LVSKLDS |
| 208A-874CDRL2 | 479 | TCGGCATCCTCCCGATACACT | 480 | 208A-874CDRL2 | SASSRYT |
| 208B-353CDRL2 | 481 | TCAGCATCCAATCGGTACACT | 482 | 208B-353CDRL2 | SASNRYT |
| 208B-793CDRL2 | 483 | TGGGCATCCACCCGGCACACT | 484 | 208B-793CDRL2 | WASTRHT |
| 208B-672CDRL2 | 485 | GCCACATCCAGTTTAGATTCT | 486 | 208B-672CDRL2 | ATSSLDS |
| 208B-408CDRL2 | 487 | AATGCAAACACCTTGGCAGAT | 488 | 208B-408CDRL2 | NANTLAD |
| 208A-207CDRL2<br>208B-826CDRL2<br>208B-395CDRL2<br>208B-517CDRL2 | 489 | GCTTCCCAGTCCATCTCTGGG | 490 | 208A-207CDRL2<br>208B-826CDRL2<br>208B-395CDRL2<br>208B-517CDRL2 | ASQSISG |
| 208B-822CDRL2 | 491 | TATGCTTCCCAATCCATCTCT | 492 | 208B-822CDRL2 | YASQSIS |
| 208A-210CDRL2 | 493 | GAGATATCCAGACGGGCTTCT | 494 | 208A-210CDRL2 | EISRRAS |
| 208B-547CDRL2 | 495 | GAAATATCCACACTGGCTTCT | 496 | 208B-547CDRL2 | EISTLAS |
| 208A-638CDRL2 | 497 | AGCACATCCAACCTGGCTTCT | 498 | 208A-638CDRL2 | STSNLAS |
| 208B-515CDRL2 | 499 | AGCACGTCCAACCCGGGTTCT | 500 | 208B-515CDRL2 | STSNPGS |
| 208A-877CDRL2 | 501 | GACACATCCGAGCTGGCTTCT | 502 | 208A-877CDRL2 | DTSELAS |
| 208B-174CDRL2 | 503 | GACACATCCAATTTGGCTTCT | 504 | 208B-174CDRL2 | DTSNLAS |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208B-612CDRL2 | 505 | GACACATTCAACCTGGTTTCT | 506 | 208B-612CDRL2 | DTFNLVS |
| 208B-911CDRL2 | 507 | ATCACATCCAACCTGGCTTCT | 508 | 208B-911CDRL2 | ITSNLAS |
| 208A-422CDRL2 208A-442CDRL2 | 509 | CGTGCATCCAACCTAGAAACT | 510 | 208A-422CDRL2 208A-442CDRL2 | RASNLET |
| 208A-967CDRL2 | 511 | CATGCATCCAACCTAAAAACT | 512 | 208A-967CDRL2 | HASNLKT |
| 208B-178CDRL2 | 513 | CGTGCATCCAACCTAGAATCT | 514 | 208B-178CDRL2 | RASNLES |
| 208A-222CDRL2 208A-605CDRL2 208B-560CDRL2 208A-557CDRL2 208A-133CDRL2 208B-556CDRL2 208B-251CDRL2 208A-110CDRL2 208A-126CDRL2 208A-920CDRL2 208A-334CDRL2 208A-741CDRL2 208A-830CDRL2 208A-1064CDRL2 208A-159CDRL2 208A-293CDRL2 208B-1094CDRL2 | 515 | TATGCATCCAACCTAGAATCT | 516 | 208A-222CDRL2 208A-605CDRL2 208B-560CDRL2 208A-557CDRL2 208A-133CDRL2 208B-556CDRL2 208B-251CDRL2 208A-110CDRL2 208A-126CDRL2 208A-920CDRL2 208A-334CDRL2 208A-741CDRL2 208A-830CDRL2 208A-1064CDRL2 208A-159CDRL2 208A-293CDRL2 208B-1094CDRL2 | YASNLES |
| 208B-1070CDRL2 | 517 | TATGCATCCAACCTTGAATGT | 518 | 208B-1070CDRL2 | YASNLEC |
| 208A-692CDRL3 208A-983CDRL3 208B-281CDRL3 208A-134CDRL3 | 519 | TTTCAAGGTTCACATGTTCCATTCACG | 520 | 208A-692CDRL3 208A-983CDRL3 208B-281CDRL3 208A-134CDRL3 | FQGSHVPFT |
| 208A-352CDRL3 208B-471CDRL3 | 521 | TTTCAAGGTTCACATGTTCCACTCACG | 522 | 208A-352CDRL3 208B-471CDRL3 | FQGSHVPLT |
| 208B-1024CDRL3 | 523 | TTTCAAGGTTCACATGTTCCGTGGACG | 524 | 208B-1024CDRL3 | FQGSHVPWTF |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208B-327CDRL3 | 525 | GCTCAAAATCTAGAACTTCCGTGGACG | 526 | 208B-327CDRL3 | AQNLELPWT |
| 208B-862CDRL3 | 527 | TCTCAAAGTACACATGTTCCGTACACG | 528 | 208B-862CDRL3 | SQSTHVPYT |
| 208B-589CDRL3 208B-1096CDRL3 | 529 | TTGCAGAGTACATATTTTCCTCTCACG | 530 | 208B-589CDRL3 208B-1096CDRL3 | LQSTYFPLT |
| 208B-189CDRL3 | 531 | TTGCAGAGTATACATTTTCCGTACACG | 532 | 208B-189CDRL3 | LQSIHFPYT |
| 208B-672CDRL3 | 533 | CTACAATATGCTAGTTCTCCTCCGACG | 534 | 208B-672CDRL3 | LQYASSPPT |
| 208A-638CDRL3 208B-515CDRL3 | 535 | CTCCAGTTTCATCGTTCCCCGTGGACG | 536 | 208A-638CDRL3 208B-515CDRL3 | LQFHRSPWT |
| 208A-967CDRL3 | 537 | CTGCAAAATAGGAAAATTCCTCTCACG | 538 | 208A-967CDRL3 | LQNRKIPLT |
| 208A-874CDRL3 | 539 | CAGCAACATTTTAGTACTCCGTGGACG | 540 | 208A-874CDRL3 | QQHFSTPWT |
| 208B-353CDRL3 | 541 | CAGCAATATAGCACCTATCCTCTCACG | 542 | 208B-353CDRL3 | QQYSTYPLT |
| 208B-793CDRL3 | 543 | CAGCAATATAGCAACTATCTCACG | 544 | 208B-793CDRL3 | QQYSNYLT |
| 208A-207CDRL3 208B-826CDRL3 208B-395CDRL3 | 545 | CAACAGAGTAACAGCTGGCCTCTCACG | 546 | 208A-207CDRL3 208B-826CDRL3 208B-395CDRL3 | QQSNSWPLT |
| 208A-210CDRL3 208B-547CDRL3 | 547 | CAGCAGTGGAATTATCCTCTCACG | 548 | 208A-210CDRL3 208B-547CDRL3 | QQWNYPLT |
| 208A-877CDRL3 | 549 | CAGCAGTGGAGTAATAAACCGCTCACG | 550 | 208A-877CDRL3 | QQWSNKPLT |
| 208B-612CDRL3 | 551 | CAACAGTACAGTGATTCCCCGTACACG | 552 | 208B-612CDRL3 | QQYSDSPYT |
| 208B-911CDRL3 | 553 | CAGCAAAGGAGTAGTTTCCCGTACACG | 554 | 208B-911CDRL3 | QQRSSFPYT |
| 208A-422CDRL3 208A-442CDRL3 | 555 | CAGCAAAGTAGGGAATATTACACG | 556 | 208A-422CDRL3 208A-442CDRL3 | QQSREYYT |
| 208B-178CDRL3 | 557 | CAGCAAAGTAATAAGGATCCATTCACG | 558 | 208B-178CDRL3 | QQSNKDPFT |
| 208B-517CDRL3 208B-822CDRL3 | 559 | CAAAATGGTCACAGTTTTCCGTGGACG | 560 | 208B-517CDRL3 208B-822CDRL3 | QNGHSFPWT |
| 208B-408CDRL3 | 561 | CAACATTTTTGGAGTGCTCCGTGGACG | 562 | 208B-408CDRL3 | QHFWSAPWT |
| 208B-174CDRL3 | 563 | CAGGAGTGGAGTAGTTACCCACTCACG | 564 | 208B-174CDRL3 | QEWSSYPLT |

APPENDIX A-DESCRIPTION OF SEQUENCES

| mAb Clone | SEQ ID | Nucleic Acid Seq | SEQ ID | mAb Clone | Amino Acid Seq |
|---|---|---|---|---|---|
| 208A-222CDRL3 208A-605CDRL3 208B-560CDRL3 208A-133CDRL3 208B-556CDRL3 208B-1070CDRL3 208B-251CDRL3 208A-110CDRL3 208A-126CDRL3 208A-920CDRL3 208A-741CDRL3 208A-830CDRL3 208A-1064CDRL3 208A-159CDRL3 208A-293CDRL3 208B-1094CDRL3 | 565 | CAGCACAGTTGGGAGTTTCCATTCACG | 566 | 208A-222CDRL3 208A-605CDRL3 208B-560CDRL3 208A-133CDRL3 208B-556CDRL3 208B-1070CDRL3 208B-251CDRL3 208A-110CDRL3 208A-126CDRL3 208A-920CDRL3 208A-741CDRL3 208A-830CDRL3 208A-1064CDRL3 208A-159CDRL3 208A-293CDRL3 208B-1094CDRL3 | QHSWEFPFT |
| 208A-557CDRL3 | 567 | CAGCACAGTTGGGATTTTCCATTCACG | 568 | 208A-557CDRL3 | QHSWDFPFT |
| 208A-334CDRL3 | 569 | CAGCACAGTTGGGATTTTCCATTCACG | 570 | 208A-334CDRL3 | QHSWGFPFT |
| HCV core 1-169 amino acid sequence | 571 | ATGTCTACCAACCCGAAACCGCAGAAAAAAA CAAACGTAACACCAACCGTCGTCCGCAGGACG TTAAATTCCCGGGTGGTGGTCAGATCGTTGGT GGTGTTTACCTGCTGCCGCGTCGTGGTCCGCG TCTGGGTGTTCGTGCTACGCGTAAAACCTCTG AACGTTCTCAGCCGCGTGGGCGTCGTCAGCCG ATCCCGAAAGCTCGTCGTCCGGAAGGTCGTAC CTGGGCTCAGCCGGGTTACCCGTGGCCGCTGT ACGGTAACGAAGGTTGCGGTTGGGCTGGTTGG CTGCTGTCTCCGCGTGGATCTCGTCCGTCTTG GGGTCCGACCGACCCGCGTCGTCGTTCTCGTA ACCTTGGTAAAGTTATCGATACCCTGACCTGC GGTTTCGCTGACCTGATGGGTTACATACCGCT GGTTGGAGCTCCGCTGGGTGGTGCTGCTCGTG CTCTGGCGCATGGCGTGCGTGTTCTGGAAGAT GGCGTCAACTATGCCACCGGTAATCTG | 572 | HCV core 1-169 amino acid sequence | MSTNPKPQKKNKRNTNRRPQDVK FPGGGQIVGGVYLLPRRGPRLGV RATRKTSERSQPRGRRQPIPKAR RPEGRTWAQPGYPWPLYGNEGCG WAGWLLSPRGSRPSWGPTDPRRR SRNLGKVIDTLTCGFADLMGYIP LVGAPLGGAARALAHGVRVLEDG VNYATGNL |
| | | | 573 | HCV 134-154 Peptide 1 | MGYIPLVGAPLGGAARALAHG |
| | | | 574 | HCV 141-161 Peptide 2 | GAPLGGAARALAHGVRVLEDG |
| | | | 575 | HCV 151-171 Peptide 3 | LAHGVRVLEDGVNYATGNLPG |
| | | | 576 | ALRZ-8 | MGYIPLVGAPLGGAARALAHGVR VLEDGVNYATGNLPGC |
| | | | 577 | ALRZ-9 | MGYIPLVGAPLGGAARALAHGVR VLEDGVNYATGNLPGQYIKANSK FIGITEL |

We claim:

1. A method for the detection of HCV protein in a test sample comprising:
   (i) contacting a test sample suspected of containing HCV with a first antibody, or antigen-binding portion thereof, which comprises heavy chain CDR1, CDR2, and CDR3 amino acid sequences of SEQ ID NO: 588, SEQ ID NO: 589, and SEQ ID NO: 590, respectively, and light chain CDR1, CDR2, and CDR3 amino acid sequences of SEQ ID NO: 585, SEQ ID NO: 586, and SEQ ID NO: 587, respectively, to form a complex between said first antibody, or said antigen-binding portion thereof, and said HCV core protein located within said test sample;
   (ii) contacting said complex formed in step (i) with a second antibody, or antigen-binding portion thereof, which specifically binds to the amino acid sequence of SEQ ID NO: 574 in the lipid binding domain of HCV core protein, to form a complex between said second antibody, or said antigen-binding portion thereof, and said complex formed in step (i); and
   (iii) detecting said complex formed in step (ii).

2. The method of claim 1, wherein said first and/or second antibody, or said antigen-binding portion thereof, is detectably labeled with a label, and wherein said detecting said complex in step (iii) comprises detecting said label.

3. The method of claim 1, wherein said HCV core protein in said complex is an HCV mini-core protein.

4. The method of claim 1, wherein said HCV core protein in said complex is a full-length HCV core protein.

5. A method for the detection of HCV protein in a test sample comprising:
   (i) contacting a test sample suspected of containing HCV with a first antibody, or antigen-binding portion thereof, which specifically binds to the amino acid sequence of SEQ ID NO: 574 in the lipid binding domain of an HCV core protein, to form a complex between said first antibody, or said antigen-binding portion thereof, and said HCV core protein located within said test sample;
   (ii) contacting said complex formed in step (i) with a second antibody, or antigen-binding portion thereof, which comprises heavy chain CDR1, CDR2, and CDR3 amino acid sequences of SEQ ID NO: 588, SEQ ID NO: 589, and SEQ ID NO: 590, respectively, and light chain CDR1, CDR2, and CDR3 amino acid sequences of SEQ ID NO: 585, SEQ ID NO: 586, and SEQ ID NO: 587, respectively, to form a complex between said second antibody, or said antigen-binding portion thereof, and said complex formed in step (i); and
   (iii) detecting said complex formed in step (ii).

6. The method of claim 1, wherein said first and/or second antibody, or said antigen-binding portion thereof, is detectably labeled with a label, and wherein said detecting said complex in step (iii) comprises detecting said label.

7. The method of claim 5, wherein said HCV core protein in said complex is an HCV mini-core protein.

8. The method of claim 5, wherein said HCV core protein in said complex is a full-length HCV core protein.

* * * * *

UNITED STATES PATENT AND TRADEMARK OFFICE
CERTIFICATE OF CORRECTION

PATENT NO. : 10,444,242 B2
APPLICATION NO. : 15/189646
DATED : October 15, 2019
INVENTOR(S) : Robert Ziemann et al.

Page 1 of 1

It is certified that error appears in the above-identified patent and that said Letters Patent is hereby corrected as shown below:

On the Title Page

Item [63], delete "application No. 15/079,013, now U.S. Pat. No. 10,197,573 as a continuation of application No. 14/138,991 and should be a divisional." and insert -- Continuation-in-part of application No. 15/079,013, filed on Mar. 23, 2016, now Pat. No. 10,197,573, which is a divisional of application No. 14/138,991, filed on December 23, 2013, now Pat. No. 9,371,374. --

Signed and Sealed this
Third Day of March, 2020

Andrei Iancu
*Director of the United States Patent and Trademark Office*